US012649939B2

(12) United States Patent (10) Patent No.: US 12,649,939 B2
Crameri et al. (45) Date of Patent: Jun. 9, 2026

(54) PROCESSES FOR THE PRODUCTION OF OLIGONUCLEOTIDES

(71) Applicant: GLAXOSMITHKLINE INTELLECTUAL PROPERTY DEVELOPMENT LIMITED, Brentford (GB)

(72) Inventors: Andreas Crameri, Stevenage (GB); David Graham Tew, Stevenage (GB)

(73) Assignee: GLAXOSMITHKLINE INTELLECTUAL PROPERTY DEVELOPMENT LIMITED, Stevenage (GB)

( * ) Notice: Subject to any disclaimer, the term of this patent is extended or adjusted under 35 U.S.C. 154(b) by 299 days.

(21) Appl. No.: 16/771,362

(22) PCT Filed: Dec. 17, 2018

(86) PCT No.: PCT/EP2018/085179
§ 371 (c)(1),
(2) Date: Jun. 10, 2020

(87) PCT Pub. No.: WO2019/121500
PCT Pub. Date: Jun. 27, 2019

(65) Prior Publication Data
US 2024/0287566 A1 Aug. 29, 2024

(30) Foreign Application Priority Data

Dec. 19, 2017 (GB) .................................... 1721307

(51) Int. Cl.
| | |
|---|---|
| *C12P 19/34* | (2006.01) |
| *C12N 9/00* | (2006.01) |
| *C12N 9/12* | (2006.01) |
| *C12N 9/22* | (2006.01) |
| *C12N 15/10* | (2006.01) |
| *C12N 15/113* | (2010.01) |
| *C12P 19/30* | (2006.01) |

(52) U.S. Cl.
CPC ............ *C12P 19/34* (2013.01); *C12N 9/1264* (2013.01); *C12N 9/22* (2013.01); *C12N 9/93* (2013.01); *C12N 15/1031* (2013.01); *C12N 15/113* (2013.01); *C12P 19/30* (2013.01); *C12N 2310/11* (2013.01); *C12N 2310/314* (2013.01); *C12N 2310/315* (2013.01); *C12N 2310/321* (2013.01); *C12N 2310/322* (2013.01); *C12N 2310/3231* (2013.01); *C12N 2310/332* (2013.01); *C12N 2310/341* (2013.01); *C12Y 605/01003* (2013.01)

(58) Field of Classification Search
CPC ........ C12P 19/34; C12P 19/30; C12N 9/1264; C12N 9/22; C12N 9/93; C12N 15/1031; C12N 15/113; C12N 2310/11; C12N 2310/314; C12N 2310/315; C12N 2310/321; C12N 2310/322; C12N 2310/3231; C12N 2310/332; C12N 2310/341; C12Y 605/01003
See application file for complete search history.

(56) References Cited

U.S. PATENT DOCUMENTS

| | | | |
|---|---|---|---|
| 5,547,843 A | 8/1996 | Studier et al. | |
| 5,602,000 A * | 2/1997 | Hyman ................... | C12P 19/34 435/6.12 |
| 5,998,175 A | 12/1999 | Akhavan-Tafti | |
| 6,004,826 A | 12/1999 | Segev | |
| 6,110,668 A | 8/2000 | Strizhov et al. | |
| 6,660,229 B2 | 12/2003 | Cantor et al. | |
| 6,867,294 B1 * | 3/2005 | Sanghvi ................. | C07H 19/04 536/25.31 |
| 7,033,753 B1 | 4/2006 | Kool | |
| 7,695,906 B2 * | 4/2010 | Schatz ................... | C12P 19/34 435/6.11 |
| 8,148,065 B1 | 4/2012 | Wallace | |
| 10,640,812 B2 | 5/2020 | Crameri et al. | |
| 2003/0008306 A1 | 1/2003 | Turnbull et al. | |
| 2003/0073081 A1 | 4/2003 | Mukai et al. | |
| 2003/0120035 A1 | 6/2003 | Gao et al. | |
| 2003/0228602 A1 | 12/2003 | Parker et al. | |
| 2004/0058330 A1 * | 3/2004 | Aevarsson ......... | C12N 15/1093 435/6.12 |
| 2004/0248104 A1 | 12/2004 | Yakhini et al. | |
| 2016/0108382 A1 * | 4/2016 | Efcavitch ....... | C12Y 207/07031 435/194 |

FOREIGN PATENT DOCUMENTS

| | | |
|---|---|---|
| CN | 1350581 A | 5/2002 |
| CN | 105506125 A | 4/2016 |
| EP | 1130113 A1 | 9/2001 |
| WO | 1989012696 A1 | 12/1989 |

(Continued)

OTHER PUBLICATIONS

Brill, "Facile Methods to Recycle Nucleosides during Solid Phase Synthesis of Oligonucleotides", Tetrahedron Letters, vol. 35, No. 19, 1994, pp. 3041-3044. (Year: 1994).*
Frank, "A new general approach for the simultaneous chemical synthesis of large numbers of oligonucleotides: segmental solid supports", (11,(13) Nucleic acids Research 4365-4377 (1983). (Year: 1983).*
Toy et al., "Soluble Polymer-Supported Organic Synthesis", Accounts of Chemical Research, 33, 546-554 (2000)). (Year: 2000).*
Mikiembo Kukwi Ki La et al: "Assembly of a biocompatible triazole-linked gene by one-pot click-DNA ligation" Nature Chemistry, vol. 9, No. 11, Sep. 11, 2017, pp. 1089-1098, ISSN: 1755-4330.

(Continued)

*Primary Examiner* — Abigail Vanhorn
*Assistant Examiner* — Stephanie L Sullivan

(57) ABSTRACT

The invention relates to novel processes using enzymes for the production of oligonucleotides, wherein said processes are suitable for use in the production of chemically modified oligonucleotides, such as those for use in therapy.

31 Claims, 25 Drawing Sheets
Specification includes a Sequence Listing.

(56)                References Cited

FOREIGN PATENT DOCUMENTS

| WO | 2000005412 | A1 | 2/2000 | | |
| WO | 2000050870 | A1 | 8/2000 | | |
| WO | 2001027326 | A2 | 4/2001 | | |
| WO | 2001029211 | A2 | 4/2001 | | |
| WO | 2001064864 | A2 | 9/2001 | | |
| WO | 2001071037 | A1 | 9/2001 | | |
| WO | WO-0164864 | A2 * | 9/2001 | ......... | C12N 15/1013 |
| WO | 2003106679 | A1 | 12/2003 | | |
| WO | 2004029223 | A2 | 4/2004 | | |
| WO | WO 2006/071568 | A2 | 7/2006 | | |
| WO | 2009043112 | A1 | 4/2009 | | |
| WO | 2009097673 | A1 | 8/2009 | | |
| WO | 2012010711 | A1 | 1/2012 | | |
| WO | 2014041337 | A1 | 3/2014 | | |
| WO | WO-2018011067 | A2 * | 1/2018 | ......... | A61K 31/7088 |

OTHER PUBLICATIONS

Markus Kramer et al: "Enzyme-Free Ligation of 5'-Phosphorylated Oligodeoxynucleotides in a DNA Nanostructure", Chemistry & Biodiversity vol. 14, No. 9, Aug. 11, 2017, p. e1700315, ISSN: 1612-1872.

A. Shivalingam et al: "Synthesis of chemically modified DNA", Biochemical Society Transactions, vol. 44, No. 3, Jun. 15, 2016, pp. 709-715, ISSN: 0300-5127.

A. H. El-Sagheer et al: "Biocompatible artificial DNA linker that is read through by DNA polymerases and is functional in *Escherichia coli*", Proceedings of the National Academy of Sciences, vol. 108, No. 28, Jul. 12, 2011, pp. 11338-11343, ISSN: 0027-8424.

Jieqiong Qiu et al: "Solid phase click ligation for the synthesis of very long oligonucleotides", Chemical Communications, vol. 49, No. 62, Jan. 1, 2013, p. 6959, ISSN: 1359-7345.

ATDBio: "Gene synthesis", Jan. 5, 2016, Retrieved from the Internet: URL:https://www.atdbio.com/content/63/Gene-synthesis [retrieved on Feb. 8, 2019].

Barany F: "The Ligase Chain Reaction in a PCR World", PCR Methods & Applicati, Cold Spring Harbor Laboratory Press, US, vol. 1, No. 1, Aug. 1, 1991, pp. 5-16, ISSN: 1054-9803.

Chen, et al., "Template-directed chemical ligation to obtain 3'-3' and 5'-5' phosphodiester DNA linkages", Scientific reports, Nature Publishing Group, England, England, doi: 10.1038/srep04595, (Apr. 4, 2014), p. 4595, Scientific reports, URL: https://www.ibg.uu.se/digitalAssets/164/c_164781-1_3-k_islam-saiful-arbete-1336.pdf, XP055511016.

Goodchild, "Conjugates of Oligonucleotides and Modified Oligonucleotides: A Review of their Synthesis and Properties," Bioconjugate Chemistry, American Chemical Society, US, US, (May 1, 1990), vol. 01., No. 03., doi:10.1021/bc00003a001, ISSN 1043-1802, pp. 165-187, XP000174627.

Hili, et al., "DNA ligase-mediated translation of DNA into densely functionalized nucleic acid polymers.", Journal of the American Chemical Society, American Chemical Society, United States, United States, (Dec. 20, 2012), vol. 135, No. 1, doi:10.1021/ja311331m, ISSN 1520-5126, pp. 98-101, XP002785248.

Karkare, et al. "Promising nucleic acid analogs and mimics: characteristic features and applications of PNA, LNA, and morpholino" 71 Applied Microbiology and Biotechnology 575-586 (2006).

Kershaw, et al., "Splint Ligation of RNA with T4 DNA Ligase", Christopher J. Kershaw, Raymond T. O'keefe, Boegel, Sebastian [Herausgeberln], Bioinformatics for Cancer Immunotherapy: Methods and Protocols, New York, NY, Springer, (Jan. 1, 2013 ), vol. 941, pp. 257-269, doi:10.1007/978-1-62703-113-4_19, ISBN 978-1-0716-0326-0, XP055523744.

Lei, et al., "A High-Fidelity Codon Set for the T4 DNA Ligase-Catalyzed Polymerization of Modified Oligonucleotides." ACS Combinatorial Science Dec. 14, 2015, (Dec. 14, 2015), vol. 17, No. 12, doi:10.1021/acscombsci.5b00119, ISSN2156-8944, pp. 716-721, XP002785249.

Lundin, et al., "Oligonucleotide Therapies: The Past and the Present", Human Gene Therapy, Mary Ann Liebert, Inc. Publishers, GB, GB , (Aug. 1, 2015), vol. 26, No. 8, doi:10.1089/hum.2015.070, ISSN 1043-034, pp. 475-485, XP055376603.

Noll, et al., "Purification of Small Interfering RNA Using Nondenaturing Anion-Exchange Chromatography", Nucleic Acid Therapeutics, Mary Ann Liebert, Inc. Publishers, US, US, (Dec. 1, 2011), vol. 21, No. 6, doi:10.1089/nat.2011.0317, ISSN 2159-3337, pp. 383-393.

Pengpumkiat, et al., "Rapid Synthesis of a Long Double-Stranded Oligonucleotide from a Single-Stranded Nucleotide Using Magnetic Beads and an Oligo Library", PLOS One, (Mar. 1, 2016), vol. 11, No. 3, doi:10.1371/journal.pone.0149774, p. e0149774.

Stark, et al., "An RNA ligase-mediated method for the efficient creation of large, synthetic RNAs", RNA, Cambridge University Press on behalf of the RNA Society, (Jan. 1, 2006), vol. 12, No. 11, doi:10.1261/rna.93506, ISSN 13558382, pp. 2014-2019.

Suzuki, et al., "Simple and Rapid Enzymatic Method for the Synthesis of Single-Strand Oligonucleotides Containing Trifluorothymidine", Nucleosides, Nucleotides & Nucleic Acids, Taylor & Francis, US, US , (Nov. 30, 2010), vol. 29, No. 11-12, doi:10.1080/15257770.2010.535803, ISSN 1525-7770, pp. 896-904.

Vanmeert, et al., "Rational design of an XNA ligase through docking of unbound nucleic acids to toroidal proteins", Nucleic Acids Research, Oxford University Press, GB, GB, (Jul. 26, 2019), vol. 47, No. 13, doi:10.1093/nar/gkz551, ISSN 0305-1048, pp. 7130-7142.

Verma, et al., "Modified oligonucleotides: synthesis and strategy for users.", Annual Review of Biochemistry, Palto Alto, CA, US, US, (Jan. 1, 1998 ), vol. 67, doi: 10.1146/annurev.biochem.67.1.99, ISSN 0066-4154, pp. 99-134.

Zhao, et al., "Effects of 2'-O-methyl nucleotide on ligation capability of T4 DNA ligase", Acta Biochimica Biophysica Sinica, Blackwell Publishing, Inc., Malden, MA, US, US, (Sep. 1, 2014), vol. 46, No. 9, doi:10.1093/abbs/gmu058, ISSN 1672-9145, pp. 727-737.

Knunyants I.L., Chemical Encyclopedia, v. 2, Soviet Encyclopedia Publishing House, Moscow, V.Z, 1990, pp. 664-665.

Ling M.M., et al., "Approaches to DNA Mutagenesis An Overview," Analytical Biochemistry, 1997, vol. 254, No. 2, pp. 157-178.

Tarantul, Explanatory Dictionary of Molecular and Cellular Biotechnology, Moscow, 2015, vol. 1, p. 411. [retrieved online https://www.ncbi.nlm.nih.gov/nlmcatalog/101685659] English Title only.

Taylor J.W., et al., 1985, vol. 13, N24, pp. 8749-8764.

Roth T.L., et al., "A Rapid and Simple Method for DNA Engineering Using Cycled Ligation Assembly," PLOS One, Sep. 16, 2014, vol. 9(9), e107329, pp. 1-9.

* cited by examiner

Experiment 2: 3' fragment 2 OMe substituted

VWD1 A, Wavelength=258nm (C:\CHEM32\1\DATA\OLIGO\OLIGO_SEQUENCE_TEMPLATE 2015-02-17 (1-34-41\E2.D)

Experiment 3: 5' fragment 2'OMe substituted

VWD1 A, Wavelength=258nm (C:\CHEM32\1\DATA\OLIGO\OLIGO_SEQUENCE_TEMPLATE 2015-02-17 11-34-41\E3.D)

Experiment 4: all fragments 2'OMe substituted

FIG. 14

PROCESSES FOR THE PRODUCTION OF OLIGONUCLEOTIDES

SEQUENCE LISTING

The instant application contains a Sequence Listing which has been submitted electronically in ASCII format and is hereby incorporated by reference in its entirety. Said ASCII copy, created on Apr. 26, 2024, is named PB66490-US_SL.txt and is 267,723 bytes in size.

FIELD OF THE INVENTION

The invention relates to novel processes using enzymes for the production of oligonucleotides, wherein said processes are suitable for use in the production of chemically modified oligonucleotides, such as those for use in therapy.

BACKGROUND TO THE INVENTION

The chemical synthesis of oligonucleotides and modified oligonucleotides via phosphoramidite chemistry is well established and has been the method of choice for synthesizing these defined sequence biopolymers for several decades. The synthetic process is usually run as a solid phase synthesis, whereby single nucleotides are added sequentially with the addition of each nucleotide requiring a cycle of several chemical steps to add and deprotect the growing oligonucleotide ("oligo") in preparation for the subsequent step. At the end of the sequential addition of nucleotides, the oligo is released from the solid phase support, further deprotection takes place, and then the crude oligonucleotide is further purified by column chromatography.

While this method may be considered routine and can be automated, there are several shortcomings to this methodology, especially if the goal is to prepare oligonucleotides at large scale as would be needed for oligonucleotide therapeutics. These shortcomings include, but are not limited to:

1) Practical limitations inherent in the use of chromatography making it unsuitable for purifying large quantities of oligonucleotide. The use of chromatography at large scale is expensive and is difficult to achieve due to the limitations on column size and performance.

2) The number of errors accumulates with the length of the oligonucleotide being synthesized. Accordingly, the linear sequential nature of the current process results in a geometric decrease in yield. For example, if the yield for each cycle of nucleotide addition is 99% then the yield of a 20 mer would be 83%.

3) Scale limitations with synthetic oligonucleotide synthesizers and downstream purification and isolation equipment: at present the maximum amount of product that can be produced in a single batch is in the order of 10 kg.

There is a need, therefore, to both reduce (or ideally eliminate) column chromatography and perform the synthesis in a way which is not purely sequential in order to increase yield.

DNA polymerase is often used to synthesize oligonucleotides for use in molecular biology and similar applications. However, DNA polymerase is unsuitable for synthesizing therapeutic oligonucleotides because of both the relatively short lengths of the oligonucleotides and the need to discriminate between nucleotides with different deoxyribose or ribose modifications. For example, therapeutic oligonucleotides are often in the range of 20 to 25 nucleotides. DNA polymerase needs at least 7 or 8 nucleotides, and optimally 18 to 22 nucleotides, as a primer in each direction so there is little to be gained in trying to synthesize a therapeutic oligo if the primers are similar in size to the desired product. Also, DNA polymerase requires all nucleotides to be present in the reaction and it relies on Watson-Crick base pairing to align incoming nucleotides. Thus, DNA polymerase is unable to discriminate between any ordering of deoxyribose or ribose modifications, such as those required by a gapmer, and the result would be a mix of deoxyribose or ribose modifications at a given position.

SUMMARY OF THE INVENTION

The invention provides a process for producing a single-stranded oligonucleotide product having at least one modified nucleotide residue, comprising:

a) providing a pool of oligonucleotides (I) that comprises segments of the product sequence, wherein at least one segment of the product sequence contains at least one modified nucleotide residue, and wherein each segment has been produced by enzymatic synthesis or solid phase synthesis;

b) providing a template oligonucleotide (II) complimentary to the sequence of the single-stranded oligonucleotide product, said template having a property that allows it to be separated from the product and recycled for use in future reactions;

c) contacting (I) and (II) in conditions to allow annealing of the segment oligonucleotides to the template oligonucleotide;

d) joining the segment oligonucleotides by using a ligase to form the product; e) changing the conditions to denature the annealed template and any impurity oligonucleotide strands, and separating the impurities;

f) changing the conditions to denature the annealed template and product oligonucleotide strands, and separating the single-stranded oligonucleotide product; and g) recycling the template oligonucleotide for use in future reactions.

The invention also provides a process for producing a double-stranded oligonucleotide product, wherein two complimentary single-stranded oligonucleotides, produced by the aforementioned process for producing a single-stranded oligonucleotide product, are mixed under conditions to allow annealing.

DESCRIPTION OF FIGURES

Figure 1A:
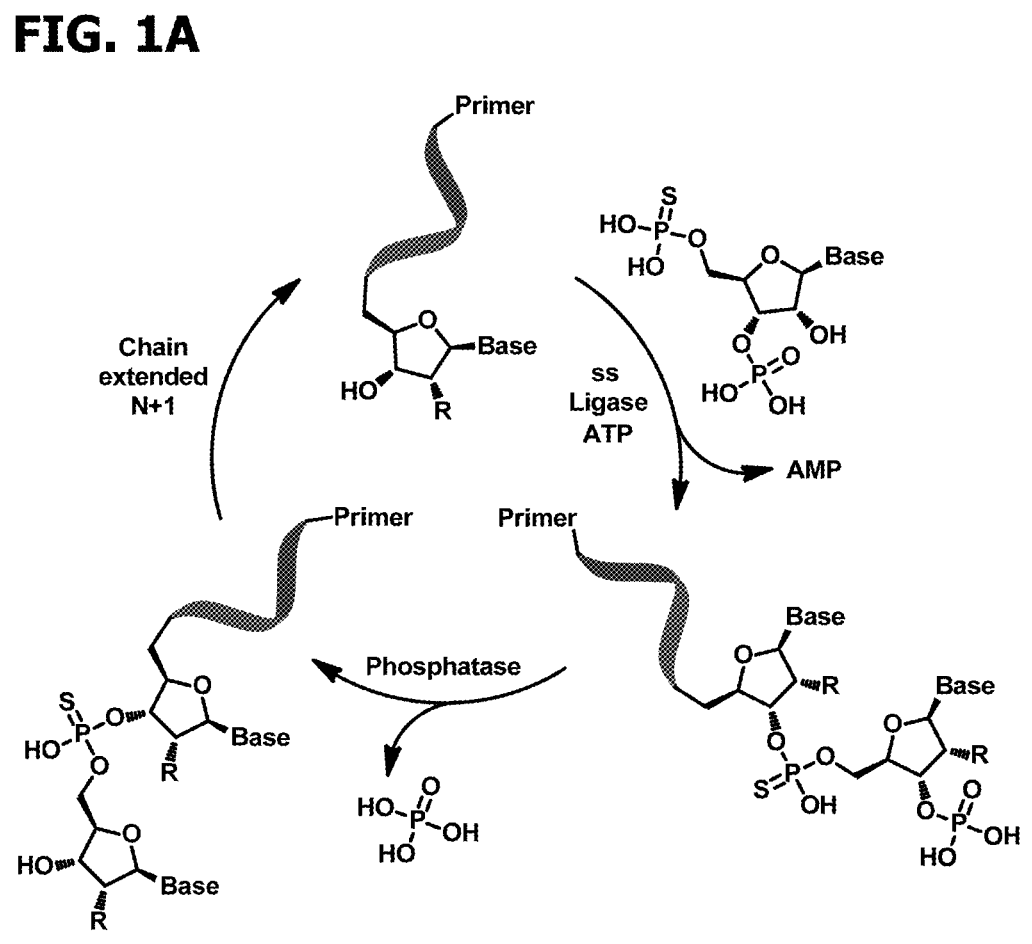

FIGS. 1a-1b Schematic of the enzymatic production of segment oligonucleotides: FIG. 1a shows 3'-extension for segment synthesis comprising a two-step reaction: addition and deprotection. The exemplary addition step involves ATP dependent ligation of nucleotide-3',5'-bis(thio)phosphate on to the 3'-OH of a single-stranded nucleic acid primer and then deprotection of the 3'-phosphate on the single-stranded oligonucleotide by a phosphatase; and FIG. 1b shows the exemplary 3'-extension (addition and deprotection) to produce a segment sequence followed by chain cleavage using a site-specific nuclease (e.g. endonuclease V—cleaves one base after inosine, i.e. at second phosphodiester bond 3' to inosine) to release the segment.

Figure 5C:
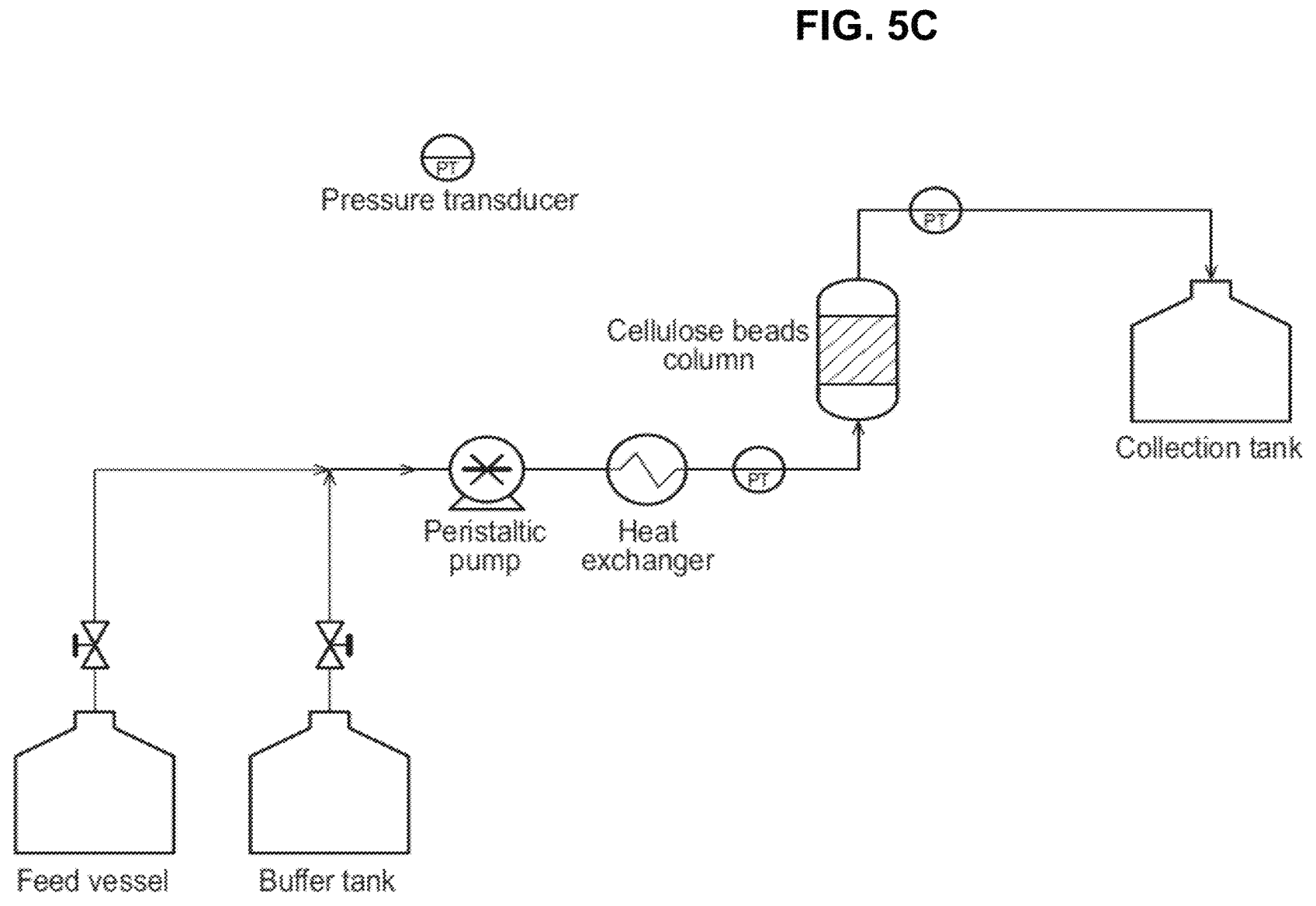

FIGS. 5a-5d Detailed schematic of the process of the invention being carried out in a flow system: FIG. 5a shows ligation chemistry section, FIG. 5b shows ligation purification section, FIG. 5c shows alternative ligation chemistry section, and FIG. 5d shows alternative purification section. N.B. sections a) and b) (alternatively c) and d)) can be performed in a single step e.g. collection vessel in a)=output from ligation step in b)).

FIG. 14 Schematic of the cross-flow filtration rig used in Example 14.

FIG. 15a is a chromatogram of the retentate solution, which remained in the filtration cell and contained mainly tri-template hub, after two diafiltration volumes; and FIG. 15b is a chromatogram of the permeate, solution enriched in the product, after two diafiltration volumes.

FIG. 16a is a chromatogram of the retentate solution, which contained mainly tri-template hub and product, after 20 diafiltration volumes; and FIG. 16b is a chromatogram of the permeate, which contained mainly segment oligonucleotides, after 20 diafiltration volumes.

FIG. 17a shows a chromatogram of the retentate solution, which contained tri-template hub only, after 20 diafiltration volumes; and FIG. 17b is a chromatogram of the permeate solution, which contained the product only, after 2 diafiltration volumes.

DETAILED DESCRIPTION OF THE INVENTION

Definitions

Figure 1B:
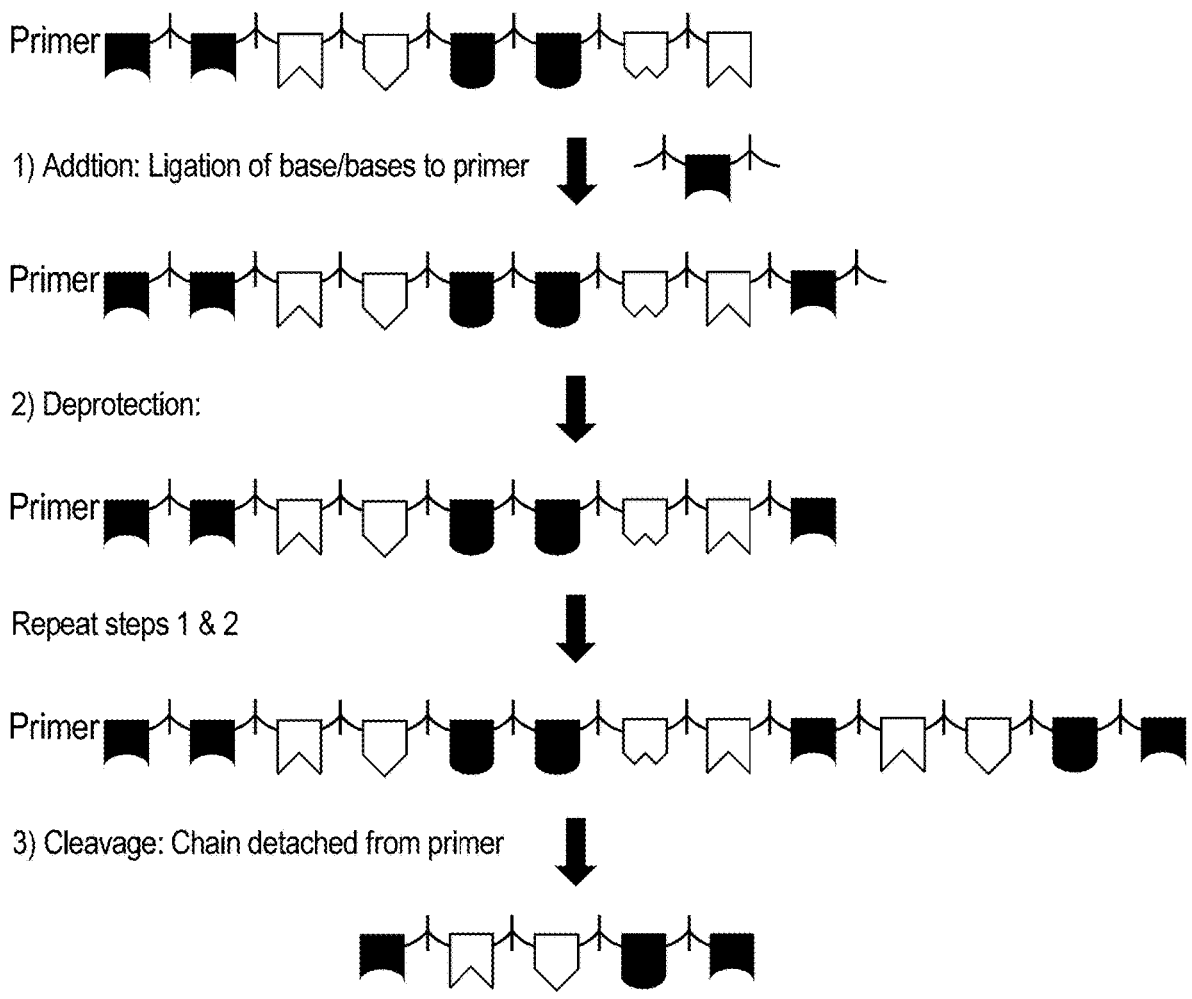
Figure 2:
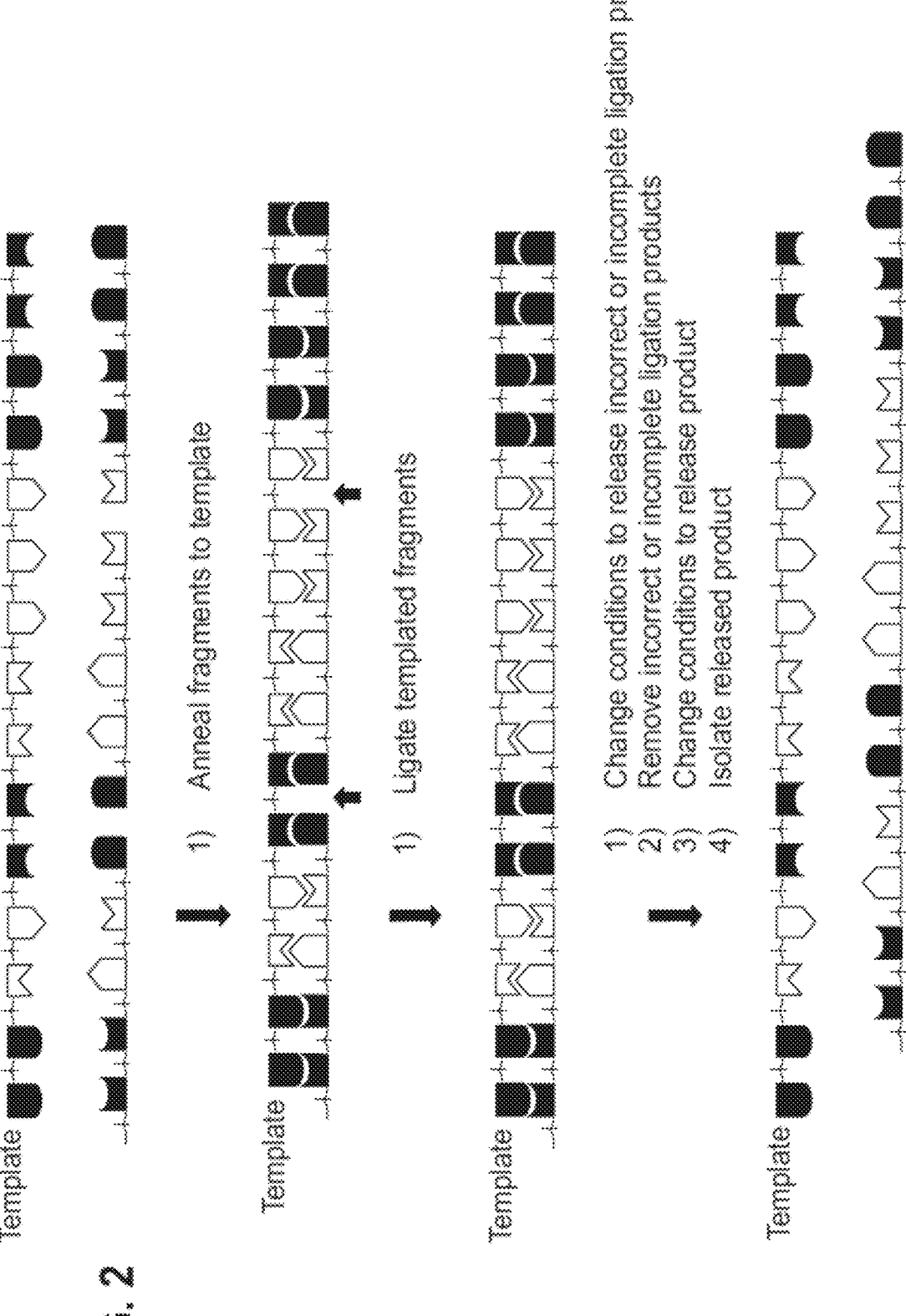
FIG. 2 Schematic of the process of the invention, including the steps of ligating the segment oligonucleotides to form the product and changing the conditions to remove impurities.

As used herein, the term "oligonucleotide", or "oligo" for short, means a polymer of nucleotide residues. These may be deoxyribonucleotides (wherein the resulting oligonucleotide is DNA), ribonucleotides (wherein the resulting oligonucleotide is RNA), modified nucleotides, or a mixture thereof. An oligonucleotide may be entirely composed of nucleotide residues as found in nature or may contain at least one nucleotide, or at least one linkage between nucleotides, that has been modified. Oligonucleotides can be single-stranded or double-stranded. An oligonucleotide of the invention may be conjugated to another molecule, e.g. N-Acetylgalactosamine (GalNAc) or multiples thereof (GalNAc clusters).

As used herein, the term "therapeutic oligonucleotide" means an oligonucleotide that has a therapeutic application, e.g. in the prevention or treatment of a condition or disease in a human or animal. Such an oligonucleotide typically contains one or more modified nucleotide residues or linkages. Therapeutic oligonucleotides act via one of several different mechanisms, including, but not limited to, antisense, splice-switching or exon-skipping, immunostimulation and RNA interference (RNAi), e.g. via microRNA (miRNA) and small interfering RNA (siRNA). A therapeutic oligonucleotide may be an aptamer. Therapeutic oligonucleotides will usually, but not always, have a defined sequence.

As used herein, the term "template" means an oligonucleotide with a sequence that is 100% complementary to the sequence of the target (or product) oligonucleotide.

Unless otherwise specified, as used herein, the term "complementary" means 100% complementary.

As used herein, the term "product" means the desired oligonucleotide, having a specific sequence, also referred to herein as a "target oligonucleotide".

As used herein, the term "pool" refers to a group of oligonucleotides that may vary in sequence, may be shorter or longer than the target sequence, and may not have the same sequence as the target sequence. The pool of oligonucleotides may be the product of oligonucleotide synthesis, e.g. solid phase chemical synthesis via phosphoramidite chemistry or enzymatic synthesis, used with or without purification. The pool of oligonucleotides may be composed of segments of the target sequence. Each segment itself may be present as a pool of that segment and may be the product of oligonucleotide synthesis, e.g. solid phase chemical synthesis via phosphoramidite chemistry or enzymatic synthesis.

As used herein, the term "annealing" means the hybridisation of complementary oligonucleotides in a sequence specific manner, e.g. the pairing of two single-stranded oligonucleotides, via the hydrogen bonds of Watson and Crick base-pairing, to form a double-stranded oligonucleotide. "Conditions to allow for annealing" will depend on the $T_m$ of the hybridised complementary oligonucleotides and will be readily apparent to a person skilled in the art. For example, the temperature for annealing may be below the $T_m$ of the hybridised oligonucleotides. Alternatively, the temperature for annealing may be close to the $T_m$ of the hybridised oligonucleotides, e.g. +/-1, 2 or 3° C. The temperature for annealing is, in general, not higher than 10° C. above the $T_m$ of the hybridised oligonucleotides. Specific conditions to allow for annealing are as outlined in the examples section.

As used herein, the term "denaturing" in relation to a double-stranded oligonucleotide is used to mean that the complementary strands are no longer annealed, i.e. the Watson and Crick base-pairing has been disrupted and the strands have dissociated. Denaturing occurs as a result of changing the conditions, for example, by raising the temperature, changing the pH, or changing the salt concentration of the buffering solution. Conditions for denaturing are well known to those skilled in the art. Denaturing a double-stranded oligonucleotide (a "duplex") as described herein results in a single-stranded product or impurity oligonucleotide and a single-stranded template oligonucleotide.

Figure 6:
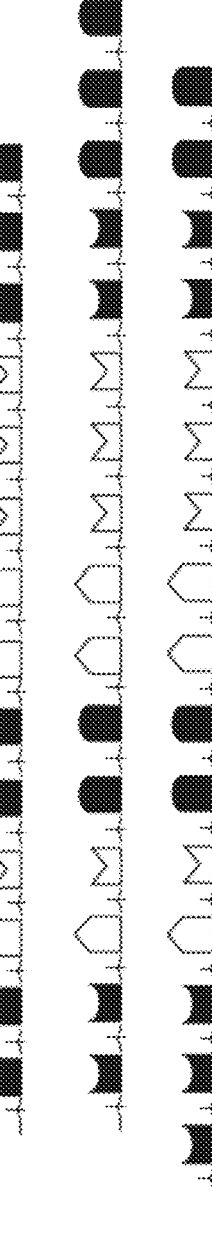
FIG. 6 Examples of impurities which may be generated during the process of the invention.

As used herein, the term "impurity" or "impurities" means oligonucleotides that do not have the desired product sequence. These oligonucleotides may include oligonucleotides that are shorter than the product (for example 1, 2, 3, 4, 5 or more nucleotide residues shorter), or that are longer than the product (for example 1, 2, 3, 4, 5 or more nucleotide residues longer). Where the production process includes a step whereby linkages are formed between segments, impurities include oligonucleotides that are remaining if one or more of the linkages fail to form. Impurities also include oligonucleotides where incorrect nucleotides have been incorporated, resulting in a mis-match when compared to the template. An impurity may have one or more of the characteristics described above. FIG. 6 shows some of the impurities that may occur.

As used herein, the term "segment" is a smaller portion of a longer oligonucleotide, in particular a smaller portion of a product or target oligonucleotide. For a given product, when all of its segments are annealed to its template and ligated together, the product is formed.

As used herein, the term "enzymatic ligation" means that the link between two adjacent nucleotides is formed enzymatically, i.e. by an enzyme. This linkage may be a naturally occurring phosphodiester bond (PO), or a modified linkage including, but not limited to, phosphorothioate (PS) or phosphoramidate (PA).

As used herein, the term "enzymatic synthesis" means the production of oligonucleotides, including segments and final product, using enzymes, e.g. ligases, transferases, phosphatases, and nucleases, in particular endonucleases. These enzymes may be wild-type enzymes or mutant enzymes. Within the scope of the present invention are mutant enzymes capable of acting on modified nucleotide or oligonucleotide substrates.

As used herein, the term "ligase" means an enzyme that catalyses the joining, i.e. covalent joining, of two oligonucleotide molecules, e.g. by formation of a phosphodiester bond between the 3' end of one oligonucleotide (or segment) and the 5' end of the same or another oligonucleotide (or segment). These enzymes are often referred to as DNA ligases or RNA ligases and utilise cofactors: ATP (eukaryotic, viral and archaeal DNA ligases) or NAD (prokaryotic DNA ligases). Despite their occurrence in all organisms, DNA ligases show a wide diversity of amino acid sequences, molecular sizes and properties (Nucleic Acids Research, 2000, Vol. 28, No. 21, 4051-4058). They are usually members of the Enzyme Class EC 6.5 as defined by the International Union of Biochemistry and Molecular Biology, i.e. ligases used to form phosphoric ester bonds. Within the scope of the invention is a ligase capable of joining an unmodified oligonucleotide to another unmodified oligonucleotide, a ligase capable of joining an unmodified oligonucleotide to a modified oligonucleotide (i.e. a modified 5' oligonucleotide to an unmodified 3' oligonucleotide, and/or an unmodified 5' oligonucleotide to a modified 3'oligonucleotide), as well as a ligase capable of joining a modified oligonucleotide to another modified oligonucleotide.

As used herein, the term "single-stranded ligase" or "ssLigase" means an enzyme, e.g. an RNA ligase, that is capable of catalysing the ATP-dependent ligation of (i) 5'-phosphorylated single-stranded RNA to the 3'-OH of a single-stranded acceptor RNA strand and (ii) the ligation of a single residue (including a modified residue), e.g. a nucleo-tide-3',5'-bisphosphate, 3',5'-thiobisphosphate or 3'-phosphate-5' thiophosphate, to the 3' end of RNA or a modified oligonucleotide (Modified Oligoribonucleotides: 17 (11), 2077-2081, 1978). An example of a ssLigase is T4 RNA ligase, which has also been shown to work on DNA substrates under certain conditions (Nucleic Acids research 7(2), 453-464, 1979). The natural function of T4 RNA ligase in *Escherichia coli* infected with T4 bacteriophage is to repair single-strand brakes to bacterial tRNA caused by bacterial defence mechanisms against viral attack. Within the scope of the invention is a ssLigase capable of joining an unmodified nucleotide to an unmodified oligonucleotide, a ssLigase capable of joining an unmodified nucleotide to a modified oligonucleotide, a ssLigase capable of joining a modified nucleotide to an unmodified oligonucleotide, as well as a ssLigase capable of joining a modified nucleotide to a modified oligonucleotide. A ssLigase according to the invention is a ligase that does not require a template oligonucleotide for ligation to occur, i.e. the ligation activity of the ligase is template-independent.

As used herein, a "thermostable ligase" is a ligase that is active at elevated temperatures, i.e. above human body temperature, i.e. above 37° C. A thermostable ligase may be active at, for example, 40° C.-65° C.; or 40° C.-90° C.; and so forth.

As used herein, a "transferase" means an enzyme that catalyses template independent joining of one nucleotide to another nucleotide or oligonucleotide. A transferase as described herein includes a terminal nucleotidyl transferase (TdT), also known as DNA nucleotidylexotransferase (DNTT) or terminal transferase. TdT is a specialised DNA polymerase that is expressed in immature, pre-B, pre-T-lymphoid cells where it enables V-D-J antibody gene junctional diversity. TdT catalyses the addition of nucleotides to the 3'terminus of a DNA molecule. A transferase as described herein includes a non-naturally occurring or mutant TdT. Within the scope of the invention is a transferase capable of joining an unmodified nucleotide to an unmodified oligonucleotide, a transferase capable of joining an unmodified nucleotide to a modified oligonucleotide, a transferase capable of joining a modified nucleotide to an unmodified oligonucleotide, as well as a transferase capable of joining a modified nucleotide to a modified oligonucleotide.

As used herein, the term "phosphatase" means an enzyme that catalyses the hydrolysis of a phosphoester to produce an alcohol. Alkaline phosphatase non-specifically catalyses the dephosphorylation of 5' and 3' ends of DNA and RNA (and modified oligonucleotides) and also hydrolyses nucleotide triphosphates (NTPs and dNTPs) and is optimally active at alkaline pH environments.

As used herein, the term "sequence-specific endonuclease" or "site-specific endonuclease" are used interchangeably and mean a nuclease that specifically cleaves a single-stranded oligonucleotide at a particular position. For example, endonuclease V cleaves RNA one base after inosine, i.e. at the second phosphodiester bond 3' to inosine. Other examples of site-specific endonucleases include the family of meganucleases, zinc finger nucleases, TALENs and Cas9.

As used herein, the term "primer" means an oligonucleotide sequence that is used as a starting point for synthesising a segment oligonucleotide of the invention. A primer comprises at least 3 nucleotides and may be attached to a support material.

As used herein, the term "modified nucleotide residue" or "modified oligonucleotide" means a nucleotide residue or oligonucleotide which contains at least one aspect of its chemistry that differs from a naturally occurring nucleotide residue or oligonucleotide. Such modifications can occur in any part of the nucleotide residue, e.g. sugar, base or phosphate. Examples of modifications of nucleotides are disclosed below.

As used herein, the term "modified ligase" means a ligase which differs from a naturally occurring, "wild-type", ligase by one or more amino acid residues. Such ligases are not found in nature. Such ligases are useful in the novel processes of the invention. Examples of modified ligases are disclosed below. The terms "modified ligase" and "mutant ligase" are used interchangeably.

As used herein, the term "modified transferase" means a transferase which differs from a naturally occurring, "wild-type", transferase by one or more amino acid residues. Such transferases are not found in nature. Such transferases are useful in the novel processes of the invention. The terms "modified transferase" and "mutant transferase" are used interchangeably.

As used herein, the term "gapmer" means an oligonucleotide having an internal "gap segment" flanked by two external "wing segments", wherein the gap segment consists of a plurality of nucleotides that support RNase H cleavage and each wing segment consists of one or more nucleotides that are chemically distinct to the nucleotides within the gap segment.

As used herein, the term "support material" means a high molecular weight compound or material that increases the molecular weight of an oligonucleotide, e.g. the template or primer, thereby allowing it to be retained, e.g. when the impurities and products are separated from the reaction mixture.

As used herein "percent identity" between a query nucleic acid sequence and a subject nucleic acid sequence is the "Identities" value, expressed as a percentage, that is calculated by the BLASTN algorithm when a subject nucleic acid sequence has 100% query coverage with a query nucleic acid sequence after a pair-wise BLASTN alignment is performed. Such pair-wise BLASTN alignments between a query nucleic acid sequence and a subject nucleic acid sequence are performed by using the default settings of the BLASTN algorithm available on the National Center for Biotechnology Institute's website with the filter for low complexity regions turned off. Importantly, a query nucleic acid sequence may be described by a nucleic acid sequence identified in one or more claims herein.

The query sequence may be 100% identical to the subject sequence, or it may include up to a certain integer number of nucleotide alterations as compared to the subject sequence such that the % identity is less than 100%. For example, the query sequence is at least 80, 85, 90, 95, 96, 97, 98, or 99% identical to the subject sequence.

STATEMENT OF THE INVENTION

In an aspect of the invention a process for producing a single-stranded oligonucleotide product, having at least one modified nucleotide residue, is provided, said process comprising:

a) providing a pool of oligonucleotides (I) that comprises segments of the product sequence, wherein at least one segment of the product sequence contains at least one modified nucleotide residue, and wherein each segment has been produced by enzymatic synthesis or solid phase synthesis;

b) providing a template oligonucleotide (II) complimentary to the sequence of the single-stranded oligonucleotide product, said template having a property that allows it to be separated from the product and recycled for use in future reactions;

c) contacting (I) and (II) in conditions to allow annealing of the segment oligonucleotides to the template oligonucleotide;

d) joining the segment oligonucleotides by using a ligase to form the product;

e) changing the conditions to denature the annealed template and any impurity oligonucleotide strands, and separating the impurities;

f) changing the conditions to denature the annealed template and product oligonucleotide strands, and separating the single-stranded oligonucleotide product; and g) recycling the template oligonucleotide for use in future reactions.

In an embodiment of the invention, one or more or all segment oligonucleotides is produced enzymatically.

In an embodiment of the invention, one or more or all segment oligonucleotides is produced using a single-stranded ligase (ssLigase). In an embodiment, the ssLigase is an RNA ligase. In an embodiment, the ssLigase is a T4 RNA ligase or modified T4 RNA ligase.

In another embodiment, the process for producing a segment oligonucleotide using a ssLigase comprises:

(i) adding a nucleotide, a dinucleotide, a trinucleotide or a tetranucleotide; which has either a phosphate, thiophosphate or dithiophosphate moiety at the 3' end; and either a phosphate, thiophosphate or dithiophosphate moiety at the 5' end; to the 3'-OH of a single-stranded oligonucleotide primer by using a ssLigase;

(ii) removing the 3'-phosphate moiety, 3'-thiophosphate moiety or 3' dithiophosphate moiety by using a phosphatase;

(iii) repeating steps (i) and (ii) to extend the oligonucleotide to produce the segment sequence; and (iv) releasing the segment oligonucleotide from the oligonucleotide primer using a sequence specific endonuclease.

In an embodiment of the invention, the process for producing a segment oligonucleotide, using a ssLigase, comprises adding a 3',5' nucleotide bisphosphate, having one or more of either of the phosphate oxygens substituted by sulphur, to the 3'-OH of a single-stranded oligonucleotide primer by using a ssLigase in step (i).

In an embodiment of the invention, the process for producing a segment oligonucleotide, using a ssLigase, comprises adding a 3',5' nucleotide bisphosphate, a 3',5' nucleotide thiophosphate (e.g. 3',5' bisthiophosphate or 3'-phosphate-5'-thiophosphate or 3'-thiophosphate-5'-phosphate) or a 3',5' nucleotide dithiophosphate (e.g. 3',5' bisdithiophosphate or 3'-phosphate-5'-dithiophosphate or 3'-dithiophosphate-5'-phosphate) to the 3'-OH of a single-stranded oligonucleotide primer by using a ssLigase in step (i).

In an embodiment of the invention, one or more segment oligonucleotides is produced using a transferase. In an embodiment of the invention, the process for producing a segment oligonucleotide using a transferase comprises:

(i) adding a nucleotide-5'-triphosphate, alpha-thiotriphosphate or alphadithiotriphosphate which has a protecting group on its 3'-OH to the 3'-OH of a single-stranded oligonucleotide primer by using a transferase;

(ii) deprotecting the 3'-position to regenerate the 3'-OH;

(iii) repeating steps (i) and (ii) to extend the oligonucleotide to produce the segment sequence;

(iv) releasing the segment oligonucleotide from the oligonucleotide primer using a sequence specific endonuclease.

In an embodiment of the invention, each segment is produced by enzymatic synthesis. In an embodiment of the invention, each segment is produced by using a ssLigase. In an embodiment of the invention, each segment is produced by using a transferase.

Using a ssLigase, e.g. an RNA ligase, a transferase or any other enzyme that is capable of adding a single nucleotide to a single-stranded oligonucleotide, in a template independent manner, allows synthesis of an oligonucleotide with a defined sequence. Such an approach could be used to produce the full oligonucleotide product by iteratively adding single bases. However, unless each synthetic cycle runs with 100% yield, sequence deletion errors will be incorporated into the final product. For example, if an oligonucleotide is extended by one nucleotide with 99% yield in a synthetic cycle, the remaining 1% will be available to react in subsequent synthetic cycles but the product formed will be one nucleotide shorter than the desired product. As the number of cycles increases then the error rate is compounded so, in this example, a 99% cycle yield would result in the formation of 20% of single base shortened sequences for the production of a 20mer.

According to the present invention, the sequential accumulation of errors is avoided by the following. Firstly, only short sequences, typically 5 to 8 nucleotides long, are synthesized by the addition of single nucleotides. This process results in short sequences that have a higher purity than long sequences as they are exposed to fewer cycles of error accumulation. Secondly, these short sequences are assembled on a complementary DNA template and then joined together. The use of a complementary template in conjunction with a ligase ensures that only short oligonucleotides that have both the correct length and the correct sequence are assembled. Accordingly, the processes of the invention results in both a higher overall yield and, importantly, higher overall sequence fidelity.

An embodiment of the invention provides a process as previously described herein, whereby denaturing the template and impurity duplex and/or denaturing the template and product duplex results from a temperature increase. In an embodiment, denaturation occurs as a result of changing the pH. In a further embodiment, denaturation occurs by changing the salt concentration in a buffering solution.

Yet another embodiment of the invention provides a process as previously disclosed herein, whereby the segment oligonucleotides are 3 to 15 nucleotides long. In a further embodiment of the invention the segments are 5 to 10 nucleotides long. In a further embodiment of the invention the segments are 5 to 8 nucleotides long. In a further embodiment of the invention the segments are 4, 5, 6, 7 or 8 nucleotides long. In a particular embodiment, there are three segment oligonucleotides: a 5' segment that is 7 nucleotides long, a central segment that is 6 nucleotides long and a 3' segment that is 7 nucleotides long, which when ligated together form an oligonucleotide that is 20 nucleotides long (a "20-mer"). In a particular embodiment, there are three segment oligonucleotides: a 5'segment that is 6 nucleotides long, a central segment that is 8 nucleotides long and a 3' segment that is 6 nucleotides long, which when ligated together form an oligonucleotide that is 20 nucleotides long (a "20-mer"). In a particular embodiment, there are three segment oligonucleotides: a 5' segment that is 5 nucleotides long, a central segment that is 10 nucleotides long and a 3' segment that is 5 nucleotides long, which when ligated together form an oligonucleotide that is 20 nucleotides long (a "20-mer"). In a particular embodiment, there are three segment oligonucleotides: a 5' segment that is 4 nucleotides long, a central segment that is 12 nucleotides long and a 3' segment that is 4 nucleotides long, which when ligated together form an oligonucleotide that is 20 nucleotides long (a "20-mer"). In a particular embodiment, there are four segment oligonucleotides: a 5' segment that is 5 nucleotides long, a 5'-central segment that is 5 nucleotides long, a central-3' segment that is 5 nucleotides long, and a 3' segment that is 5 nucleotides long, which when ligated together form an oligonucleotide that is 20 nucleotides long (a "20-mer").

One embodiment of the invention provides a process as previously described herein, whereby the product is 10 to 200 nucleotides long. In a further embodiment of the invention the product is 15 to 30 nucleotides long. In an embodiment of the invention, the product is 21, 22, 23, 24, 25, 26, 27, 28, 29 or 30 nucleotides long. In an embodiment of the invention, the product is 20 nucleotides long, a "20-mer". In an embodiment of the invention, the product is 21 nucleotides long, a "21-mer". In an embodiment of the invention, the product is 22 nucleotides long, a "22-mer". In an embodiment of the invention, the product is 23 nucleotides long, a "23-mer". In an embodiment of the invention, the product is 24 nucleotides long, a "24-mer". In an embodiment of the invention, the product is 25 nucleotides long, a "25-mer". In an embodiment of the invention, the product is 26 nucleotides long, a "26-mer". In an embodiment of the invention, the product is 27 nucleotides long, a "27-mer". In an embodiment of the invention, the product is 28 nucleotides long, a "28-mer". In an embodiment of the invention, the product is 29 nucleotides long, a "29-mer". In an embodiment of the invention, the product is 30 nucleotides long, a "30-mer".

In an embodiment of the invention, the process is a process for producing a therapeutic oligonucleotide. In an embodiment of the invention, the process is a process for producing a single-stranded therapeutic oligonucleotide. In an embodiment of the invention, the process is a process for producing a double-stranded therapeutic oligonucleotide.

Another embodiment of the invention provides a process as previously disclosed herein, wherein the property that allows the template to be separated from the product is that the template is attached to a support material. In a further embodiment of the invention, the support material is a soluble support material. In a yet further embodiment of the invention the soluble support material is selected from the group consisting of: polyethylene glycol, a soluble organic polymer, DNA, a protein, a dendrimer, a polysaccharide, an oligosaccharide, and a carbohydrate. In an embodiment of the invention the support material is polyethylene glycol (PEG). In a further embodiment of the invention, the support material is an insoluble support material. In a further embodiment of the invention the support material is a solid support material. In a yet further embodiment, the solid support material is selected from the group consisting of: a glass bead, a polymeric bead, a fibrous support, a membrane, a streptavidin coated bead and cellulose. In an embodiment, the solid support material is a streptavidin coated bead. In a further embodiment, the solid support material is part of the reaction vessel itself, e.g. a reaction wall.

Figures 3, 4:
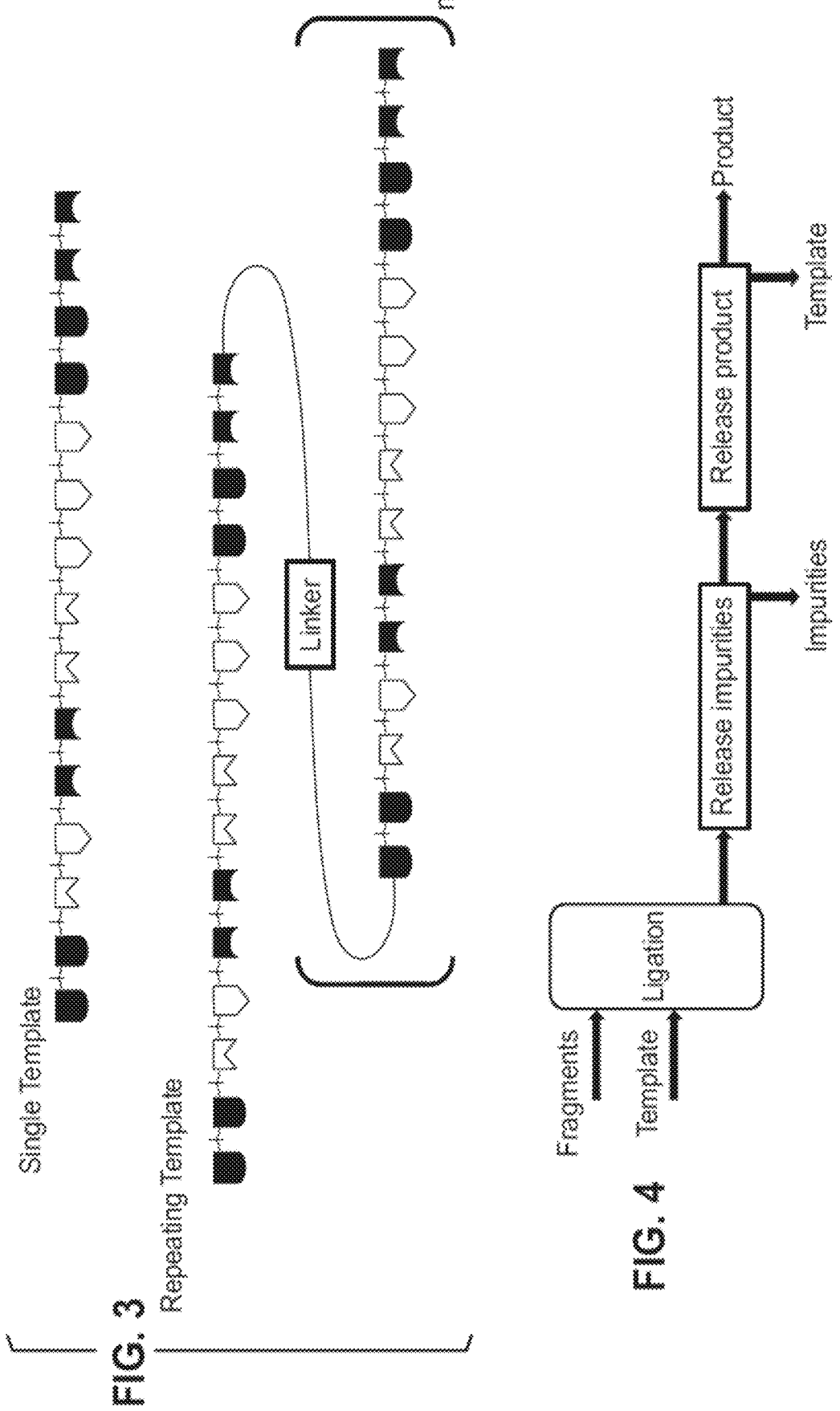
FIG. 3 Schematic of multiple template configurations.
FIG. 4 Basic schematic of the process of the invention being carried out in a flow system.
Figure 5A:
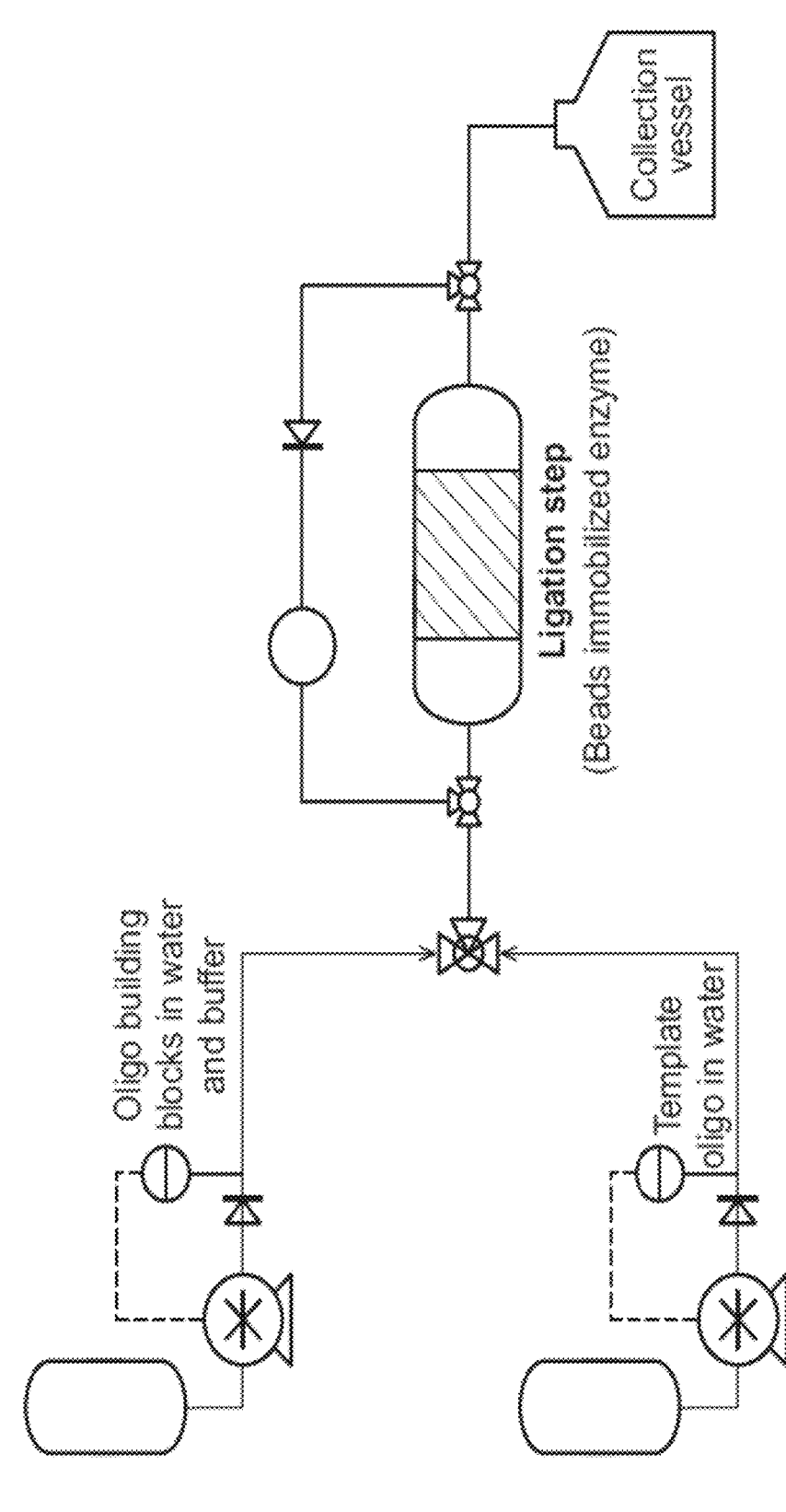
Figure 5B:
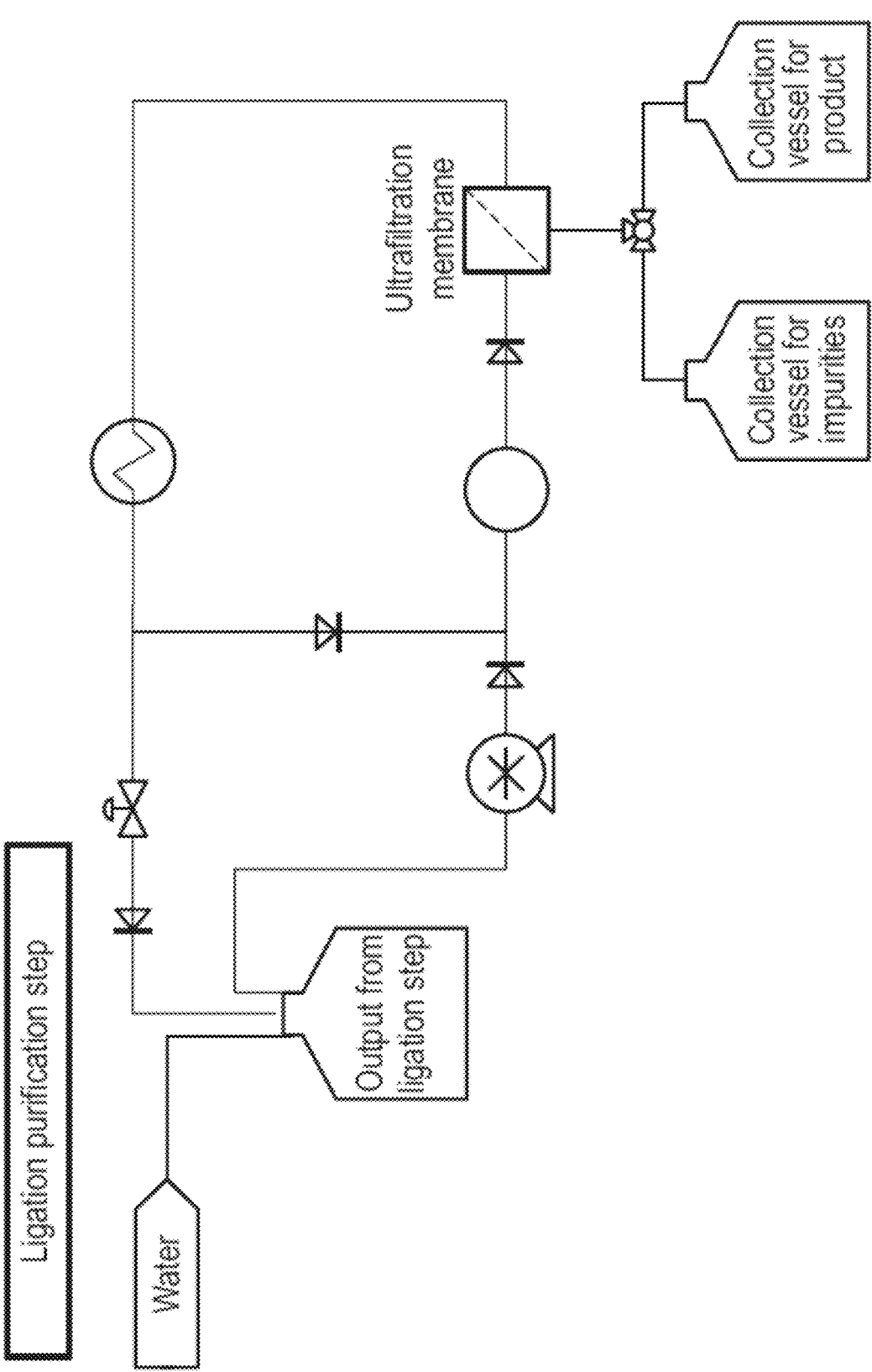
Figure 5D:
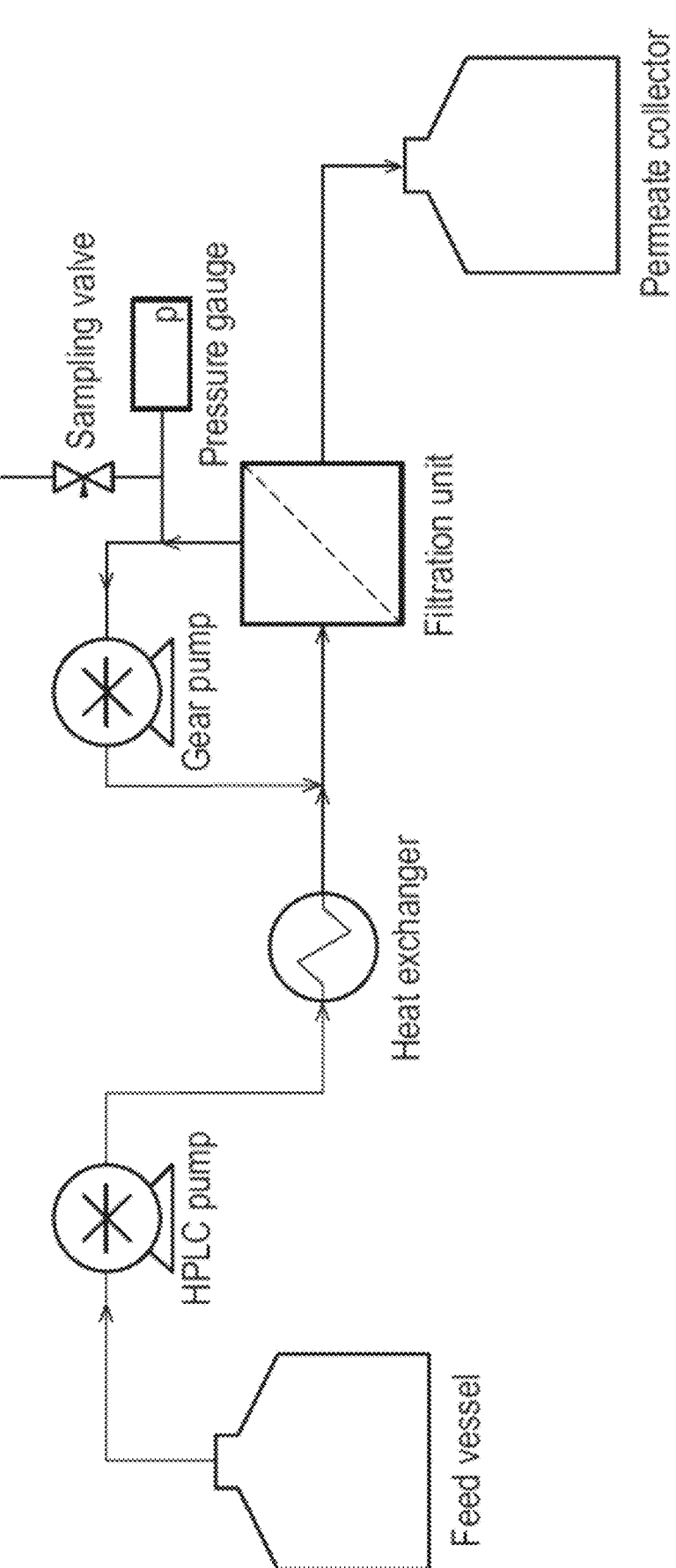

One embodiment of the invention provides a process as previously disclosed herein, wherein multiple, repeated copies of the template are attached in a continuous manner via a single attachment point to the support material. The multiple repeated copies of the template may be separated by a linker, e.g. as shown in FIG. 3. The multiple repeated copies of the template may be direct repeats, i.e. they are not separated by a linker.

In another embodiment of the invention, the template is attached to the support material at multiple attachment points.

Yet another embodiment of the invention provides a process as previously disclosed herein, wherein the property that allows the template to be separated from the product is the molecular weight of the template. For example, repeated copies of the template sequence may be present on a single oligonucleotide, with or without a linker sequence.

Another embodiment of the invention provides a process as previously disclosed herein, wherein the template, or the template and support material, are recycled for use in future reactions, for example as detailed below. Another embodiment of the invention provides a process as previously disclosed herein, wherein the reaction is carried out using a continuous or semi-continuous flow process, for example as shown in FIG. 4 or FIG. 5a-5d.

In an embodiment of the invention, the process is for large scale manufacture of oligonucleotides, in particular therapeutic oligonucleotides. In the context of the present invention, large scale manufacture of oligonucleotides means manufacture at a scale greater than or equal to 1 litre, e.g. the process is carried out in a 1 L or larger reactor. Alternatively, or in addition, in the context of the present invention large scale manufacture of oligonucleotides means manufacture at gram scale of product, in particular the production of greater than or equal to 10 grams of product. In an embodiment of the invention, the amount of oligonucleotide product produced is at gram scale. In an embodiment of the invention the amount of product produced is greater than or equal to: 1, 2, 3, 4, 5, 6, 7, 8, 9, 10, 20, 30, 40, 50, 60, 70, 80, 90 or 100 grams. In an embodiment of the invention, the amount of oligonucleotide product produced is greater than or equal to: 150, 200, 250, 300, 350, 400, 450, 500, 550, 600, 650, 700, 750, 800, 850, 900, 950 grams. In an embodiment of the invention, the amount of oligonucleotide product produced is 500 grams or greater. In an embodiment of the invention, the oligonucleotide product produced is at kilogram scale. In an embodiment of the invention, the amount of oligonucleotide product produced is 1 kg or more. In an embodiment of the invention, the amount of oligonucleotide product produced is greater than or equal to: 1, 2, 3, 4, 5, 6, 7, 8, 9, 10 kg. In an embodiment of the invention, the amount of oligonucleotide product produced is greater than or equal to: 15, 20, 25, 30, 35, 40, 45, 50, 55, 60, 65, 70, 75, 80, 85, 90, 95 or 100 kg.

In an embodiment of the invention, the amount of product produced is between 10 grams and 100 kg. In an embodiment of the invention, the amount of product produced is between 10 grams and 50 kg. In an embodiment of the invention, the amount of product produced is between 100 grams and 100 kg. In an embodiment of the invention, the amount of product produced is between 100 grams and 50 kg. In an embodiment of the invention, the amount of product produced is between 500 grams and 100 kg. In an embodiment of the invention, the amount of product produced is between 500 grams and 50 kg. In an embodiment of the invention, the amount of product produced is between 1 kg and 50 kg. In an embodiment of the invention, the amount of product produced is between 10 kg and 50 kg.

In an embodiment of the invention, oligonucleotide manufacture takes place at a scale greater than or equal to: 2, 3, 4, 5, 6, 7, 8, 9, 10 litres, e.g. in a 2, 3, 4, 5, 6, 7, 8, 9 or 10 L reactor. In an embodiment of the invention, oligonucleotide manufacture takes place at a scale greater than or equal to: 20, 25, 30, 35, 40, 45, 50, 55, 60, 65 70, 75, 80, 85, 90, 95, 100 litres, e.g. in a 20, 25, 30, 35, 40, 45, 50, 55, 60, 65 70, 75, 80, 85, 90, 95, 100 L reactor. In an embodiment of the invention, oligonucleotide manufacture takes place at a scale greater than or equal to: 150, 200, 250, 300, 350, 400, 450, 500, 550, 600, 650, 700, 750, 800, 850, 900, 950, 1000 litres, e.g. in 150, 200, 250, 300, 350, 400, 450, 500, 550, 600, 650, 700, 750, 800, 850, 900, 950, 1000 L reactor.

In an embodiment of the invention, the reactor volume is about 10,000 L, about 5000 L, about 2000 L, about 1000 L, about 500 L, about 125 L, about 50 L, about 20 L, about 10 L, or about 5 L.

In an embodiment of the invention, the reactor volume is between 5 and 10,000 L, between 10 and 5000 L, between 20 and 2000 L, or between 50 and 1000 L.

An oligonucleotide in accordance with the present invention may have at least one backbone modification, and/or at least one sugar modification and/or at least one base modification compared to an RNA or DNA-based oligonucleotide.

In an embodiment of the invention, one or more segment oligonucleotides have at least one backbone modification, and/or at least one sugar modification and/or at least one base modification compared to an RNA or DNA-based oligonucleotide. In an embodiment, all of the segment oligonucleotides have at least one backbone modification. In an embodiment, at least one of the segments has a completely modified backbone. In an embodiment of the invention, all of the segments have a completely modified backbone. In an embodiment, the backbone of all of the segment oligonucleotides consists of phosphorothioate linkages. In an embodiment, two or more of the segments have at least one sugar modification and/or at least one base modification compared to an RNA or DNA-based oligonucleotide. In an embodiment, the "wing" segments comprise at least one sugar modification. In an embodiment, the "wing" segments consist entirely of modified sugars. In an embodiment, the "wing" segments consist entirely of 2'-MOE-modified sugars.

One embodiment of the invention provides a process as previously disclosed herein, wherein the product contains at least 1 modified nucleotide residue. In a further embodiment, the modification is at the 2' position of the sugar moiety.

Oligonucleotides used in the process of the invention may include sugar modifications, i.e. a modified version of the ribosyl moiety, such as 2'-O-modified RNA such as 2'-O-alkyl or 2'-O-(substituted)alkyl e.g. 2'-O-methyl, 2'-O-(2-cyanoethyl), 2'-O-(2-methoxy)ethyl (2'-MOE), 2'-O-(2-thiomethyl)ethyl, 2'-O-butyryl, 2'-O-propargyl, 2'-O-allyl, 2'-O-(3-amino)propyl, 2'-O-(3-(dimethylamino)propyl), 2'-O-(2-amino)ethyl, 2'-O-(2-(dimethylamino)ethyl); 2'-deoxy (DNA); 2'-O-(haloalkoxy)methyl (Arai K. et al. Bioorg. Med. Chem. 2011, 21, 6285) e.g. 2'-O-(2-chloroethoxy) methyl (MCEM), 2'-O-(2, 2-dichloroethoxy)methyl (DCEM); 2'-O-alkoxycarbonyl e.g. 2'-O-[2-(methoxycarbonyl)ethyl](MOCE), 2'-O-[2-(N-methylcarbamoyl)ethyl] (MCE), 2'-O-[2-(N, N-dimethylcarbamoyl)ethyl](DCME); 2'-halo e.g. 2'-F, FANA (2'-F arabinosyl nucleic acid); carbasugar and azasugar modifications; 3'-O-alkyl e.g. 3'-O-methyl, 3'-O-butyryl, 3'-O-propargyl; and their derivatives.

In an embodiment of the invention, the sugar modification is selected from the group consisting of 2'-Fluoro (2'-F), 2'-O-methyl (2'-OMe), 2'-O-methoxyethyl (2'-MOE), and 2'-amino. In a yet further embodiment, the modification is 2'-MOE.

Other sugar modifications include "bridged" or "bicyclic" nucleic acid (BNA), e.g. locked nucleic acid (LNA), xylo-LNA, α-L-LNA, B3-D-LNA, cEt (2'-0,4'-C constrained ethyl) LNA, cMOEt (2'-0,4'-C constrained methoxyethyl) LNA, ethylene-bridged nucleic acid (ENA), tricyclo DNA; unlocked nucleic acid (UNA); cyclohexenyl nucleic acid (CeNA), altriol nucleic acid (ANA), hexitol nucleic acid (HNA), fluorinated HNA (F-HNA), pyranosyl-RNA (p-RNA), 3'-deoxypyranosyl-DNA (p-DNA); morpholino (as e.g. in PMO, PPMO, PMOPlus, PMO-X); and their derivatives.

Oligonucleotides used in the process of the invention may include other modifications, such as peptide-base nucleic acid (PNA), boron modified PNA, pyrrolidine-based oxy-peptide nucleic acid (POPNA), glycol- or glycerol-based nucleic acid (GNA), threose-based nucleic acid (TNA), acyclic threoninol-based nucleic acid (aTNA), oligonucleotides with integrated bases and backbones (ONIBs), pyrrolidine-amide oligonucleotides (POMs); and their derivatives.

In an embodiment of the invention, the modified oligonucleotide comprises a phosphorodiamidate morpholino oligomer (PMO), a locked nucleic acid (LNA), a peptide nucleic acid (PNA), a bridged nucleic acid (BNA) such as (S)-cEt-BNA, or a SPIEGELMER.

In a further embodiment, the modification is in the nucleobase. Base modifications include modified versions of the natural purine and pyrimidine bases (e.g. adenine, uracil, guanine, cytosine, and thymine), such as inosine, hypoxanthine, orotic acid, agmatidine, lysidine, 2-thiopyrimidine (e.g. 2-thiouracil, 2-thiothymine), G-clamp and its derivatives, 5-substituted pyrimidine (e.g. 5-methylcytosine, 5-methyluracil, 5-halouracil, 5-propynyluracil, 5-propynylcytosine, 5-aminomethyluracil, 5-hydroxymethyluracil, 5-aminomethylcytosine, 5-hydroxymethylcytosine, Super T), 2,6-diaminopurine, 7-deazaguanine, 7-deazaadenine, 7-aza-2, 6-diaminopurine, 8-aza-7-deazaguanine, 8-aza-7-deazaadenine, 8-aza-7-deaza-2, 6-diaminopurine, Super G, Super A, and N4-ethylcytosine, or derivatives thereof; $N^2$-cyclopentylguanine (cPent-G), $N^2$-cyclopentyl-2-aminopurine (cPent-AP), and $N^2$-propyl-2-aminopurine (Pr-AP), or derivatives thereof; and degenerate or universal bases, like 2, 6-difluorotoluene or absent bases like abasic sites (e.g. 1-deoxyribose, 1,2-dideoxyribose, 1-deoxy-2-O-methylribose; or pyrrolidine derivatives in which the ring oxygen has been replaced with nitrogen (azaribose)). Examples of derivatives of Super A, Super G and Super T can be found in U.S. Pat. No. 6,683,173. cPent-G, cPent-AP and Pr-AP were shown to reduce immunostimulatory effects when incorporated in siRNA (Peacock H. et al. J. Am. Chem. Soc. (2011), 133, 9200).

In an embodiment of the invention, the nucleobase modification is selected from the group consisting of 5-methyl pyrimidines, 7-deazaguanosines and abasic nucleotides. In an embodiment, the modification is a 5-methyl cytosine.

Oligonucleotides used in the process of this invention may include a backbone modification, e.g. a modified version of the phosphodiester present in RNA, such as phosphorothioate (PS), phosphorodithioate (PS2), phosphonoacetate (PACE), phosphonoacetamide (PACA), thiophosphonoacetate, thiophosphonoacetamide, phosphorothioate prodrug, H-phosphonate, methyl phosphonate, methyl phosphonothioate, methyl phosphate, methyl phosphorothioate, ethyl phosphate, ethyl phosphorothioate, boranophosphate, boranophosphorothioate, methyl boranophosphate, methyl boranophosphorothioate, methyl boranophosphonate, methylboranophosphonothioate, and their derivatives. Another modification includes phosphoramidite, phosphoramidate, N3'→P5' phosphoramidate, phosphordiamidate, phosphorothiodiamidate, sulfamate, dimethylenesulfoxide, sulfonate, triazole, oxalyl, carbamate, methyleneimino (MMI), and thioacetamido nucleic acid (TANA); and their derivatives.

In a further embodiment, the modification is in the backbone and is selected from the group consisting of: phosphorothioate (PS), phosphoramidate (PA) and phosphorodiamidate. In an embodiment of the invention, the modified oligonucleotide is a phosphorodiamidate morpholino oligomer (PMO). A PMO has a backbone of methylenemorpholine rings with phosphorodiamidate linkages. In an embodiment of the invention the product has a phosphorothioate (PS) backbone.

In an embodiment of the invention, the oligonucleotide comprises a combination of two or more modifications as disclosed above. A person skilled in the art will appreciate that there are many synthetic derivatives of oligonucleotides.

In an embodiment of the invention, the product is a gapmer. In an embodiment of the invention, the wing segments comprise backbone and sugar modifications and the central or 'gap' segment comprises backbone modifications, but no sugar modifications. In an embodiment of the invention, the 5' and 3' wings of the gapmer comprise or consist of 2'-MOE modified nucleotides. In an embodiment of the invention the gap segment of the gapmer comprises or consists of nucleotides containing hydrogen at the 2' position of the sugar moiety, i.e. is DNA-like. In an embodiment of the invention the 5' and 3' wings of the gapmer consist of 2'MOE modified nucleotides and the gap segment of the gapmer consists of nucleotides containing hydrogen at the 2' position of the sugar moiety (i.e. deoxynucleotides). In an embodiment of the invention the 5' and 3' wings of the gapmer consist of 2'MOE modified nucleotides and the gap segment of the gapmer consists of nucleotides containing hydrogen at the 2' position of the sugar moiety (i.e. deoxynucleotides) and the linkages between all of the nucleotides are phosphorothioate linkages.

One embodiment of the invention provides a process as previously described herein, wherein the resulting product is greater than 90% pure. In a further embodiment, the product is greater than 95% pure. In a further embodiment, the product is greater than 96% pure. In a further embodiment, the product is greater than 97% pure. In a further embodiment, the product is greater than 98% pure. In a further embodiment, the product is greater than 99% pure. Purity of an oligonucleotide may be determined using any suitable method, e.g. high-performance liquid chromatography (HPLC) or mass spectrometry (MS), in particular, liquid chromatography-MS (LC-MS), HPLC-MS or capillary electrophoresis mass spectrometry (CEMS).

In an embodiment of the invention the oligonucleotide produced is an antisense oligonucleotide. In an embodiment of the invention the oligonucleotide produced is an aptamer. In an embodiment of the invention the oligonucleotide produced is a miRNA. In an embodiment of the invention, the product is a therapeutic oligonucleotide.

Yet another embodiment of the invention provides a process for producing double-stranded oligonucleotides, wherein 2 complimentary single-stranded oligonucleotides are produced by the method of any preceding embodiment and then mixed under conditions to allow annealing, such conditions being readily apparent to a skilled person. In an embodiment, the product is a siRNA.

In an embodiment of the invention, there are substantially no nucleotides in the reaction vessel for ligating the segments. In an embodiment of the invention, there are no nucleotides in the reaction vessel for ligating the segments. In another embodiment of the invention, the reaction vessel for ligating the segments does not comprise a pool of nucleotides, i.e. the reaction is substantially free to completely free of nucleotides.

The invention herein disclosed utilises the properties of oligonucleotide binding to provide an improved process for their production. By providing a template oligonucleotide with 100% complementarity to the target sequence, and controlling the reaction conditions so that the product can be released and separated under specific conditions, a product with a high degree of purity can be obtained.

Denaturing the Product (or Impurity):Template Duplex and Separating the Product (or Impurity) from the Template Releasing the product (or any impurities) from the template requires the Watson-Crick base pairing between the template oligonucleotide strand and the product (or impurity) to be broken (i.e. denaturing the duplex). The product (or impurity) can then be separated from the template, which can occur as two separate steps, or as one combined step.

Releasing and separating the product (or impurity) can occur as one step, if the process is carried out in a column reactor. Running in a buffer that alters the pH or salt concentration, or contains a chemical agent that disrupts the base pairing (such as formamide or urea) will cause denaturation of the oligonucleotide strands, and the product (or impurity) will be eluted in the buffer.

When the process is carried out in other reaction vessels, the release and separation of the product (or impurity) can occur as a two-step process. First, the Watson-Crick base pairs are disrupted to denature the strands, and then the product (or impurity) is separated from the template, e.g. removed from the reaction vessel. When releasing and separating the product is carried out as a two-step process, the breaking of the Watson-Crick base pairs can be achieved by altering the buffer conditions (pH, salt) or by introducing a chemical disrupting agent (formamide, urea). Alternatively, raising the temperature will also cause the dissociation of the two strands, i.e. denaturation. The product (or impurities) can then be separated (and also removed from the reaction vessel, if desired) via methods including molecular weight-based separation, charge based separation, hydrophobicity-based separation, specific sequence-based separation or a combination of these methods.

When the process is carried out in a continuous or semi-continuous flow reactor, the release and separation of the product (or impurity) can be in either one step or two steps. For example, releasing and separating the product (or impurity) in one step could be affected by increasing the temperature to cause dissociation of the two strands, and separating the released strands on the basis of molecular weight in the same part of the reactor that is used to elevate the temperature. Releasing and separating the product (or impurity) in two steps could be affected by increasing the temperature to cause dissociation of the two strands in one part of the reactor and separating the released strands on the basis of molecular weight in a different part of the reactor.

Specifically Releasing and Separating Impurities from the Template, but Retaining the Product on the Template Impurities arise when an incorrect nucleotide is incorporated into the oligonucleotide strand during chain extension, or when the chain extension reaction terminates early. Impurities also arise when the reaction includes the step of ligating segment oligonucleotides and one or more of the ligation steps fail to happen. The kinds of impurities which can arise are illustrated in FIG. 6.

The properties of Watson-Crick base pairing can be exploited to specifically release any impurities bound to the template prior to the release of the product. Each double-stranded oligonucleotide will dissociate under specific conditions, and those conditions are different for sequences which do not have 100% complementarity when compared to sequences with 100% complementarity. Determining such conditions is within the remit of a skilled person.

A common way of denaturing oligonucleotides is by raising the temperature. The temperature at which half of the base pairs are dissociated, i.e. when 50% of the duplex is in the single-stranded state, is called the melting temperature, $T_m$. The most reliable and accurate means of determining the melting temperature is empirically. However, this is cumbersome and not usually necessary. Several formulas can be used to calculate $T_m$ values (Nucleic Acids Research 1987, 15 (13): 5069-5083; PNAS 1986, 83 (11): 3746-3750; Biopolymers 1997, 44 (3): 217-239) and numerous melting temperature calculators can be found on-line, hosted by reagent suppliers and universities. It is known that for a given oligonucleotide sequence, a variant with all phosphorothioate linkages will melt at a lower temperature than a variant with all phosphodiester linkages. Increasing the number of phosphorothioate linkages in an oligonucleotide tends to lower the $T_m$ of the oligonucleotide for its intended target.

To specifically separate the impurities from a reaction mixture, first the melting temperature of the product:template duplex is calculated. Then the reaction vessel is heated to a first temperature, e.g. a temperature below the melting temperature of the product:template duplex, for example 1, 2, 3, 4, 5, 6, 7, 8, 9 or 10 degrees centigrade below the melting temperature. This heating step causes the denaturing of oligonucleotides which are not the product, i.e. are not 100% complimentary to the template, from the template. These denatured oligonucleotides can then be removed from the reaction vessel using one of the methods disclosed above, e.g. molecular weight-based separation, charge based separation, hydrophobicity-based separation, specific sequence-based separation or a combination of these methods. Then, the reaction vessel will be raised to a second, higher, temperature, e.g. above the calculated melting temperature, for example 1, 2, 3, 4, 5, 6, 7, 8, 9 or 10 degrees centigrade above the melting temperature, to cause the denaturing of the product from the template. The product can then be separated (and removed from the reaction vessel) using one of the methods disclosed above, e.g. molecular weight-based separation, charge-based separation, hydrophobicity-based separation, specific sequence-based separation or a combination of these methods.

A similar process can be used when the disrupting agent is an agent which causes a change in pH or salt concentration or is a chemical disrupting agent. The disrupting agent is increased in concentration until just below the concentration at which the product would dissociate, to cause the denaturing of oligonucleotides which are not the product from the template. These impurities can then be removed from the reaction vessel using one of the methods disclosed above. The disrupting agent is then increased in concentration to above the concentration at which the product dissociates from the template. The product can then be removed from the reaction vessel using one of the methods disclosed above.

The product obtained from a process such as disclosed above has a high degree of purity without the need for further purification steps. For example, the product obtained is greater than 95% pure.

Properties of the Template

The template requires a property which allows it to be retained in the reaction vessel when the product is removed, to prevent it from becoming an impurity in the product. In other words, the template has properties that allow it to be separated from the product. In one embodiment of the invention, this retention is achieved by coupling the template to a supporting material. This coupling results in a template-support complex which has a high molecular weight, and can therefore be retained in the reaction vessel when impurities and product are removed, for example by filtration.

The template can be coupled to a solid support material such as polymeric beads, fibrous supports, membranes, streptavidin coated beads and cellulose. The template can also be coupled to a soluble support material such as polyethylene glycol, a soluble organic polymer, DNA, a protein, a dendrimer, a polysaccharide, an oligosaccharide and a carbohydrate.

Each support material can have multiple points where a template can be attached, and each attachment point can have multiple templates attached, e.g. in the manner shown in FIG. 3.

The template may have a high molecular weight itself, without being attached to a support material, for example, it may be a molecule with multiple copies of the template, e.g. separated by a linker, in the manner shown in FIG. 3.

The ability to retain the template in the reaction vessel also allows the template to be recycled for future reactions, either by being recovered or by use in a continuous or semi-continuous flow process.

Methods of Separating the Template from the Product (or Impurities)

The properties of the template, as disclosed above, allow separation of the template and product, or separation of the template bound product and impurities. Molecular weight-based separation, charge-based separation, hydrophobicity-based separation, specific sequence-based separation or a combination of these methods can be used.

In the case where the template is attached to a solid support, separation of the template from the product, or separation of impurities from the product bound to the template, is achieved by washing the solid support under appropriate conditions as would be readily apparent to a person skilled in the art. In cases where the template is coupled to a soluble support or is itself composed of repeating template sequences, separation of template from product or separation of template bound product from impurities can be achieved by means of a molecular weight-based separation, for example by using techniques such as ultra-filtration or nano-filtration where the filter material is chosen so that the larger molecule is retained by the filter and the smaller molecule passes through.

In cases where a single separation step of impurity from template product complex, or separation of product from template, is not efficient enough, multiple sequential filtration steps can be employed to increase separation efficiency and so generate a product that meets the desired purity.

It is desirable to provide a process for separation of such oligonucleotides which is efficient and applicable on an industrial production scale. "Therapeutic oligonucleotides: The state of the art in purification technologies" Sanghvi et.

al. Current Opinion in Drug Discovery (2004) Vol. 7 No. 8 reviews processes used for oligonucleotide purification.

WO 01/55160 A1 discloses purification of oligonucleotides by forming imine linkages with contaminants and then removing the imine-linked impurities with chromatography or other techniques. "Size Fractionation of DNA Fragments Ranging from 20 to 30000 Base Pairs by Liquid/Liquid chromatography" Muller et al. Eur. J. Biochem (1982) 128-238 discloses use of a solid column of microcrystalline cellulose on which has been deposited a PEG/dextran phase for separation of nucleotide sequences. "Separation and identification of oligonucleotides by hydrophilic interaction chromatography." Easter et. al. The Analyst (2010); 135(10) discloses separation of oligonucleotides using a variant of HPLC employing a solid silica support phase. "Fractionation of oligonucleotides of yeast soluble ribonucleic acids by countercurrent distribution" Doctor et al. Biochemistry (1965) 4(1) 49-54 discloses use of a dry solid column packed with dry DEAE-cellulose. "Oligonucleotide composition of a yeast lysine transfer ribonucleic acid" Madison et al; Biochemistry, 1974, 13(3) discloses use of solid phase chromatography for separation of nucleotide sequences.

Liquid-liquid chromatography is a known separation method. "Countercurrent Chromatography The Support-Free Liquid Stationary Phase" Billardello, B.; Berthod, A; Wilson & Wilson's Comprehensive Analytical Chemistry 38; Berthod, A., Ed.; Elsevier Science B.V.: Amsterdam (2002) pp 177-200 provides a useful general description of liquid-liquid chromatography. Various liquid-liquid chromatography techniques are known. One such technique is liquid-liquid counter current chromatography (termed herein "CCC"). Another known technique is centrifugal partition chromatography (termed herein "CPC").

The above disclosed methods and those methods set out in WO 2013/030263 may be used to separate a product oligonucleotide, e.g. from the template and/or an impurity.

Ligases for Use in the Processes of the Invention, i.e. Ligation Step (d)

In an embodiment of the invention, the ligase is an ATP dependent ligase. ATP dependent ligases range in size from 30 to >100 kDa. In an embodiment of the invention, the ligase is an NAD dependent ligase. NAD dependent enzymes are highly homologous and are monomeric proteins of 70-80 kDa. In an embodiment of the invention, the ligase is a thermostable ligase. A thermostable ligase may be derived from a thermophilic bacterium.

In an embodiment of the invention, the ligase is a template-dependent ligase.

In an embodiment of the invention, the ligase is a wild-type Enterobacteria phage CC31 DNA ligase (SEQ ID NO:6) or a wild-type *Shigella* phage Shf125875 DNA ligase (SEQ ID NO:8).

In an embodiment of the invention, the ligase is a modified ligase. For example, a modified ligase includes a modified T4 DNA ligase, a modified Enterobacteria phage CC31 ligase, a modified *Shigella* phage Shf125875 ligase and a modified *Chlorella* ligase.

In an embodiment, wild-type T4 DNA ligase is modified at amino acid position 368 or amino acid position 371 of SEQ ID NO:3.

In an embodiment, the mutant ligase comprises or consists of SEQ ID NO:3 wherein the amino acid at position 368 is R or K.

In an embodiment, the mutant ligase comprises or consists of SEQ ID NO:3 wherein the amino acid at position 371 is any one of the following amino acids: L, K, Q, V, P, R.

In an embodiment, the corresponding residue(s) disclosed above in relation to T4 DNA ligase are mutated in any one of Enterobacteria phage CC31 ligase, *Shigella* phage Shf125875 ligase and *Chlorella* ligase. Conserved regions of DNA ligases are disclosed in Chem. Rev. 2006, 106, 687-699 and Nucleic Acids Research, 2000, Vol. 28, No. 21, 4051-4058. In an embodiment, the ligase is modified in a linker region.

In an embodiment of the invention, the ligase comprises or consists of SEQ ID NO:23 or a ligase with at least 90% sequence identity thereto, excluding a wild-type ligase e.g. Enterobacteria phage CC31 ligase.

In an embodiment of the invention, the ligase comprises or consists of any one of the following amino acid sequences: SEQ ID NOs:10-28.

In an embodiment of the invention, the ligase is immobilised, e.g. on a bead.

Oligonucleotides Used as Starting Materials

The oligonucleotides used as a starting material for the processes of the invention are herein described as being a "pool" and a definition thereof is provided above. The pool is a non-homogenous set of oligonucleotides. The oligonucleotides which form the pool will have been produced by other oligonucleotide production methods, e.g. solid phase or enzymatic synthesis, and will therefore likely contain impurities.

The pool is composed of segments of the product oligonucleotides, which are then joined together whilst assembled on the template. Each segment will be a non-homogeneous set with impurities of differing lengths and/or incorrectly incorporated residues.

Producing the Segment Oligonucleotides Using Enzymes 1) ssLigase, e.g. RNA Ligase ssLigase catalyses the ATP driven addition of, for example, 3',5' nucleotide bisphosphates, 3',5' nucleotide thiophosphates (e.g. 3',5' bisthiophosphate or 3'-phosphate-5'-thiophosphate or 3'-thiophosphate-5'-phosphate) or 3'5' nucleotide dithiophosphates (e.g. 3',5' bisdithiophosphate or 3'-phosphate-5'-dithiophosphate or 3'-dithiophosphate-5'-phosphate) to the 3'-OH of a short oligonucleotide (primer) in a template-independent manner. A skilled person would appreciate that diphosphates (or dithiophosphates) or triphosphates (or other oligophosphate where one or more oxygen atoms has been substituted by sulphur) at the 3' position of the sugar moiety may also be used, although the additional phosphate (or thiophosphate) moieties are not required. An equivalently modified dinucleotide, trinucleotide or tetranucleotide may be used instead of the aforementioned individual nucleotides. The oligonucleotide primer is usually a minimum of three nucleotides long. The resulting oligonucleotide of this addition reaction is one nucleotide longer than the starting oligonucleotide (or two, three or four nucleotides longer than the starting oligonucleotide if a dinucleotide, trinucleotide or tetranucleotide is used, respectively). The new 3' position is now phosphorylated. In order to add a subsequent nucleotide, the 3' phosphate of the growing oligonucleotide is removed to generate a 3'-OH by hydrolysis. This hydrolysis is typically done using a phosphatase enzyme as shown in FIG. 1*a*.

2) Transferase

Terminal deoxynucleotidyl transferase (TdT) enzymes catalyse the addition of 3'-protected nucleotide triphosphates, e.g. protected by a 3'-O-azidomethyl, 3-aminoxy or 3-O-allyl group, to the 3'-OH of a short oligonucleotide (primer) in a template-independent manner. This oligonucleotide primer is usually a minimum of three nucleotides long.

Suitable methods are set out, for example, in EP2796552, U.S. Pat. No. 8,808,989, WO16128731 A1 and WO16139477 A1.

The primer oligonucleotide used in the above described ssLigase and transferase methods for producing segment oligonucleotides can:

(1) be retained as part of the segment oligonucleotide if desired, or (2) be cleaved from the product oligonucleotide to allow separation of the desired product and allow for the possibility of recycling to make further segment oligonucleotides. Cleavage of the primer from the segment oligonucleotide can be performed using a sequence specific nuclease and an appropriate design of primer and segment such that the cleavage is both effective and precise.

EXAMPLES

Abbreviations

OMe O-Methyl
MOE O-Methoxyethyl (DNA backbone) or Methoxyethyl (RNA backbone)
CBD Cellulose Binding Domain
HPLC high performance liquid chromatography
PBS phosphate buffered saline
HAA Hexylammonium acetate
SDS PAGE sodium dodecyl sulphate polyacrylamide gel electrophoresis
LCMS liquid chromatography mass spectrometry
PO phosphodiester
DTT dithiothreitol
Ni-NTA Nickel nitrilotriacetic acid
/3Phos/ 3'-Phosphate group
/5Phos/ 5' Phosphate group
(p) phosphate group
PS or * phosphorothioate
/ideoxyl/ 2' deoxyInosine
5mC 5-Methylcytosine
BSA Bovine serum albumin
LNA locked nucleic acid
WT wild-type

Example 1: Oligonucleotide (DNA) Segment Assembly and Ligation with Wild-Type T4 DNA Ligase 1.1 Chemical Synthesis of Starting and Control Sequences In order to demonstrate that multiple short oligonucleotides ("segments") could be assembled in the correct order on a complementary template strand and ligated to give the desired final product ("target"), the segments, target and template sequences, as detailed in Table 1, were chemically synthesised using standard methods.

1.2 HPLC Analysis

HPLC analysis was carried out using an Agilent ZORBAX Eclipse Plus XDB-C18 column (4.6×150 mm, 5 μm dp. Agilent P/N 993967-902) running at 0.2 ml/min while absorbance was monitored at 258 nm. The column was maintained at 60° C. 20 μl of sample was injected and a gradient from 20-31% buffer B was run over 20 minutes before being stepped up to 80% buffer B for 5 minutes.

Buffer A: 75 ml 1 M HAA, 300 ml isopropyl alcohol, 200 ml acetonitrile, 4425 ml water Buffer B: 650 ml isopropyl alcohol, 350 ml acetonitrile

TABLE 1

| Name | Sequence | % HPLC purity | Amount (mg) |
|---|---|---|---|
| 5'-segment | 5'-GGC CAA-3' | 100.0 | 21.6 |
| centre segment | 5'-(p)ACC TCG GC-3' | 96.9 | 58.1 |
| 3'-segment | 5'-(p)T TAC CT-3' | 98.8 | 39.8 |
| Target | 5'-GGC CAA ACC TCG GCT TAC CT-3' (SEQ ID NO: 1) | 98.4 | 101.7 |
| Biotinylated template | 5'-biotin TT TAG GTA AGC CGA GGT TTG GCC-3' (SEQ ID NO: 2) | 96.9 | 130.7 |

(p) phosphate 1.3 Oligonucleotide Assembly and Ligation Method with Commercial T4 DNA Ligase (SEQ ID NO:3)

The 5' segment, centre segment and 3' segment were assembled on the template: each segment and the template was dissolved in water at a concentration of 1 mg/ml and then mixed as follows.

| | |
|---|---|
| 5'-segment | 2 µl |
| centre segment | 2 µl |
| 3-segment | 2 µl |
| biotinylated template | 2 µl |
| H₂O | 36 µl |

The combined oligonucleotide solution was incubated at 94° C. for 5 minutes and cooled to 37° C. before incubating at 37° C. for a further 5 minutes to allow the segments to anneal to the template. 2 µl (equivalent to 2 µg) T4 DNA ligase (NEB) and 4 µl of 1×T4 DNA Ligation Buffer (NEB) were then added and the reaction (total reaction volume 50 µl) was incubated at room temperature for one hour. Following this, 40 µl of streptavidin coated magnetic beads were added and the suspension incubated at room temperature for 10 minutes to allow the biotinylated template to bind to the streptavidin beads. The streptavidin beads were washed with 2×100 µl PBS to remove unbound segments. The wash was analysed by HPLC. The reaction mixture was then incubated at 94° C. for 10 minutes to separate the bound ligation products (or any bound segments) from the template before being rapidly cooled on ice to 'melt' the DNA and stop reannealing of the oligonucleotides products (or segments) to the template. Analysis of the ligation reaction was then carried out by HPLC.

1.4 Oligonucleotide Assembly and Ligation Method with in-House T4 DNA Ligase Bead Slurry 1.4.1 Bead Slurry Generation T4 ligase (SEQ ID NO:4) fused at the N-terminal to a cellulose binding domain (CBD) was produced using standard cloning, expression and extraction methods. This T4 ligase amino acid sequence differs from the commercial T4 ligase sequence (SEQ ID NO:3) in that the N-terminal methionine (M) has been replaced with glycine and serine (GS). These amino acid substitutions were done to aid the generation and expression of the CBD fusion protein. CBD-T4 ligase fusion protein was expressed in BL21 A1 cells (INVITROGEN). Supernatant was harvested and was added to 600 µl of PERLOZA™ 100 (PERLOZA™) beads and shaken at 26° C. for 1 hour. The PERLOZA™ cellulose beads were then collected and washed with 2 ml buffer (50 mM Tris pH 8.0, 200 mM NaCl, 0.1% Tween 20, 10% Glycerol) followed by 5 ml PBS and were finally resuspended in 200 µl PBS (10 mM PO₄³⁻, 137 mM NaCl, 2.7 mM KCl pH 7.4). In order to analyse protein expression, 15 µl of the PERLOZA™ bead slurry was mixed with 5 µl of SDS loading buffer and incubated at 80° C. for 10 minutes before being run on a SDS PAGE gradient gel (4-20%) according to a standard protocol.

1.4.2 Oligonucleotide Assembly and Ligation Using Bead Slurry

For T4 ligase bound to PERLOZA™ beads, the assembly and ligation method in 1.3 above was modified as follows. In the initial segment mixture, 36 µl of H₂O was reduced to 8 µl H₂O. After annealing, 2 µl of commercial T4 DNA ligase was replaced by 20 µl of PERLOZA™ bead slurry. Prior to adding the streptavidin magnetic beads, the PERLOZA™ beads were spun down and the supernatant removed. The streptavidin magnetic beads were added to the supernatant and incubated at room temperature for 10 minutes to allow the biotinylated template to bind to the streptavidin beads.

1.5 Results and Conclusions

The product, template and all three segment oligonucleotides were clearly resolved in the control chromatogram.

Figure 7:
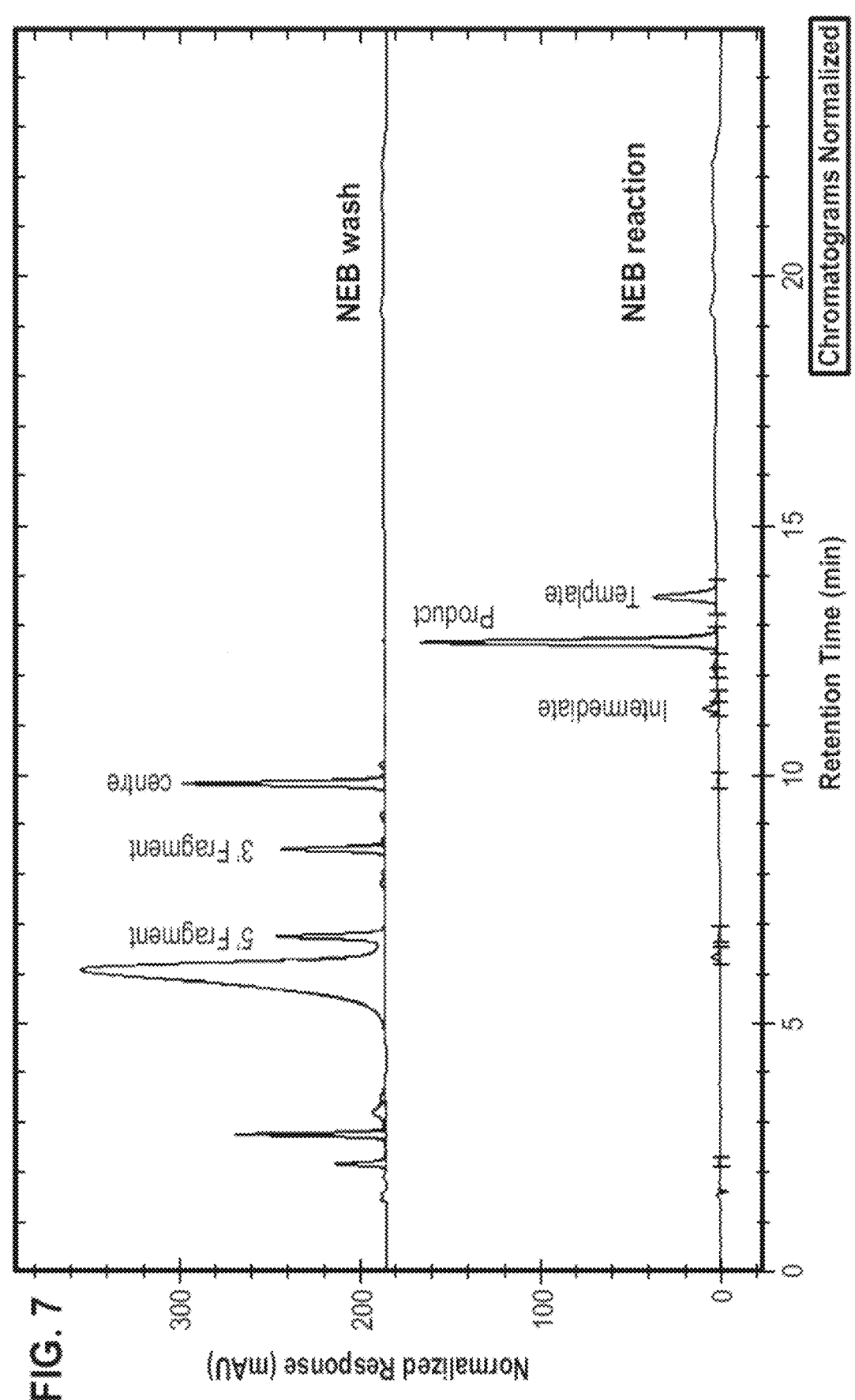
FIG. 7 Chromatogram showing the results of a ligation reaction using commercial NEB T4 ligase (SEQ ID NO:3) and unmodified DNA (Example 1).
Figure 8:
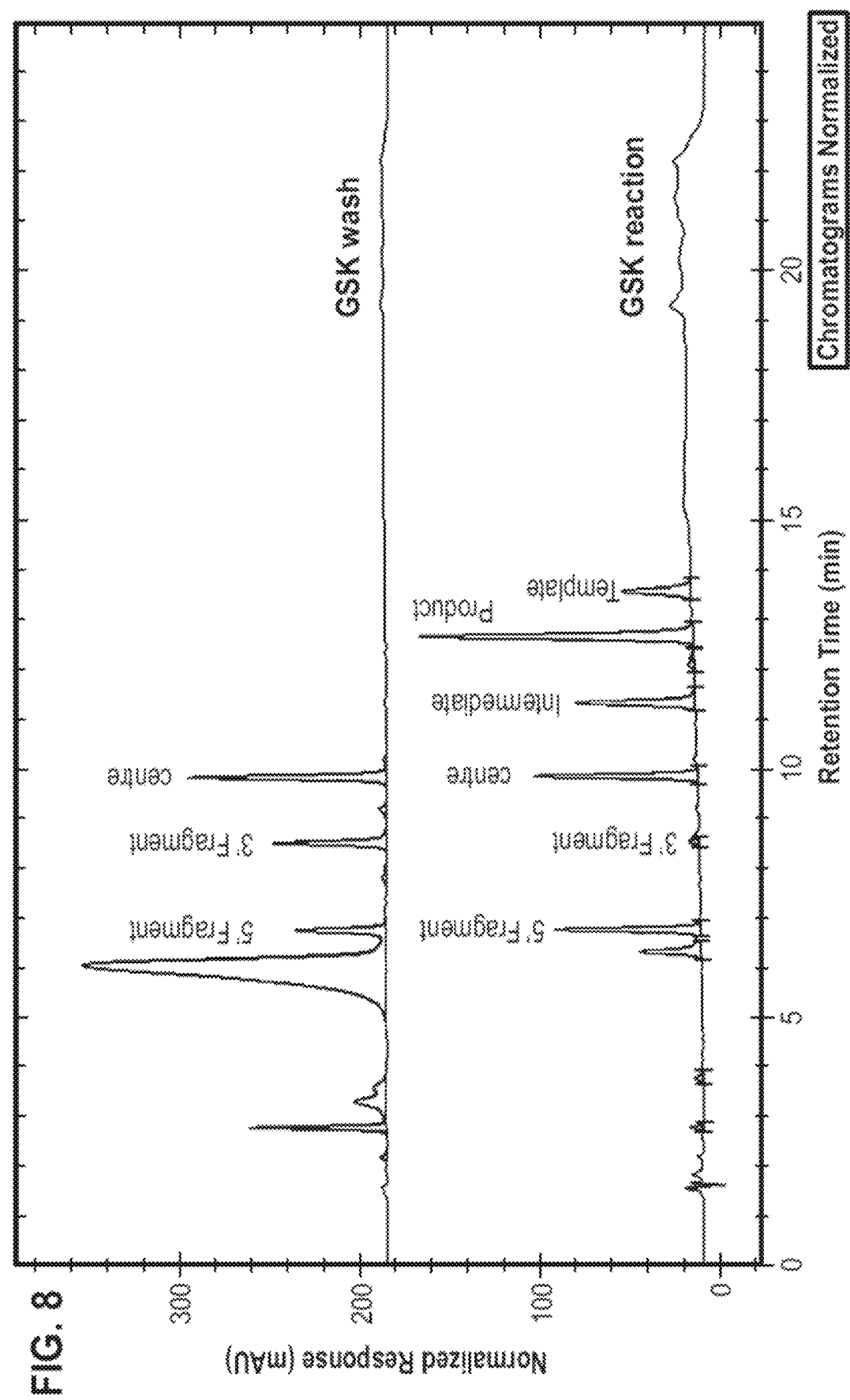
FIG. 8 Chromatogram showing the results of a ligation reaction using PERLOZA™ bound T4 ligase (SEQ ID NO:4) and unmodified DNA (Example 1).

HPLC analysis of the ligase reactions showed that some unligated oligonucleotide segments remained, but commercial T4 DNA ligase (NEB) was able to catalyse ligation of the three segments to generate the desired product oligonucleotide (FIG. 7). The PERLOZA™ bead bound T4 DNA ligase appeared to be less efficient at ligation of the oligonucleotide segments, with oligonucleotide segments appearing in both the control wash sample and the reaction sample (FIG. 8). However, it is difficult to be sure whether the same amount of enzyme was added on the beads compared to the commercial enzyme, so a direct comparison of ligation efficiency was not possible.

Example 2: 2'-OMe Ribose Modified Oligonucleotide Segment Assembly and Ligation with Wild-Type T4 DNA Ligase 2.1 2' OMe at Each Nucleotide Position in Every Segment In order to determine whether T4 DNA ligase was able to ligate oligonucleotide segments with modification at the 2' position of the ribose ring, oligonucleotide segments were synthesized with the same sequence as for Example 1, but the 2' position of the ribose ring was substituted with an OMe group and thymidine was replaced by uridine as shown below.

TABLE 2

| Name | Sequence | % HPLC purity | Amount (mg) |
|---|---|---|---|
| 5'-segment 2'-OMe | 5'-GGC CAA-3' | 21 | 97.8 |
| centre segment 2'-OMe | 5'-(p)ACC UCG GC-3' | 15.5 | 97.7 |
| 3'-segment 2'-OMe | 5'-(p)U UAC CU-3' | 21.2 | 98.1 |
| Target 2'-OMe | 5'-GGC CAA ACC UCG GCU UAC CU-3' (SEQ ID NO: 5) | 88 | 96.9 |

(p) = phosphate

Assembly, ligation and HPLC analysis were carried out using the methods of Example 1, with both commercial NEB ligase and T4 ligase CBD fusion bound to PERLOZA™ beads. The amount of water used in the reaction mix for the commercial T4 DNA ligase (NEB) experiment was 26 μl, rather than 36 μl, so that the final reaction volume was 40 μl. The amount of water used in the reaction mix for the in-house T4 DNA ligase bead slurry experiment was 23 μl, and the amount of beads used was 5 μl, so that the final reaction volume was also 40 μl. Control experiments using unmodified DNA as opposed to 2'-OMe DNA were run in parallel.

The results from the control experiments were in accordance with Example 1. No product was detected using HPLC for the 2'-OMe experiments indicating that T4 DNA ligase is unable to ligate fully 2'-OMe modified oligonucleotide segments regardless of whether a commercial T4 DNA ligase or in-house T4 DNA ligase CBD fusion bound to PERLOZA™ beads was used.

2.2 2'-OMe at Each Nucleotide Position in a Single Segment

Using a 1 mg/ml solution of each oligonucleotide the reactions as detailed in table 3 were set up.

The processed reactions were split in two: half were analysed by HPLC as described for Example 1 (section 1.2). The other half of the sample was retained for mass spectrometry to confirm the HPLC results.

Figure 9A:
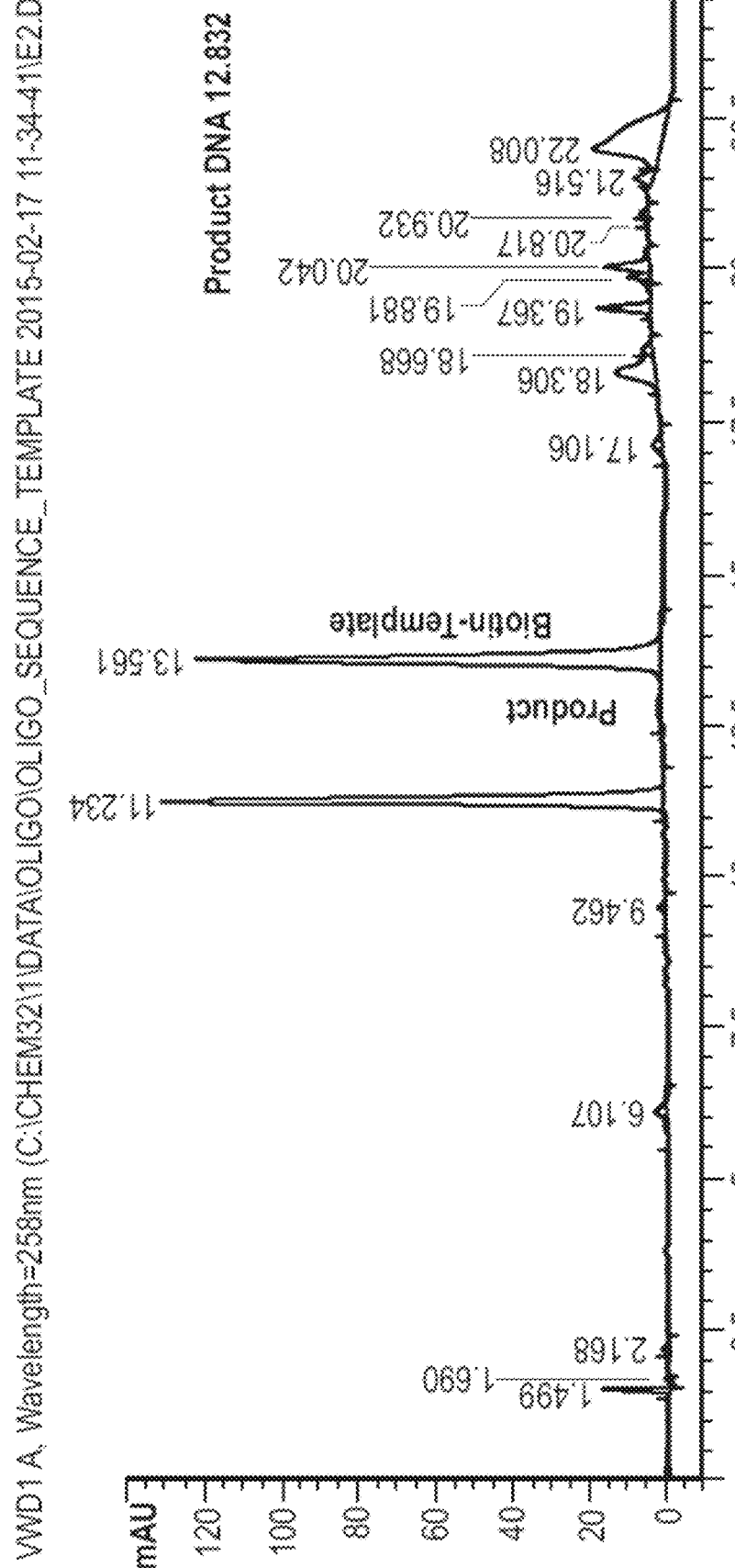
FIGS. 9a-9c Chromatogram showing the results of a ligation reaction using PERLOZA™ bound T4 ligase expressed according to Example 2 and 2'-OMe modified oligonucleotide fragments.
Figure 9B:
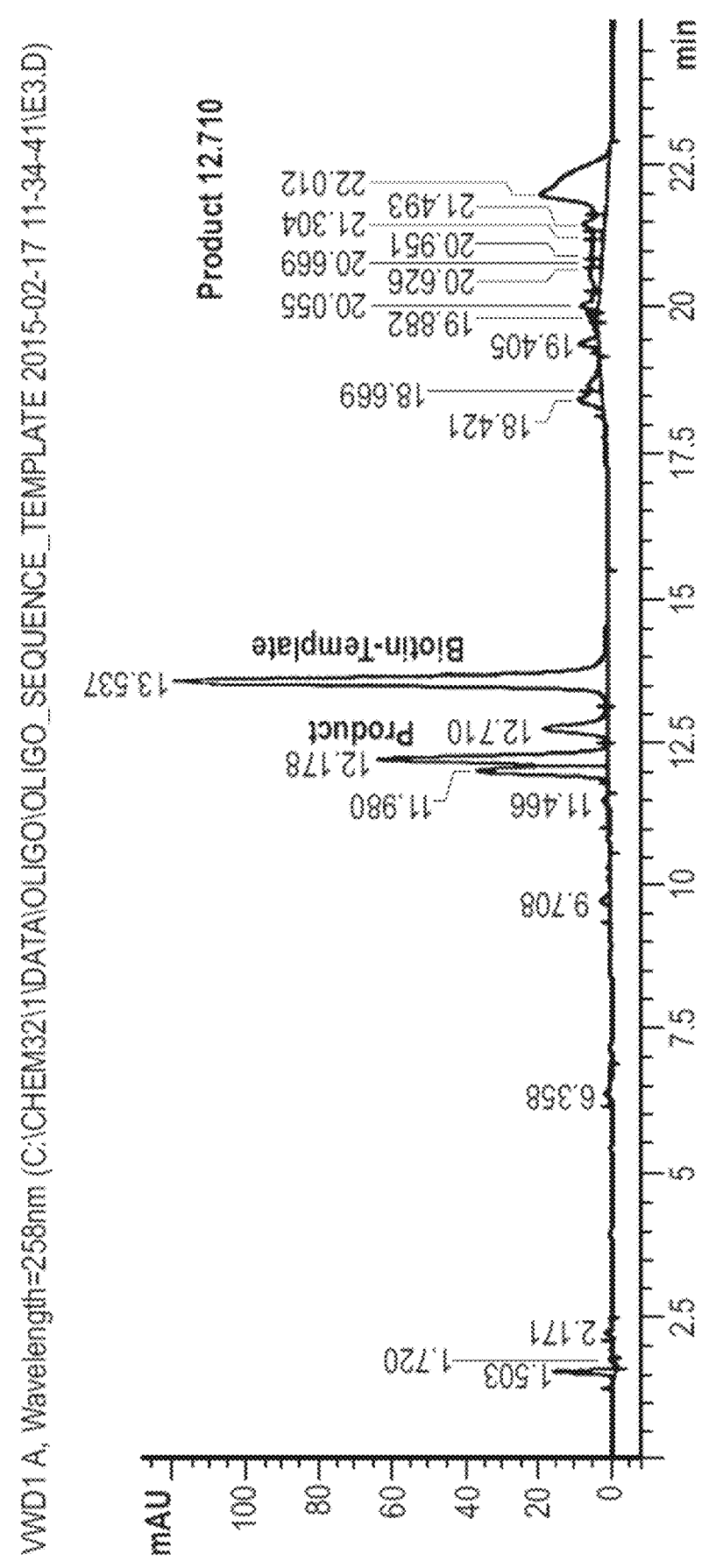
Figure 9C:
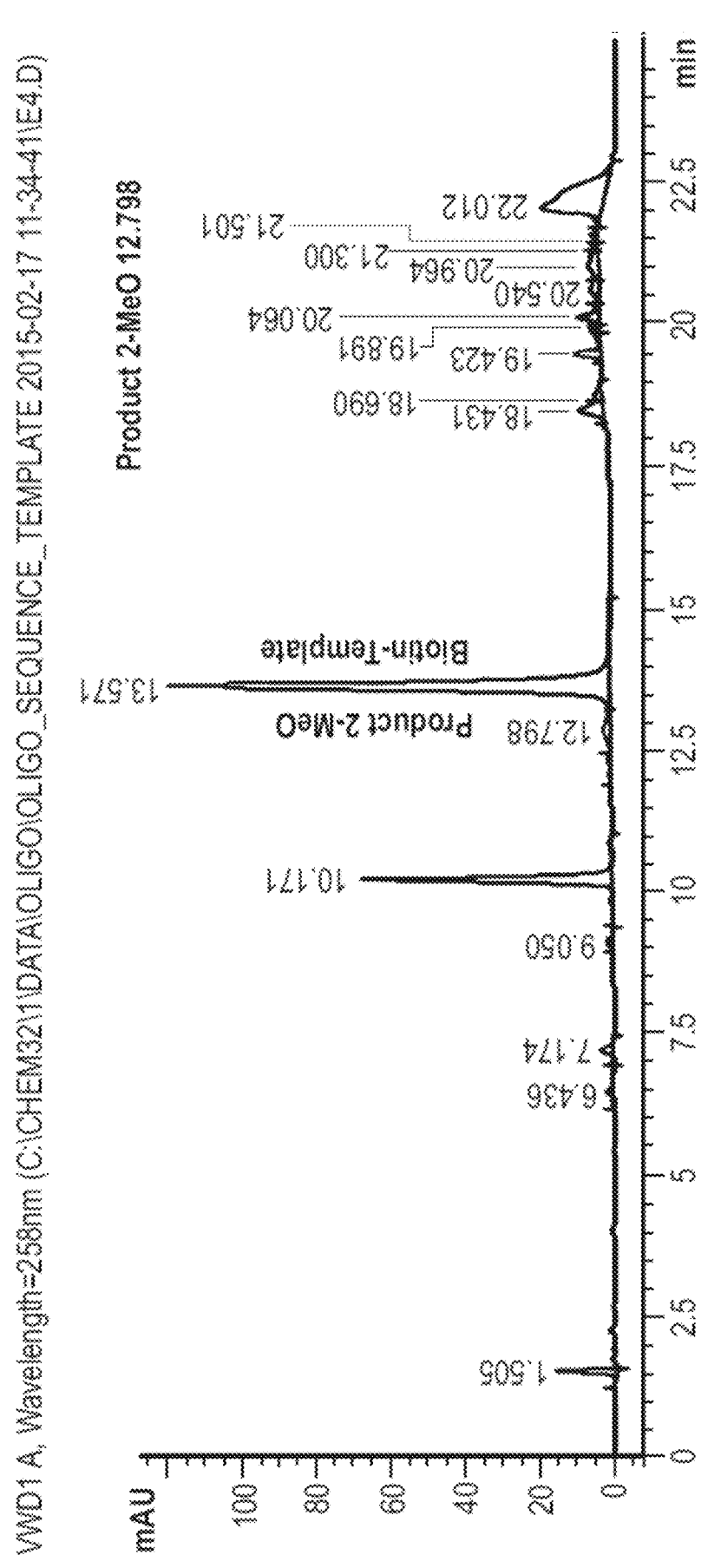

Ligation of unmodified oligonucleotide segments (experiment 5) proceeded as expected to produce full length product. A small amount of ligation was seen when the 5' segment was 2'-OMe substituted (Experiment 3) as shown in FIG. 9B, but no ligation was seen when the 3' segment was 2'-OMe substituted (Experiment 2; FIG. 9A). No significant product was seen when all three segments were 2'-OMe substituted (Experiment 4; FIG. 9C) in accordance with 2.1.

2.3 Conclusion

Wild-type T4 DNA ligase is poor at ligating 2'-OMe substituted oligonucleotide segments, but is slightly less sensitive to modification of the 5' oligonucleotide segment than the 3' segment.

Example 3: 2'-OMe Ribose Modified Oligonucleotide Segment Assembly and Ligation with Wild-Type and Mutant Ligases 3.1 Materials Wild-type Enterobacteria phage ligase CC31 (SEQ ID NO:6), wild-type *Shigella* phage Shf125875 ligase (SEQ ID

TABLE 3

| Experiment 1 (No ligase control) | Experiment 2 (single 2'-OMe segment - 3') | Experiment 3 (single 2'-OMe segment - 5') | Experiment 4 (all 2'-OMe) | Experiment 5 (all unmodified) | Volume (μl) |
|---|---|---|---|---|---|
| template | template | template | template | template | 2 |
| 5' segment | 5' segment | 2'-OMe substituted 5' segment | 2'-OMe substituted 5' segment | 5' segment | 2 |
| 3' segment | 2'-OMe substituted 3' segment | 3' segment | 2'-OMe substituted 3' segment | 3' segment | 2 |
| Centre segment | Centre segment | Centre segment | 2'-OMe substituted Centre segment | Centre segment | 2 |
| H₂O | H₂O | H₂O | H₂O | H₂O | up to 40 total |

Assembly and ligation were carried out using the methods of Example 1 with commercial NEB ligase and in-house PERLOZA™ bound T4 DNA ligase.

Reactions were incubated at 94° C. for 5 minutes, followed by incubation for 5 minutes at 37° C. to allow for annealing. 4 μl of 1×NEB T4 DNA ligation buffer was added to each reaction along with 5 μl (approximately 2 μg) of in-house T4 DNA ligase or 2 μl (approximately 2 μg) commercial T4 DNA ligase (apart from Experiment 1 which was a no ligase control) and the ligation reaction was allowed to proceed for 2 hours at room temperature. Streptavidin magnetic beads were then added to each reaction and the reactions heated to 94° C. before rapid cooling on ice as described in Example 1 to separate the template from starting materials and products.

NO:8), and 10 mutant T4 ligases of SEQ ID NO:10-19, each fused at the N-terminus to a CBD, were produced using standard cloning, expression and extraction methods. As disclosed in 1.4.1, in order to generate and express the CBD fusion proteins the N-terminal methionine (M) was replaced with glycine and serine (GS) in each case (e.g. SEQ ID NO:7 for Enterobacteria phage ligase CC31 and SEQ ID NO:9 for *Shigella* phage Shf125875 ligase).

The following oligonucleotides were synthesized by standard solid phase methods.

TABLE 4

| Name | Sequence | % HPLC purity | Amount (mg) |
|---|---|---|---|
| 5'-segment | 5'-(OMe)G(OMe)G(OMe)C(OMe)C(OMe)AA-3' | 99.35 | 24.7 |
| centre segment | 5'-(p)ACC TCG GC-3' | 96.9 | 58.1 |
| 3' segment | 5'-(p)TTA CCT-3' | 97.88 | 29.5 |
| Biotinylated template | 5'-biotin TT TAG GTA AGC CGA GGT TTG GCC-3' (SEQ ID NO: 2) | 96.9 | 130.7 |

N.B. OMe indicates 2' methoxy substitution on the ribose ring
(p) = phosphate
*note that the first 5 nucleotides are 2'-OMe modified (GGCCA), but the final A is not

3.2 Oligonucleotide Assembly and Ligation Method with Ligase Bead Slurries

3.2.1 Bead Slurry Generation

Ligases fused to CBD were bound to PERLOZA™ beads as described in 1.4 to generate a bead slurry.

3.2.2 Oligonucleotide Assembly and Ligation Using Bead Slurry

Ligation reactions were prepared with the components below to a final volume of 50 μL in a 96 well plate:

| | |
|---|---|
| 2 μL | ~1 mg/mL 5' (2'-OMe) segment |
| 2 μL | ~1 mg/mL centre segment |
| 2 μL | ~1 mg/mL 3' segment |
| 2 μL | ~1 mg/mL template |
| 5 μL | NEB T4 DNA ligase buffer |
| 22 μL | H$_2$O |
| 15 μL | PERLOZA bound bead slurry |

The reaction was incubated for 15 minutes at room temperature prior to the addition of PERLOZA™ bead slurry to allow segments to anneal to the template. PER-LOZA™ bead slurry was added and the reaction incubated at room temperature for 1 hour. After the hour incubation, the solution was transferred into an ACOPREP™ advance 350 filter plate (PN 8082) and the filter plate was placed on top of an ABGENE™ superplate (Thermo Scientific, #AB-2800) and centrifuged for 10 minutes at 4,000 rpm to remove the PERLOZA™ bead slurry. Solutions were then analysed by HPLC using the method described in Example 1 (section 1.2).

Each oligonucleotide assembly and ligation was repeated 6 times for each ligase.

3.3 Results and Conclusions

Wild-type Enterobacteria phage CC31 ligase (SEQ ID NO:6) and wild-type *Shigella* phage Shf125875 ligase (SEQ ID NO:8) are able to ligate a 2' OMe substituted 5' segment containing five 2'-OMe nucleobases and one deoxynucleobase to a segment containing only unmodified DNA. In addition, whilst wild-type T4 DNA ligase (SEQ ID NO:3 and 4) is poor at performing this reaction, as shown in Example 2 and reconfirmed here, a number of mutations at positions 368 and 371 confer the ability to ligate a 2'-OMe substituted 5' segment containing five 2' OMe nucleobases and one deoxynucleobase to a segment containing only unmodified DNA on the ligase (SEQ ID NO:10-19).

Example 4: 2' MOE Ribose Modified and 5-Methyl Pyrimidine Modified Oligonucleotide Segment Assembly and Ligation with Mutant DNA Ligases

4.1 Materials

Modified oligonucleotide segments as set out in table 5 below were synthesised by standard solid phase-based methods.

TABLE 5

| Segment | Sequence | MW | Mass (mg) | % purity |
|---|---|---|---|---|
| centre segment | 5'-(p)dCdCdTdCdGdG-3' | 2044.122 | 39 | 98.96 |
| MOE 3'-segment | 5'-(p)dCdTmTmAmCmCmT-3' | 2699.679 | 52 | 97.79 |
| MOE 5'-segment | 5'-mGmGmCmCmAdAdA-3' | 2644.771 | 48 | 99.13 |

(p) = phosphate, mX = MOE bases, dX = DNA bases
all 5-methyl pyrimidines

Mutant DNA ligases (SEQ ID NO:20-28) based upon wild-type Enterobacteria phage CC31 ligase, wild-type T4 ligase and wild-type *Shigella* phage Shf125875 ligase were each fused at the N-terminus to a cellulose binding domain (CBD), using standard cloning, expression and extraction methods. Ligases fused to CBD were bound to PERLOZA™ beads as described in 1.4 to generate a bead slurry. In order to release the ligases from the PERLOZA™ beads, 2 μl of TEV protease was added to the slurry and incubated overnight at 4° C. The cleaved protein, now lacking the cellulose binding domain, was collected by centrifugation for 10 min at 4000 rpm.

4.2 Method

The reaction was set up as follows:

| | |
|---|---|
| centre segment | 20 μM final |
| MOE 3' segment | 20 μM final |
| MOE 5' segment | 20 μM final |
| Template | 20 μM final |
| NEB T4 DNA ligase buffer | 5 μl |
| mutant DNA ligase | 15 μl |
| H$_2$O | To make final reaction 50 μl |

All components were mixed and vortexed prior to addition of DNA ligase. Reactions were incubated for 1 hour at 35° C. After 1-hour reactions were stopped by heating at 95° C. for 5 minutes in a PCR block.

Samples were analysed by both HPLC and LCMS to confirm product identity according to the HPLC protocol used in Example 1 (section 1.2). Controls of commercial NEB T4 DNA ligase and a negative control (H$_2$O instead of any ligase) were included.

4.3 Results and Conclusions

Figure 10A:
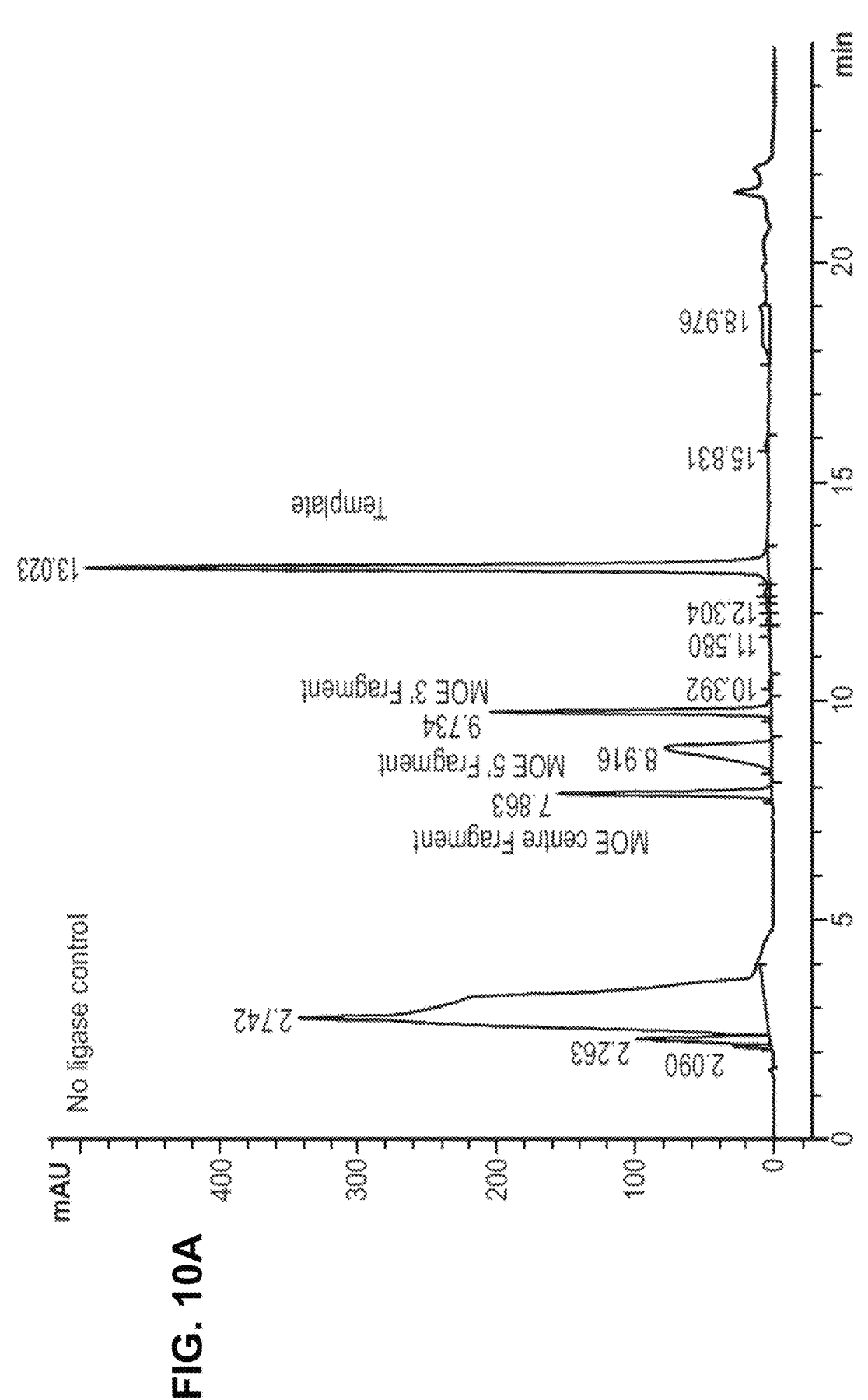
FIGS. 10a-10b HPLC traces for Example 4: Upper trace (FIG. 10a)—No ligase control. Lower trace (FIG. 10b)—clone A4. Product and template co-elute in this HPLC method. Two intermediate ligation fragments (segments) can be seen in the Clone A4 trace at 10.3 and 11.2 minutes.
Figure 10B:
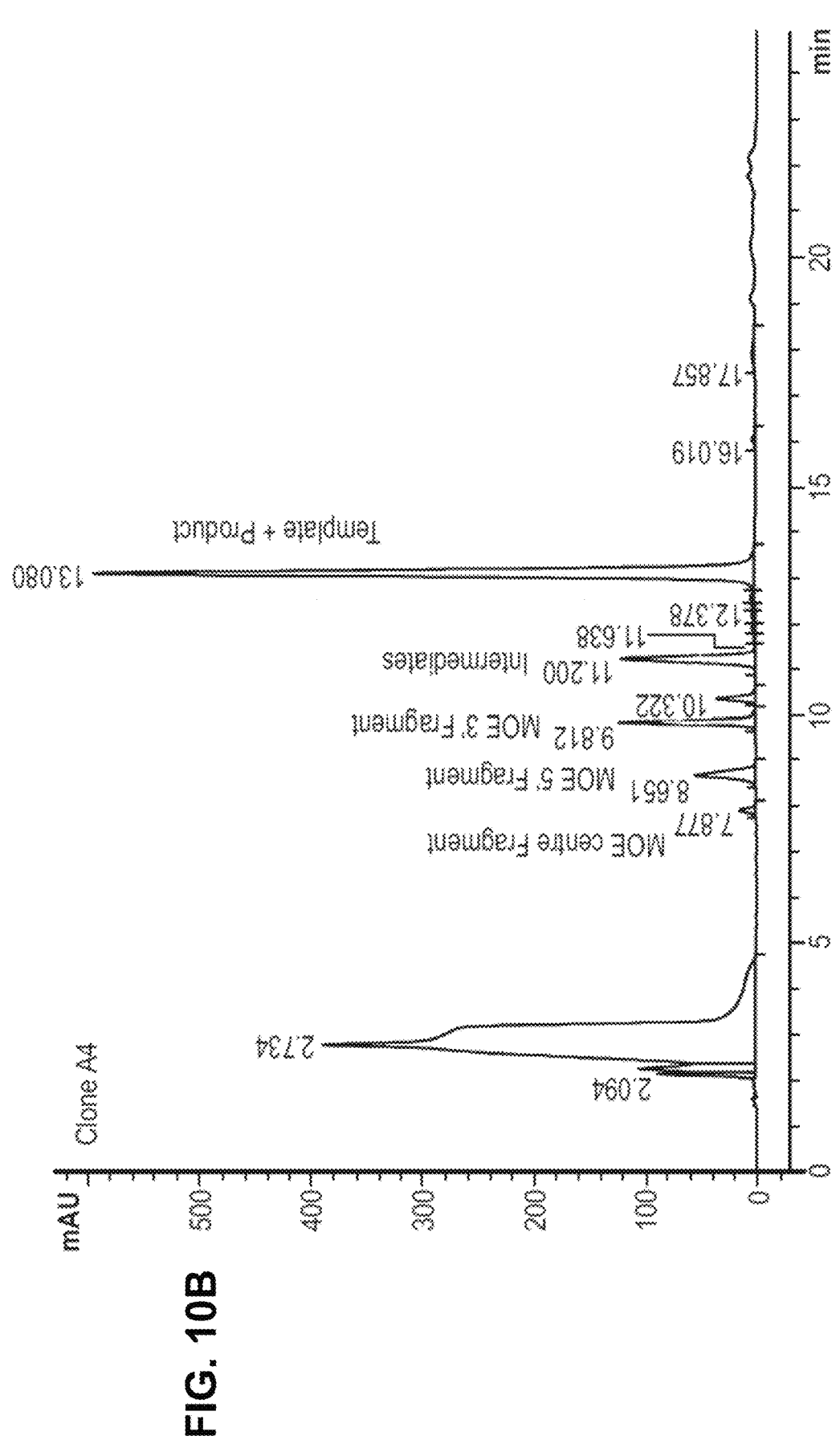

FIGS. 10*a*-10*b* show the HPLC traces for the control reaction and the reaction catalysed by SEQ ID NO:23 (clone A4—mutant Enterobacteria phage CC31 ligase). The product and template co-elute using this HPLC method so product appears as an increase in the peak area of the product+template peak. In the mutant ligase trace of FIG. 10*b* not only does the product+template peak increase but two new peaks appear at 10.3 and 11.2 minutes. These peaks correspond to the ligation of the centre segment with either the MOE 5'segment or the MOE 3'segment. Also, the input segment peaks are substantially smaller than the control in line with product and intermediate peaks increasing. The NEB commercial T4 ligase trace of FIG. 10*a* showed a slight increase in the peak area for template+product, a small amount of intermediate ligation product along with a concomitant decrease in input oligonucleotide segments. The mutant ligase (SEQ ID NO:23), however, showed substantially greater product+template peak area and concomitant reduction in peak areas for input oligonucleotide segments. Thus, the mutant ligase (SEQ ID NO:23) is a much more effective ligase for the 2' MOE substituted segments than commercial T4 DNA ligase. Similar improvements were shown for the other mutant ligases (SEQ ID NO:20, 21, 24-28).

Example 5: Effect of Different Nucleotide Pairing at the Ligation Site 5.1 Materials Mutant Enterobacteria phage CC31 ligase (SEQ ID NO:23) fused at the N-terminal to a cellulose binding domain (CBD) was produced using standard cloning, expression and extraction methods. Extracted CBD-mutant Enterobacteria phage CC31 ligase fusion protein was added to 25 ml of PERLOZA™ 100 (PERLOZA™) cellulose beads and shaken at 20° C. for 1 hour. The PERLOZA™ beads were then collected and washed with 250 ml buffer (50 mM Tris pH 8.0, 200 mM NaCl, 0.1% Tween 20, 10% Glycerol) followed by 250 ml PBS and were finally re-suspended in 10 ml PBS (10 mM $PO_4^{3-}$, 137 mM NaCl, 2.7 mM KCl pH 7.4). In order to analyse protein expression, 15 μl of the PERLOZA™ bead slurry was mixed with 5 μl of SDS loading buffer and incubated at 80° C. for 10 minutes before being run on a SDS PAGE gradient gel (4-20%) according to a standard protocol. For the release of the ligase from the beads, 70 μl of TEV protease was added and incubated overnight at 4° C. with shaking. Ligase was collected by washing the digested beads with 80 ml of PBS. The ligase was then concentrated down to 1.2 ml using an Amicon 30 Kd MCO filter.

The following biotinylated DNA template oligonucleotides (table 6) and DNA segment oligonucleotides (table 7) were synthesized by standard solid phase methods. Please note that the nucleotides in bold are the ones present at the ligation site (i.e. those nucleotides that were joined together in the ligation reaction—table 7; and those nucleotides that are complementary to those joined via the ligation reaction—table 6).

TABLE 6

| Template number | Sequence (nucleotides complementary to junction nucleotides are in bold) | SEQ ID NO |
|---|---|---|
| 1 | 5'-biotin TTTGGTGCGAAGCAGACTGAGGC-3' | 30 |
| 2 | 5'-biotin TTTGGTGCGAAGCAGAGTGAGGC-3' | 31 |
| 3 | 5'-biotin TTTGGTGCGAAGCAGATTGAGGC-3' | 32 |
| 4 | 5'-biotin TTTGGTGCGAAGCAGAATGAGGC-3' | 33 |
| 5 | 5'-biotin TTTGGTGCGAAGCAGTCTGAGGC-3' | 34 |
| 6 | 5'-biotin TTTGGTGCGAAGCAGTGTGAGGC-3' | 35 |
| 7 | 5'-biotin TTTGGTGCGAAGCAGTTTGAGGC-3' | 36 |
| 8 | 5'-biotin TTTGGTGCGAAGCAGTATGAGGC-3' | 37 |
| 9 | 5'-biotin TTTGGTGCGAAGCAGCCTGAGGC-3' | 38 |
| 10 | 5'-biotin TTTGGTGCGAAGCAGCGTGAGGC-3' | 39 |
| 11 | 5'-biotin TTTGGTGCGAAGCAGCTTGAGGC-3' | 40 |
| 12 | 5'-biotin TTTGGTGCGAAGCAGCATGAGGC-3' | 41 |
| 13 | 5'-biotin TTTGGTGCGAAGCAGGCTGAGGC-3' | 42 |
| 14 | 5'-biotin TTTGGTGCGAAGCAGGGTGAGGC-3' | 43 |
| 15 | 5'-biotin TTTGGTGCGAAGCAGGTTGAGGC-3' | 44 |
| 16 | 5'-biotin TTTGGTGCGAAGCAGGATGAGGC-3' | 45 |

TABLE 7

| Segment | Identifier | Sequence (junction nucleotides are in bold) |
|---|---|---|
| 5' | A | 5'-GCCTCAG-3' |
| 5' | B | 5'-GCCTCAC-3' |
| 5' | C | 5'-GCCTCAA-3' |
| 5' | D | 5'-GCCTCAT-3' |
| 3' | E | 5'-(p)TCTGCT-3' |
| 3' | F | 5'-(p)ACTGCT-3' |
| 3' | G | 5'-(p)CCTGCT-3' |
| 3' | H | 5'-(p)GCTGCT-3' |

(p) = phosphate

N.B. please note that, unlike previous examples, the ligation reactions in this example involve joining two segments together: a 5'-segment and a 3'-segment, i.e. there is no centre segment.

5.2 Method

Reactions were set up as follows:

TABLE 8

| Template | 5'-segment | 3'-segment |
|---|---|---|
| 1 | A | E |
| 2 | B | E |
| 3 | C | E |
| 4 | D | E |
| 5 | A | F |
| 6 | B | F |
| 7 | C | F |
| 8 | D | F |
| 9 | A | H |
| 10 | B | H |
| 11 | C | H |
| 12 | D | H |
| 13 | A | G |
| 14 | B | G |
| 15 | C | G |
| 16 | D | G |

For each 50 μL reaction:

3' segment (1 mM stock, 20 μM final) 1 μl

| | |
|---|---|
| 3' segment (1 mM stock, 20 μM final) | 1 μl |
| 5' segment (1 mM stock, 20 μM final) | 1 μl |
| Template (1 mM stock, 20 μM final) | 1 μl |
| NEB DNA ligase buffer (for T4 ligase) | 5 μl |
| Mutant CC31 DNA ligase (0.45 mM stock, 90 μM final) | 10 μl |
| H₂O | up to 50 μl |

Each reaction mix was incubated at 35° C. both for 30 minutes and 1 hour. Each reaction was terminated by heating at 95° C. for 5 minutes. HPLC analysis was carried out.

5.3 Results and Conclusions

All of the reactions produced a product peak after 1 hour incubation in HPLC analysis. Accordingly, the ligation method works for all combinations of nucleotides at the junctions to be joined. Optimisation to improve product yield is possible, but was not necessary as the results were conclusive and it was clear that the reaction was working for all combinations of nucleotides at the junctions to be joined.

Example 6: Effect of Different Modifications at the Ligation Site 6.1 Materials

Mutant Enterobacteria phage CC31 ligase (SEQ ID NO:23) was produced as described in 5.1 and *Chlorella* virus DNA ligase (SEQ ID NO:29, commercially available as SplintR ligase, NEB) was purchased.

The following biotinylated template oligonucleotide and segment oligonucleotides (table 9) were synthesized by standard solid phase methods.

TABLE 9

| Name | Sequence (junction modification in bold) |
|---|---|
| Template | 5'-biotin TTTAGGTAAGCCGAGGTT TGGCC-3' (SEQ ID NO: 2) |
| 5' segment (WT) | 5'-GGCCAAA-3' |
| 5' segment (Mo1) | 5'-GGCCAA**(OMe)A**-3' |
| 5' segment (Mo2) | 5'-GGCCAA**(F)A**-3' |
| centre segment (WT) | 5'-(p)CCTCGG-3' |
| centre segment (Mo4A) | 5'-(p)**(OMe)**CCTCGG-3' |
| centre segment (Mo5A) | 5'-(p)**(F)**CCTCGG-3' |
| centre segment (Mo7) | 5'(p)**(Me)**CCTCGG-3' |
| 3' segment (WT) | 5'-(p)CTTACCT-3' |
| 3' segment (Mo8) | 5'-(p)**(Me)**CTTACCT3' |

OMe indicates 2' methoxy substitution on the ribose ring
F indicates 2' fluoro substitution on the ribose ring
All remaining sugar residues are deoxyribose residues
Me indicates 5-methyl cytosines 6.2 Method Reactions were set up as follows:

TABLE 10

| Reaction | 5' segment | Centre segment | 3' segment |
|---|---|---|---|
| 1 | WT | WT | WT |
| 2 | WT | Mo4A | WT |
| 3 | WT | Mo5A | WT |
| 4 | WT | Mo7 | WT |
| 5 | Mo1 | WT | WT |
| 6 | Mo1 | Mo4A | WT |
| 7 | Mo1 | Mo5A | WT |
| 8 | Mo1 | Mo7 | WT |
| 9 | Mo2 | WT | WT |
| 10 | Mo2 | Mo4A | WT |
| 11 | Mo2 | Mo5A | WT |
| 12 | Mo2 | Mo7 | WT |
| 13 | WT | WT | Mo8 |
| 14 | WT | Mo4A | Mo8 |
| 15 | WT | Mo5A | Mo8 |
| 16 | WT | Mo7 | Mo8 |
| 17 | Mo1 | WT | Mo8 |
| 18 | Mo1 | Mo4A | Mo8 |
| 19 | Mo1 | Mo5A | Mo8 |
| 20 | Mo1 | Mo7 | Mo8 |
| 21 | Mo2 | WT | Mo8 |
| 22 | Mo2 | Mo4A | Mo8 |
| 23 | Mo2 | Mo5A | Mo8 |
| 24 | Mo2 | Mo7 | Mo8 |

For each 50 µL reaction:

| | |
|---|---|
| 3'-segment (1 mM, stock, 20 µM final) | 1 µl |
| centre segment (1 mM, stock, 20 µM final) | 1 µl |
| 5'-segment (1 mM, stock, 20 µM final) | 1 µl |
| Template (1 mM, stock, 20 µM final) | 1 µl |
| H₂O | up to 50 µl |

For Mutant Enterobacteria phage CC31 ligase (SEQ ID NO:23)

| | |
|---|---|
| DNA ligase buffer (50 mM Tris-HCl, 1 mM DTT) | 5 µl |
| Mutant CC31 DNA ligase (0.45 mM) | 10 µl |
| MnCl₂ (50 mM) | 5 µl |
| ATP (10 mM) | 10 µl |

Whereas for *Chlorella* virus DNA ligase (SEQ ID NO:29, commercially available as SplintR ligase, NEB)

| | |
|---|---|
| NEB DNA ligase buffer (for Chlorella) | 5 µl |
| Chlorella virus DNA ligase | 2 µl |

Each reaction mix was incubated at 20° C. 1 hour. Each reaction was terminated by heating at 95° C. for 10 minutes. HPLC analysis was carried out using the method of Example 1.

6.3 Results and Conclusions

All of the reactions produced a product peak in HPLC analysis. Accordingly, the ligation method works for all combinations of modifications tested at the junctions to be joined. Optimisation to improve product yield is possible, but was not necessary as the results were conclusive and it was clear that the reaction was working for all combinations of modifications tested at the junctions to be joined.

Example 7: Ability to Use Different Numbers of Segments to Build Larger Oligonucleotides 7.1 Materials Mutant Enterobacteria phage CC31 ligase (SEQ ID NO:23) was produced as described in 5.1.

The following biotinylated template DNA oligonucleotides and DNA segment oligonucleotides (table 11) were synthesized by standard solid phase methods.

TABLE 11

| Name | Sequence |
|---|---|
| Template | 5'-biotin TTTGGTGCGAAGCAGAAGGTA AGCCGAGGTTTGGCC-3' (SEQ ID NO: 47) |
| 5' segment (1) | 5'-GGCCAAA-3' |
| centre segment (2) | 5'-(p)CCTCGG-3' |

TABLE 11-continued

| Name | Sequence |
|---|---|
| centre segment/ 3'segment (5) | 5'-(p)TCTGCT-3' |
| centre segment (3) | 5'-(p)CTTACCT-3' |
| 3' segment (4) | 5'-(p)TCGCACC-3' |

(p) = phosphate, 7.2 Method

Reactions were set up as follows:

TABLE 12

| 5' segment | Centre segment(s) | 3' segment | Total number of segments |
|---|---|---|---|
| 1 | 2 and 3 | 5 | 4 |
| 1 | 2, 3 and 5 | 4 | 5 |

Reactions were run in phosphate buffered saline, pH=7.04 in a total volume of 100 µl and set up as follows:—
Template (20 µM final)
Each segment (20 µM final)
MgCl₂ (10 mM final)
ATP (100 µM final)
Mutant CC31 DNA ligase (25 µM final)

Each reaction was incubated at 28° C. overnight before being terminated by heating at 94° C. for 1 minute. Products were analysed by HPLC mass spec.

7.3 Results and Conclusions

The reaction using 4 segments produced a fully ligated product of 27 base pairs in length. The reaction using 5 segments produced a product of 33 base pairs in length. In both cases the observed mass of the product was in concordance with that expected for the desired sequence. In conclusion, it is clearly possible to assemble multiple segments to generate oligonucleotides of the desired length and sequence as defined by the appropriate complementary template sequence.

Example 8: Assembly and Ligation of 5-10-5 Segments to Form a Gapmer, Wherein the 5' and the 3'Segments Comprise (i) 2'-OMe Ribose Sugar Modifications, (ii) Phosphorothioate Linkages or (iii) 2'-OMe Ribose Sugar Modifications and Phosphorothioate Linkages; and Wherein the Central Segment is Unmodified DNA 8.1 Materials Mutant Enterobacteria phage CC31 ligase (SEQ ID NO:23) was produced as described in 5.1 the following biotinylated template DNA oligonucleotide and segment oligonucleotides (table 13) were synthesized by standard solid phase methods.

TABLE 13

| Name | Sequence |
|---|---|
| Template | 5'-biotin TTTGGTGCGAAGCAGACTGAGGC-3' (SEQ ID NO: 30) |
| 3' segment (3OMe) | 5'-(p)(OMe)G(OMe)C(OMe)C(OMe)T(OMe)C-3' |
| 3' segment (3PS + OMe) | 5'-(p)(OMe)G*(OMe)C*(OMe)C*(OMe)T*(OMe)C-3' |

TABLE 13-continued

| Name | Sequence |
|------|----------|
| 3' segment (3PS) | 5'-(p)G*C*C*T*C-3' |
| centre segment (D) | 5'-(p)AGTCTGCTTC-3' |
| 5' segment (5OMe) | 5'-(OMe)G(OMe)C(OMe)A(OMe)C(OMe)C-3' |
| 5' segment (5PS+OMe) | 5'-(OMe)G*(OMe)C*(OMe)A*(OMe)C*(OMe)C-3' |
| 5' segment (5PS) | 5'-G*C*A*C*C-3' |

OMe indicates 2' methoxy substitution on the ribose ring
All remaining sugar residues are deoxyribose residues
*phosphorothioate 8.2 Method
Reactions were set up as follows:

TABLE 14

| Reaction | 3' segment | Centre segment(s) | 5' segment |
|----------|-----------|-------------------|-----------|
| 1 | 3PS | D | 5PS |
| 2 | 3OMe | D | 5OMe |
| 3 | 3PS + OMe | D | 5PS + OMe |

Each of reactions 1, 2 and 3 were set up in 100 μl final volume in phosphate buffered saline with the following components:—

| | |
|--|--|
| 3' segment | 20 μM final |
| Centre segment | 20 μM final |
| 5' segment | 20 μM final |
| Template | 20 μM final |
| MgCl₂ | 10 mM final |
| ATP | 50 μM final |
| Enzyme | 25 μM final |

Each reaction mix was incubated at 20° C. overnight. Each reaction was terminated by heating at 95° C. for 10 minutes. HPLC mass spec analysis was carried out.

8.3 Results and Conclusions
Product oligonucleotide corresponding to the successful ligation of all three fragments was produced in all three reactions.

Accordingly, mutant Enterobacteria phage CC31 ligase (SEQ ID NO:23) is able to ligate 3 segments together to form a 'gapmer' where the 5' and 3"wings' have a phosphorothioate backbone, whereas the central region has a phosphodiester backbone, and all the sugar residues in the gapmer are deoxyribose residues. Enterobacteria phage CC31 ligase (SEQ ID NO:23) is also able to ligate 3 segments together to form a 'gapmer' where the 5' and 3' 'wings' have 2'-methoxyribose (2'-OMe) residues, whereas the central region has deoxyribose residues, and all of the linkages are phosphodiester linkages. Finally, Enterobacteria phage CC31 ligase (SEQ ID NO:23) is able to ligate 3 segments together to form a 'gapmer' where the 5' and 3"wings' have the combined modifications (a phosphorothioate backbone and 2'-methoxyribose residues), whereas the central region has deoxyribose residues and phosphodiester linkages.

Example 9: Assembly and Ligation of Segments Comprising Locked Nucleic Acids (LNA)

9.1 Materials
Mutant Enterobacteria phage CC31 ligase (SEQ ID NO:23) was produced as described in 5.1. A mutant *Staphy-*

*lococcus aureus* NAD dependent ligase (NAD-14) was produced as described in 13.1 The following biotinylated template DNA oligonucleotide and segment oligonucleotides (table 15) were synthesized by standard solid phase methods.

TABLE 15

| Name | Sequence |
|------|----------|
| Template | 5'-biotin TTTGGTGCGAA GCAGACTGAGGC-3' (SEQ ID NO: 30) |
| 5'-segment | 5'- GCCTCAG-3' |
| LNA 5'-segment (oligo 1) | 5'-GCCTCA(LNA)G-3' |
| Centre segment | 5'-(p)TCTGCT-3' |
| LNA centre segment (oligo 2) | 5'-(p)(LNA)TCTGCT-3' |

(p) = phosphate
LNA = locked nucleic acid 9.2 Method
Reactions were set up as follows:

| Reaction volume 100 μl | |
|------------------------|--|
| Template | 20 μM final |
| Enzyme | 25 μM final |
| All oligonucleotide segments | 20 μM final |

Reactions were set up varying enzyme (mutant Enterobacteria phage CC31 ligase (SEQ ID NO:23) or NAD-14), divalent cation (Mg²⁺ or Mn²⁺) and combinations of oligonucleotide segments as set out in Table 16.

TABLE 16

| Enzyme | SEQ ID NO: 23 | SEQ ID NO: 23 | NAD-14 | NAD-14 |
|--------|---------------|---------------|--------|--------|
| Divalent cation | 10 mM MgCl₂ | 10 mM MnCl₂ | 10 mM MgCl₂ | 10 mM MnCl₂ |
| Cofactor | 100 μM ATP | 100 μM ATP | 100 μM NAD | 100 μM NAD |
| Buffer | PBS, pH = 7.04 | PBS, pH = 7.04 | 50 mM KH₂PO₄, pH 7.5 | 50 mM KH₂PO₄, pH 7.5 |
| 5' segment + Centre segment | Product | Product | Product | Product |
| Oligo 1 + Centre segment | Product | Product | Product | Product |

TABLE 16-continued

| Enzyme | SEQ ID NO: 23 | SEQ ID NO: 23 | NAD-14 | NAD-14 |
|---|---|---|---|---|
| 5' segment + Oligo 2 | Product | Product | Product | Product |
| Oligo 1 + oligo 2 | No product | No product | No product | No product |

Each reaction mix was incubated at 28° C. overnight. Each reaction was terminated by heating at 94° C. for 1 minute. HPLC mass spec. analysis was carried out.

9.3 Results and Conclusions

Product oligonucleotide was produced in control reaction reactions (unmodified oligonucleotides only) and where a single locked nucleic acid was included in one segment at the ligation junction regardless of whether it was on the 3' or 5' side of the junction. When locked nucleic acids were included at both sides (oligo 1+oligo 2) no product was detected. The data was similar for both enzymes and regardless of whether Mg2+ or Mn2+ were used.

Enzyme mutations and/or selection screens could be carried out to identify an enzyme capable of ligating segments with a locked nucleic acid at both the 3' and 5' side of the junction.

Example 10: Assembly and Ligation of Three Segments (7-6-7) to Form a Gapmer Wherein The 5' and the 3' Segments Comprise 2' MOE Ribose Sugar Modifications and all Linkages are Phosphorothioate Linkages, Using a Variant of Enterobacteria Phage CC31 Ligase in the Presence of Mg$^{2+}$ or Mn$^{2+}$ 10.1 Phosphorothioate Bond Formation In order to determine whether a mutant Enterobacteria phage CC31 ligase (SEQ ID NO:23) was able to ligate modified oligonucleotide segments with a phosphorothioate backbone, 2' MOE ribose sugar modifications and 5-methylated pyrimidine bases, reactions were performed using the oligonucleotide segments shown in table 15. Reactions were performed in the presence of Mg$^{2+}$ and Mn$^{2+}$ ions.

10.2 Materials

Oligonucleotides were chemically synthesised using standard methods as shown below:

TABLE 17

| Name | Sequence |
|---|---|
| 5'-segment 2'-MOE PS | 5'-mG*mG*mC*mC*mA*dA*dA-3' |
| centre segment PS | 5'-(p)*dC*dC*dT*dC*dG*dG -3' |
| 3'-segment 2'-MOE PS | 5'-(p)*dC*dT*mU*mA*mC*mC*mU-3' |
| Biotinylated template | 5'-biotin dT dT dT dA dG dG dT dA dA dG dC dC dG dA dG dG dT dT dT dG dG dC dC-3' (SEQ ID NO: 2) |

(p)* = 5'-phosphorothioate, * = phosphorothioate linkage, mX = MOE bases, dX = DNA bases all segments and product have 5-methyl pyrimidines (with the exception of the template)
mT and m (Me)U are considered to be equivalent N.B. the target 2'MOE PS molecule produced by ligation of the segments in table 17, when hybridised to the biotinylated template shown in table 17, is: 5'-mG*mG*mC*mC* mA*dA*dA*dC*dC*dT*dC*dG* dG*dC*dT*mU*mA*mC*mC*mU-3' (SEQ ID NO:1)

Purified mutant Enterobacteria phage CC31 ligase (SEQ ID NO:23) was prepared as described in example 5.1. HPLC analysis was carried out.

10.3 Oligonucleotide Assembly and Ligation Method with Enterobacteria Phage CC31 Ligase Variant (SEQ ID NO:23)

Reactions were prepared as follows:

MgCl$_2$ Reaction

| | |
|---|---|
| 10 × T4 DNA ligase buffer (NEB)* | 5 µl |
| template | 20 µM final concentration |
| 5' segment 2' MOE PS | 20 µM final concentration |
| centre segment PS | 20 µM final concentration |
| 3' segment 2' MOE PS | 20 µM final concentration |
| ligase (24.3 µM) | 10 µl |
| water | made up to 50 µL |

*1 × buffer contains 50 mM Tris-HCl, 10 mM MgCl$_2$, 1 mM ATP, 10 mM DTT, pH 7.5

MnCl$_2$ Reaction

| | |
|---|---|
| 10 × ligase buffer* | 5 µl |
| ATP (10 mM) | 5 µl |
| MnCl$_2$ (50 mM) | 5 µl |
| template | 20 µM final concentration |
| 5' segment 2' MOE PS | 20 µM final concentration |
| centre segment PS | 20 µM final concentration |
| 3' segment 2' MOE PS | 20 µM final concentration |
| ligase (24.3 µM) | 10 µl |
| water | made up to 50 µL |

*1 × buffer contains 50 mM Tris-HCl, 10 mM DTT, pH 7.5

The final reactions contained 20 µM of each segment and template, 5 mM MgCl$_2$ or 5 mM MnCl$_2$, 1 mM ATP, 50 mM Tris-HCl, 10 mM DTT, pH 7.5 and 4.9 µM ligase. Additional reactions were prepared containing no enzyme and served as a negative control. Reactions were incubated for 16 hours at 25° C. and then quenched by heating to 95° C. for 5 minutes. Precipitated proteins were cleared by centrifugation and samples were analysed by HPLC.

10.4 Results and Conclusion

Product, template and segment oligonucleotides were clearly resolved in the control chromatogram and no ligation was observed. Ligase reactions performed in the presence of 5 mM MgCl$_2$ led to the formation of an intermediate product formed from the ligation of the 5' segment and centre segments, but no full-length product was detected. Ligase reactions performed in the presence of MnCl$_2$ produced both full length product and intermediate (5' segment plus centre segment intermediate). Both ligase reactions showed that unligated oligonucleotide segments remained. However, optimisation of the protocol is possible in order to maximise product yield.

Example 11: Assembly and Ligation of Three Segments (7-6-7) to Form a Gapmer Wherein the 5' and the 3' Segments Comprise 2' MOE Ribose Sugar Modifications and all Linkages are Phosphorothioate Linkages, Using Wild-Type *Chlorella* Virus DNA Ligase in the Presence of Native Mg$^{2+}$ 11.1 Materials In order to determine whether *Chlorella* virus DNA ligase (SEQ ID NO:29, commercially available as SplintR ligase, NEB) was able to ligate modified oligonucleotide segments with a phosphorothioate backbone, 2' MOE ribose sugar modifications and 5-methylated pyrimidine bases reactions were performed using the oligonucleotide segments shown in example 10.2 table 17. Reactions were performed at 25° C., 30° C. and 37° C. to investigate the effect of temperature on the enzyme activity.

11.2 Oligonucleotide Assembly and Ligation Method with Commercial *Chlorella* Virus DNA Ligase (SEQ ID NO:29)

Each Oligonucleotide segment and template were dissolved in nuclease free water as detailed below:

| | |
|---|---|
| Biotinylated template | 249.6 ng/µl |
| 5' segment 2' MOE PS | 182.0 ng/µl |
| Centre segment PS | 534.0 ng/µl |
| 3' segment 2' MOE PS | 531.0 ng/µl |

Reactions were prepared as follows:

| | |
|---|---|
| 10× buffer (NEB)* | 6 µl |
| template | 3.8 µl |
| 5' segment 2' MOE PS | 18.1 µl |
| centre segment PS | 4.8 µl |
| 3' segment 2' MOE PS | 6.3 µl |
| water | 15 µl |
| SplintR ligase (25 U/µl) | 6 µl |

*1× buffer contains 50 mM Tris-HCl, 10 mM MgCl$_2$, 1 mM ATP, 10 mM DTT, pH 7.5

The final reactions contained 20 µM of each segment and template, 50 mM Tris-HCl, 10 mM MgCl$_2$, 1 mM ATP, 10 mM DTT, pH 7.5 and 2.5 U/µl ligase. Reactions were incubated at 25° C., 30° C. and 37° C. Additional reactions were prepared containing no enzyme and served as a negative control. Following 16 hours incubation, reactions were quenched by heating to 95° C. for 10 minutes. Precipitated proteins were cleared by centrifugation and samples were analysed by HPLC.

11.3 Results and Conclusion

Product, template and segment oligonucleotides were clearly resolved in the control chromatogram and no ligation was observed. HPLC analysis of the ligase reactions showed that unligated oligonucleotide segments remained, but *Chlorella* virus DNA ligase was able to successfully ligate the segments. The activity of the ligase increased with increasing temperature. At 25° C. the *Chlorella* virus DNA ligase was able to successfully ligate the 5' segment and centre segment but no full-length product was observed. At 30° C. and 37° C., full length product was detected in addition to the intermediate formed from 5' segment and centre segment.

Example 12: Screening a Panel of 15 ATP and NAD Ligases for Activity Towards the Ligation of Three Segments (7-6-7) to Form a Gapmer Wherein the 5' and the 3' Segments Comprise 2' MOE Ribose Sugar Modifications and all Linkages are Phosphorothioate Linkages 12.1 Materials Wild-type ATP and NAD dependent ligases described in table 18 and 19 were each fused at the N-terminus to a CBD. Genes were synthesised, cloned into pET28a and expressed in *E. coli* BL21(DE3) using standard cloning, expression and extraction methods.

TABLE 18

| ATP dependent Ligases | | |
|---|---|---|
| Name | Origin | SEQ ID |
| M1I5D1_Pbcv | Paramecium bursaria Chlorella virus NE-JV-4 | SEQ ID NO: 48 |
| M1I998_Pbcv | Paramecium bursaria Chlorella virus NYs1 | SEQ ID NO: 49 |
| M1HX09_Pbcv | Paramecium bursaria Chlorella virus NE-JV-09 | SEQ ID NO: 50 |
| M1HULO_Atcv | Acanthocystis turfacea Chlorella virus Canal-1 | SEQ ID NO: 51 |
| M1HRK1_Atcv | Acanthocystis turfacea Chlorella virus Br0604L | SEQ ID NO: 52 |
| M1I273_Atcv | Acanthocystis turfacea Chlorella virus NE-JV-2 | SEQ ID NO: 53 |
| M1I600_Atcv | Acanthocystis turfacea Chlorella virus TN603.4.2 | SEQ ID NO: 54 |
| M1H4A4_Atcv | Acanthocystis turfacea Chlorella virus GM0701.1 | SEQ ID NO: 55 |
| F5B464_Sphage | Synechococcus phage S-CRM01 | SEQ ID NO: 56 |
| A0A0F9M1S3 | marine sediment metagenome - uncharacterized protein | SEQ ID NO: 57 |

TABLE 19

| NAD dependent ligases | | |
|---|---|---|
| Name | Origin | SEQ ID |
| MtNAD | Mycobacterium tuberculosis (strain ATCC 25618/H37Rv) | SEQ ID NO: 58 |
| EfNAD | Enterococcus faecalis (strain ATCC 700802/V583) | SEQ ID NO: 59 |
| HiNAD | Haemophilus influenzae (strain ATCC 51907/DSM 11121/ KW20/Rd) | SEQ ID NO: 60 |

TABLE 19-continued

| NAD dependent ligases | | |
| --- | --- | --- |
| Name | Origin | SEQ ID |
| SaNAD | *Staphylococcus aureus* | SEQ ID NO: 61 |
| SpNAD | *Streptococcus pneumoniae* (strain P1031) | SEQ ID NO: 62 |

CBD-Ligase fusions were bound to PERLOZA™ beads as described in 1.4 with the following modifications. CBD-ligase fusion proteins were grown from a single colony of BL21(DE3) cells (NEB) and grown in a 50 mL expression culture. The cells were harvested by centrifugation, resuspended in 5-10 mL Tris-HCl (50 mM, pH 7.5) and lysed by sonication. The lysate was cleared by centrifugation and 1 mL of PERLOZA™ 100 (PERLOZA™) beads (50% slurry, pre-equilibrated with 50 mM Tris-HCl pH 7.5) was added to the supernatant which was shaken at 20° C. for 1 hour. The PERLOZA™ cellulose beads were then collected and washed with 30 ml buffer (50 mM Tris pH 8.0, 200 mM NaCl, 0.1% Tween 20, 10% Glycerol) followed by 10 ml Tris-HCl (50 mM, pH 7.5) and were finally re-suspended in 1 mL Tris-HCl (50 mM, pH 7.5). In order to analyse protein expression, 20 µl of the PERLOZA™ bead slurry was mixed with 20 µl of SDS loading buffer and incubated at 95° C. for 5 minutes before being run on a SDS PAGE gradient gel (4-20%) according to a standard protocol.

12.2 2' MOE and Phosphorothioate Modified Oligonucleotide Assembly and Ligation Method Modified oligonucleotide segments with a phosphorothioate backbone, 2' MOE ribose sugar modifications and 5-methylated pyrimidine bases shown in example 10.2 table 17 were used. Each oligonucleotide segment and template was dissolved in nuclease free water as detailed below:

| | |
| --- | --- |
| Biotinylated template | 1500 ng/µl |
| 5' segment 2' MOE PS | 1008 ng/µl |
| Centre segment PS | 725 ng/µl |
| 3' segment 2' MOE PS | 1112 ng/µl |

ATP Assay mix was prepared as follows:

| | |
| --- | --- |
| template | 85.6 µl |
| 5' segment 2' MOE PS | 43.5 µl |
| centre segment PS | 46.8 µl |
| 3' segment 2' MOE PS | 40.1 µl |
| DTT 1M | 8 µl |
| MgCL2 1M | 4 µl |
| ATP (50 mM) | 16 µl |
| Tris 0.5M | 80 µl |
| water | 476 µl |

NAD Assay mix was prepared as follows:

| | |
| --- | --- |
| template | 85.6 µl |
| 5' segment 2' MOE PS | 43.5 µl |
| centre segment PS | 46.8 µl |
| 3' segment 2' MOE PS | 40.1 µl |
| DTT 1M | 8 µl |
| MgCL2 1M | 4 µl |
| NAD (50 mM) | 1.6 µl |
| Tris 0.5M | 80 µl |
| water | 490.4 µl |

Each immobilized protein (40 µl, 50% PERLOZA™ bead slurry) was pipetted into a PCR tube. The beads were pelleted by centrifugation and the supernatant was removed by pipetting. Assay mix (40 µl) was added to each reaction (The final reactions contained 20 µM of each segment and template, 50 mM Tris-HCl, 10 mM MgCl₂, 1 mM ATP or 100 µM NAD, 10 mM DTT, pH 7.5, and 40 µl of ligase on PERLOZA™ beads). A reaction containing no protein served as a negative control. Reactions were incubated for 18 hours at 30° C. and then quenched by heating to 95° C. for 10 minutes. Precipitated proteins were cleared by centrifugation and samples were analysed by HPLC.

12.3 Results and Conclusion

The product, template and segment oligonucleotides were clearly resolved in the control chromatogram and no ligation was observed. HPLC analysis of the ligase reactions showed that all proteins catalyzed the successful ligation of the 5' segment and centre segment to form an intermediate product, but only some ligases catalyzed the ligation of all three segments to yield the full-length product as described in table 20. The NAD dependent ligase from *Staphylococcus aureus* (SaNAD, SEQ ID NO:61) yielded the most full length product. Optimisation to improve product yield is possible and within the skilled person's skill set.

TABLE 20

| Gene name | SED ID NO | Conversion (%)* | |
| --- | --- | --- | --- |
| | | intermediate | product |
| M1I5D1_Pbcv | 48 | 5.0 | 0.8 |
| M1I998_Pbcv | 49 | 5.1 | 0.0 |
| M1HX09_Pbcv | 50 | 14.4 | 6.6 |
| M1HULO_Atcv | 51 | 9.5 | 2.0 |
| M1HRK1_Atcv | 52 | 2.8 | 9.4 |
| M1I273_Atcv | 53 | 12.0 | 6.4 |
| M1I600_Atcv | 54 | 8.8 | 5.1 |
| M1H4A4_Atcv | 55 | 2.1 | 0.0 |
| F5B464_Sphage | 56 | 2.1 | 0.0 |
| A0A0F9M1S3_ms_metagenome | 57 | 1.4 | 0.0 |
| MtNAD | 58 | 7.1 | 0.0 |
| EfNAD | 59 | 19.1 | 0.0 |
| HiNAD | 60 | 0.3 | 0.0 |
| SaNAD | 61 | 10.5 | 11.8 |
| SpNAD | 62 | 19.0 | 0.0 |

*Conversion was calculated from the HPLC peak area relative to the template which is not consumed in the reaction and serves as an internal standard. Conversion = product area/(template + product area)*100

Example 13: Semi-Continuous Ligation Reaction 13.1 Materials

A mutant *Staphylococcus aureus* ligase (NAD-14) fused at the N-terminal to a CBD was produced using standard cloning, expression and extraction methods. CBD-NAD-14 mutant ligase was then bound to PERLOZA™ beads: 50 ml of protein lysate was added to 7.5 ml PERLOZA™ beads, incubated at room temperature for 1 hour and then the beads were collected in a glass column (BioRad Econo-Column 10 cm length, 2.5 cm diameter #7372512). The beads were washed with 200 ml Buffer Y (50 mM Tris8, 500 mM NaCl, 0.1% Tween 20, 10% Glycerol), then with 200 ml Buffer Z (50 mM Tris8, 200 mM NaCl, 0.1% Tween 20, 10% Glycerol) and 200 ml PBS. The estimated concentration of mutant NAD-14 ligase on the beads was 69 µM of ligase per ml of beads.

The following template DNA oligonucleotide and segment oligonucleotides (table 21) were synthesized by standard solid phase methods.

TABLE 21

| Segment | Sequence | MW | % HPLC purity |
|---|---|---|---|
| Template 3 | 5' TTTGGTGCGAAGCAGACTGA GGC-3' (SEQ ID NO: 30) | | |
| centre segment | 5'-(p)dTdCdTdGdCdT-3' | 1865.4 | 97.5 |
| MOE 3'-segment | 5'-(p)dTdCmGmCmAmCmC-3' | 2546.7 | 98.0 |
| MOE 5'-segment | 5'-mGmCmCmYmCdAdG-3' | 2492.7 | 98.3 |

Figure 11:
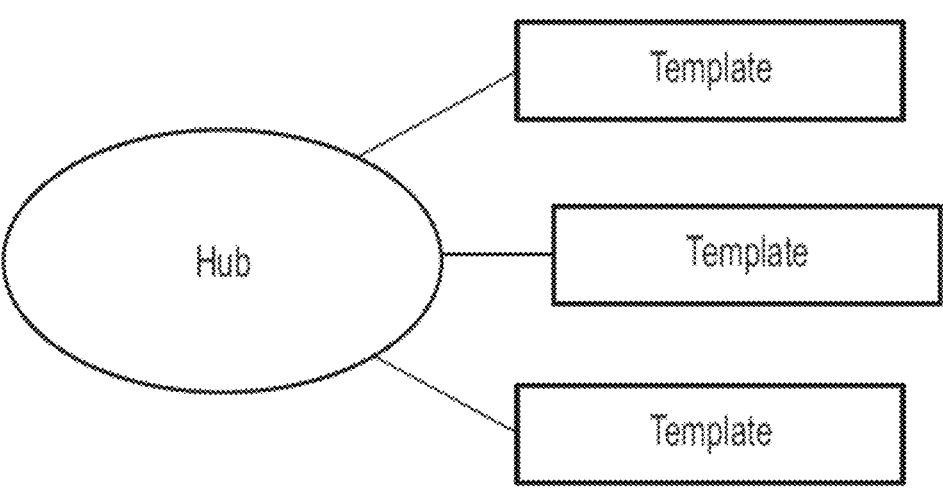
FIG. 11 Schematic of the "tri-template hub" used in Example 13, comprising a support material referred to as the "hub" and three template sequences.

(p) = phosphate, mX = MOE bases, dX = DNA bases
all 5-methyl pyrimidines
all linkages are phosphodiester linkages A "tri-template hub" (approximately 24 kDa) comprising a support material referred to as the "hub" and three template sequences, was produced (FIG. 11). Each copy of the template was covalently attached, at its own individual attachment point, to the "hub". The "tri-template hub" molecule has a higher molecular weight than the target (product) oligonucleotide (100% complementary to the template sequence), thereby allowing it to be retained when the impurities and products are separated from the reaction mixture. It should be noted that in this particular case the template sequence was SEQ ID NO:30 and three copies were attached to the hub. In the following example, a tri-template hub is also produced, but with a different template sequence. Accordingly, as the template sequence varies between examples, so too does the tri-template hub.

The following reaction mix (total volume 5 ml) was prepared:

| | | |
|---|---|---|
| 250 µl | 1M KH₂PO₄, pH 7.5 | (50 mM final) |
| 108 µl | 0.07011M centre segment | (1.5 mM final) |
| 137 µl | 0.05481M 3'-segment | (1.5 mM final) |
| 168 µl | 0.04461M 5'-segment | (1.5 mM final) |
| 750 µl | 0.00387M Hub (Template) | (0.55 mM final) |
| 350 µl | 50 mM NAD⁺ | (3.5 mM final) |
| 1000 µl | 50 mM MgCl₂ | (10 mM final) |
| 2237 µl | Nuclease free H₂O | |

13.2 Methods

Figure 12:
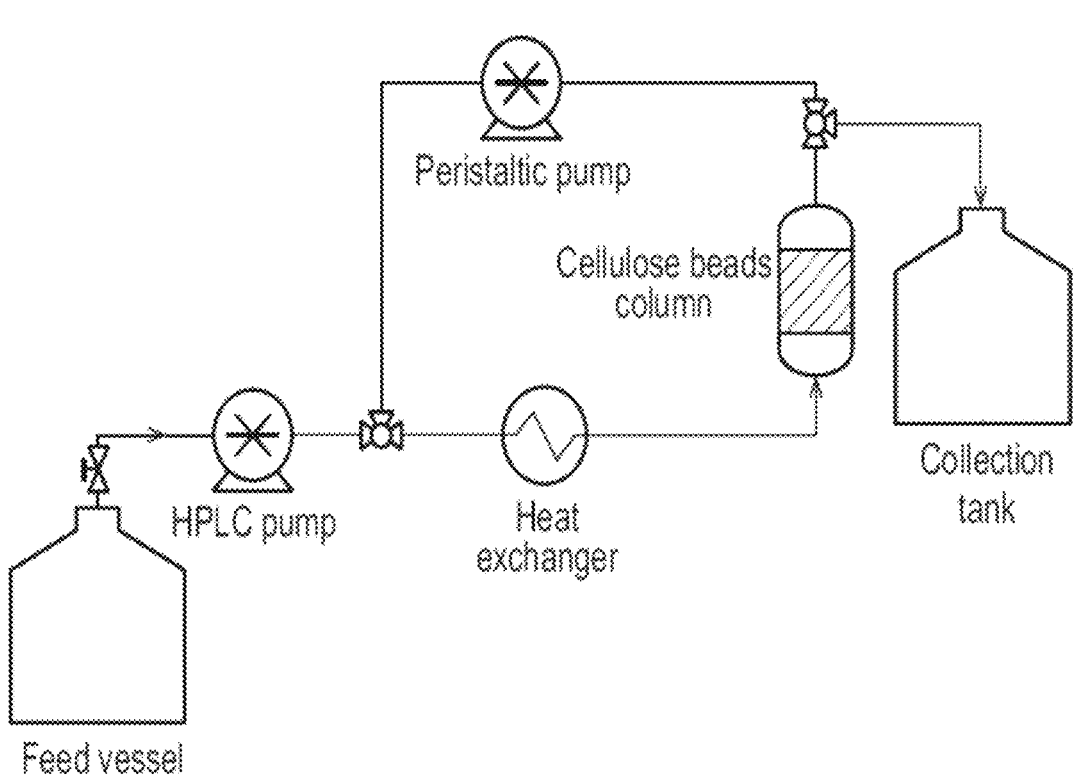
FIG. 12 Schematic of the semi-continuous ligation rig used in Example 13.

A semi-continuous system was set up as shown in FIG. 12.

4 ml of PERLOZA™ beads and immobilised mutant NAD-14 ligase were packed into a Pharmacia XK16 column (B). A water bath and peristaltic pump (C) was used to keep the temperature of the column, using the column water compartment, at 30° C. The beads were equilibrated by running 120 ml (30×column volume) of buffer containing 50 mM KH₂PO₄ at pH7.5 for 120 minutes at 1 ml/min. An AKTA explorer pump A1 (A) was used to create the flow through the Pharmacia XK16 column.

Following column equilibration, the 5 ml reaction mix (mixed well by vortexing) was loaded onto the column, collected in the reservoir tube (D) and recirculated through the column using the AKTA explorer A1 pump. The reaction mix was recirculated through the system at a flow rate of 1 ml/min in continuous circulation mode for 16 hours. Samples were collected after 30 minutes, 60 minutes, 90 minutes, 4 hours, 5 hours, 6 hours, 7 hours, 14 hours and 16 hours for HPLC analysis.

13.3 Results and Conclusions

TABLE 22

| Sample | 5'-segment (%) | Centre segment (%) | 3'-segment (%) | 5' + centre intermediate (%) | Product (%) |
|---|---|---|---|---|---|
| 30 min | 7.80 | 11.00 | 24.00 | 39.40 | 4.40 |
| 60 min | 3.30 | 4.50 | 18.80 | 41.50 | 18.90 |
| 90 min | 2.10 | 2.80 | 15.10 | 33.80 | 34.40 |
| 4 hr | 1.80 | 2.40 | 9.60 | 19.20 | 56.80 |
| 5 hr | 1.72 | 2.40 | 8.30 | 15.70 | 61.50 |
| 6 hr | 1.69 | 2.50 | 8.60 | 15.90 | 69.40 |
| 7 hr | 1.70 | 2.40 | 8.30 | 14.80 | 70.90 |
| 14 hr | 2.00 | 2.70 | 1.60 | 5.40 | 88.10 |
| 16 hr | 0.80 | 1.90 | 1.70 | 3.30 | 89.50 |

The percentage of each segment, intermediate and product is expressed as fractional peak area relative to the tri-template hub peak area.

In conclusion, the semi-continuous flow reaction worked and after 16 hours the reaction was almost complete.

Example 14: Separating Oligonucleotides of Different Sizes by Filtration: a) Separation of a 20-Mer Oligonucleotide (SEQ ID NO:1) and a Hub Comprising Three Non-Complementary 20-Mer Oligonucleotides (SEQ ID NO:30); (b) Separation of a 20-Mer Oligonucleotide (SEQ ID NO:1) from Segment 6-Mer and 8-Mer Oligonucleotides (See Table 1) and a Hub Comprising Three Complementary 20-Mer Oligonucleotides (SEQ ID NO:2)

14.1 Materials

All oligonucleotides used were synthesized by standard solid phase methods.

A tri-template hub, as described in 13.1 (FIG. 11), was used.

A variety of filters of varying molecular weight cut-offs and from different manufacturers were used as shown in tables 23 and 24.

14.2 Methods 14.2.1 Dead-End Filtration Set-Up and Protocol for Screening of Polymeric Membranes: (Protocol 1)

Figure 13:
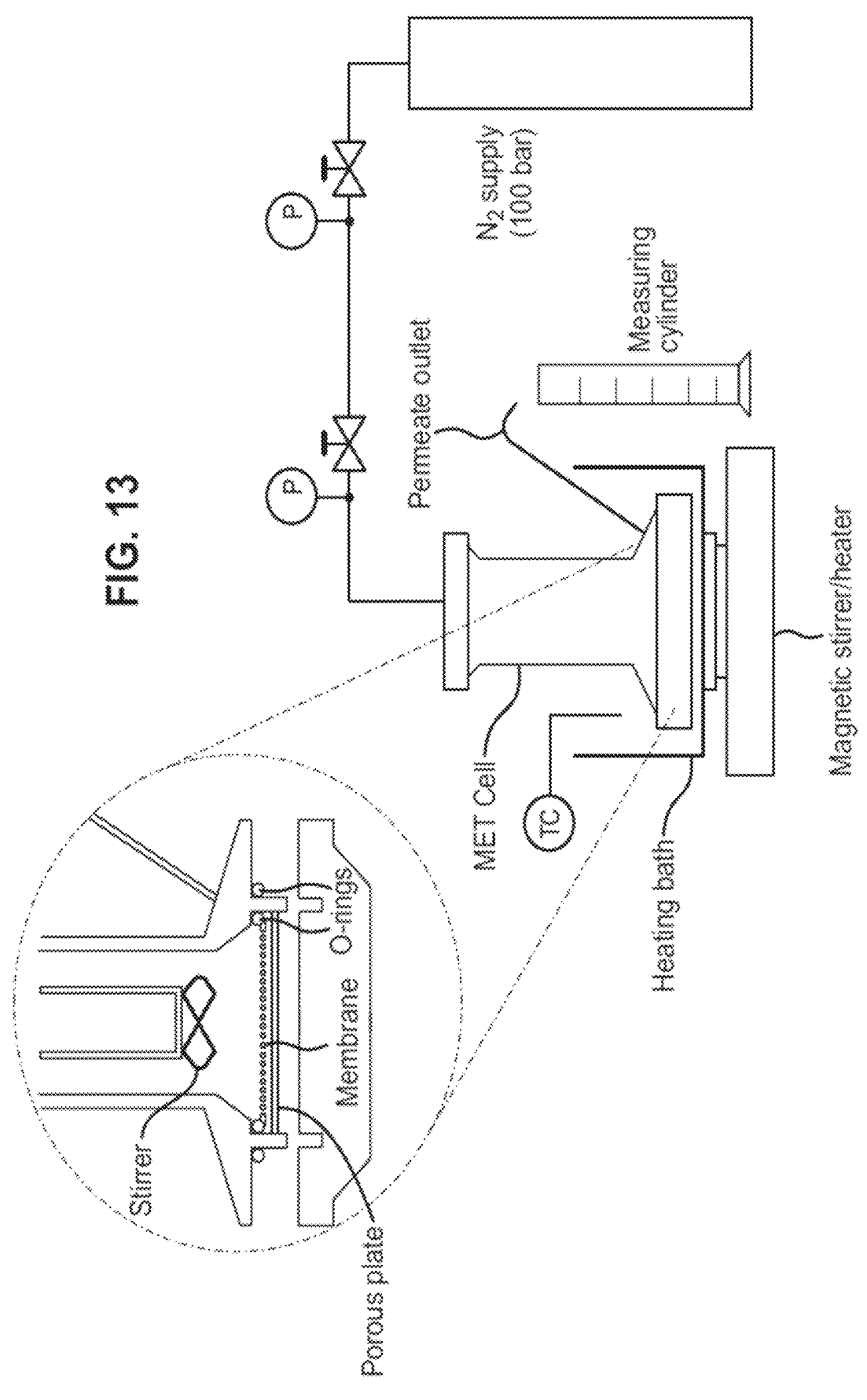
FIG. 13 Schematic of the dead-end filtration rig used in Example 14.

A dead-end filtration rig was set-up as shown in FIG. 13 comprising a MET dead-end filtration cell placed in a water bath sitting on a magnetic stirrer and hotplate. Pressure inside the cell was provided from a flow of nitrogen.

The coupon of membrane (14 cm²) to be tested was first cut to the appropriate size and placed in the cell. The membrane was first conditioned with HPLC grade water (200 ml) and then with PBS buffer (200 ml). The cell was then depressurised, the remaining PBS solution was removed and replaced by a solution containing oligonucleotides (40 ml of oligonucleotides in PBS at a 1 g/L concentration). The cell was placed on a hot stirrer plate and the solution was heated to the desired temperature while being stirred using magnetic agitation. Pressure was applied to the cell (aiming for approximately 3.0 bar; the actual pressure was recorded in each case). Stirring of the solution was either stopped or continued and permeate solution was collected (approximately 20 ml) and analysed by HPLC. Flux was recorded. The system was then depressurised to allow sampling and analysis by HPLC of the retentate solution. More PBS buffer (20 ml) was then added to the filtration cell and the previous procedure was repeated 3 times. The membrane was finally washed with PBS buffer.

All samples were analysed by HPLC without any dilution.

14.2.2 Cross-Flow Filtration Set-Up and Protocol for Screening of Polymeric Membranes: (Protocol 2)

Figure 14:
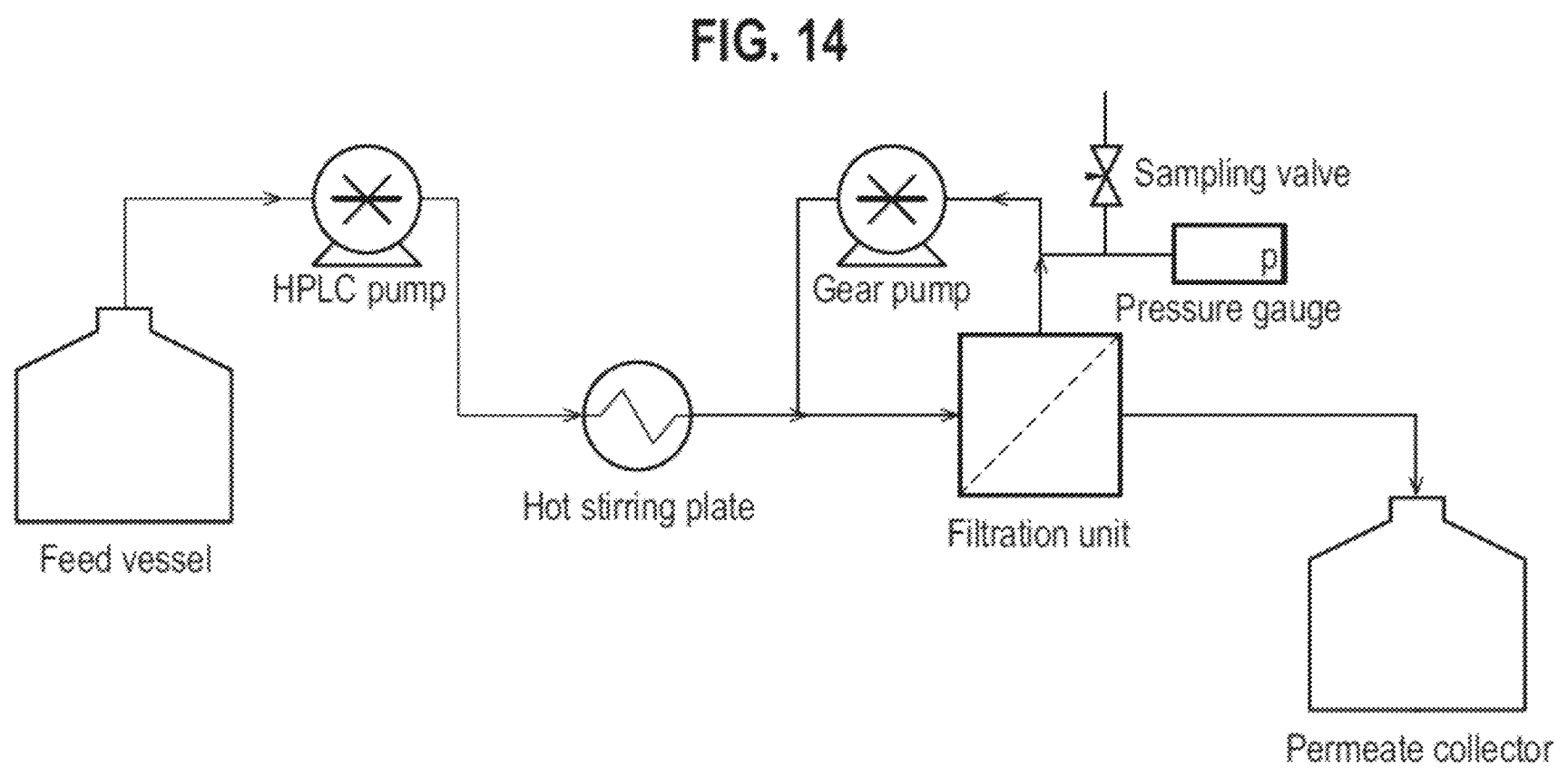

A cross-flow filtration rig was set-up as shown in FIG. 14. The feed vessel (1) consisting of a conical flask contained the oligonucleotide solution to be purified. The solution was pumped to a cross-flow filtration cell (4) using an HPLC pump (2) while temperature within the cell was maintained using a hot plate (3). The solution within the cell was recirculated using a gear pump (6). A pressure gauge (5) enabled the pressure to be read during the experiment. Samples of the retentate solution were taken from the sampling valve (7) while the permeate solution was sampled from the permeate collection vessel (8).

The coupon of membrane to be tested was first cut to the appropriate size and placed in the cell. The system was washed with a PBS solution (100 ml). Temperature of the In the case of the experiment using the Snyder membrane having a 5 kDa molecular weight cut off (lot number 120915R2) and SEQ ID NO:46 and SEQ ID NO:30 the above methodology was modified as follows. The coupon of membrane to be tested was first cut to the appropriate size and placed in the cell. The system was washed with a Potassium phosphate solution (100 ml, 50 mM, pH 7.5). Temperature of the solution was adjusted to the desired set point. A solution containing oligonucleotide products in potassium phosphate (approximately 1 g/L) was added to ethylenediaminetetraacetic acid (EDTA) (230 μL of a 500 mM solution). The solution was then fed into the system. Potassium phosphate buffer was then pumped into the system using the HPLC pump at a flow rate matching the flow rate of the permeate solution (typically 4 ml/min). Pressure was recorded using the pressure gauge. The retentate solution was sampled for HPLC analysis every 5 diafiltration volumes. The permeate solution was sampled for HPLC analysis every diafiltration volume. The experiment was stopped after 15 diafiltration volumes 14.3 Results

TABLE 23

| results for the dead-end filtration experiments following protocol 1 (14.2.1) | | | | | | | |
|---|---|---|---|---|---|---|---|
| | | | | | | Rejection (%) | |
| Stirring (Yes or No) | Membrane | MWCO (kDa) | Lot number | SEQ ID NO | Temp. (° C.) | Product | Tri-template hub |
| Yes | NADIR | 10 | 226162 | 1 and 30 | 60 | 38 | 96 |
| Yes | NADIR | 10 | 226162 | 1 and 2 | 60 | 90 | 98 |
| | | | | | 80 | 40 | 43 |
| Yes | NADIR | 10 | 226162 | 1 and 2 | 60 | 83 | 92 |
| | | | | | 65 | 77 | 84 |
| | | | | | 70 | 38 | 41 |
| | | | | | 75 | 12 | 20 |
| Yes | NADIR | 5 | 226825 | 1 and 2 | 60 | 97 | 95 |
| | | | | | 65 | 99 | 93 |
| | | | | | 70 | 97 | 92 |
| | | | | | 75 | 90 | 95 |
| No | NADIR | 5 | 226825 | 1 and 2 | 75 | 66 | 96 |
| No | NADIR | 10 | 226162 | 1 and 2 | 75 | 80 | 80 |
| No | Snyder | 5 | 120915R2 | 1 and 2 | 75 | 97 | 98 |
| No | Osmonics | 5 | 622806PT | 1 and 2 | 75 | 99 | 98 |
| No | Osmonics | 10 | 622806PW | 1 and 2 | 75 | 86 | 95 |

MWCO = molecular weight cut-off

55 solution was adjusted to the desired set point. A solution containing oligonucleotide products in PBS (7.5 ml at 1 g/L) was fed into the system. PBS solution was then pumped into the system using the HPLC pump at a flow rate matching the flow rate of the permeate solution (typically 3 ml/min). Pressure was recorded using the pressure gauge. The retentate solution was sampled for HPLC analysis every 5 diafiltration volumes. The permeate solution was sampled for HPLC analysis every diafiltration volume. The experiment was stopped after 20 diafiltration volumes.

Figure 15A:
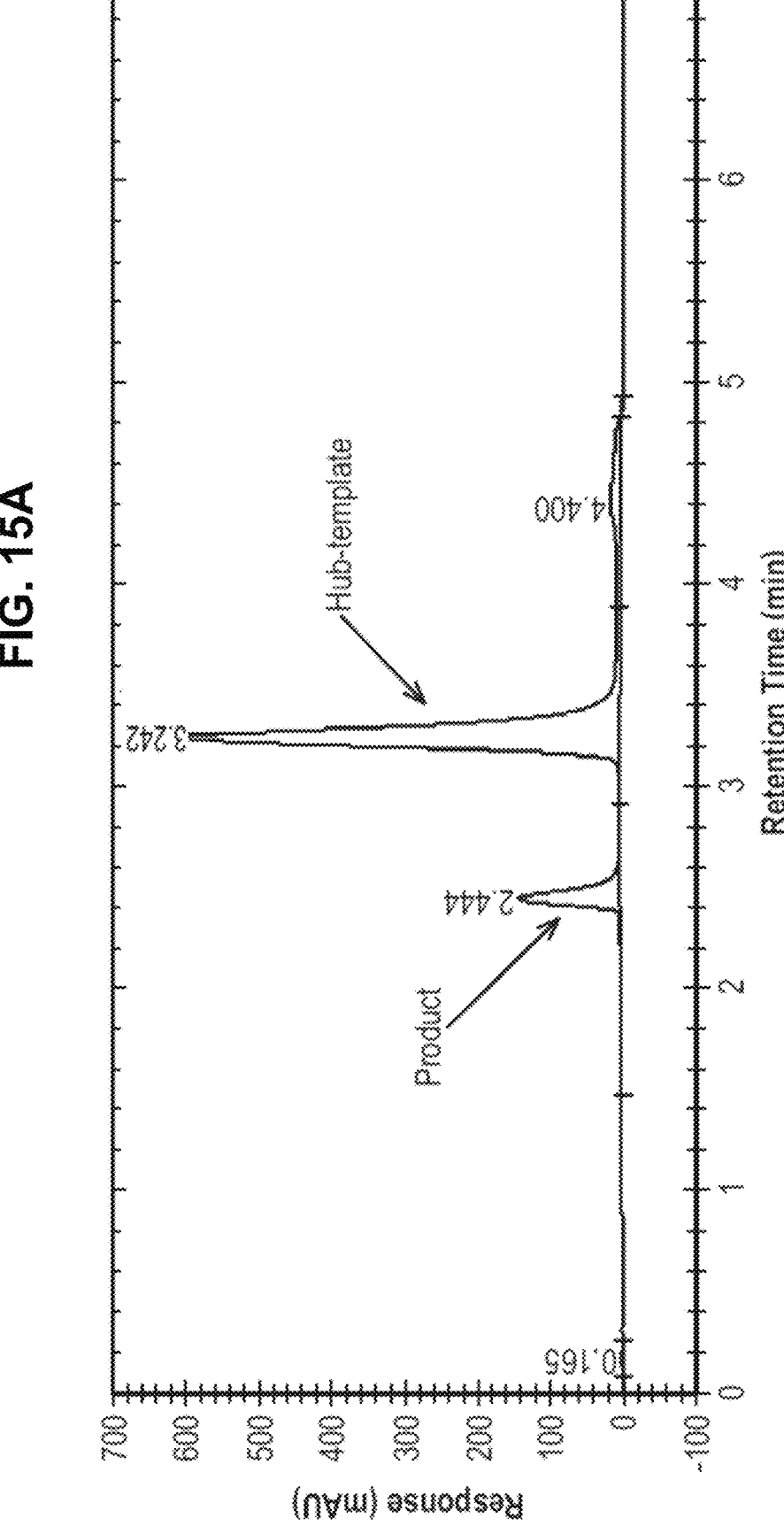
FIGS. 15a-15b Chromatograms showing the results from the dead-end filtration experiments using the 10 kDa MWCO NADIR membrane at 60° C. in Example 14.
Figure 15B:
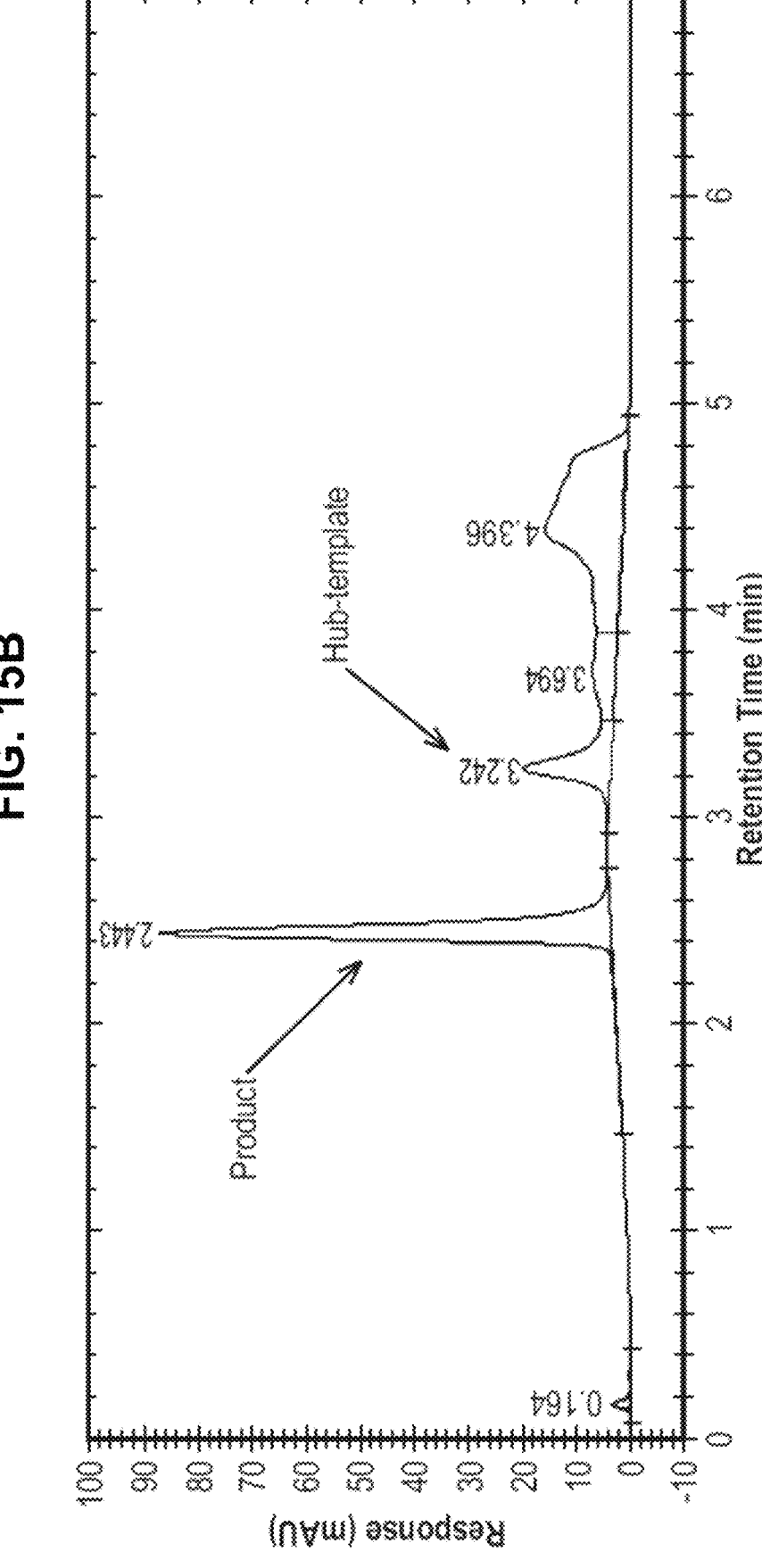

In the experiment using the 10 kDa MWCO NADIR membrane at 60° C., clear separation between the product sequence (SEQ ID NO:1) and the non-complementary tri-template hub (comprising SEQ ID NO:30) was demonstrated. FIG. 15a shows a chromatogram of the retentate solution, which remained in the filtration cell and contained mainly tri-template hub, after two diafiltration volumes; and FIG. 15b shows a chromatogram of the permeate, solution enriched in the product, after two diafiltration volumes.

TABLE 24

| | | | | | | | | Rejection (%) | | | | |
|---|---|---|---|---|---|---|---|---|---|---|---|---|
| | | | | | | | | | | | | Tri-template |
| Membrane | MWCO (kDa) | Lot number | SEQ ID NO | Temp. (° C.) | Pressure | Diafiltration volume | Segment 1 | Segment 2 | Segment 3 | Product | hub |
| Osmonics | 10 | 622806PW | 1 and 2 | 75 | 3.1 | 0 | N/A | N/A | N/A | 100 | 88 |
| | | | | | | 5 | N/A | N/A | N/A | 64 | 88 |
| | | | | | | 10 | N/A | N/A | N/A | 40 | 82 |
| | | | | | | 15 | N/A | N/A | N/A | 12 | 74 |
| Snyder | 5 | 120915R2 | 1 and 2 | 75 | 3.1 | 0 | N/A | N/A | N/A | 100 | 100 |
| | | | | 82 | | 5 | N/A | N/A | N/A | 88 | 100 |
| | | | | 75 | | 10 | N/A | N/A | N/A | 98 | 100 |
| | | | | 75 | | 15 | N/A | N/A | N/A | 98 | 100 |
| | | | | 75 | | 20 | N/A | N/A | N/A | 96 | 100 |
| Snyder | 5 | 120915R2 | 1 and 2 | 85 | 3.1 | 0 | N/A | N/A | N/A | 99 | 99 |
| | | | | | | 5 | N/A | N/A | N/A | 63 | 99 |
| | | | | | | 10 | N/A | N/A | N/A | 79 | 99 |
| | | | | | | 15 | N/A | N/A | N/A | 100 | 98 |
| | | | | | | 20 | N/A | N/A | N/A | 100 | 99 |
| Snyder | 5 | 120915R2 | 1 and 2+ segments from table 1 | 50 | 3.0 | 0 | 100 | 100 | 100 | 100 | 100 |
| | | | | | | 5 | 39 | 39 | 40 | 100 | 100 |
| | | | | | | 10 | 82 | 86 | 86 | 100 | 100 |
| | | | | | | 15 | 77 | 81 | 79 | 100 | 100 |
| | | | | | | 20 | * | * | * | 100 | 100 |
| Snyder | 5 | 120915R2 | 1 and 2 | 80 | 3.1 | 0 | N/A | N/A | N/A | 96 | 100 |
| | | | | | | 5 | N/A | N/A | N/A | 22 | 96 |
| | | | | | | 10 | N/A | N/A | N/A | 10 | 100 |
| | | | | | | 20 | N/A | N/A | N/A | 38 | 100 |
| Snyder | 5 | 120915R2 | 46 and 30 | 80 | 3.4 | 0 | N/A | N/A | N/A | 98 | 100 |
| | | | | | | 5 | N/A | N/A | N/A | 83 | 100 |
| | | | | | | 10 | N/A | N/A | N/A | 68 | 100 |
| | | | | | | 15 | N/A | N/A | N/A | 72 | 100 |

Figure 16A:
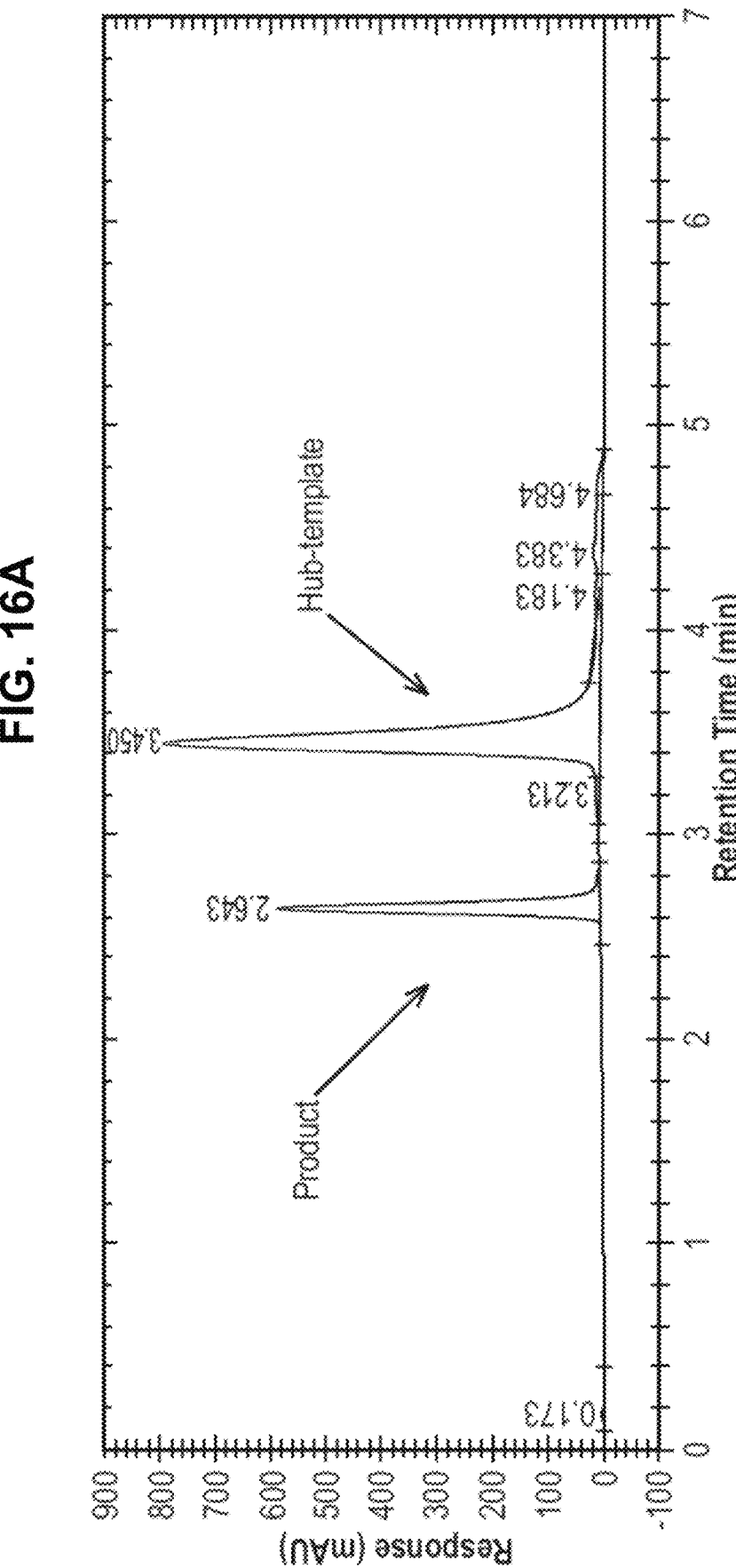
FIGS. 16a-16b Chromatograms showing the results from the cross-flow filtration experiments using the 5 kDa MWCO Snyder membrane at 50° C. and 3.0 bar pressure, in Example 14.
Figure 16B:
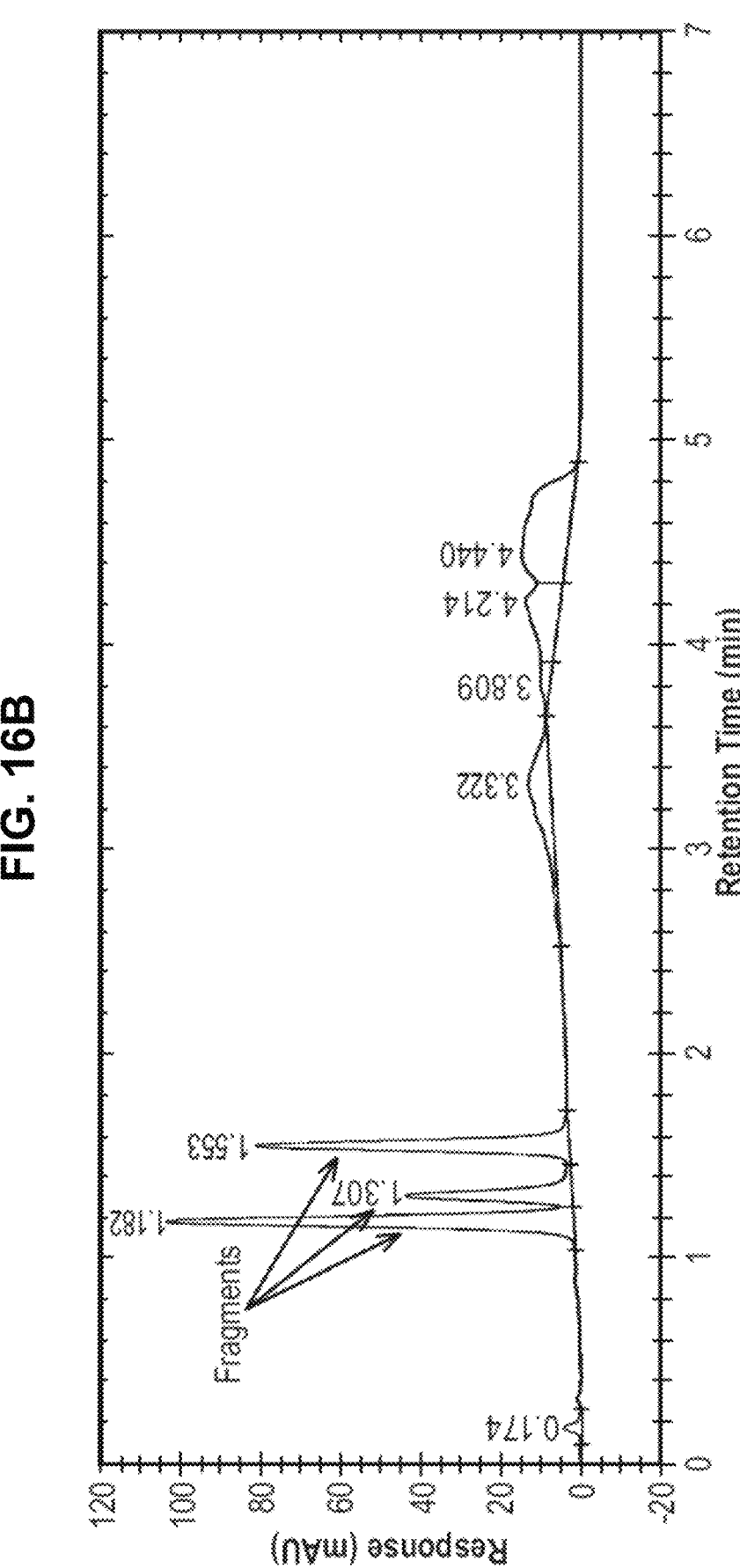

MWCO = molecular weight cut-off
* concentration of solutes too low preventing meaningful analysis In the experiment using the 5 kDa MWCO Snyder membrane at 50° C. and 3.0 bar pressure, clear separation between the segment sequences (see table 1) and the complementary tri-template hub (comprising SEQ ID NO:2) and product (SEQ ID NO:1) was demonstrated. FIG. 16*a* shows a chromatogram of the retentate solution, which contained mainly tri-template hub and product, after 20 diafiltration volumes; and FIG. 16*b* shows a chromatogram of the permeate, which contained mainly segment oligonucleotides, after 20 diafiltration volumes.

Figure 17A:
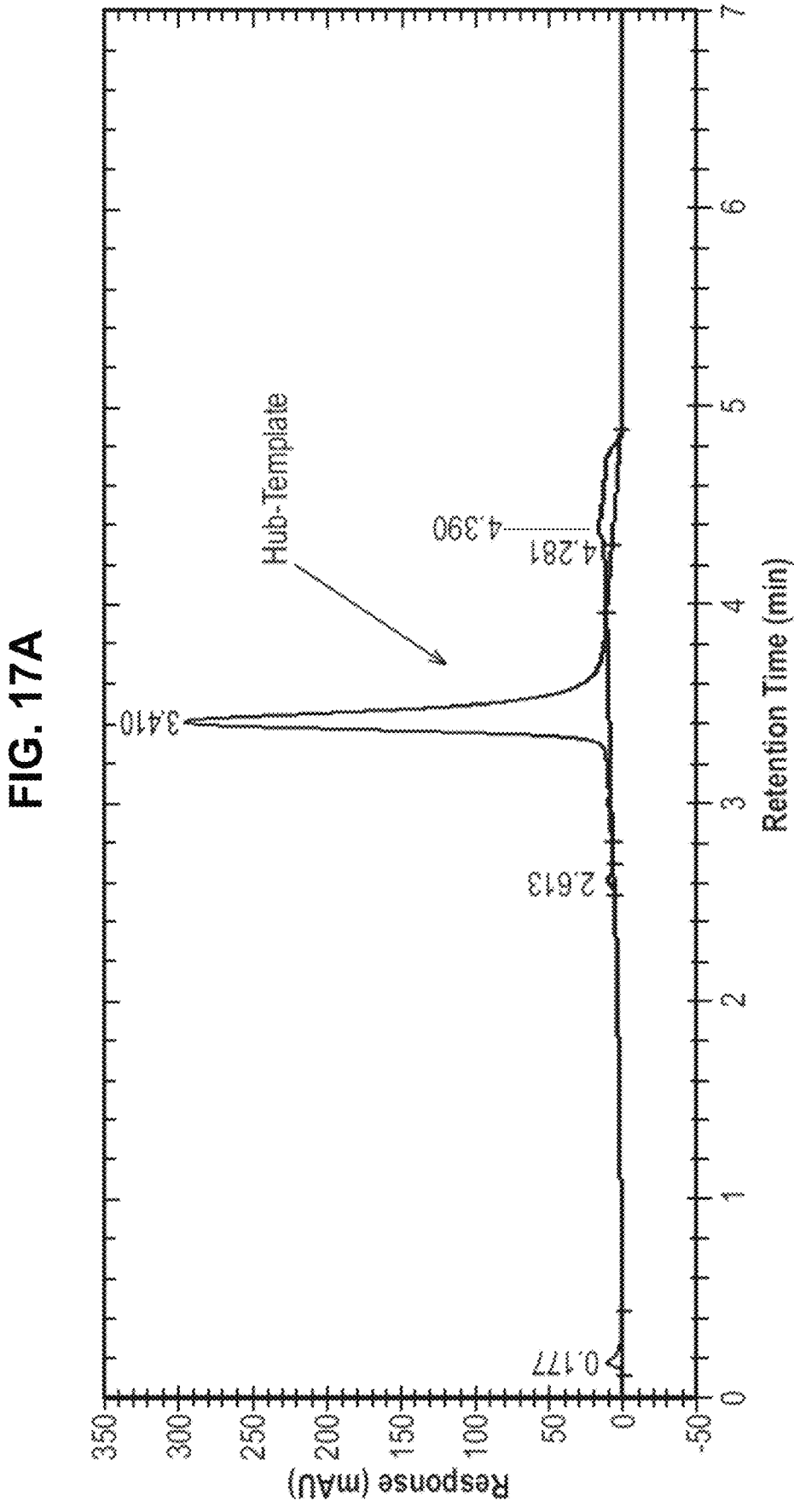
FIGS. 17a-17b Chromatograms showing the results from the cross-flow filtration experiments using the 5 kDa MWCO Snyder membrane at 80° C. and 3.1 bar pressure, in Example 14.
Figure 17B:
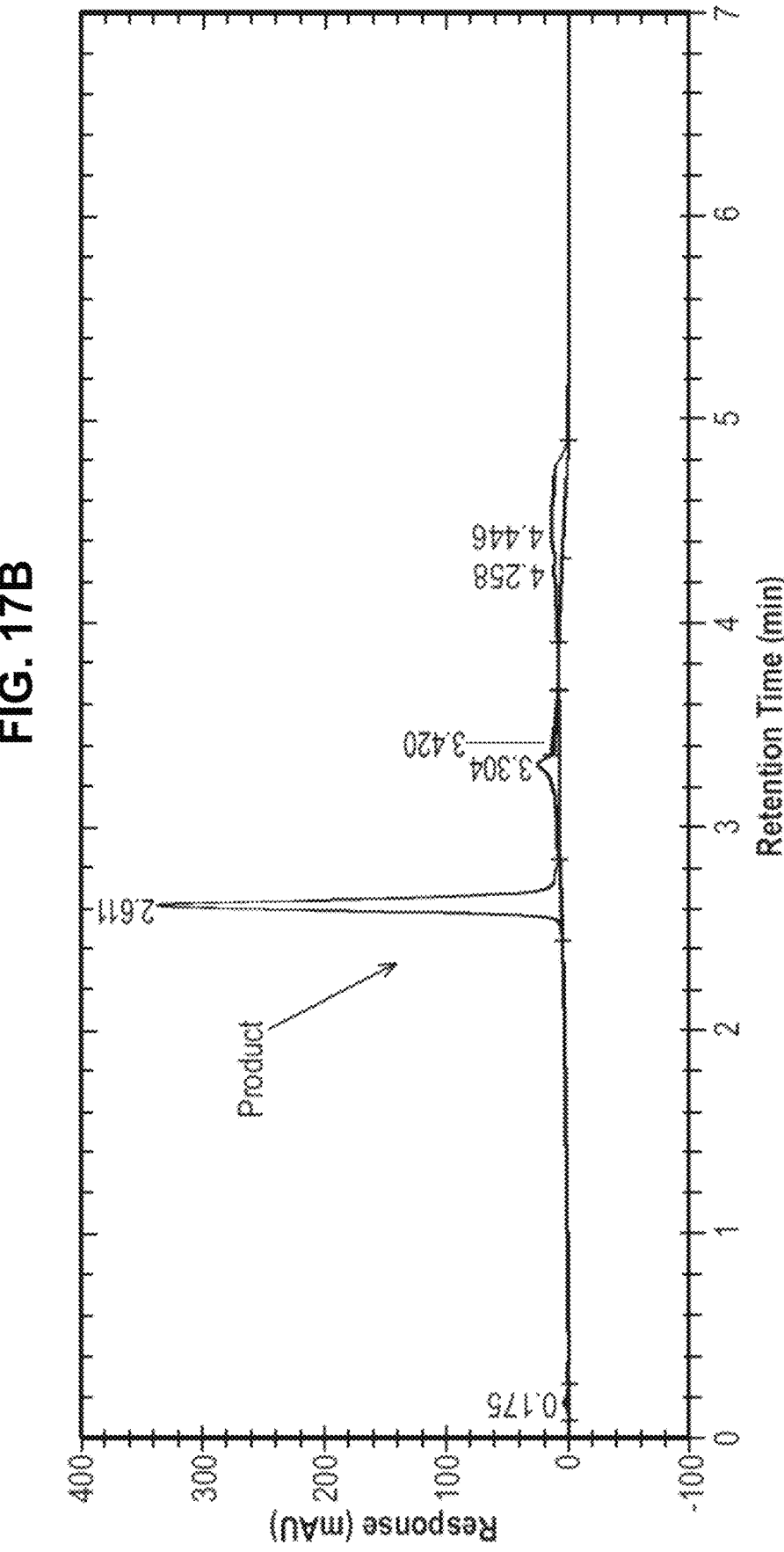

In the experiment using the 5 kDa MWCO Snyder membrane at 80° C. and 3.1 bar pressure, clear separation between the complementary tri-template hub (comprising SEQ ID NO:2) and product (SEQ ID NO:1) was demonstrated. FIG. 17*a* shows a chromatogram of the retentate solution, which contained tri-template hub only, after 20 diafiltration volumes; and FIG. 17*b* shows a chromatogram of the permeate solution, which contained the product only, after 2 diafiltration volumes.

14.4 Conclusions

Oligonucleotides of different lengths and molecular weights can be separated using filtration. As shown above, the type of membrane and the conditions, such as temperature, affect the level of separation. For a given set of oligonucleotides of different lengths/molecular weights, suitable membranes and conditions can be selected to allow the required separation. For example, we have demonstrated that segment oligonucleotides (shortmers of 6 and 8 nucleotides in length), as outlined in table 1, can be separated from the product oligonucleotide (20-mer oligonucleotide having SEQ ID NO:1) and tri-template hub (comprising 3×20-mer of SEQ ID NO:2 attached to a solid support), and the product oligonucleotide and tri-template hub can, in turn, be separated from each other.

Example 15: 3' Extension by Single Base Ligation for Oligonucleotide Synthesis with 2'-OMe Base Modification and Phosphate Linkages Wild-type ssLigases (SEQ ID NO:63 to 83) were each fused at the N-terminus to a histidine tag consisting of 6×His. Genes were synthesised, cloned into pET28a and protein encoding the gene produced in *E. coli* BL21(DE3) Star using standard cloning, expression and extraction methods.

Proteins were purified using Ni-NTA using standard methods and used directly.

Reactions were set up as per table 25 below, with addition of ligase last. Reactions were incubated at 25° C. for 20 hours. Reactions were then quenched by heating to 95° C. for 15 min, centrifuged at 4000×g for 15 min and 10 μL of supernatant transferred to an HPLC vial. Reactions were then analysed by HPLC for the presence of SEQ ID NO:85.

TABLE 25

| | Final concentration in reaction (mM) | Volume per reaction (μL) |
|---|---|---|
| Primer: (2'-OMe) - SEQ ID NO: 84 | 0.125 | 2.5 |
| Monomer: Adenosine-3,5-bisphosphate (2'OMe pAp) | 1 | 2 |
| Adenosine triphosphate trisodium (ATP) | 0.25 | 0.5 |
| Magnesium Chloride (MgCl₂) | 10 | 0.2 |
| Ligase - SEQ ID NO: 63 to 83 | | 5 |
| Buffer (20 mM Tris, 30 mM NaCl at pH 8) | | 9.8 |
| Final reaction volume: | | 20 |

TABLE 26

Results from reactions:

| Gene name | SED ID NO | Conversion (%) to product* |
|---|---|---|
| Enterobacteria phage T4 RNA ligase 1 - 'Rnl1' | 63 | 23.9 |
| Enterobacteria phage T4 RNA ligase 2 - 'Rnl2' | 64 | 12.1 |
| Aeromonas virus Aeh1 ligase - 'RNA3' | 65 | 15.7 |
| Klebsiella phage JD18 ligase - 'RNA6' | 66 | 25.5 |
| Stenotrophomonas phage IME13 ligase - 'RNA8' | 67 | 29.9 |
| Escherichia phage JSE ligase - 'RNA9' | 68 | 16.7 |
| Acinetobacter phage Acj61 ligase - 'RNA16' | 69 | 18.0 |
| Vibrio phage VH7D ligase - 'RNA20' | 70 | 14.4 |
| Escherichia phage JS98 ligase - 'RNA22' | 71 | 23.9 |
| Escherichia phage vB_EcoM_112 ligase - 'RNA23' | 72 | 24.7 |
| Aeromonas phage CC2 ligase - 'RNA28' | 73 | 19.3 |
| Enterobacteria phage RB69 ligase - 'RNA29' | 74 | 19.1 |
| Acinetobacter phage Ac42 ligase - 'RNA31 | 75 | 24.2 |

Example 16: 3' Extension by Single Base Ligation for Oligonucleotide Synthesis with 2'-OMe Base Modification and Phosphorothioate Linkages Wild-type ssLigases (SEQ ID NO:63 to 83) were each fused at the N-terminus to a histidine tag consisting of 6×His. Genes were synthesised, cloned into pET28a and protein encoding the gene produced in *E. coli* BL21(DE3) Star using standard cloning, expression and extraction methods. Proteins were purified using Ni-NTA using standard methods and used directly.

Reactions were set up as per table 27 below, with addition of ligase last. Reactions were incubated at 25° C. for 20 hours. Reactions were then quenched by heating to 95° C. for 15 min, centrifuged at 4000×g for 15 min and 10 μL of supernatant transferred to an HPLC vial. Reactions were then analysed by HPLC for the presence of SEQ ID NO:85.

TABLE 27

| | Final concentration in reaction (mM) | Volume per reaction (L) |
|---|---|---|
| Primer: (2'-OMe) - SEQ ID NO: 84 | 0.125 | 2.5 |
| Monomer: Adenosine-3-phosphate-5-thiophosphate (2'OMe psAp) | 1 | 2 |
| Adenosine triphosphate trisodium (ATP) | 0.25 | 0.5 |
| Magnesium Chloride (MgCl₂) | 10 | 0.2 |
| Ligase - SEQ ID NO: 63 to 83 | | 5 |
| Buffer (20 mM Tris, 30 mM NaCl at pH 8) | | 9.8 |
| Final reaction volume: | | 20 |

TABLE 26-continued

Results from reactions:

| Gene name | SED ID NO | Conversion (%) to product* |
|---|---|---|
| Pectobacterium phage CBB ligase - 'RNA33' | 76 | 0.0 |
| Aeromonas phage phiAS5 ligase - 'RNA35 | 77 | 22.4 |
| Salmonella phage vB_SenMS16 ligase - 'RNA36 | 78 | 22.0 |
| Vibrio phage KVP40 ligase - 'RNA39' | 79 | 20.2 |
| Campylobacter virus CP220 ligase - 'RNA49' | 80 | 10.4 |
| Pseudomonas phage phiPMW ligase - 'RNA59' | 81 | 2.2 |
| Pseudomonas phage vB_PaeM_C2-10_Ab1 ligase - 'RNA61' | 82 | 3.4 |
| Butyrivibrio proteoclasticus ligase - 'RNA82' | 83 | 2.3 |

*Conversion (%) to product - % area of Primer N peak vs. Product N + 1(pi) peak at wavelength 258 nm

TABLE 28

Results from reactions:

| Gene name | SED ID NO | Conversion (%) to product* |
|---|---|---|
| Enterobacteria phage T4 RNA ligase 1 - 'Rnl1' | 63 | 0 |
| Enterobacteria phage T4 RNA ligase 2 - 'Rnl2' | 64 | 0 |
| Aeromonas virus Aeh1 ligase - 'RNA3' | 65 | 0 |
| Klebsiella phage JD18 ligase - 'RNA6' | 66 | 0.8 |
| Stenotrophomonas phage IME13 ligase - 'RNA8' | 67 | 2.8 |
| Escherichia phage JSE ligase - 'RNA9' | 68 | 1.5 |
| Acinetobacter phage Acj61 ligase - 'RNA16' | 69 | 0 |
| Vibrio phage VH7D ligase - 'RNA20' | 70 | 0 |
| Escherichia phage JS98 ligase - 'RNA22' | 71 | 0 |
| Escherichia phage vB_EcoM_112 ligase - 'RNA23' | 72 | 0 |
| Aeromonas phage CC2 ligase - 'RNA28' | 73 | 0 |
| Enterobacteria phage RB69 ligase - 'RNA29' | 74 | 0 |
| Acinetobacter phage Ac42 ligase - 'RNA31 | 75 | 1.2 |
| Pectobacterium phage CBB ligase - 'RNA33' | 76 | 0 |
| Aeromonas phage phiAS5 ligase - 'RNA35 | 77 | 0 |

TABLE 28-continued

| | | SED ID NO | Conversion (%) to product* |
|---|---|---|---|
| Gene name | | | |
| *Salmonella* phage vB__SenMS16 ligase - 'RNA36 | | 78 | 0 |
| Vibrio phage KVP40 ligase - 'RNA39' | | 79 | 0 |
| Campylobacter virus CP220 ligase - 'RNA49' | | 80 | 0 |
| Pseudomonas phage phiPMW ligase - 'RNA59' | | 81 | 0 |
| Pseudomonas phage vB__PaeM__C2-10__Ab1 ligase - 'RNA61' | | 82 | 0 |
| Butyrivibrio proteoclasticus ligase - 'RNA82' | | 83 | 0 |

*Conversion (%) to product - % area of Primer N peak vs. Product N + 1(pi) peak at wavelength 258 nm

Example 17: 3' Extension by Single Base Ligation for Oligonucleotide Synthesis with 2'MOE Base Modification and Phosphorothioate Linkages Wild-type ssLigases (SEQ ID NO:63 to 83) were each fused at the N-terminus to a histidine tag consisting of 6×His. Genes were synthesised, cloned into pET28a and protein encoding the gene produced in *E. coli* BL21(DE3) Star using standard cloning, expression and extraction methods. Proteins were purified using Ni-NTA using standard methods and used directly.

Reactions were set up as per table 29 below, with addition of ligase last. Reactions were incubated at 25° C. for 20 hours. Reactions were then quenched by heating to 95° C. for 15 min, centrifuged at 4000×g for 15 min and 10 μL of supernatant transferred to an HPLC vial. Reactions were then analysed by HPLC for the presence of SEQ ID NO:87.

TABLE 29

| | Final concentration in reaction (mM) | Volume per reaction (μl) |
|---|---|---|
| Primer: (2-'MOE) - SEQ ID NO: 86 | 0.125 | 2.5 |
| Monomer: Adenosine-3-phosphate-5-thiophosphate (2'MOE psAp) | 1 | 2 |
| Adenosine triphosphate trisodium (ATP) | 0.25 | 0.5 |
| Magnesium Chloride (MgCl₂) | 10 | 0.2 |
| Ligase - SEQ ID NO: 63 to 83 | | 5 |
| Buffer (20 mM Tris, 30 mM NaCl at pH 8) | | 9.8 |
| Final reaction volume: | | 20 |

TABLE 30

Results from reactions:

| Gene name | SED ID NO | Conversion (%) to product* |
|---|---|---|
| Enterobacteria phage T4 RNA ligase 1 - 'Rnl1' | 63 | 0 |
| Enterobacteria phage T4 RNA ligase 2 - 'Rnl2' | 64 | 0 |
| Aeromonas virus Aeh1 ligase - 'RNA3' | 65 | 0 |
| Klebsiella phage JD18 ligase - 'RNA6' | 66 | 0 |
| Stenotrophomonas phage IME13 ligase - 'RNA8' | 67 | 0.4 |
| *Escherichia* phage JSE ligase - 'RNA9' | 68 | 0 |
| Acinetobacter phage Acj61 ligase - 'RNA16' | 69 | 0 |
| Vibrio phage VH7D ligase - 'RNA20' | 70 | 0 |
| *Escherichia* phage JS98 ligase - 'RNA22' | 71 | 0 |
| *Escherichia* phage vB__EcoM__112 ligase - 'RNA23' | 72 | 0 |
| Aeromonas phage CC2 ligase - 'RNA28' | 73 | 0 |
| Enterobacteria phage RB69 ligase - 'RNA29' | 74 | 0 |
| Acinetobacter phage Ac42 ligase - 'RNA31 | 75 | 0.2 |
| Pectobacterium phage CBB ligase - 'RNA33' | 76 | 0 |

TABLE 30-continued

Results from reactions:

| Gene name | SED ID NO | Conversion (%) to product* |
|---|---|---|
| Aeromonas phage phiAS5 ligase - 'RNA35 | 77 | 0 |
| *Salmonella* phage vB__SenMS16 ligase - 'RNA36 | 78 | 0 |
| Vibrio phage KVP40 ligase - 'RNA39' | 79 | 0 |
| Campylobacter virus CP220 ligase - 'RNA49' | 80 | 0 |
| Pseudomonas phage phiPMW ligase - 'RNA59' | 81 | 0 |
| Pseudomonas phage vB__PaeM__C2-10__Ab1 ligase 'RNA61' | 82 | 0.5 |
| Butyrivibrio proteoclasticus ligase - 'RNA82' | 83 | 0 |

*Conversion (%) to product - % area of Primer N peak vs. Product N + 1(pi) peak at wavelength 258 nm

Example 18: 3' Extension by Single Base Ligation for Oligonucleotide Synthesis with 2'H Base Modification and Phosphate Linkages Wild-type ssLigases (SEQ ID NO:63 to 83) were each fused at the N-terminus to a histidine tag consisting of 6×His. Genes were synthesised, cloned into pET28a and protein encoding the gene produced in *E. coli* BL21(DE3) Star using standard cloning, expression and extraction methods. Proteins were purified using Ni-NTA using standard methods and used directly.

Reactions were set up as per table 31 below, with addition of ligase last. Reactions were incubated at 25° C. for 20 hours. Reactions were then quenched by heating to 95° C. for 15 min, centrifuged at 4000×g for 15 min and 10 μL of supernatant transferred to an HPLC vial. Reactions were then analysed by HPLC for the presence of SEQ ID NO:87. to 35

TABLE 31

| | Final concentration in reaction (mM) | Volume per reaction (μL) |
|---|---|---|
| Primer: (2'H) - SEQ ID NO: 86 | 0.125 | 2.5 |
| Monomer: Adenosine-3-phosphate-5-thiophosphate (2'MOE psAp) | 1 | 2 |
| Adenosine triphosphate trisodium (ATP) | 0.25 | 0.5 |
| Magnesium Chloride (MgCl₂) | 10 | 0.2 |
| Ligase - SEQ ID NO: 63 to 83 | | 5 |
| Buffer (20 mM Tris, 30 mM NaCl at pH 8) | | 9.8 |
| Final reaction volume: | | 20 |

TABLE 32

Results from reactions:

| Gene name | SED ID NO | Conversion (%) to product* |
|---|---|---|
| Enterobacteria phage T4 RNA ligase 1 - 'Rnl1' | 63 | 6.3 |
| Enterobacteria phage T4 RNA ligase 2 - 'Rnl2' | 64 | 0 |
| Aeromonas virus Aeh1 ligase - 'RNA3' | 65 | 0 |
| Klebsiella phage JD18 ligase - 'RNA6' | 66 | 2.3 |
| Stenotrophomonas phage IME13 ligase - 'RNA8' | 67 | 5.1 |
| *Escherichia* phage JSE ligase - 'RNA9' | 68 | 1.1 |
| Acinetobacter phage Acj61 ligase - 'RNA16' | 69 | 0 |
| Vibrio phage VH7D ligase - 'RNA20' | 70 | 0 |
| *Escherichia* phage JS98 ligase - 'RNA22' | 71 | 0 |
| *Escherichia* phage vB_EcoM_112 ligase - 'RNA23' | 72 | 0 |
| Aeromonas phage CC2 ligase - 'RNA28' | 73 | 2.3 |
| Enterobacteria phage RB69 ligase - 'RNA29' | 74 | 0 |
| Acinetobacter phage Ac42 ligase - 'RNA31 | 75 | 0 |
| Pectobacterium phage CBB ligase - 'RNA33' | 76 | 2.2 |
| Aeromonas phage phiAS5 ligase - 'RNA35 | 77 | 0 |
| *Salmonella* phage vB_SenMS16 ligase - 'RNA36 | 78 | 0 |
| Vibrio phage KVP40 ligase - 'RNA39' | 79 | 0 |
| Campylobacter virus CP220 ligase - 'RNA49' | 80 | 0 |
| Pseudomonas phage phiPMW ligase - 'RNA59' | 81 | 0 |
| Pseudomonas phage vB_PaeM_C2-10_Ab1 ligase - 'RNA61' | 82 | 1.3 |
| Butyrivibrio proteoclasticus ligase - 'RNA82' | 83 | 0 |

*Conversion (%) to product - % area of Primer N peak vs. Product N + 1(pi) peak at wavelength 258 nm

Example 19: 3' Extension by Single Base Ligation for Oligonucleotide Synthesis with 2'MOE Base Modification and Phosphate Linkages Wild-type ssLigases (SEQ ID NO:63 to 83) were each fused at the N-terminus to 6×His. Genes were synthesised, cloned into pET28a and protein encoding the gene produced in *E. coli* BL21(DE3) Star using standard cloning, expression and extraction methods. Proteins were purified using Ni-NTA using standard methods and used directly.

Reactions were set up as per table 33, with addition of ligase last. Reactions were incubated at 25° C. for 20 hours. Reactions were then quenched by heating to 95° C. for 15 min, centrifuged at 4000×g for 15 min and 10 µL of supernatant transferred to an HPLC vial. Reactions were then analysed by HPLC for the presence of SEQ ID NO:87.

TABLE 33

| | Final concentration in reaction (mM) | Volume per reaction (µL) |
|---|---|---|
| Primer: (2'MOE) - SEQ ID NO: 86 | 0.125 | 2.5 |
| Monomer: Adenosine-3,5-bisphosphate (2'MOE pAp) | 1 | 2 |
| Adenosine triphosphate trisodium (ATP) | 0.25 | 0.5 |
| Magnesium Chloride (MgCl₂) | 10 | 0.2 |
| Ligase - SEQ ID NO: 63 to 83 | | 5 |
| Buffer (20 mM Tris, 30 mM NaCl at pH 8) | | 9.8 |
| Final reaction volume: | | 20 |

TABLE 34

Results from reactions:

| Gene name | SEQ ID NO | Conversion (%) to product* |
|---|---|---|
| Enterobacteria phage T4 RNA ligase 1 - 'Rnl1' | 63 | 1.4 |
| Enterobacteria phage T4 RNA ligase 2 - 'Rnl2' | 64 | 0 |
| Aeromonas virus Aeh1 ligase - 'RNA3' | 65 | 0 |
| Klebsiella phage JD18 ligase - 'RNA6' | 66 | 3.9 |
| Stenotrophomonas phage IME13 ligase - 'RNA8' | 67 | 8.8 |
| *Escherichia* phage JSE ligase - 'RNA9' | 68 | 0 |
| Acinetobacter phage Acj61 ligase - 'RNA16' | 69 | 0 |
| Vibrio phage VH7D ligase - 'RNA20' | 70 | 0 |
| *Escherichia* phage JS98 ligase - 'RNA22' | 71 | 0 |
| *Escherichia* phage vB_EcoM_112 ligase - 'RNA23' | 72 | 1.2 |
| Aeromonas phage CC2 ligase - 'RNA28' | 73 | 0 |
| Enterobacteria phage RB69 ligase - 'RNA29' | 74 | 1.1 |
| Acinetobacter phage Ac42 ligase - 'RNA31 | 75 | 4.0 |
| Pectobacterium phage CBB ligase - 'RNA33' | 76 | 0 |
| Aeromonas phage phiAS5 ligase - 'RNA35 | 77 | 0 |
| *Salmonella* phage vB_SenMS16 ligase - 'RNA36 | 78 | 0 |
| Vibrio phage KVP40 ligase - 'RNA39' | 79 | 0 |
| Campylobacter virus CP220 ligase - 'RNA49' | 80 | 0 |
| Pseudomonas phage phiPMW ligase - 'RNA59' | 81 | 0 |
| Pseudomonas phage vB_PaeM_C2-10_Ab1 ligase - 'RNA61' | 82 | 1.3 |
| Butyrivibrio proteoclasticus ligase - 'RNA82' | 83 | 0 |

*Conversion (%) to product - % area of Primer N peak vs. Product N + 1(pi) peak at wavelength 258 nm

Example 20: Optimisation of 3' Extension by Single Base Ligation for Oligonucleotide Synthesis with 2'OMe Base Modification and Phosphate Linkages Wild-type ssLigase (SEQ ID NO:67) was fused at the N-terminus to 6×His. Gene was synthesised, cloned into pET28a and protein encoding the gene produced in *E. coli* BL21(DE3) Star using standard cloning, expression and extraction methods. Protein was purified using Ni-NTA using standard methods and used directly. Protein concentration was determined via microfluidic capillary electrophoresis.

Reactions were set up as per table 35, with addition of ligase last. Reactions were incubated at 25° C. for 18 hours. Reactions were then quenched by heating to 95° C. for 15 min, centrifuged at 4000×g for 15 min and 10 µL of supernatant transferred to an HPLC vial. Reactions were then analysed by HPLC for the presence of SEQ ID NO:85.

TABLE 35

| | Final concentration in reaction (mM) | Volume per reaction (µL) |
|---|---|---|
| Primer: (2'OMe) - SEQ ID NO: 84 | 0.125 | 2.5 |
| Monomer: Adenosine-3,5-bisphosphate (2'OMe pAp) | 1 | 2 |
| Adenosine triphosphate trisodium (ATP) | 0.25 | 0.5 |
| Magnesium Chloride (MgCl₂) | 10 | 0.2 |
| Ligase - SEQ ID NO: 67 | 0.025 | 10 |
| Buffer (20 mM Tris, 30 mM NaCl at pH 8) | | 4.8 |
| Final reaction volume: | | 20 |

TABLE 36

| Results from reaction: | | |
| --- | --- | --- |
| Gene name | SEQ ID NO | Conversion (%) to product* |
| Stenotrophomonas phage IME13 ligase - 'RNA8' | 67 | 66.9 |

*Conversion (%) to product - % area of Primer N peak vs. Product N + 1(pi) peak at wavelength 258 nm

Example 21: Optimisation of 3' Extension by Single Base Ligation for Oligonucleotide Synthesis with 2'MOE Base Modification and Phosphate Linkages Wild-type ssLigase (SEQ ID NO:67) was fused at the N-terminus to 6×His. Gene was synthesised, cloned into pET28a and protein encoding the gene produced in E. coli BL21(DE3) Star using standard cloning, expression and extraction methods. Protein was purified using Ni-NTA using standard methods and used directly. Protein concentration was determined via microfluidic capillary electrophoresis.

Reactions were set up as per table 37, with addition of ligase last. Reactions were incubated at 25° C. for 12 hours. Reactions were then quenched by heating to 95° C. for 15 min, centrifuged at 4000×g for 15 min and 10 μL of supernatant transferred to an HPLC vial. Reactions were then analysed by HPLC for the presence of SEQ ID NO:87.

TABLE 37

| | Final concentration in reaction (mM) | Volume per reaction (μL) |
| --- | --- | --- |
| Primer: (2'MOE) - SEQ ID NO: 86 | 0.125 | 2.5 |
| Monomer: Adenosine-3,5-bisphosphate (2'MOE pAp) | 1 | 2 |
| Adenosine triphosphate trisodium (ATP) | 0.25 | 0.5 |
| Magnesium Chloride (MgCl₂) | 10 | 0.2 |
| Ligase - SEQ ID NO: 67 | 0.025 | 10 |
| Buffer (20 mM Tris, 30 mM NaCl at pH 8) | | 4.8 |
| Final reaction volume: | | 20 |

TABLE 38

| Results from reaction: | | |
| --- | --- | --- |
| Gene name | SEQ ID NO | Conversion (%) to product* |
| Stenotrophomonas phage IME13 ligase - 'RNA8' | 67 | 26.0 |

*Conversion (%) to product - % area of SEQ ID NO: 86 peak vs. SEQ ID NO: 87 peak at wavelength 258 nm

Example 22: Reactions Comparing WT to Mutants—3' Extension by Single Base Ligation for Oligonucleotide Synthesis with 2'MOE Base Modification and Phosphate Linkages Wild-type or Mutant ssLigases (SEQ ID NO:67 and 88 to 92) were each fused at the N-terminus to 6×His. Genes were synthesised, cloned into pET28a and protein encoding the gene produced in E. coli BL21(DE3) Star using standard cloning, expression and extraction methods. Proteins were purified using Ni-NTA using standard methods and used directly. Protein concentration was determined via microfluidic capillary electrophoresis.

Reactions were set up as per table 39, with addition of ligase last. Reactions were incubated at 25° C. for 24 hours. Reactions were then quenched by heating to 70° C. for 30 min, centrifuged at 4000×g for 15 min and 10 μL of supernatant transferred to an HPLC vial. Reactions were then analysed by HPLC for the presence of SEQ ID NO:87.

TABLE 39

| | Final concentration in reaction (mM) | Volume per reaction (μL) |
| --- | --- | --- |
| Primer: (2'MOE) - SEQ ID NO: 86 | 0.1 | 3 |
| Monomer: Adenosine-3,5-bisphosphate (2'MOE pAp) | 1 | 3 |
| Adenosine triphosphate trisodium (ATP) | 0.25 | 0.68 |
| Magnesium Chloride (MgCl₂) | 10 | 0.3 |
| Ligase - SEQ ID NO: 67 or 88 to 92 | 0.01 | 7.5 |
| Buffer (20 mM Tris at pH 8) | | 15.53 |
| Final reaction volume: | | 30 |

TABLE 40

| Results from reactions: | | |
| --- | --- | --- |
| Gene name | SEQ ID NO | Conversion (%) to product* |
| Stenotrophomonas phage IME13 ligase - 'RNA8' | 67 | 18.34 |
| Mutant ligase (Stenotrophomonas phage IME13 backbone) protein sequence | 88 | 74.18 |
| Mutant ligase (Stenotrophomonas phage IME13 backbone) protein sequence | 89 | 72.34 |
| Mutant ligase (Stenotrophomonas phage IME13 backbone) protein sequence | 90 | 75.75 |
| Mutant ligase (Stenotrophomonas phage IME13 backbone) protein sequence | 91 | 73.99 |
| Mutant ligase (Stenotrophomonas phage IME13 backbone) protein sequence | 92 | 55.05 |

*Conversion (%) to product - % area of SEQ ID NO: 86 vs. SEQ ID NO: 87 peak at wavelength 258 nm

Example 23: Reactions Comparing WT to Mutants—3' Extension by Single Base Ligation for Oligonucleotide Synthesis with 2'MOE Base Modification and Phosphorothioate Linkages Wild-type or Mutant ssLigases (SEQ ID NO:67 and 88 to 92) were each fused at the N-terminus to 6×His. Genes were synthesised, cloned into pET28a and protein encoding the gene produced in E. coli BL21(DE3) Star using standard cloning, expression and extraction methods. Proteins were purified using Ni-NTA using standard methods and used directly. Protein concentration was determined via microfluidic capillary electrophoresis.

Reactions were set up as per table 41, with addition of ligase last. Reactions were incubated at 25° C. for 24 hours. Reactions were then quenched by heating to 70° C. for 30 min, centrifuged at 4000×g for 15 min and 10 μL of supernatant transferred to an HPLC vial. Reactions were then analysed by HPLC for the presence of SEQ ID NO:87.

TABLE 41

| | Final concentration in reaction (mM) | Volume per reaction (μL) |
|---|---|---|
| Primer: (2'MOE) - SEQ ID NO: 86 | 0.1 | 3 |
| Monomer: Adenosine-3-phosphate-5-thiophosphate (2'OMe psAp) | 1 | 3 |
| Adenosine triphosphate trisodium (ATP) | 0.25 | 0.68 |
| Magnesium Chloride (MgCl₂) | 10 | 0.3 |
| Ligase - SEQ ID NO: 67 or 88 to 92 | 0.01 | 7.5 |
| Buffer (20 mM Tris at pH 8) | | 15.53 |
| Final reaction volume: | | 30 |

TABLE 42

Results from reactions:

| Gene name | SEQ ID NO | Conversion (%) to product* |
|---|---|---|
| Stenotrophomonas phage IME13 ligase - 'RNA8' | 67 | 0 |
| Mutant ligase (Stenotrophomonas phage IME13 backbone) protein sequence | 88 | 19.81 |
| Mutant ligase (Stenotrophomonas phage IME13 backbone) protein sequence | 89 | 6.05 |
| Mutant ligase (Stenotrophomonas phage IME13 backbone) protein sequence | 90 | 12.56 |
| Mutant ligase (Stenotrophomonas phage IME13 backbone) protein sequence | 91 | 12.44 |
| Mutant ligase (Stenotrophomonas phage IME13 backbone) ligase protein sequence | 92 | 0 |

*Conversion (%) to product - % area of SEQ ID NO: 86 vs. SEQ ID NO: 87 peak at wavelength 258 nm

Example 24: 3' Extension by Single Base Ligation for Oligonucleotide Synthesis with 2'MOE Base Modification and Phosphorothioate Linkages—Adenosine Mutant ssLigase (SEQ ID NO:88) was fused at the N-terminus to 6×His. Gene was synthesised, cloned into pET28a and protein encoding the gene produced in *E. coli* BL21(DE3) Star using standard cloning, expression and extraction methods. Proteins were purified using Ni-NTA using standard methods and used directly. Protein concentration was determined via microfluidic capillary electrophoresis.

Reactions were set up as per table 43, with addition of ligase last. Reactions were incubated at 25° C. for 24 hours. Reactions were then quenched by heating to 70° C. for 30 min, centrifuged at 4000×g for 15 min and 10 μL of supernatant transferred to an HPLC vial. Reactions were then analysed by HPLC and LCMS for the presence of SEQ ID NO:87.

TABLE 43

| | Final concentration in reaction (mM) | Volume per reaction (μL) |
|---|---|---|
| Primer: (2'MOE) - SEQ ID NO: 86 | 0.05 | 10 |
| Monomer: Adenosine-3-phosphate-5-thiophosphate (2'OMe psAp) | 0.5 | 10 |
| Adenosine triphosphate trisodium (ATP) | 2 | 40 |

TABLE 43-continued

| | Final concentration in reaction (mM) | Volume per reaction (μL) |
|---|---|---|
| Magnesium Chloride (MgCl₂) | 10 | 2 |
| Ligase - SEQ ID NO: 88 | 0.01 | 21.7 |
| Buffer (20 mM Tris at pH 8) | | 116.3 |
| Final reaction volume: | | 200 |

TABLE 44

Results from reaction:

| Gene name | SEQ ID NO | Conversion (%) to product* |
|---|---|---|
| Mutant ligase (Stenotrophomonas phage IME13 backbone) protein sequence | 88 | 94.39 |

*Conversion (%) to product - % area of SEQ ID NO: 86 peak vs. SEQ ID NO: 87 peak at wavelength 258 nm

Example 25: 3' Extension by Single Base Ligation for Oligonucleotide Synthesis with 2'MOE Base Modification and Phosphorothioate Linkages—5-Methylcytidine Mutant ssLigase (SEQ ID NO:88) was fused at the N-terminus to 6×His. Gene was synthesised, cloned into pET28a and protein encoding the gene produced in *E. coli* BL21(DE3) Star using standard cloning, expression and extraction methods. Protein was purified using Ni-NTA using standard methods and used directly. Protein concentration was determined via microfluidic capillary electrophoresis.

Reactions were set up as per table 45, with addition of ligase last. Reactions were incubated at 25° C. for 24 hours. Reactions were then quenched by heating to 70° C. for 30 min, centrifuged at 4000×g for 15 min and 10 μL of supernatant transferred to an HPLC vial. Reactions were then analysed by HPLC and LCMS for the presence of SEQ ID NO:93.

TABLE 45

| | Final concentration in reaction (mM) | Volume per reaction (μL) |
|---|---|---|
| Primer: (2'MOE) - SEQ ID NO: 86 | 0.05 | 10 |
| Monomer: 5-Methylcytidine-3-phosphate-5-thiophosphate (2'OMe psCp) | 0.5 | 10 |
| Adenosine triphosphate trisodium (ATP) | 2 | 40 |
| Magnesium Chloride (MgCl₂) | 10 | 2 |
| Ligase - SEQ ID NO: 88 | 0.01 | 21.7 |
| Buffer (20 mM Tris at pH 8) | | 116.3 |
| Final reaction volume: | | 200 |

TABLE 46

| Results from reaction: | | |
|---|---|---|
| Gene name | SEQ ID NO | Conversion (%) to product* |
| Mutant ligase (*Stenotrophomonas phage* IME13 backbone) protein sequence | 88 | 69.27 |

*Conversion (%) to product - % area of SEQ ID NO: 86 peak vs. SEQ ID NO: 93 peak at wavelength 258 nm

Example 26: 3' Extension by Single Base Ligation for Oligonucleotide Synthesis with 2'MOE Base Modification and Phosphorothioate Linkages—Thymidine Mutant ssLigase (SEQ ID NO:88) was fused at the N-terminus to 6×His. Gene was synthesised, cloned into pET28a and protein encoding the gene produced in *E. coli* BL21(DE3) Star using standard cloning, expression and extraction methods. Protein was purified using Ni-NTA using standard methods and used directly. Protein concentration was determined via microfluidic capillary electrophoresis.

Reactions were set up as per table 47, with addition of ligase last. Reactions were incubated at 25° C. for 24 hours. Reactions were then quenched by heating to 70° C. for 30 min, centrifuged at 4000×g for 15 min and 10 µL of supernatant transferred to an HPLC vial. Reactions were then analysed by HPLC and LCMS for the presence of SEQ ID NO:94.

TABLE 47

| | Final concentration in reaction (mM) | Volume per reaction (µL) |
|---|---|---|
| Primer: (2'MOE) - SEQ ID NO: 86 | 0.05 | 10 |
| Monomer: Thymidine-3-phosphate-5-thiophosphate (2'OMe psCp) | 0.5 | 10 |
| Adenosine triphosphate trisodium (ATP) | 2 | 40 |
| Magnesium Chloride (MgCl$_2$) | 10 | 2 |
| Ligase - SEQ ID NO: 88 | 0.01 | 21.7 |
| Buffer (20 mM Tris at pH 8) | | 116.3 |
| Final reaction volume: | | 200 |

TABLE 48

| Results from reaction: | | |
|---|---|---|
| Gene name | SEQ ID NO | Conversion (%) to product* |
| Mutant ligase (*Stenotrophomonas phage* IME13 backbone) protein sequence | 88 | 94.38 |

*Conversion (%) to product - % area of SEQ ID NO: 86 peak vs. SEQ ID NO: 94 peak at wavelength 258 nm

Example 27: 3' Extension by Single Base Ligation for Oligonucleotide Synthesis with 2'MOE Base Modification and Phosphorothioate Linkages, Followed by 3' Dephosphorylation and a Second Single Base Ligation and Second Dephosphorylation—Reaction Sequence Mutant ssLigase (SEQ ID NO:88) and wild-type phosphatase (SEQ ID NO:95) were fused at the N-terminus to 6×His. Genes were synthesised, cloned into pET28a and protein encoding the gene produced in *E. coli* BL21(DE3) Star using standard cloning, expression and extraction methods. Proteins were purified using Ni-NTA using standard methods and used directly. Protein concentration was determined via microfluidic capillary electrophoresis.

First ligation reaction was set up as per table 49, with addition of ligase last. Reactions were incubated at 25° C. for 24 hours. Reactions were then quenched by heating to 70° C. for 30 min, centrifuged at 4000×g for 15 min and 10 µL of supernatant transferred to an HPLC vial. Reactions were then analysed by HPLC and LCMS for the presence of SEQ ID NO:87. The remainder of the reactions were purified by ion-exchange chromatography, lyophilised and used directly in first deprotection (i.e. dephosphorylation).

TABLE 49

| | Final concentration in reaction (mM) | Volume per reaction (µL) |
|---|---|---|
| Primer: (2'MOE) - SEQ ID NO: 86 | 0.05 | 10 |
| Monomer: Adenosine-3-phosphate-5-thiophosphate (2'MOE psAp) | 0.5 | 10 |
| Adenosine triphosphate trisodium (ATP) | 2 | 40 |
| Magnesium Chloride (MgCl$_2$) | 10 | 2 |
| Ligase - SEQ ID NO: 88 | 0.01 | 21.7 |
| Buffer (20 mM Tris at pH 8) | | 116.3 |
| Final reaction volume: | | 200 |

TABLE 50

| Results from first ligation reaction: | | |
|---|---|---|
| Gene name | SEQ ID NO | Conversion (%) to product* |
| Mutant ligase (*Stenotrophomonas phage* IME13 backbone) protein sequence | 88 | 94.99 |

*Conversion (%) to product - % area of SEQ ID NO: 86 peak vs. SEQ ID NO: 87 peak at wavelength 258 nm First deprotection/dephosphorylation reaction was set up as per table 51, with addition of phosphatase last. Reactions were incubated at 37° C. for 24 hours. Reactions were then quenched by heating to 70° C. for 30 min, centrifuged at 4000×g for 15 min and 10 µL of supernatant transferred to an HPLC vial. Reactions were then analysed by HPLC and LCMS for the presence of SEQ ID NO:96. The remainder of the reactions were purified by ion-exchange chromatography, lyophilised and used directly in the second the ligation reaction.

TABLE 51

| | Final concentration in reaction (mM) | Volume per reaction (µL) |
|---|---|---|
| First ligation product: (2'MOE) - SEQ ID NO: 84 | 0.05 | 10 |
| Phosphatase - SEQ ID NO 95 | 0.00036 | 20 |
| Buffer (20 mM Tris at pH 8) | | 170 |
| Final reaction volume: | | 200 |

TABLE 52

Results from first dephosphorylation reaction:

| Gene name | SEQ ID NO | Conversion (%) to product* |
|---|---|---|
| Wild type phosphatase (*Pandalus borealis*) protein sequence - 'SAP' | 95 | 96.44 |

*Conversion (%) to product - % area of SEQ ID NO: 85 peak vs. SEQ ID NO: 96 peak at wavelength 258 nm Second ligation reaction was set up as per table 53, with addition of ligase last. Reactions were incubated at 25° C. for 24 hours. Reactions were then quenched by heating to 70° C. for 30 min, centrifuged at 4000×g for 15 min and 10 μL of supernatant transferred to an HPLC vial. Reactions were then analysed by HPLC and LCMS for the presence of SEQ ID NO:96. The remainder of the reactions were purified by ion-exchange chromatography, lyophilised and used directly in the second deprotection/dephosphorylation reaction.

TABLE 53

| | Final concentration in reaction (mM) | Volume per reaction (μL) |
|---|---|---|
| First deprotection product: (2'MOE) - SEQ ID NO: 96 | 0.05 | 10 |
| Monomer: Adenosine-3-phosphate-5-thiophosphate (2'MOE psAp) | 0.5 | 10 |
| Adenosine triphosphate trisodium (ATP) | 2 | 40 |
| Magnesium Chloride (MgCl$_2$) | 10 | 2 |
| Ligase - SEQ ID NO: 88 | 0.01 | 21.7 |
| Buffer (20 mM Tris at pH 8) | | 116.3 |
| Final reaction volume: | | 200 |

TABLE 54

Results from second ligation reaction:

| Gene name | SEQ ID NO | Conversion (%) to product* |
|---|---|---|
| Mutant ligase (*Stenotrophomonas phage* IME13 backbone) protein sequence | 88 | 91.15 |

*Conversion (%) to product - % area of SEQ ID NO: 97 peak vs. SEQ ID NO: 96 peak at wavelength 258 nm Second deprotection/dephosphorylation reaction was set up as per table 55, with addition of phosphatase last. Reactions were incubated at 37° C. for 24 hours. Reactions were then quenched by heating to 70° C. for 30 min, centrifuged at 4000×g for 15 min and 10 μL of supernatant transferred to an HPLC vial. Reactions were then analysed by HPLC and LCMS for the presence of SEQ ID NO:98.

TABLE 55

| | Final concentration in reaction (mM) | Volume per reaction (μL) |
|---|---|---|
| Second ligation product: (2'MOE) - SEQ ID NO: 97 | 0.05 | 10 |
| Phosphatase - SEQ ID NO: 94 | 0.00036 | 20 |
| Buffer (20 mM Tris at pH 8) | | 170 |
| Final reaction volume: | | 200 |

TABLE 56

Results from second dephosphorylation reaction:

| Gene name | SEQ ID NO | Conversion (%) to product* |
|---|---|---|
| Wild type phosphatase (*Pandalus borealis*) protein sequence - 'SAP' | 95 | 92.63 |

*Conversion (%) to product - % area of SEQ ID NO: 97 peak vs. SEQ ID NO: 98 peak at wavelength 258 nm

Example 28: Specific Chain Cleavage by Endonuclease for Release of Segment or Product Oligonucleotide Sequence Having 2'MOE Base Modifications and Phosphorothioate Linkages Wild-type endonuclease (SEQ ID NO:100) was fused at the N-terminus to CBD. Genes were synthesised, cloned into pET28a and protein encoding the gene produced in *E. coli* BL21(DE3) A1 using standard cloning, expression and extraction methods. Proteins were purified by binding to beaded cellulose followed by cleavage with TEV protease using standard methods and used directly.

Reaction was set up as per table 58, with addition of endonuclease last. Reaction was incubated at 65° C. for 16 hours. Reaction was then quenched by heating to 95° C. for 5 min, centrifuged at 4000×g for 15 min and 10 μL of supernatant transferred to an HPLC vial. Reaction was then analysed by HPLC and LCMS for the presence of SEQ ID NO:101 and ACT1A (specific modifications set out in table 57).

TABLE 57

| SEQ ID NO | Sequence |
|---|---|
| 99 | ACT/ideoxyl/A*G*A*5mC(MOE)*5mC(MOE)*A(MOE)*5mC(MOE)*G(MOE) |
| 101 | /5phos/G*A*5mC(MOE)*5mC(MOE)*A(MOE)*5mC(MOE)*G(MOE) |
| N/A | ACT1A |

TABLE 58

| | Final concentration in reaction (mM) | Volume per reaction (µL) |
|---|---|---|
| Oligonucleotide: (2'MOE, PS) - SEQ ID NO: 99 | 20 | 2 |
| Endonuclease - SEQ ID NO: 100 | | 88 |
| Buffer (50 mM Sodium chloride, 10 mM Tris-HCl, 10 mM Magnesium Chloride, 100 µg/mL BSA at pH 7.9) | | 10 |
| Final reaction volume: | | 100 |

TABLE 59

Results from reaction:

| Gene name | SEQ ID NO | Conversion (%) to product* |
|---|---|---|
| Wild type *Archaeoglobus fulgidus* endonuclease V endonuclease | 100 | 47.69 |

*Conversion (%) to product - % area of SEQ ID NO: 100 peak vs. SEQ ID NO: 101 and ACTIA peak at wavelength 258 nm

OVERALL CONCLUSIONS

The inventors have shown that it is possible to synthesize oligonucleotides enzymatically in solution, including oligonucleotides with a range of therapeutically relevant chemical modifications, starting from simple water and air stable nucleoside derivatives, firstly by using an RNA ligase enzyme to produce short oligonucleotide segments and secondly by assembling the short segments on a complementary template. The segments can then be ligated together to produce a product oligonucleotide which can be separated from both impurities and its complementary template in an efficient process that is scalable and suitable for large scale therapeutic oligonucleotide manufacture.

By synthesizing oligonucleotides in solution, the inventors have avoided the scale up constraints imposed by solid phase methods. In using the inherent properties of DNA to recognise complementary sequences specifically and bind complementary sequences with an affinity that reflects both the fidelity of the complementary sequence and the length of the complementary sequence, the inventors have been able to produce oligonucleotides of high purity without the need for chromatography, which both improves the efficiency of the production process and the scalability of the process. By recovering the template in an unchanged state during the separation process the inventors are able to reuse the template for further rounds of synthesis and so have avoided the economic consequences of having to make one equivalent of template for every equivalent of product oligonucleotide formed.

Finally, although wild type ligases are known to ligate normal DNA and RNA effectively, we have shown that modifications to DNA or RNA result in decreased ligation efficiency and multiple modifications to the DNA or RNA are additive in their effect on decreasing the efficiency of ligation which can, in some cases render the DNA or RNA ligase completely ineffective. We have shown that by appropriate mutation and evolution of DNA and RNA ligases, ligation efficiency can be restored and appropriately modified DNA and RNA ligases are effective catalysts for synthesizing oligonucleotides which contain multiple modifications.

SEQUENCE LISTING

| SEQ ID NO | Sequence Identifier |
|---|---|
| 1 | Example 1 desired product oligonucleotide sequence ("target") |
| 2 | Example 1-4, 6, 10 and 11 template oligonucleotide sequence |
| 3 | Wild-type T4 DNA ligase protein sequence |
| 4 | Wild-type T4 DNA ligase protein sequence (when fused to CBD) |
| 5 | Example 2 target sequence |
| 6 | Wild-type *Enterobacteria* phage CC31 DNA ligase protein sequence |
| 7 | Wild-type *Enterobacteria* phage CC31 DNA ligase protein sequence (when fused to CBD) |
| 8 | Wild-type *Shigella* phage Shf125875 DNA ligase protein sequence |
| 9 | Wild-type *Shigella* phage Shf125875 DNA ligase protein sequence (when fused to CBD) |
| 10 | Mutant ligase (T4 backbone) protein sequence |
| 11 | Mutant ligase (T4 backbone) protein sequence |
| 12 | Mutant ligase (T4 backbone) protein sequence |
| 13 | Mutant ligase (T4 backbone) protein sequence |
| 14 | Mutant ligase (T4 backbone) protein sequence |
| 15 | Mutant ligase (T4 backbone) protein sequence |
| 16 | Mutant ligase (T4 backbone) protein sequence |

-continued

| SEQ ID NO | Sequence Identifier |
|---|---|
| 17 | Mutant ligase (T4 backbone) protein sequence |
| 18 | Mutant ligase (T4 backbone) protein sequence |
| 19 | Mutant ligase (T4 backbone) protein sequence |
| 20 | Mutant ligase (T4 backbone) protein sequence |
| 21 | Mutant ligase (T4 backbone) protein sequence |
| 22 | Mutant ligase (T4 backbone) protein sequence |
| 23 | Mutant ligase (*Enterobacteria* phage CC31 backbone-clone A4) protein sequence |
| 24 | Mutant ligase (*Enterobacteria* phage CC31 backbone) protein sequence |
| 25 | Mutant ligase (*Enterobacteria* phage CC31 backbone) protein sequence |
| 26 | Mutant ligase (*Enterobacteria* phage CC31 backbone) protein sequence |
| 27 | Mutant ligase (*Enterobacteria* phage CC31 backbone) protein sequence |
| 28 | Mutant ligase (*Shigella phage* Shf125875 backbone) protein sequence |
| 29 | Wild-type *Chlorella ligase* protein sequence |
| 30 | Example 5, 8 and 9 template oligonucleotide sequence |
| 31 | Example 5 template oligonucleotide sequence |
| 32 | Example 5 template oligonucleotide sequence |
| 33 | Example 5 template oligonucleotide sequence |
| 34 | Example 5 template oligonucleotide sequence |
| 35 | Example 5 template oligonucleotide sequence |
| 36 | Example 5 template oligonucleotide sequence |
| 37 | Example 5 template oligonucleotide sequence |
| 38 | Example 5 template oligonucleotide sequence |
| 39 | Example 5 template oligonucleotide sequence |
| 40 | Example 5 template oligonucleotide sequence |
| 41 | Example 5 template oligonucleotide sequence |
| 42 | Example 5 template oligonucleotide sequence |
| 43 | Example 5 template oligonucleotide sequence |
| 44 | Example 5 template oligonucleotide sequence |
| 45 | Example 5 template oligonucleotide sequence |
| 46 | Example 14 "20 mer" oligonucleotide sequence |
| 47 | Example 7 template oligonucleotide sequence |
| 48 | *Paramecium bursaria* Chlorella virus NE-JV-4 ligase |
| 49 | *Paramecium bursaria* Chlorella virus NYs1 ligase |
| 50 | *Paramecium bursaria* Chlorella virus NE-JV-1 ligase |
| 51 | *Acanthocystis turfacea* Chlorella virus Canal-1 ligase |
| 52 | *Acanthocystis turfacea* Chlorella virus Br0604L ligase |
| 53 | *Acanthocystis turfacea* Chlorella virus NE-JV-2 ligase |
| 54 | *Acanthocystis turfacea* Chlorella virus TN603.4.2 ligase |
| 55 | *Acanthocystis turfacea* Chlorella virus GM0701.1 ligase |

-continued

| SEQ ID NO | Sequence Identifier |
|---|---|
| 56 | *Synechococcus* phage S-CRM01 ligase |
| 57 | marine sediment metagenome ligase |
| 58 | *Mycobacterium tuberculosis* (strain ATCC 25618/H37Rv) ligase |
| 59 | *Enterococcus faecalis* (strain ATCC 700802/V583) ligase |
| 60 | *Haemophilus influenzae* (strain ATCC 51907/DSM 11121/KW20/Rd) ligase |
| 61 | *Staphylococcus aureus* ligase |
| 62 | *Streptococcus pneumoniae* (strain P1031) ligase |
| 63 | Wild-type *Enterobacteria* phage T4 RNA ligase 1 protein sequence-'Rnl1' |
| 64 | Wild-type *Enterobacteria* phage T4 RNA ligase 2 protein sequence-'Rnl2' |
| 65 | Wild-type *Aeromonas* virus Aeh1 ligase protein sequence-'RNA3' |
| 66 | Wild-type *Klebsiella* phage JD18 ligase protein sequence-'RNA6' |
| 67 | Wild-type *Stenotrophomonas* phage IME13 ligase protein sequence-'RNA8' |
| 68 | Wild-type *Escherichia* phage JSE ligase protein sequence-'RNA9' |
| 69 | Wild-type *Acinetobacter* phage Acj61 ligase protein sequence-'RNA16' |
| 70 | Wild-type *Vibrio* phage VH7D ligase protein sequence-'RNA20' |
| 71 | Wild-type *Escherichia* phage JS98 ligase protein sequence-'RNA22' |
| 72 | Wild-type *Escherichia* phage vB_EcoM_112 ligase protein sequence-'RNA23' |
| 73 | Wild-type *Aeromonas* phage CC2 ligase protein sequence-'RNA28' |
| 74 | Wild-type *Enterobacteria* phage RB69 ligase protein sequence-'RNA29' |
| 75 | Wild-type *Acinetobacter* phage Ac42 ligase protein sequence-'RNA31 |
| 76 | Wild-type *Pectobacterium* phage CBB ligase protein sequence-'RNA33' |
| 77 | Wild-type *Aeromonas* phage phiAS5 ligase protein sequence-'RNA35 |
| 78 | Wild-type *Salmonella* phage vB_SenMS16 ligase protein sequence-'RNA36 |
| 79 | Wild-type *Vibrio* phage KVP40 ligase protein sequence-'RNA39' |
| 80 | Wild-type *Campylobacter* virus CP220 ligase protein sequence-'RNA49' |
| 81 | Wild-type *Pseudomonas* phage phiPMW ligase protein sequence-'RNA59' |
| 82 | Wild-type *Pseudomonas* phage vB_PaeM_C2-10_Ab1 ligase protein sequence-'RNA61' |
| 83 | Wild-type *Butyrivibrio proteoclasticus* ligase protein sequence-'RNA82' |
| 84 | Example 15 and 16 primer oligonucleotide sequence |
| 85 | Example 15 and 16 product oligonucleotide sequence |
| 86 | Example 17 primer oligonucleotide sequence |
| 87 | Example 17 product oligonucleotide sequence |
| 88 | Mutant ligase (*Stenotrophomonas* phage IME13 backbone) protein sequence |
| 89 | Mutant ligase (*Stenotrophomonas* phage IME13 backbone) protein sequence |
| 90 | Mutant ligase (*Stenotrophomonas* phage IME13 backbone) protein sequence |
| 91 | Mutant ligase (*Stenotrophomonas* phage IME13 backbone) protein sequence |
| 92 | Mutant ligase (*Stenotrophomonas* phage IME13 backbone) protein sequence |
| 93 | Example 26 product oligonucleotide sequence |

| SEQ ID NO | Sequence Identifier |
|---|---|
| 94 | Example 26 product oligonucleotide sequence |
| 95 | Wild type phosphatase (*Pandalus borealis*) protein sequence-'SAP' |
| 96 | Example 27 product oligonucleotide sequence |
| 97 | Example 27 product oligonucleotide sequence |
| 98 | Example 27 product oligonucleotide sequence |
| 99 | Example 28 product oligonucleotide sequence |
| 100 | Wild type *Archaeoglobus fulgidus* endonuclease V endonuclease |
| 101 | Example 28 product oligonucleotide sequence |

SEQ ID NO: 1
GGCCAAACCTCGGCTTACCT

SEQ ID NO: 2
TTTAGGTAAGCCGAGGTTTGGCC

SEQ ID NO: 3
MILKILNEIASIGSTKQKQAILEKNKDNELLKRVYRLTYSRGLQYYIKKWPKPGIATQSFGMLTLTDMLDFIEFTLA
TRKLTGNAAIEELTGYITDGKKDDVEVLRRVMMRDLECGASVSIANKVWPGLIPEQPQMLASSYDEKGINKNIKF
PAFQSLKADGARCFAEVRGDELDDVRLLSRAGNEYLGLDLLKEELIKMTAEARQIHPEGVLIDGELVYHEQVKKE
PEGLDFLFDAYPENSKAKEFAEVAESRTASNGIANKSLKGTISEKEAQCMKFQVWDYVPLVEIYSLPAFRLKYDVR
FSKLEQMTSGYDKVILIENQVVNNLDEAKVIYKKYIDQGLEGIILKNIDGLWENARSKNLYKFKEVIDVDLKIVGIY
PHRKDPTKAGGFILESECGKIKVNAGSGLKDKAGVKSHELDRTRIMENQNYYIGKILECECNGWLKSDGRTDYV
KLFLPIAIRLREDKTKANTFEDVFGDFHEVTGL

SEQ ID NO: 4
GSILKILNEIASIGSTKQKQAILEKNKDNELLKRVYRLTYSRGLQYYIKKWPKPGIATQSFGMLTLTDMLDFIEFTL
ATRKLTGNAAIEELTGYITDGKKDDVEVLRRVMMRDLECGASVSIANKVWPGLIPEQPQMLASSYDEKGINKNIK
FPAFAQLKADGARCFAEVRGDELDDVRLLSRAGNEYLGLDLLKEELIKMTAEARQIHPEGVLIDGELVYHEQVKK
EPEGLDFLFDAYPENSKAKEFAEVAESRTASNGIANKSLKGTISEKEAQCMKFQVWDYVPLVEIYSLPAFRLKYDV
RDSKLEQMTSGYDKVILIENQVVNNLDEAKVIYKKYIDQGLEGIILKNIDGLWENARSKNLYKFKEVIDVDLKIVGI
YPHRKDPTKAGGFILESECGKIKVNAGSGLKDKAGVKSHELDRTRIMENQNYYIGKILECECNGWLKSDGRTDY
VKLFLPIAIRLREDKTKANTFEDVFGDFHEVTGL

SEQ ID NO: 5
GGC CAA ACC UCG GCU UAC CU

SEQ ID NO: 6
MILDIINEIASIGSTKEKAIRRHKDNELLKRVFRMTYDGLKQYYIKKWDTRPKGDIHLTLEDMLYLLEEKLAKRV
VTGNAAKEKLEIALSQTSDADAEVVKKVLLRDLRCGASRSIANKVWKNLIPEQPQMLASSYDEKGIEKNIKFPAFA
QLKADGARAFAEVRGDELDDVKILSRAGNEYLGLDLLKQQLIEMTKEARERHPGGVMIDGELVYHASTLPAGPLD
DIFGDLPELSKAKEFKEESRTMSNGLANKSLKGTISAKEAAGMKFQVWDYVPLDVVYSEGKQSGFAYDVRFRALE
LMVQGYSQMILIENHIVHNLDEAKVIYRKYVDEGLEGIILKNIGAFWENTRSKNLYKFKEVITIDLRIVDIYEHSKQ
PGKAGGFYLESECGLIKVKAGSGLKDKPGKDAHELDRTRIWENKNDYIGGVLESECNGWLAAEGRTDYVKLFLPI
AIKMRRDKDVANTFADIWGDFHEVTGL

SEQ ID NO: 7
GSILDIINEIASIGSTKEKEAIIRRHKDNELLKRVFRMTYDGLKQYYIKKWDTRPKGDIHLTLEDMLYLLEEKLAKR
VVTGNAAKEKLEIALSQTSDADAEVVKKVLLRDLRCGASRSIANKVWKNLIPEQPQMLASSYDEKGIEKNIKFPAF
AQLKADGARAFAEVRGDELDDVKILSRAGNEYLGLDLLKQQLIEMTKEARERHPGGVMIDGELVYHASTLPAGPL
DDIFGDLPELSKAKEFKEESRTMSNGLANKSLKGTISAKEAAGMKFQVWDYVPLDVVYSEGKQSGFAYDVRFRA
LELMVQGYSQMILIENHIVHNLDEAKVIYRKYVDEGLEGIILKNIGAFWENTRSKNLYKFKEVITIDLRIVDIYEHS
KQPGKAGGFYLESECGLIKVKAGSGLKDKPGKDAHELDRTRIWENKNDYIGGVLESECNGWLAAEGRTDYVKLF
LPIAIKMRRDKDVANTFADIWGDFHEVTGL

SEQ ID NO: 8
MILDILNQIAAIGSTKTKQEILKKNKDNKLLERVYRLTYARGIQYYIKKWPGPGERSQAYGLLELDDMLDFIEFTLA
TRKLTGNAAIKELMGYIADGKPDDVEVLRRVMMRDLEVGASVSIANKVWPGLIQLQPQMLASAYDEKLITKNIK
WPAFAQLKADGARCFAEVRDDGVQFFSRAGNEYHGLTLLADELMEMTKEARERHPNGVLIDGELVYHSFDIKKA
VSSGNDLSFLFGDNEESEEVQVADRSTSNGLANKSLQGTISPKEAEGMVLQAWDYVPLDEVYSDGKIKGQKYDV
RFAALENMAEGFKRIEPIENQLVHNLDEAKVVYKKYVDQGLEGIILKNRDSYWENKRSKNLIKFKEVIDIALEVVG
YYEHSKDPNKLGGVELVSRCRRITTDCGSGFKDTTHKTVDGVKVLIPLDERHDLDRERLMAEAREGKLIGRIADC
ECNGWVHSKGREGTVGIFLPIIKGFRFDKTEADSFEDVFGPWSQTGL

SEQ ID NO: 9
GSILDILNQIAAIGSTKTKQEILKKNKDNKLLERVYRLTYARGIQYYIKKWPGPGERSQAYGLLELDDMLDFIEFTL
ATRKLTGNAAIKELMGYIADGKPDDVEVLRRVMMRDLEVGASVSIANKVWPGLIQLQPQMLASAYDEKLITKNIK
WPAFAQLKADGARCFAEVRDDGVQFFSRAGNEYHGLTLLADELMEMTKEARERHPNGVLIDGELVYHSFDIKKA
VSSGNDLSFLFGDNEESEEVQVADRSTSNGLANKSLQGTISPKEAEGMVLQAWDYVPLDEVYSDGKIKGQKYDV

-continued

---

| SEQ ID NO | Sequence Identifier |
|---|---|

RFAALENMAEGFKRIEPIENQLVHNLDEAKVVYKKYVDQGLEGIILKNRDSYWENKRSKNLIKFKEVIDIALEVVG
YYEHSKDPNKLGGVELVSRCRRITTDCGSGFKDTTHKTVDGVKVLIPLDERHDLDRERLMAEAREGKLIGRIADC
ECNGWVHSKGREGTVGIFLPIIKGFRFDKTEADSFEDVFGPWSQTGL

SEQ ID NO: 10
MILKILNEIASIGSTKQKQAILEKNKDNELLKRVYRLTYSRGLQYYIKKWPKPGIATQSFGMLTLTDMLDFIEFTLA
TRKLTGNAAIEELTGYITDGKKDDVEVLRRVMMRDLECGASVSIANKVWPGLIPEQPQMLASSYDEKGINKNIKF
PAFAQLKADGARCFAEVRGDELDDVRLLSRAGNEYLGLDLLKEELIKMTAEARQIHPEGVLIDGELVYHEQVKKE
PEGLDFLFDAYPENSKAKEFAEVAESRTASNGIANKSLKGTISEKEAQCMKFQVWDYVPLVEIYSLPAFRLKYDVR
FSKLEQMTSGYDKVILIENQVVNNLDEAKVIYKKYIDQGLEGIILKNIDGLWENARSKNLYKFKRVIDVDLKIVGIY
PHRKDPTKAGGFILESECGKIKVNAGSGLKDKAGVKSHELDRTRIMENQNYYIGKILECECNGWLKSDGRTDYV
KLFLPIAIRLREDKTKANTFEDVFGDFHEVTGL

SEQ ID NO: 11
MILKILNEIASIGSTKQKQAILEKNKDNELLKRVYRLTYSRGLQYYIKKWPKPGIATQSFGMLTLTDMLDFIEFTLA
TRKLTGNAAIEELTGYITDGKKDDVEVLRRVMMRDLECGASVSIANKVWPGLIPEQPQMLASSYDEKGINKNIKF
PAFAQLKADGARCFAEVRGDELDDVRLLSRAGNEYLGLDLLKEELIKMTAEARQIHPEGVLIDGELVYHEQVKKE
PEGLDFLFDAYPENSKAKEFAEVAESRTASNGIANKSLKGTISEKEAQCMKFQVWDYVPLVEIYSLPAFRLKYDVR
FSKLEQMTSGYDKVILIENQVVNNLDEAKVIYKKYIDQGLEGIILKNIDGLWENARSKNLYKFKGVIDVDLKIVGIY
PHRKDPTKAGGFILESECGKIKVNAGSGLKDKAGVKSHELDRTRIMENQNYYIGKILECECNGWLKSDGRTDYV
KLFLPIAIRLREDKTKANTFEDVFGDFHEVTGL

SEQ ID NO: 12
MILKILNEIASIGSTKQKQAILEKNKDNELLKRVYRLTYSRGLQYYIKKWPKPGIATQSFGMLTLTDMLDFIEFTLA
TRKLTGNAAIEELTGYITDGKKDDVEVLRRVMMRDLECGASVSIANKVWPGLIPEQPQMLASSYDEKGINKNIKF
PAFAQLKADGARCFAEVRGDELDDVRLLSRAGNEYLGLDLLKEELIKMTAEARQIHPEGVLIDGELVYHEQVKKE
PEGLDFLFDAYPENSKAKEFAEVAESRTASNGIANKSLKGTISEKEAQCMKFQVWDYVPLVEIYSLPAFRLKYDVR
FSKLEQMTSGYDKVILIENQVVNNLDEAKVIYKKYIDQGLEGIILKNIDGLWENARSKNLYKFKKVIDVDLKIVGIY
PHRKDPTKAGGFILESECGKIKVNAGSGLKDKAGVKSHELDRTRIMENQNYYIGKILECECNGWLKSDGRTDYV
KLFLPIAIRLREDKTKANTFEDVFGDFHEVTGL

SEQ ID NO: 13
MILKILNEIASIGSTKQKQAILEKNKDNELLKRVYRLTYSRGLQYYIKKWPKPGIATQSFGMLTLTDMLDFIEFTLA
TRKLTGNAAIEELTGYITDGKKDDVEVLRRVMMRDLECGASVSIANKVWPGLIPEQPQMLASSYDEKGINKNIKF
PAFAQLKADGARCFAEVRGDELDDVRLLSRAGNEYLGLDLLKEELIKMTAEARQIHPEGVLIDGELVYHEQVKKE
PEGLDFLFDAYPENSKAKEFAEVAESRTASNGIANKSLKGTISEKEAQCMKFQVWDYVPLVEIYSLPAFRLKYDVR
FSKLEQMTSGYDKVILIENQVVNNLDEAKVIYKKYIDQGLEGIILKNIDGLWENARSKNLYKFKEVILVDLKIVGIY
PHRKDPTKAGGFILESECGKIKVNAGSGLKDKAGVKSHELDRTRIMENQNYYIGKILECECNGWLKSDGRTDYV
KLFLPIAIRLREDKTKANTFEDVFGDFHEVTGL

SEQ ID NO: 14
MILKILNEIASIGSTKQKQAILEKNKDNELLKRVYRLTYSRGLQYYIKKWPKPGIATQSFGMLTLTDMLDFIEFTLA
TRKLTGNAAIEELTGYITDGKKDDVEVLRRVMMRDLECGASVSIANKVWPGLIPEQPQMLASSYDEKGINKNIKF
PAFAQLKADGARCFAEVRGDELDDVRLLSRAGNEYLGLDLLKEELIKMTAEARQIHPEGVLIDGELVYHEQVKKE
PEGLDFLFDAYPENSKAKEFAEVAESRTASNGIANKSLKGTISEKEAQCMKFQVWDYVPLVEIYSLPAFRLKYDVR
FSKLEQMTSGYDKVILIENQVVNNLDEAKVIYKKYIDQGLEGIILKNIDGLWENARSKNLYKFKEVIKVDLKIVGIY
PHRKDPTKAGGFILESECGKIKVNAGSGLKDKAGVKSHELDRTRIMENQNYYIGKILECECNGWLKSDGRTDYV
KLFLPIAIRLREDKTKANTFEDVFGDFHEVTGL

SEQ ID NO: 15
MILKILNEIASIGSTKQKQAILEKNKDNELLKRVYRLTYSRGLQYYIKKWPKPGIATQSFGMLTLTDMLDFIEFTLA
TRKLTGNAAIEELTGYITDGKKDDVEVLRRVMMRDLECGASVSIANKVWPGLIPEQPQMLASSYDEKGINKNIKF
PAFAQLKADGARCFAEVRGDELDDVRLLSRAGNEYLGLDLLKEELIKMTAEARQIHPEGVLIDGELVYHEQVKKE
PEGLDFLFDAYPENSKAKEFAEVAESRTASNGIANKSLKGTISEKEAQCMKFQVWDYVPLVEIYSLPAFRLKYDVR
FSKLEQMTSGYDKVILIENQVVNNLDEAKVIYKKYIDQGLEGIILKNIDGLWENARSKNLYKFKEVIQVDLKIVGIY
PHRKDPTKAGGFILESECGKIKVNAGSGLKDKAGVKSHELDRTRIMENQNYYIGKILECECNGWLKSDGRTDYV
KLFLPIAIRLREDKTKANTFEDVFGDFHEVTGL

SEQ ID NO: 16
MILKILNEIASIGSTKQKQAILEKNKDNELLKRVYRLTYSRGLQYYIKKWPKPGIATQSFGMLTLTDMLDFIEFTLA
TRKLTGNAAIEELTGYITDGKKDDVEVLRRVMMRDLECGASVSIANKVWPGLIPEQPQMLASSYDEKGINKNIKF
PAFAQLKADGARCFAEVRGDELDDVRLLSRAGNEYLGLDLLKEELIKMTAEARQIHPEGVLIDGELVYHEQVKKE
PEGLDFLFDAYPENSKAKEFAEVAESRTASNGIANKSLKGTISEKEAQCMKFQVWDYVPLVEIYSLPAFRLKYDVR
FSKLEQMTSGYDKVILIENQVVNNLDEAKVIYKKYIDQGLEGIILKNIDGLWENARSKNLYKFKEVIVVDLKIVGIY
PHRKDPTKAGGFILESECGKIKVNAGSGLKDKAGVKSHELDRTRIMENQNYYIGKILECECNGWLKSDGRTDYV
KLFLPIAIRLREDKTKANTFEDVFGDFHEVTGL

SEQ ID NO: 17
MILKILNEIASIGSTKQKQAILEKNKDNELLKRVYRLTYSRGLQYYIKKWPKPGIATQSFGMLTLTDMLDFIEFTLA
TRKLTGNAAIEELTGYITDGKKDDVEVLRRVMMRDLECGASVSIANKVWPGLIPEQPQMLASSYDEKGINKNIKF
PAFAQLKADGARCFAEVRGDELDDVRLLSRAGNEYLGLDLLKEELIKMTAEARQIHPEGVLIDGELVYHEQVKKE
PEGLDFLFDAYPENSKAKEFAEVAESRTASNGIANKSLKGTISEKEAQCMKFQVWDYVPLVEIYSLPAFRLKYDVR
FSKLEQMTSGYDKVILIENQVVNNLDEAKVIYKKYIDQGLEGIILKNIDGLWENARSKNLYKFKEVIRVDLKIVGIY
PHRKDPTKAGGFILESECGKIKVNAGSGLKDKAGVKSHELDRTRIMENQNYYIGKILECECNGWLKSDGRTDYV
KLFLPIAIRLREDKTKANTFEDVFGDFHEVTGL

-continued

---

SEQ ID NO Sequence Identifier

---

SEQ ID NO: 18
MILKILNEIASIGSTKQKQAILEKNKDNELLKRVYRLTYSRGLQYYIKKWPKPGIATQSFGMLTLTDMLDFIEFTLA
TRKLTGNAAIEELTGYITDGKKDDVEVLRRVMMRDLECGASVSIANKVWPGLIPEQPQMLASSYDEKGINKNIKF
PAFAQLKADGARCFAEVRGDELDDVRLLSRAGNEYLGLDLLKEELIKMTAEARQIHPEGVLIDGELVYHEQVKKE
PEGLDFLFDAYPENSKAKEFAEVAESRTASNGIANKSLKGTISEKEAQCMKFQVWDYVPLVEIYSLPAFRLKYDVR
FSKLEQMTSGYDKVILIENQVVNNLDEAKVIYKKYIDQGLEGIILKNIDGLWENARSKNLYKFKEAIDVDLKIVGIY
PHRKDPTKAGGFILESECGKIKVNAGSGLKDKAGVKSHELDRTRIMENQNYYIGKILECECNGWLKSDGRTDYV
KLFLPIAIRLREDKTKANTFEDVFGDFHEVTGL

SEQ ID NO: 19
MILKILNEIASIGSTKQKQAILEKNKDNELLKRVYRLTYSRGLQYYIKKWPKPGIATQSFGMLTLTDMLDFIEFTLA
TRKLTGNAAIEELTGYITDGKKDDVEVLRRVMMRDLECGASVSIANKVWPGLIPEQPQMLASSYDEKGINKNIKF
PAFAQLKADGARCFAEVRGDELDDVRLLSRAGNEYLGLDLLKEELIKMTAEARQIHPEGVLIDGELVYHEQVKKE
PEGLDFLFDAYPENSKAKEFAEVAESRTASNGIANKSLKGTISEKEAQCMKFQVWDYVPLVEIYSLPAFRLKYDVR
FSKLEQMTSGYDKVILIENQVVNNLDEAKVIYKKYIDQGLEGIILKNIDGLWENARSKNLYKFKEKIDVDLKIVGIY
PHRKDPTKAGGFILESECGKIKVNAGSGLKDKAGVKSHELDRTRIMENQNYYIGKILECECNGWLKSDGRTDYV
KLFLPIAIRLREDKTKANTFEDVFGDFHEVTGL

SEQ ID NO: 20
MILKILNEIASIGSTKQKQAILEKNKDNELLKRVYRLTYSRGLQYYIKKWPKPGIATQSFGMLTLTDMLDFIEFTLA
TRKLTGNAAIEELTGYITDGKKDDVEVLRRVMMRDLECGASVSIANKVWPGLIPEQPQMLASSYDEKGINKNIKF
PAFAQLKADGARCFAEVRGDELDDVRLLSRAGNEYLGLDLLKEELIKMTAEARQIHPEGVLIDGELVYHEQVKKE
PEGLDFLFDAYPENSKAKEFAEVAESRTASNGIANKSLKGTISEKEAQCMKFQVWDYVPLVEIYSLPAFRLKYDVR
FSKLEQMTSGYDKVILIENQVVNNLDEAKVIYKKYIDQGLEGIILKNIDGLWENARSKNLYKFKRVIVVDLKIVGIY
PHRKDPTKAGGFILESECGKIKVNAGSGLKDKAGVKSHELDRTRIMENQNYYIGKILECECNGWLKSDGRTDYV
KLFLPIAIRLREDKTKANTFEDVFGDFHEVTGL

SEQ ID NO: 21
MILKILNEIASIGSTKQKQAILEKNKDNELLKRVYRLTYSRGLQYYIKKWPKPGIATQSFGMLTLTDMLDFIEFTLA
TRKLTGNAAIEELTGYITDGKKDDVEVLRRVMMRDLECGASVSIANKVWPGLIPEQPQMLASSYDEKGINKNIKF
PAFAQLKADGARCFAEVRGDELDDVRLLSRAGNEYLGLDLLKEELIKMTAEARQIHPEGVLIDGELVYHEQVKKE
PEGLDFLFDAYPENSKAKEFAEVAESRTASNGIANKSLKGTISEKEAQCMKFQVWDYVPLVEIYSLPAFRLKYDVR
FSKLEQMTSGYDKVILIENQVVNNLDEAKVIYKKYIDQGLEGIILKNIDGLWENARSKNLYKFKKVIEVDLKIVGIY
PHRKDPTKAGGFILESECGKIKVNAGSGLKDKAGVKSHELDRTRIMENQNYYIGKILECECNGWLKSDGRTDYV
KLFLPIAIRLREDKTKANTFEDVFGDFHEVTGL

SEQ ID NO: 22
MILKILNEIASIGSTKQKQAILEKNKDNELLKRVYRLTYSRGLQYYIKKWPKPGIATQSFGMLTLTDMLDFIEFTLA
TRKLTGNAAIEELTGYITDGKKDDVEVLRRVMMRDLECGASVSIANKVWPGLIPEQPQMLASSYDEKGINKNIKF
PAFAQLKADGARCFAEVRGDELDDVRLLSRAGNEYLGLDLLKEELIKMTAEARQIHPEGVLIDGELVYHEQVKKE
PEGLDFLFDAYPENSKAKEFAEVAESRTASNGIANKSLKGTISEKEAQCMKFQVWDYVPLVEIYSLPAFRLKYDVR
FSKLEQMTSGYDKVILIENQVVNNLDEAKVIYKKYIDQGLEGIILKNIDGLWENARSKNLYKFKKVIHVDLKIVGIY
PHRKDPTKAGGFILESECGKIKVNAGSGLKDKAGVKSHELDRTRIMENQNYYIGKILECECNGWLKSDGRTDYV
KLFLPIAIRLREDKTKANTFEDVFGDFHEVTGL

SEQ ID NO: 23
MILDIINEIASIGSTKEKEAIIRRHKDNELLKRVFRMTYDGKLQYYIKKWDTRPKGDIHLTLEDMLYLLEEKLAKRV
VTGNAAKEKLEIALSQTSDADAEVVKKVLLRDLRCGASRSIANKVWKNLIPEQPQMLASSYDEKGIEKNIKFPAFA
QLKADGARAFAEVRGDELDDVKILSRAGNEYLGLDLLKQQLIEMTKEARERHPEGVMIDGELVYHASTLPAGPLD
DIFGDLPELSKAKEFKEESRTMSNGLANKSLKGTISAKEAAGMKFQVWDYVPLDVVYSEGKQSGFAYDVRFRALE
LMVQGYSQMILIENHIVHNLDEAKVIYRKYVDEGLEGIILKNIGAFWENTRSKNLYKFKRVIVIDLRIVDIYEHSKQ
PGKAGGFYLESECGLIKVKAGSGLKDKPGKDAHELDRTRIWENKNDYIGGVLESECNGWLAAEGRTDYVKLFLPI
AIKMRRDKDVANTFADIWGDFHEVTGL

SEQ ID NO: 24
MILDIINEIASIGSTKEKEAIIRRHKDNELLKRVFRMTYDGKLQYYIKKWDTRPKGDIHLTLEDMLYLLEEKLAKRV
VTGNAAKEKLEIALSQTSDADAEVVKKVLLRDLRCGASRSIANKVWKNLIPEQPQMLASSYDEKGIEKNIKFPAFA
QLKADGARAFAEVRGDELDDVKILSRAGNEYLGLDLLKQQLIEMTKEARERHPGGVMIDGELVYHASTLPAGPLD
DIFGDLPELSKAKEFKEESRTMSNGLANKSLKGTISAKEAAGMKFQVWDYVPLDVVYSEGKQSGFAYDVRFRALE
LMVQGYSQMILIENHIVHNLDEAKVIYRKYVDEGLEGIILKNIGAFWENTRSKNLYKFKKVIKIDLRIVDIYEHSKQ
PGKAGGFYLESECGLIKVKAGSGLKDKPGKDAHELDRTRIWENKNDYIGGVLESECNGWLAAEGRTDYVKLFLPI
AIKMRRDKDVANTFADIWGDFHEVTGL

SEQ ID NO: 25
MILDIINEIASIGSTKEKEAIIRRHKDNELLKRVFRMTYDGKLQYYIKKWDTRPKGDIHLTLEDMLYLLEEKLAKRV
VTGNAAKEKLEIALSQTSDADAEVVKKVLLRDLRCGASRSIANKVWKNLIPEQPQMLASSYDEKGIEKNIKFPAFA
QLKADGARAFAEVRGDELDDVKILSRAGNEYLGLDLLKQQLIEMTKEARERHPGGVMIDGELVYHASTLPAGPLD
DIFGDLPELSKAKEFKEESRTMSNGLANKSLKGTISAKEAAGMKFQVWDYVPLDVVYSEGKQSGFAYDVRFRALE
LMVQGYSQMILIENHIVHNLDEAKVIYRKYVDEGLEGIILKNIGAFWENTRSKNLYKFKGVIFIDLRIVDIYEHSKQ
PGKAGGFYLESECGLIKVKAGSGLKDKPGKDAHELDRTRIWENKNDYIGGVLESECNGWLAAEGRTDYVKLFLPI
AIKMRRDKDVANTFADIWGDFHEVTGL

SEQ ID NO: 26
MILDIINEIASIGSTKEKEAIIRRHKDNELLKRVFRMTYDGKLQYYIKKWDTRPKGDIHLTLEDMLYLLEEKLAKRV
VTGNAAKEKLEIALSQTSDADAEVVKKVLLRDLRCGASRSIANKVWKNLIPEQPQMLASSYDEKGIEKNIKFPAFA
QLKADGARAFAEVRGDELDDVKILSRAGNEYLGLDLLKQQLIEMTKEARERHPGGVMIDGELVYHASTLPAGPLD
DIFGDLPELSKAKEFKEESRTMSNGLANKSLKGTISAKEAAGMKFQVWDYVPLDVVYSEGKQSGFAYDVRFRALE

SEQ ID NO    Sequence Identifier

LMVQGYSQMILIENHIVHNLDEAKVIYRKYVDEGLEGIILKNIGAFWENTRSKNLYKFKGVILIDLRIVDIYEHSKQ
PGKAGGFYLESECGLIKVKAGSGLKDKPGKDAHELDRTRIWENKNDYIGGVLESECNGWLAAEGRTDYVKLFLPI
AIKMRRDKDVANTFADIWGDFHEVTGL

SEQ ID NO: 27
MILDIINEIASIGSTKEKEAIIRRHKDNELLKRVFRMTYDGKLQYYIKKWDTRPKGDIHLTLEDMLYLLEEKLAKRV
VTGNAAKEKLEIALSQTSDADAEVVKKVLLRDLRCGASRSIANKVWKNLIPEQPQMLASSYDEKGIEKNIKFPAFA
QLKADGARAFAEVRGDELDDVKILSRAGNEYLGLDLLKQQLIEMTKEARERHPGGVMIDGELVYHASTLPAGPLD
DIFGDLPELSKAKEFKEESRTMSNGLANKSLKGTISAKEAAGMKFQVWDYVPLDVVYSEGKQSGFAYDVRFRALE
LMVQGYSQMILIENHIVHNLDEAKVIYRKYVDEGLEGIILKNIGAFWENTRSKNLYKFKRVIFIDLRIVDIYEHSKQ
PGKAGGFYLESECGLIKVKAGSGLKDKPGKDAHELDRTRIWENKNDYIGGVLESECNGWLAAEGRTDYVKLFLPI
AIKMRRDKDVANTFADIWGDFHEVTGL

SEQ ID NO: 28
MILDILNQIAAIGSTKTKQEILKKNKDNKLLERVYRLTYARGIQYYIKKWPGPGERSQAYGLLELDDMLDFIEFTLA
TRKLTGNAAIKELMGYIADGKPDDVEVLRRVMMRDLEVGASVSIANKVWPGLIQLQPQMLASAYDEKLITKNIK
WPAFAQLKADGARCFAEVRDDGVQFFSRAGNEYHGLTLLADELMEMTKEARERHPNGVLIDGELVYHSFDIKKA
VSSGNDLSFLFGDNEESEEVQVADRSTSNGLANKSLQGTISPKEAEGMVLQAWDYVPLDEVYSDGKIKGQKYDV
RFAALENMAEGFKRIEPIENQLVHNLDEAKVVYKKYVDQGLEGIILKNRDSYWENKRSKNLIKFKRVIVIALEVVG
YYEHSKDPNKLGGVELVSRCRRITTDCGSGFKDTTHKTVDGVKVLIPLDERHDLDRERLMAEAREGKLIGRIADC
ECNGWVHSKGREGTVGIFLPIIKGFRFDKTEADSFEDVFGPWSQTGL

SEQ ID NO: 29
MAITKPLLAATLENIEDVQFPCLATPKIDGIRSVKQTQMLSRTFKPIRNSVMNRLLTELLPEGSDGEISIEGATFQD
TTSAVMTGHKMYNAKFSYYWFDYVTDDPLKKYIDRVEDMKNYITVHPHILEHAQVKIIPLIPVEINNITELLQYER
DVLSKGFEGVMIRKPDGKYKFGRSTLKEGILLKMKQFKDAEATIISMTALFKNTNTKTKDNFGYSKRSTHKSGKV
EEDVMGSIEVDYDGVVFSIGTGFDADQRRDFWQNKESYIGKMVKFKYFEMGSKDCPRFPVFIGIRHEEDR

SEQ ID NO: 30
TTTGGTGCGAAGCAGACTGAGGC

SEQ ID NO: 31
TTTGGTGCGAAGCAGAGTGAGGC

SEQ ID NO: 32
TTTGGTGCGAAGCAGATTGAGGC

SEQ ID NO: 33
TTTGGTGCGAAGCAGAATGAGGC

SEQ ID NO: 34
TTTGGTGCGAAGCAGTCTGAGGC

SEQ ID NO: 35
TTTGGTGCGAAGCAGTGTGAGGC

SEQ ID NO: 36
TTTGGTGCGAAGCAGTTTGAGGC

SEQ ID NO: 37
TTTGGTGCGAAGCAGTATGAGGC

SEQ ID NO: 38
TTTGGTGCGAAGCAGCCTGAGGC

SEQ ID NO: 39
TTTGGTGCGAAGCAGCGTGAGGC

SEQ ID NO: 40
TTTGGTGCGAAGCAGCTTGAGGC

SEQ ID NO: 41
TTTGGTGCGAAGCAGCATGAGGC

SEQ ID NO: 42
TTTGGTGCGAAGCAGGCTGAGGC

SEQ ID NO: 43
TTTGGTGCGAAGCAGGGTGAGGC

SEQ ID NO: 44
TTTGGTGCGAAGCAGGTTGAGGC

SEQ ID NO: 45
TTTGGTGCGAAGCAGGATGAGGC

-continued

| SEQ ID NO | Sequence Identifier |
| --- | --- |

SEQ ID NO: 46
GCCUCAGTCTGCTTCGCACC

SEQ ID NO: 47
TTTGGTGCGAAGCAGAAGGTAAGCCGAGGTTTGGCC

SEQ ID NO: 48
MAITKPLLAATLENIEDVQFPCLATPKIDGIRSVKQTQMLSRTFKPIRNSVMNRLLTELLPEGSDGEISIEGATFQD
TTSAVMTGHKMYNAKFSYYWFDYVTDDPLKKYSDRVEDMKNYITAHPHILDHEQVKIIPLIPVEINNITELLQYE
RDVLSKGFEGVMIRKPDGKYKFGRSTLKEGILLKMKQFKDAEATIISMTALFKNTNTKTKDNFGYSKRSTHKNGK
VEEDVMGSIEVDYDGVVFSIGTGFDADQRRDFWQNKESYIGKMVKFKYFEMGSKDCPRFPVFIGIRHEEDH

SEQ ID NO: 49
MTIAKPLLAATLENLDDVKFPCLVTPKIDGIRSLKQQHMLSRTFKPIRNSVMNKLLSELLPEGADGEICIEDSTFQA
TTSAVMTGHKVYDEKFSYYWFDYVVDDPLKSYTDRVNDMKKYVDDHPHILEHEQVKIIPLIPVEINNIDELSQYE
RDVLAKGFEGVMIRRPDGKYKFGRSTLKEGILLKMKQFKDAEATIISMSPRLKNTNAKSKDNLGYSKRSTHKSGK
VEEETMGSIEVDYDGVVFSIGTGFDDEQRKHFWENKDSYIGKLLLFKYFEMGSKDAPRFPVFIGIRHEEDC

SEQ ID NO: 50
MTAIQKPLLAASFKKLTVADVKYPVFATPKLDGIRALKIDGAFVSRTFKPIRNRAIADALQDLLPNGSDGEILSGST
FQDASSAVMTAKAGIGANTIFYWFDYVKDDPNKPYLDRMTDMENYLKERPEILNDDRIKIVPLIPKKIETKDELD
TFEKICLDQGFEGVMIRSGAGKYKFGRSTEKEGILIKIKQFEDDEAVVIGFTPMQTNTNDKSMNELGDMKRSSHK
DGKVNLDTLGALEVDWNGITFSIGTGFDHALRDKLWSERDKLIGKIVKFKYFAQGVKTAPRFPVFIGFRDPDDM

SEQ ID NO: 51
MAIQKPLLAASLKKMSVGDLTFPVFATPKLDGIRALKVGGTIVSRTFKPVRNSAISEVLASILPDGSDGEILSGKTF
QESTSTVMTADAGLGSGTMFFWFDYVKDDPNKGYLDRIADMKSFTDRHPEILKDKRVTIVPLFPKKIDTTEELHE
FEKWCLDQGFEGVMVRNAGGKYKFGRSTEKEQILVKIKQFEDDEAVVIGVSALQTNTNDKKLNQLGEMRRTSH
QDGKVELEMLGALDVDWNGIRFSIGTGFDRDTRVDLWKRREGVIGKIVKFKYFSQGIKTAPRFPVFLGFRDKDDM

SEQ ID NO: 52
MAIQKPLLAASLKKLSVDDLTFPVYATPKLDGIRALKIDGTLVSRTFKPIRNTTISKVLTSLLPDGSDGEILSGKTFQ
DSTSTVMSADAGIGSGTTFFWFDYVKDDPNKGYLDRIADIKKFIDCRPEILKDSRVIIVPLFPKKIDTAEELNVFEK
WCLDQGFEGVMVRNAGGKYKFGRSTEKEQILVKIKQFEDDEAVVIGVSALQTNTNDKKVNELGEMRRTSHQDG
KVDLDMLGALDVDWNGIRFGIGTGFDKDTREDLWKRRDSIIGKIVKFKYFSQGVKTAPRFPVFLGFRDKNDM

SEQ ID NO: 53
MAIQKPLLAASLKKLSVDDLTFPVYATPKLDGIRALKIDGTIVSRTFKPIRNTTISNVLMSLLPDGSDGEILSGKTF
QDSTSTVMSADAGIGSGTTFFWFDYVKDDPDKGYLDRIADMKKFVDSHPEILKDRRVTIVPLIPKKIDTVEELNV
FEQWCLDQGFEGVMVRNAGGKYKFGRSTEKEQILVKIKQFEDDEAVVIGVSALQTNVNDKKMNELGDMRRTSH
KDGKIDLEMLGALDVEWNGIRFGIGTGFDKDTREDLWKKRDSIIGKVVKFKYFSQGIKTAPRFPVFLGFRDENDM

SEQ ID NO: 54
MAIQKPLLAASLKKMSVDNLTFPVYATPKLDGIRALKIDGTLVSRTFKPIRNTTISKVLASLLPDGSDGEILSGKTF
QDSTSTVMTTDAGIGSDTTFFWFDYVKDDPDKGYLDRIADMKTFVDQHPEILKDSCVTIVPLFPKKIDTPEELHV
FEKWCLDQGFEGVMVRTAGGKYKFGRSTEKEQILVKIKQFEDDEAVVIGVSALQTNTNDKKLNQLGEMRRTSH
QDGKVDLDMLGALDVDWNGIRFSIGTGFDKDTREDLWKQRDSIVGKVVKFKYFSQGIKTAPRFPVFLGFRDENDM

SEQ ID NO: 55
MAIQKPLLAASLKKMSVDDLTFPVYTTPKLDGIRALKIDGTLVSRTFKPVRNSAISEVLASLLPDGSDGEILSGKTF
QDSTSTVMTTDAGIGSDTTFFWFDYVKDDPNKGYLDRIADMKTFIDQHPEMLKDNHVTIVPLIPKKIDTVEELNI
FEKWCLDQGFEGVMVRNAGGKYKFGRSTEKEQILVKIKQFEDDEAVVIGVSALQTNTNDKKLNQLGEMRRTSH
QDGKIDLEMLGALDVDWNGIRFSIGTGFDRDTRVDLWKRRDGIVGRTIKFKYFGQGIKTAPRFPVFLGFRDKDDM

SEQ ID NO: 56
MLAGNFDPKKAKFPYCATPKIDGIRFLMVNGRALSRTFKPIRNEYIQKLLSKHLPDGIDGELTCGDTFQSSTSAIM
RIAGEPDFKAWIFDYVDPDSTSILPFIERFDQISDIIYNGPIPFKHQVLGQSILYNIDDLNRYEEACLNEGYEGVML
RDPYGTYKFGRSSTNEGILLKVKRFEDAEATVIRIDEKMSNQNIAEKDNFGRTKRSSCLDGMVPMETTGALFVRN
SDGLEFSIGSGLNDEMRDEIWKNKSSYIGKLVKYKYFPQGVKDLPRHPVFLGFRDPDDM

SEQ ID NO: 57
MDAHELMKLNEYAERQNQKQKKQITKPMLAASLKDITQLDYSKGYLATQKLDGIRALMIDGKLVSRTFKPIRNN
HIREMLEDVLPDGADGEIVCPGAFQATSSGVMSANGEPEFIYYMFDYVKDDITKEYWRRTQDMVQWLINQGPT
RTPGLSKLKLLVPTLIKNYDHLKTYETECIDKGFEGVILRTPDSPYKCGRSTAKQEWLLKLKRFADDEAVVIGFTEK
MHNDNEATKDKFGHTVRSSHKENKRPAGTLGSLIVRDIKTEIEFEIGTGFDDELRQKIWDARPEWDGLCVKYKH
FAISGVKEKPRFPSFIGVRDVEDM

SEQ ID NO: 58
MSSPDADQTAPEVLRQWQALAEEVREHQFRYYVRDAPIISDAEFDELLRRLEALEEQHPELRTPDSPTQLVGGA
GFATDFEPVDHLERMLSLDNAFTADELAAWAGRIHAEVGDAAHYLCELKIDQVALSLVYREGRLTRASTRGDGR
TGEDVTLNARTIADVPERLTPGDDYPVPEVLEVRGEVFFRLDDFQALNASLVEEGKAPFANPRNSAAGSLRQKDP
AVTARRRLRMICHGLGHVEGFRPATLHQAYLALRAWGLPVSEHTTLATDLAGVRERIDYWGEHRHEVDHEIDG
VVVKVDEVALQRRLGSTSRAPRWAIAYKYPPEEAQTKLLDIRVNVGRTGRITPFAFMTPVKVAGSTVGQATLHN
ASEIKRKGVLIGDTVVIRKAGDVIPEVLGPVVELRDGSEREFIMPTTCPECGSPLAPEKEGDADIRCPNARGCPGQ
LRERVFHVASRNGLDIEVLGYEAGVALLQAKVIADEGELFALTERDLLRTDLFRTKAGELSANGKRLLVNLDKAKA
APLWRVLVALSIRHVGPTAARALATEFGSLDAIAAASTDQLAAVEGVGPTIAAAVTEWFAVDWHREIVDKWRAA
GVRMVDERDESVPRTLAGLTIVVTGSLTGFSRDDAKEAIVARGGKAAGSVSKKTNYVVAGDSPGSKYDKAVELG
VPILDEDGFRRLLADGPASRT

SEQ ID NO Sequence Identifier

SEQ ID NO: 59
MEQQPLTLTAATTRAQELRKQLNQYSHEYYVKDQPSVEDYVYDRLYKELVDIETEFPDLITPDSPTQRVGGKVLS
GFEKAPHDIPMYSLNDGFSKEDIFAFDERVRKAIGKPVAYCCELKIDGLAISLRYENGVFVRGATRGDGTVGENIT
ENLRTVRSVPMRLTEPISVEVRGECYMPKQSFVALNEEREENGQDIFANPRNAAAGSLRQLDTKIVAKRNLNTFL
YTVADFGPMKAKTQFEALEELSAIGFRTNPERQLCQSIDEVWAYIEEYHEKRSTLPYEIDGIVIKVNEFALQDELG
FTVKAPRWAIAYKFPPEEAETVVEDIEWTIGRTGVVTPTAVMAPVRVAGTTVSRASLHNADFIQMKDIRLNDHVI
IYKAGDIIPEVAQVLVEKRAADSQPYEMPTHCPICHSELVHLDEEVALRCINPKCPAQIKEGLNHFVSRNAMNIDG
LGPRVLAQMYDKGLVKDVADLYFLTEEQLMTLDKIKEKSANNIYTAIQGSKENSVERLIFGLGIRHVGAKAAKILA
EHFGDLPTLSRATAEEIVALDSIGETIADSVVTYFENEEVHELMAELEKAQVNLTYKGLRTEQLAEVESPFKDKTV
VLTGKLAQYTREEAKEKIENLGGKVTGSVSKKTDIVVAGEDAGSKLTKAESLGVTVWNEQEMVDALDASHF

SEQ ID NO: 60
MTNIQTQLDNLRKTLRQYEYEYHVLDNPSVPDSEYDRLFHQLKALELEHPEFLTSDSPTQRVGAKPLSGFSQIRH
EIPMLSLDNAFSDAEFNAFVKRIEDRLILLPKPLTFCCEPKLDGLAVSILYVNGELTQAATRGDGTTGEDITANIRT
IRNVPLQLLTDNPPARLEVRGEVFMPHAGFERLNKYALEHNEKTFANPRNAAAGSLRQLDPNITSKRPLVLNAYGI
GIAEGVDLPTTHYARLQWLKSIGIPVNPEIRLCNGADEVLGFYRDIQNKRSSLGYDIDGTVLKINDIALQNELGFI
SKAPRWAIAYKFPAQEELTLLNDVEFQVGRTGAITPVAKLEPVFVAGVTVSNATLHNGDEIERLNIAIGDTVVIRR
AGDVIPQIIGVLHERRPDNAKPIIFPTNCPVCDSQIIRIEGEAVARCTGGLFCAAQRKEALKHFVSRKAMDIDGVG
GKLIEQLVDRELIHTPADLFKLDLTTLTRLERMGAKSAENALNSLENAKSTTLARFIFALGIREVGEATALNLANHF
KTLDALKDANLEELQQVPDVGEVVANRIFIFWREAHNVAVVEDLIAQGVHWETVEVKEASENLFKDKTVVLTGT
LTQMGRNEAKALLQQLGAKVSGSVSSKTDFVIAGDAAGSKLAKAQELNITVLTEEEFLAQITR

SEQ ID NO: 61
MADLSSRVNELHDLLNQYSYEYYVEDNPSVPDSEYDKLLHELIKIEEEHPEYKTVDSPTVRVGGEAQASFNKVNH
DTPMLSLGNAFNEDDLRKFDQRIREQIGNVEYMCELKIDGLAVSLKYVDGYFVQGLTRGDGTTGEDITENLKTIH
AIPLKMKEPLNVEVRGEAYMPRRSFLRLNEEKEKNDEQLFANPRNAAAGSLRQLDSKLTAKRKLSVFIYSVNDFT
DFNARSQSEALDELDKLGFTTNKNRARVNNIDGVLEYIEKWTSQRESLPYDIDGVIKVNDLDQQDEMGFTQKS
PRWAIAYKFPAEEVVTKLLDIELSIGRTGVVTPTAILEPVKVAGTTVSRASLHNEDLIHDRDIRIGDSVVVKKAGDI
IPEVVRSIPERRPEDAVTYHMPTHCPSCGHELVRIEGEVALRCINPKCQAQLVEGLIHFVSRQAMNIDGLGTKIIQ
QLYQSELIKDVADIFYLTEEDLLPLDRMGQKKVDNLLAAIQQAKDNSLENLLFGLGIRHLGVKASQVLAEKYETID
RLLTVTEAELVEIHDIGDKVAQSVVTYLENEDIRALIQKLKDKHVNMIYKGIKTSDIEGHPEFSGKTIVLTGKLHQ
MTRNEASKWLASQGAKVTSSVTKNTDVVIAGEDAGSKLTKAQSLGIEIWTEQQFVDKQNELNS

SEQ ID NO: 62
MNKRMNELVALLNRYATEYYTSDNPSVSDSEYDRLYRELVELETAYPEQVLADSPTHRVGGKVLDGFEKYSHQY
PLYSLQDAFSREELDAFDARVRKEVAHPTYICELKIDGLSISLTYEKGILVAGVTRGDGSIGENITENLKRVKDIPL
TLPEELDITVRGECYMPRASFDQVNQARQENGEPEFANPRNAAAGSLRQLDTDTAVVAKRNLATFLYQEASPSTRD
SQEKGLKYLEQLGFVVNPKRILAENIDEIWNFIQEVGQERENLPYDIDGVVIKVNDLASQEELGFTVKAPKWAVA
YKFPAEEKEAQLLSVDWTVGRTGVVTPTANLTPVQLAGTTVSRATLHNVDYIAEKDIRKDDTVIVYKAGDIIPAV
LRVVESKRVSEEKLDIPTNCPSCNSDLLHFEDEVALRCINPRCPAQIMEGLIHFASRDAMNITGLGPSIVEKLFAAN
LVKDVADIYRLQEEDFLLLEGVKEKSAAKLYQAIQASKENSAEKLLFGLGIRHVGSKASQLLLQYFHSIENLYQADS
EEVASIESLGGVIAKSLQTYFATEGSEILLRELKETGVNLDYKGQTVVADAALSGLTVVLTGKLERLKRSEAKSKLE
SLGAKVTGSVSKKTDLVVVGADAGSKLQKAQELGIQVRDEAWLESL

SEQ ID NO: 63
MQELFNNLMELCKDSQRKFFYSDDVSASGRTYRIFSYNYASYSDWLLPDALECRGIMFEMDGEKPVRIASRPME
KFFNLNENPFTMNIDLNDVDYILTKEDGSLVSTYLDGDEILFKSKGSIKSEQALMANGILMNINHHRLRDRLKELA
EDGFTANFEFVAPTNRIVLAYQEMKIILLNVRENETGEYISYDDIYKDATLRPYLVERYEIDSPKWIEEAKNAENIE
GYVAVMKDGSHFKIKSDWYVSLHSTKSSLDNPEKLFKTIIDGASDDLKAMYADDEYSYRKIEAFETTYLKYLDRA
LFLVLDCHNKHCGKDRKTYAMEAQGVAKGAGMDHLFGIIMSLYQGYDSQEKVMCEIEQNFLKNYKKFIPEGY

SEQ ID NO: 64
MPFKKYSSLENHYNSKFIEKLYSLGLTGGEWVAREKIHGTNFSLIIERDKVTCAKRTGPILPAEDFFGYEIILKNYAD
SIKAVQDIMETSAVVSYQVFGEFAGPGIQKNVDYCDKDFYVFDIIVTTESGDVTYVDDYMMESFCNTFKFKMAPL
LGRGKFEELIKLPNDLDSVVQDYNFTVDHAGLVDANKCVWNAEAKGEVFTAEGYVLKPCYPSWLRNGNRVAIKC
KNSKFSEKKKSDKPIKAKVELSEADNKLVGILACYVTLNRVNNVISKIGEIGPKDFGKVMGLTVQDILEETSREGIT
LTQADNPSLIKKELVKMVQDVLRPAWIELVS

SEQ ID NO: 65
MQSIKELYQNLINLCVDDNTKFYFAETVTSLGTKVRIFDYHVAGYNDWIRPDAMASRGIMFEMNGEIPVRIMSR
PMDKFFNYSEVIGWEKLETAGNMKMPDLNKIAYVIDKRDGSLISTYLDISGEIKNLLLKSKASIRSNQANDASVW
LYQEDHKDLLEFCTAYAENGFTVNMEWTAPHNQIVLCYNEHQLRILNIRHNETGEYVDFGELQKDPTFVKYAAD
FPEVPGDGKAWIDEVYQMTGIEGFVVVMEDYQMFKLKTDWYVALHHTKDSINNSERLIYACAENCTDDLRQMF
RDDENSLQKIEIFDNHFRDVVMDAMKKLTEAYEKYRGMERRDYAINMNNDFKNERHWFNIAMQMFAQRPDFS
MTDEIVAVIKKYPKTFIPKGY

SEQ ID NO: 66
MLELYKNLMNLCESSEVAKFFYKDFTGPMDGKFRVFSYHYASYSEWLKPDALECRGIMFEMDGDTPIRIASRPM
EKFFNLNENPMTMGIDISDVEYIMDKADGSLVSSYVDDGYLYLKSKTSLYSDQARQASALLNSEEYSSLHQVILEL
ALDGYTVNMEFVSPNNRVVLAYQEPQLFVLNVRNNTTGEYIKYDDLYANAKIRPYLINAYGISDPTTWVEGVRAL
EGVEGEYIAVLNTGQRFVKTEWYSALHHTKDSITSNERLFASVVSANSDDLRSLFAGDEYAIKKISAFEQAYLDYL
GKSLELCQSFYDEYRGRARKDYAIAAQKATVNQRHLFGVIMNMYEGTVDVDKLLKDLERVFLKYWAGYVPKEYE
KEIEISEE

-continued

---

SEQ ID NO  Sequence Identifier

---

SEQ ID NO: 67
MSRTIELFNNLMSVVEKSEKGNFYFKDVITSMGTKARIFSYFIASYTDWLQDDALECRGIMFELNDKNEPVRIMA
RPMQKFFNLKENPMTIGLDLTKMIGLMEKADGSLISSYHDQGYVYLKSKAAIFSDQANKAMALLNSPAYEKLRDA
IVRAGSDFTFNMEYVGPSNRVVLPYEEEELIVLNVRHNETGQYVEFSTLLDDPLIRHRMIGVYPCPDWSKVTPEE
WEAATRAETDIEGVIGIMPDGQLFKLKTDWYSSLHRTKDSINNNKALFQSIKERASDDLRGMFSDDNAALAKIE
AFESAYIDTVAKYHKICAEVFLRFARFLIVEVFAIEAQARMKDCRYLFSIVMQQYGRDWDGELAVEKIEEHIIKEYA
TYVPMAYR

SEQ ID NO: 68
MEHKLCQQKKTTKKVLALFKNLMALCDGSDTFYYKDEITAMQTRMRIFSYLYLSKPEMWNKPDALECRGIMFEI
DDKDRPVRIASRPMEKFFNLGENDRARFKPEDVEMVMDKMDGSLVSTYIDNGYVQLKSKAALYSSQAERANGLL
YSEKYADLRAKIADIGSDYTFNFEYTAPSNRIVVEYSEPSLTLLNVRHNVTGEYVPHQMLFADAILRPHLVNALQV
DSARFSNILDEVRTAEGIEGIVARTKDGQMFKVKSEWYIGVHNIKNTSMFPNNLIYYVVESETDDLRAAYEGEPE
ALERIELFEEAFRSILRNAFTTATEFYNAHAGEDRKTYASNATIESRKHGDAQSYIFMCLMIAFDGLDYDRILASM
KTYYLRNYKKLIPADKIDW

SEQ ID NO: 69
MKELFDNLMALQDPNDISKFFYKDVVTQPGTKCRIFSYNYAAYSDWLLPGALESRGIMFELDADNQPVRVMARP
MEKFFNLEENPFTMDLDLSQLEYAMTKADGSLISTYVDQGYLYTKSKGSISSSQAIESKQLLLDINYKPLAERALE
LAKDGFTCNFEYVAPNNRIVLNYAKKDLILLNVRHNETGEYVPMAELQKDPVLRNYLIDVYPPREDIDTNEMIKEI
REMVDIEGFVFQHASGLKFKLKTEWYSNLHRVKDTLNNSEALFMVVAGGSDDMKSLFTDDLSRTKIESFETAFL
DYLKKTSNFVFDLQRQLIGSDRKTYAIECQTILRNTDQLELFGVMMELYKGADQEQTIKNINVVFMKNYKKYVPA
GFETLKNEY

SEQ ID NO: 70
MNVQELYKNLMSLADDAEGKFFFADHLSPLGEKFRVFSYHIASYSDWLLPGALEARGIMFQLDDNDEMIRIVSRP
MEKFFNLNENPFTMELDLTTTVQLMDKADGSLISTYLSGENFALKSKTSIFSEQAVAANRYIKKPENRDLWEFCD
DCTQAGLTVNMEWCAPNNRIVLEYPEAKLVILNIRDNETGDYVSFDDIPQSALMRVKQWLVDEYDPATAHEPDF
VEKLRDTKGIEGMILRLLANGQSVKIKTQWYVDLHSQKDSVNVPKKLVTTILNGNHDDLYALFADDKPTIERIREF
DSHVTKTLTNSFNAVRQFYARNRHLARKDYAIAGQKVLKPWEFGVAMIAYQKQTVEGVYESLVTAYLKRPELAIP
EKYLNGV

SEQ ID NO: 71
MIELYDNLMTLVKNSTKSKFFFKDFQSALGVNYRIFSYNYASYSDWLEDGALECRGIMFEMDENGPVRIAARPM
QKFFNLDENPLTIGLDLSQENIDLVMAKEDGSLISTFMDRQYLSVKSKGSIHSSMVHDSLRFLRLPENEAFAARLE
EITKAGYTCNLEYVSPTNRIVLAYQETNLILLNVRNNETGEYIPYAELFKDGALRKHLVKSYELSEGDFVDNIRKQE
GIEGFIFVLKDGTFFKLKTAWYSALHHTKDSINNNERLFEVVVAGGTDDLRGLFSTDSFAIEKINAFERIHLDYLE
QSLALLEAAYSQLKGRDRKDYAVTGQLILKDFPGLFSILMQAYVDGINYDTVMDQINSVFLKNHKAQIPEKYLKEI
VVE

SEQ ID NO: 72
MVLYSKHKRGYTMQELFNNLMELCKDSQRKFFYSDDVSASGRTYRIFSYNYASYSDWLLPDALECRGIMFEMDG
EKPVRIASRPMEKFFNLNENPFTMNIDLNDVDYILTKEDGSLVSTYLDGDEILFKSKGSIKSEQALMANGILMNIN
HHQLRDRLKELAEDGFTANFEFVAPTNRIVLAYQEMKIILLNVRENETGEYISYDDIYKDAILRPYLVERYEIDSPK
WVEEAKNAENIEGYVAVMKDGSHFKIKSDWYVSLHSTKSSLDNPEKLFKTIIDGASDDLKAMYADDEYSYRKIEA
FETTYLKYLDRALFLVLDCHNKHCGKDRKTYAMEAQGVAKGAGMDHLFGIIMSLYQGYDSQEKVMCEIEQNFLK
NYKKFIPEGY

SEQ ID NO: 73
MKELYNNLLKLTEEHGDCFFFRDHWSSIGNHFRVFSYHIAGLTQWMLPDALECRGIMFELINGEPYRIASRPMEK
FFNLAERQAWNLTNSGVVGLDKLELDYSNIDRYEDKADGSLMSSYHFIDPEDDNRINYMLKSKTSINSDQANDA
NRWLVNHTDLLDFIIDCEEAGYTVNLEWCSPKNQIVIMYPEESLKILNVRHRDTGEYYSNNSLIRSPVFRKYAVD
QPMFEEGTDVNTAISNMYNETGIEGYILVMRDGSRVKIKTTSYVARHKLKDSITNNKDLVIAVAQGVSDDLRQLF
LDDSLSLTKIQEFEDHVVSVAGSTYTKIREAHKACAGMERREYAISMQNTFKQDRMFFNIVMKMFQAPDLEVMP
EIMSVIIKYPDEFVPTKWK

SEQ ID NO: 74
MEKLYYNLLSLCKSSSDRKFFYSDDVSPIGKKYRIFSYNFASYSDWLLPDALECRGIMFEMDGETPLRIASRPMEK
FFNLNENPFTLSIDLNDVKYLMTKEDGSLVSTYLDGNMVRFKSKGSIKSDQAASATSILLDINHKDLADRLLELCN
DGFTANFEYVAPSNKIVLTYPEKRLILLNIRDNNTGKYIEYDDIYLDPVFRKYLVDRFEAPEGDWVPGVKSSTNIE
GYVAVMKDGSHFKLKTDWYVALHTTRDSISSPEKLFLAIMNGASDDLKAMYADDEFSFKKVELFEKAYLDFLDRS
FYICLDAYDKHKGKDRKTYAIEAQAICKGAQSPWLFGIIMNLYQGGSKEQMMTALESVFIKNHKNFIPEGY

SEQ ID NO: 75
MNELYNNLMTLIEPGKMSRFFLRDAVTPFGTRVRMFGYNYASYTDWLLPDALEARGIMFEMDENDQPIRVMAR
PMEKFFNLGENPFTIDLDLSTIEYFMDKSDGSLISSYVDNDTLFMKSKMSIGSVQAVAARQVIQDYVHRDLHDRV
LELAKDGFTCNFEYVAPDNRVVILYPERALVLLNVRNNETGEYVHIEELKRDPVLRRYLVNNYVIDPENFDQDTFV
NDIYQMVDIEGYVFRLMTGQHVKIKTEWYKMLHYAKDTINNNEALFAITVAAQLDDVRSLYSDDYALGKINKFE
EVFLGFLDTRLPILLNLHKELNGSSRKDYAIKSQTYFKQANELYLFGIFMQMFEGVPPREQLVEKLSEAFMKNYKL
FVPPEYDKVVEYDN

SEQ ID NO: 76
MRTKQIFDDLMNLTAKNDAFMWKDFVSPAGGLFRIFSYRLASYSDFLEPNALECRGSMFKVDDEGNFVGIASRT
PMKFFNAYENPFTMYDKDTLSSEIAVVMDKLDGSIISTFMDVDFVVRTKSHASLHSDHAYNSTAMLIADKELYNE
VHYAESMGYTVNMEYTSPEYRIVLPYQEDNLTVLNLRHRETGELLIGERLKEFSKILYERSVFAKHGEIDATFPMK
ETLKESIDAVRGMADIEGYVLILKDGRMCKIKTDWYCALHFTKDSINVDSRLYDAIITGASDDLKQMFSTDLYAM
KKIEKMEQLIFSCYNKLVHDVESFYEENKHLERKEYALKVQSTLPNELGMPGLAFSLYASKPVDYKGQMLKYMKD
VLVNFEV

-continued

---

SEQ ID NO Sequence Identifier

---

SEQ ID NO: 77
MQSIKELYQNLVNLCVDDNTKFFFSETVTSLGTKVRIFDYHVAGYNDWIRPDAMACRGIMFEMNGEIPVRIMSR
PMDKFFNYSEVIGWEKLETHGNMKMPDLSKIKFVIDKRDGSLISTFMDVDNLLLKSKGSIRSNQANDASVWLYQ
DDQADLLEFCRAYAKEGFTVNMEWTAPHNQIVLCYTDHQLRILNIRHNETGEYVDFAELQKDSVFRKYAADFYE
VPQDGAEWIKNVYGMTGIEGYVVVMEDYQMFKLKTDWYVALHHTKDSINDSKRLISACAENATDDLRQMFRD
DPNSLAKIEVFDAKFRDVVSSAMQALTNAYSKYKALERREYAISMTNEFKNERHWFNIAMQMFSTRPDFSLADEI
VAVIKKYPEKFVPQGY

SEQ ID NO: 78
MKELFDNLMNLCNDTDESRFFYRDDISPSGLKYRIFSYNYASYSDWLLPDALECRGIMFEMIDGVPVRIASRPME
KFFNLNETPFTMNLDLSNAVHMMKKEDGSLVSSYLDGNILRFKSKSSLKSEQAYLSSAMLTSITHEALLWRLLELA
RDGFTANFEYVSPENRIVLAYQKKDLILLNIRENDTGAYVPYNEIAKDPVLRQYLVESYEIPEGDFVSDIKAMEGIE
GYVFVMDNGLRFKLKTDWYTALHHTKDSITKNDRLFEVIVNNASDDLKGLFSNDAYSLKKINKFEEVYLDYLRRS
LSFISTSYQKLRGLDRKTYAGEAKRLADAERLPFLFTILMLMFNDSMDYDTTIKKVNELFMKNYKTFIPKEYE

SEQ ID NO: 79
MTTQELYNHLMTLTEDAEGKFFFADHISPLGEKLRVFSYHIASYSDWLLPGALEARGIMFQLDEQDKMVRIVSRP
MEKFFNLNENPFTMDLDLTTTVQLMDKADGSLISTYLTGENFALKSKTSIFSEQAVAANRYIKLPENRDLWEFCD
DLTQAGCTVNMEWCAPNNRIVLEYPEAKLVILNIRDNETGDYVSFDDIPLPALMRVKKWLVDEYDPETAHVDDF
VEKLRATKGIEGMILRLANGQSVKIKTQWYVDLHSQKDSVNVPKKLVTTILNNNHDDLYALFADDKPTIDRIREF
DSHVSKTVSASFHAVSQFYVKNRHMSRKDYAIAGQKALKPWEFGVAMIAYQKKTVEGVYEALVGAYLKRPELLIP
EKYLNEA

SEQ ID NO: 80
MNYLELKNMAENLKDSNYRSTKLNNFKFYTYIFSDYKNFKENNTFFIRGLMIDSKSILNKDTLAPGISIPMPKFFNI
NENEDWLLPDSTNLEDFTIVTKYDGSLMIPYEYDGIKFRTKMSIDNDQTKLANKYIKNNPDILDLIKNNPDTQYF
FELISPLNRIVVDYNKTELKLIAELDLRTLEFKIHETNEFNFKDLNIKTLKDLKDYINTISNYEGVILQHKVTKKVYKL
KTQEYLDLHNTMTNLDLKVIYKMILEETIDDVLPKLSPEAVAYIDSVSNSVKVKLNEILDSIDSNYIKTKDLETPAL
YIKDLNIDPIAKDCLFKLCKNKLNLDDVLNQVKKSMLKYNKLRDIKVFLKWIH

SEQ ID NO: 81
MKVIEFLKNAPSITDGLASLHLELGIKAKIYEDEGLIVLNYSQIDSPKTHPIVQECRGLIIDNDLTVVARPFDRFFNY
GEALNVMPEIDWENASIFEKVDGSLIKIYFHKGRWEVATRGTAFAESECMGHGITFKELVFNALKVHDDDGFQY
LMNNAYLFRDTTYLFELTCVENRVVRHYHGYNLHFLAARDNVSGNYSEECRDWLRSPDCILYGIVKHPKRYALG
SADEALQAAKELKNLDEGFIVYQNAVPIAKIKSPAYVAVHHIRGEGLNPKRIMELVLSGEHDEYLSYFPEDRPIIQP
YVDSLLDMLNIIAVTYPRLNQATTPKAFAAAIKHAGIDKQKASVYFMARRDNKDPVQVFHGMKTTFKMDMLRK
WMMV

SEQ ID NO: 82
MPNCRIEIRRSRMEGNLNIAMYKDLIANKLVTVKHFNGMSIIKYARKVFYENLWNEHPLLLEARGHVFDQHSGD
CIVRPFEKVFNLGENGAGSFLHPKFRVRLIEKVNGFMFSVTKHNGSLIFSTTGSLTSDYVALGQKYVSNNPDDYIA
GFTYNFEICSPDDPHIVEEEEGAYLIGIRDIFTGGQLSEYILDSHALGVTDHSSVKILRPEHIECSWEHAKGLLSSC
EKEGYMVQTGLGTVKCKSTHYLGKKFIMRMGSKKVNSMYQDPAGFKQTLDEEFYPLVDFLVNEVEEVRFTEMT
DAQRRLLIETYFDMARI

SEQ ID NO: 83
MKSRILEFIKNNPDTWEEKLNEKFIRTNHNGDLVCFKYATEADFSDPLVCEARGIIIDVAQLVVVCWPFDKFFNV
QEKYAADIDWNSARVLEKIDGSMIKLFWYKGAWRFATSSTCDAKDAAIPGYNELTYADIIARAENVNEIPFEELN
KDYTYIFELVSPLSQIVVRYEMTELFFLTARNNLTGEELDTELLQFRRPRSFALKSMNECLDAALALNKGDEIEDE
GFVVVDEKHNRVKIKSPAYVAMHRLSTNKVFTVKRMAEFFCNGEDLSKLAKDFPANAHIIKYYDWQFAEMKHKA
EDMMLYSRRLYEEYDHDRKAVAMTIKDSPYAWAGFRAIGNDKDITDIMAVLAPANVEKLIVEYPEISN

SEQ ID NO: 84
ACUCCUCGGU

SEQ ID NO: 85
ACUCCUCGGUA

SEQ ID NO: 86
ACTCATCGAT

SEQ ID NO: 87
ACTCATCGATA

SEQ ID NO: 88
MSRTIELFNNLMSVVEKSEKGNFYFKDVITSMGTKARIFSHKIASYTDWLQDDALECRGIMFELNDKNEPVRIMA
RPMQKFFNLKENPMTIGLDLTKMIGLMEKADGSLISSYHDQGYVYLKSKTSIFSDQANKAMALLNSPAYEKLRDA
IVRAGSDFTFNMEYVGPSNRVVLPYEEEELIVLNVRHNETGQYVEFSTLLDDPLIRHRMIGVYPCPDWSKVTPEE
WEAATRAETDIEGVIGIMPDGQLFKLKTDWYSSLGRTKFSINNNKALHQSIKERASVALRGMFSDDNAALAKIEA
FESAYIDTVAKYHKICAEVFLRFARFLIVEVFAIEAQARMKDCRYLFSIVMQQYGRDWDGELAVEKIEEHIIKEYAT
YVPMAYR

SEQ ID NO: 89
MSRTIELFNNLMSVVEKSEKGNFYFKDVITSMGTKARIFSHQIASYTDWLQDDALECRGIMFELNDKNEPVRIMA
RPMQKFFNLKENPMTIGLDLTKMIGLMEKADGSLISSYHDQGYVYLKSKTSIFSDQANKAMALLNSPAYEKLRDA
IVRAGSDFTFNMEYVGPSNRVVLPYEEEELIVLNVRHNETGQYVEFSTLLDDPLIRHRMIGVYPCPDWSKVTPEE
WEAATRAETDIEGVIGIMPDGQLFKLKTDWYSSLGRTKFSINNNKALHQSIKERASGALRGMFSDDNAALAKIEA

SEQ ID NO  Sequence Identifier

FESAYIDTVAKYHKICAEVFLRFARFLIVEVFAIEAQARMKDCRYLFSIVMQQYGRDWDGELAVEKIEEHIIKEYAT
YVPMAYR

SEQ ID NO: 90
MSRTIELFNNLMSVVEKSEKGNFYFKDVITSMGTKARIFSYFIASYTDWLQDDALECRGIMFELNDKNEPVRIMA
RPMQKFFNLKENPMTIGLDLTKMIGLMEKADGSLISSYHDQGYVYLKSKTSIFSDQANKAMALLNSPAYEKLRDA
IVRAGSDFTFNMEYVGPSNRVVLPYEEEELIVLNVRHNETGQYVEFSTLLDDPLIRHRMIGVYPCPDWSKVTPEE
WEAATRAETDIEGVIGIMPDGQLFKLKTDWYSSLGRTKYSINNNKALNQSIKERASVALRGMFSDDNAALAKIEA
FESAYIDTVAKYHKICAEVFLRFARFLIVEVFAIEAQARMKDCRYLFSIVMQQYGRDWDGELAVEKIEEHIIKEYAT
YVPMAYR

SEQ ID NO: 91
MSRTIELFNNLMSVVEKSEKGNFYFKDVITSMGTKARIFSHNIASYTDWLQDDALECRGIMFELNDKNEPVRIMA
RPMQKFFNLKENPMTIGLDLTKMIGLMEKADGSLISSYHDQGYVYLKSKTTIFSDQANKAMALLNSPAYEKLRDA
IVRAGSDFTFNMEYVGPSNRVVLPYEEEELIVLNVRHNETGQYVEFSTLLDDPLIRHRMIGVYPCPDWSKVTPEE
WEAATRAELHDIEGVIGIMPDGQLFKLKTDWYSSLGRTKYSINNNKALHQSIKERASVDLRGMFSDDNAALAKIE
AFESAYIDTVAKYHKICAEVFLRFARFLIVEVFAIEAQARMKDCRYLFSIVMQQYGRDWDGELAVEKIEEHIIKEYA
TYVPMAYR

SEQ ID NO: 92
MSRTIELFNNLMSVVEKSEKGNFYFKDVITSMGTKARIFSHKIASYTDWLQDDALECRGIMFELNDKNEPVRIMA
RPMQKFFNLKENPMTIGLDLTKMIGLMEKADGSLISSYHDQGYVYLKSKAAIFSDQANKAMALLNSPAYEKLRDA
IVRAGSDFTFNMEYVGPSNRVVLPYEEEELIVLNVRHNETGQYVEFSTLLDDPLIRHRMIGVYPCPDWSKVTPEE
WEAATRAETDIEGVIGIMPDGQLFKLKTDWYSSLHRTKDSINNNKALFQSIKERASDDLRGMFSDDNAALAKIE
AFESAYIDTVAKYHKICAEVFLRFARFLIVEVFAIEAQARMKDCRYLFSIVMQQYGRDWDGELAVEKIEEHIIKEYA
TYVPMAYR

SEQ ID NO: 93
ACTCATCGATC

SEQ ID NO: 94
ACTCATCGATT

SEQ ID NO: 95
MEEDKAYWNKDAQDALDKQLGIKLREKQAKNVIFFLGDGMSLSTVTAARIYKGGLTGKFEREKISWEEFDFAAL
SKTYNTDKQVTDSAASATAYLTGVKTNQGVIGLDANTVRTNCSYQLDESLFTYSIAHWFQEAGRSTGVVTSTRV
THATPAGTYAHVADRDWENDSDVVHDREDPEICDDIAEQLVFREPGKNFKVIMGGGRRGFFPEEALDIEDGIPG
EREDGKHLITDWLDDKASQGATASYVWNRDDLLAVDIRNTDYLMGLFSYTHLDTVLTRDAEMDPTLPEMTKVA
IEMLTKDENGFFLLVEGGRIDHMHHANQIRQSLAETLDMEEAVSMALSMTDPEETIILVTADHGHTLTITGYADR
NTDILDFAGISDLDDRRYTILDYGSGPGYHITEDGKRYEPTEEDLKDINFRYASAAPKHSATHDGTDVGIWVNGP
FAHLFTGVYEENYIPHALAYAACVGTGRTFCD

SEQ ID NO: 96
ACTCATCGATA

SEQ ID NO: 97
ACTCATCGATAA

SEQ ID NO: 98
ACTCATCGATAA

SEQ ID NO: 99
ACTIAGACCACG

SEQ ID NO: 100
MLQMNLEELRRIQEEMSRSVVLEDLIPLEELEYVVGVDQAFISDEVVSCAVKLTFPELEVVDKAVRVEKVTFPYIPT
FLMFREGEPAVNAVKGLVDDRAAIMVDGSGIAHPRRCGLATYIALKLRKPTVGITKKRLFGEMVEVEDGLWRLLD
GSETIGYALKSCRRCKPIFISPGSYISPDSALELTRKCLKGYKLPEPIRIADKLTKEVKRELTPTSKLK

SEQ ID NO: 101
GACCACG

The invention claimed is:

1. A process for producing a single-stranded oligonucleotide product, wherein the single-stranded oligonucleotide product comprises at least one modified nucleotide residue selected from the group consisting of modification at the 2' position of the sugar moiety, modification of the nucleobase, and modification of the backbone of the nucleotide residue, wherein the process comprises:

a) providing a pool of oligonucleotides comprising segments of the single-stranded oligonucleotide product, wherein at least one segment comprises the at least one modified nucleotide residue, and wherein at least one segment is produced by enzymatic synthesis using a single-stranded ligase (ssLigase);

b) providing a template oligonucleotide having a sequence complementary to the sequence of the single-stranded oligonucleotide product, wherein the template oligonucleotide has a property that allows it to be separated from the single-stranded oligonucleotide product;

c) contacting the pool of oligonucleotides with the template oligonucleotide in conditions to allow annealing of the segments to the template oligonucleotide;

d) joining the segments by enzymatic ligation with a ligase to form the single-stranded oligonucleotide product annealed to the template oligonucleotide and impurity oligonucleotide strands annealed to the template oligonucleotide;

e) changing the conditions to denature the annealed template oligonucleotide and any impurity oligonucleotide strands, and separating the impurity oligonucleotide strands from the annealed template oligonucleotide and single-stranded oligonucleotide product;

f) changing the conditions to denature the annealed template oligonucleotide and the single-stranded oligonucleotide product, and separating the single-stranded oligonucleotide product; and g) recycling the template oligonucleotide, wherein a process for producing the at least one segment using a ssLigase comprises:

(i) adding a 3',5' nucleotide bisphosphate, having at least one phosphate oxygens substituted by sulphur, to the 3'-OH of a single-stranded oligonucleotide primer by using the ssLigase;

(ii) removing the 3'-phosphate, 3'-thiophosphate or 3'-dithiophosphate by using a phosphatase;

(iii) repeating steps (i) and (ii) to produce the segment attached to the single-stranded oligonucleotide primer;

(iv) releasing the segment from the single-stranded oligonucleotide primer by using a sequence specific endonuclease.

2. The process according to claim 1, wherein each segment is produced by enzymatic synthesis.

3. The process according to claim 1, wherein the 3',5' nucleotide bisphosphate is selected from the group consisting of a 3',5' bisthiophosphate, a 3'-phosphate-5'-thiophosphate, a 3'-thiophosphate-5'-phosphate, a 3',5' bisdithiophosphate, a 3'-phosphate-5'-dithiophosphate, and a 3'-dithiophosphate-5'-phosphate.

4. The process according to claim 1, wherein at least one segment is produced using a transferase.

5. The process according to claim 4, wherein the process for producing the segment using a transferase comprises:

(i) adding a nucleotide-5'-triphosphate, alpha-thiotriphosphate or alphadithiotriphosphate, which has a protecting group on its 3'-OH, to the 3'-OH of a single-stranded oligonucleotide primer, by using a transferase;

(ii) deprotecting the 3'-position to regenerate the 3'-OH;

(iii) repeating steps (i) and (ii) to produce the segment attached to the single-stranded oligonucleotide primer; and (iv) releasing the segment from the single-stranded oligonucleotide primer by using a sequence specific endonuclease.

6. The process according to claim 1, wherein each segment is produced by enzymatic synthesis using a ssLigase.

7. The process according to claim 1, wherein the process is semi-continuous or continuous.

8. The process according to claim 1, wherein the single-stranded oligonucleotide product is produced at gram or kilogram scale and/or the process is carried out in a 1 L or larger reactor.

9. The process according to claim 1, whereby the denaturing results from a temperature increase, a change in pH, or a change in salt concentration in a buffering solution.

10. The process according to claim 9, wherein the process includes two steps of increasing the temperature: i) to denature annealed template oligonucleotide and impurity oligonucleotide strands and ii) to denature annealed template oligonucleotide and single stranded oligonucleotide product.

11. The process according to claim 1, wherein each segment is independently 3 to 15 nucleotides long.

12. The process according to claim 1, wherein the single-stranded oligonucleotide product is 10 to 200 nucleotides long.

13. The process according to claim 12, wherein the single-stranded oligonucleotide product is 20 nucleotides long and comprises three segments comprising:

(i) a 5' segment that is 7 nucleotides long, a central segment that is 6 nucleotides long and a 3' segment that is 7 nucleotides long;

(ii) a 5' segment that is 6 nucleotides long, a central segment that is 8 nucleotides long and a 3' segment that is 6 nucleotides long;

(iii) a 5' segment that is 5 nucleotides long, a central segment that is 10 nucleotides long and a 3' segment that is 5 nucleotides long;

(iv) a 5' segment that is 4 nucleotides long, a central segment that is 12 nucleotides long and a 3' segment that is 4 nucleotides long; or (v) a 5' segment that is 3 nucleotides long, a central segment that is 14 nucleotides long and a 3' segment that is 3 nucleotides long.

14. The process according to claim 12, wherein the single-stranded oligonucleotide product is 20-30 nucleotides long.

15. The process according to claim 1, wherein the template oligonucleotide is attached to a support material.

16. The process according to claim 15, wherein multiple, repeated copies of the template oligonucleotide are attached via a single attachment point to the support material.

17. The process according to claim 15, wherein the template oligonucleotide is attached to the support material at multiple attachment points.

18. The process according to claim 15, wherein the support material is selected from the group consisting of polyethylene glycol, an organic polymer, DNA, a protein, a dendrimer, a polysaccharide, an oligosaccharide, and a carbohydrate.

19. The process according to claim 18, wherein the support material is polyethylene glycol.

20. The process according to claim 15, wherein the support material is selected from the group consisting of a glass bead, a polymeric bead, a fibrous support, a membrane, a streptavidin coated bead, and cellulose, or the support material is part of the reaction vessel itself.

21. The process according to claim 1, wherein the modification is at the 2' position of the sugar moiety and the modification is selected from the group consisting of 2'-F, 2'-OMe, 2'-MOE, and 2'-amino, or wherein the oligonucleotide comprises a phosphorodiamidate morpholino oligomer (PMO), a locked nucleic acid (LNA), a peptide nucleic acid (PNA), or a bridged nucleic acid (BNA).

22. The process according to claim 1, wherein the modification is in the nucleobase and the modification is selected from the group consisting of a 5-methyl pyrimidine, a 7-deazaguanosine and an abasic nucleotide.

23. The process according to claim 1, wherein the modification is in the backbone and the modification is selected from the group consisting of phosphorothioate, phosphoramidate and phosphorodiamidate.

24. The process according to claim 1, wherein the resulting single-stranded oligonucleotide product is at least 90% pure.

25. The process according to claim 24, wherein the resulting single-stranded oligonucleotide product is at least 98% pure.

26. The process according to claim 1, wherein the single-stranded oligonucleotide product is a gapmer.

27. A process for producing a double-stranded oligonucleotide product, wherein two (2) complementary single-stranded oligonucleotides are each produced by the process according to claim 1 and are mixed under conditions to allow annealing.

28. The process according to claim 1, wherein the single-stranded oligonucleotide product is a therapeutic oligonucleotide.

29. The process according to claim 1, wherein the ssLigase is an RNA ligase.

30. The process according to claim 1, wherein the property that allows the template oligonucleotide to be separated from the single-stranded oligonucleotide product is molecular weight of the template oligonucleotide.

31. The process according to claim 30, wherein repeated copies of the template oligonucleotide are joined together to form a single oligonucleotide, with or without a linker between each copy of template oligonucleotide.

\* \* \* \* \*

SEQUENCE LISTING

<160> NUMBER OF SEQ ID NOS: 101

<210> SEQ ID NO 1
<211> LENGTH: 20
<212> TYPE: DNA
<213> ORGANISM: Artificial Sequence
<220> FEATURE:
<223> OTHER INFORMATION: Example 1 desired product oligonucleotide
      sequence ("target")

<400> SEQUENCE: 1
ggccaaacct cggcttacct                                                                    20

<210> SEQ ID NO 2
<211> LENGTH: 23
<212> TYPE: DNA
<213> ORGANISM: Artificial Sequence
<220> FEATURE:
<223> OTHER INFORMATION: Example 1-4, 6, 10 and 11 template
      oligonucleotide sequence

<400> SEQUENCE: 2
tttaggtaag ccgaggtttg gcc                                                                23

<210> SEQ ID NO 3
<211> LENGTH: 487
<212> TYPE: PRT
<213> ORGANISM: Enterobacteria phage T4

<400> SEQUENCE: 3

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

-continued

```
Glu Ile Tyr Ser Leu Pro Ala Phe Arg Leu Lys Tyr Asp Val Arg Phe
    290             295             300

Ser Lys Leu Glu Gln Met Thr Ser Gly Tyr Asp Lys Val Ile Leu Ile
305             310             315             320

Glu Asn Gln Val Val Asn Asn Leu Asp Glu Ala Lys Val Ile Tyr Lys
            325             330             335

Lys Tyr Ile Asp Gln Gly Leu Glu Gly Ile Ile Leu Lys Asn Ile Asp
            340             345             350

Gly Leu Trp Glu Asn Ala Arg Ser Lys Asn Leu Tyr Lys Phe Lys Glu
        355             360             365

Val Ile Asp Val Asp Leu Lys Ile Val Gly Ile Tyr Pro His Arg Lys
    370             375             380

Asp Pro Thr Lys Ala Gly Gly Phe Ile Leu Glu Ser Glu Cys Gly Lys
385             390             395             400

Ile Lys Val Asn Ala Gly Ser Gly Leu Lys Asp Lys Ala Gly Val Lys
            405             410             415

Ser His Glu Leu Asp Arg Thr Arg Ile Met Glu Asn Gln Asn Tyr Tyr
            420             425             430

Ile Gly Lys Ile Leu Glu Cys Glu Cys Asn Gly Trp Leu Lys Ser Asp
        435             440             445

Gly Arg Thr Asp Tyr Val Lys Leu Phe Leu Pro Ile Ala Ile Arg Leu
    450             455             460

Arg Glu Asp Lys Thr Lys Ala Asn Thr Phe Glu Asp Val Phe Gly Asp
465             470             475             480

Phe His Glu Val Thr Gly Leu
            485

<210> SEQ ID NO 4
<211> LENGTH: 488
<212> TYPE: PRT
<213> ORGANISM: Artificial Sequence
<220> FEATURE:
<223> OTHER INFORMATION: Wild type T4 DNA ligase protein sequence (when
      fused to CBD)

<400> SEQUENCE: 4

Gly Ser Ile Leu Lys Ile Leu Asn Glu Ile Ala Ser Ile Gly Ser Thr
1               5               10              15

Lys Gln Lys Gln Ala Ile Leu Glu Lys Asn Lys Asp Asn Glu Leu Leu
            20              25              30

Lys Arg Val Tyr Arg Leu Thr Tyr Ser Arg Gly Leu Gln Tyr Tyr Ile
        35              40              45

Lys Lys Trp Pro Lys Pro Gly Ile Ala Thr Gln Ser Phe Gly Met Leu
    50              55              60

Thr Leu Thr Asp Met Leu Asp Phe Ile Glu Phe Thr Leu Ala Thr Arg
65              70              75              80

Lys Leu Thr Gly Asn Ala Ala Ile Glu Glu Leu Thr Gly Tyr Ile Thr
            85              90              95

Asp Gly Lys Lys Asp Asp Val Glu Val Leu Arg Arg Val Met Met Arg
            100             105             110

Asp Leu Glu Cys Gly Ala Ser Val Ser Ile Ala Asn Lys Val Trp Pro
            115             120             125

Gly Leu Ile Pro Glu Gln Pro Gln Met Leu Ala Ser Ser Tyr Asp Glu
    130             135             140

Lys Gly Ile Asn Lys Asn Ile Lys Phe Pro Ala Phe Ala Gln Leu Lys
```

-continued

```
            145               150               155               160

Ala Asp Gly Ala Arg Cys Phe Ala Glu Val Arg Gly Asp Glu Leu Asp
                        165               170               175

Asp Val Arg Leu Leu Ser Arg Ala Gly Asn Glu Tyr Leu Gly Leu Asp
                        180               185               190

Leu Leu Lys Glu Glu Leu Ile Lys Met Thr Ala Glu Ala Arg Gln Ile
                        195               200               205

His Pro Glu Gly Val Leu Ile Asp Gly Glu Leu Val Tyr His Glu Gln
                210               215               220

Val Lys Lys Glu Pro Glu Gly Leu Asp Phe Leu Phe Asp Ala Tyr Pro
        225               230               235               240

Glu Asn Ser Lys Ala Lys Glu Phe Ala Glu Val Ala Glu Ser Arg Thr
                        245               250               255

Ala Ser Asn Gly Ile Ala Asn Lys Ser Leu Lys Gly Thr Ile Ser Glu
                        260               265               270

Lys Glu Ala Gln Cys Met Lys Phe Gln Val Trp Asp Tyr Val Pro Leu
                        275               280               285

Val Glu Ile Tyr Ser Leu Pro Ala Phe Arg Leu Lys Tyr Asp Val Arg
                290               295               300

Phe Ser Lys Leu Glu Gln Met Thr Ser Gly Tyr Asp Lys Val Ile Leu
        305               310               315               320

Ile Glu Asn Gln Val Val Asn Asn Leu Asp Glu Ala Lys Val Ile Tyr
                        325               330               335

Lys Lys Tyr Ile Asp Gln Gly Leu Glu Gly Ile Ile Leu Lys Asn Ile
                        340               345               350

Asp Gly Leu Trp Glu Asn Ala Arg Ser Lys Asn Leu Tyr Lys Phe Lys
                        355               360               365

Glu Val Ile Asp Val Asp Leu Lys Ile Val Gly Ile Tyr Pro His Arg
                370               375               380

Lys Asp Pro Thr Lys Ala Gly Gly Phe Ile Leu Glu Ser Glu Cys Gly
        385               390               395               400

Lys Ile Lys Val Asn Ala Gly Ser Gly Leu Lys Asp Lys Ala Gly Val
                        405               410               415

Lys Ser His Glu Leu Asp Arg Thr Arg Ile Met Glu Asn Gln Asn Tyr
                        420               425               430

Tyr Ile Gly Lys Ile Leu Glu Cys Glu Cys Asn Gly Trp Leu Lys Ser
                        435               440               445

Asp Gly Arg Thr Asp Tyr Val Lys Leu Phe Leu Pro Ile Ala Ile Arg
                450               455               460

Leu Arg Glu Asp Lys Thr Lys Ala Asn Thr Phe Glu Asp Val Phe Gly
        465               470               475               480

Asp Phe His Glu Val Thr Gly Leu
                        485
```

```
<210> SEQ ID NO 5
<211> LENGTH: 20
<212> TYPE: RNA
<213> ORGANISM: Artificial Sequence
<220> FEATURE:
<223> OTHER INFORMATION: Example 2 target sequence

<400> SEQUENCE: 5
ggccaaaccu cggcuuaccu                                                    20

<210> SEQ ID NO 6
```

-continued

```
<211> LENGTH: 482
<212> TYPE: PRT
<213> ORGANISM: Unknown
<220> FEATURE:
<223> OTHER INFORMATION: Description of Unknown:
      Enterobacteria phase CC31

<400> SEQUENCE: 6

Met Ile Leu Asp Ile Ile Asn Glu Ile Ala Ser Ile Gly Ser Thr Lys
1               5                   10                  15

Glu Lys Glu Ala Ile Ile Arg Arg His Lys Asp Asn Glu Leu Leu Lys
            20                  25                  30

Arg Val Phe Arg Met Thr Tyr Asp Gly Lys Leu Gln Tyr Tyr Ile Lys
        35                  40                  45

Lys Trp Asp Thr Arg Pro Lys Gly Asp Ile His Leu Thr Leu Glu Asp
    50                  55                  60

Met Leu Tyr Leu Leu Glu Glu Lys Leu Ala Lys Arg Val Val Thr Gly
65                  70                  75                  80

Asn Ala Ala Lys Glu Lys Leu Glu Ile Ala Leu Ser Gln Thr Ser Asp
                85                  90                  95

Ala Asp Ala Glu Val Val Lys Lys Val Leu Leu Arg Asp Leu Arg Cys
            100                 105                 110

Gly Ala Ser Arg Ser Ile Ala Asn Lys Val Trp Lys Asn Leu Ile Pro
        115                 120                 125

Glu Gln Pro Gln Met Leu Ala Ser Ser Tyr Asp Glu Lys Gly Ile Glu
    130                 135                 140

Lys Asn Ile Lys Phe Pro Ala Phe Ala Gln Leu Lys Ala Asp Gly Ala
145                 150                 155                 160

Arg Ala Phe Ala Glu Val Arg Gly Asp Glu Leu Asp Asp Val Lys Ile
            165                 170                 175

Leu Ser Arg Ala Gly Asn Glu Tyr Leu Gly Leu Asp Leu Leu Lys Gln
            180                 185                 190

Gln Leu Ile Glu Met Thr Lys Glu Ala Arg Glu Arg His Pro Gly Gly
        195                 200                 205

Val Met Ile Asp Gly Glu Leu Val Tyr His Ala Ser Thr Leu Pro Ala
    210                 215                 220

Gly Pro Leu Asp Asp Ile Phe Gly Asp Leu Pro Glu Leu Ser Lys Ala
225                 230                 235                 240

Lys Glu Phe Lys Glu Glu Ser Arg Thr Met Ser Asn Gly Leu Ala Asn
            245                 250                 255

Lys Ser Leu Lys Gly Thr Ile Ser Ala Lys Glu Ala Ala Gly Met Lys
        260                 265                 270

Phe Gln Val Trp Asp Tyr Val Pro Leu Asp Val Val Tyr Ser Glu Gly
        275                 280                 285

Lys Gln Ser Gly Phe Ala Tyr Asp Val Arg Phe Arg Ala Leu Glu Leu
    290                 295                 300

Met Val Gln Gly Tyr Ser Gln Met Ile Leu Ile Glu Asn His Ile Val
305                 310                 315                 320

His Asn Leu Asp Glu Ala Lys Val Ile Tyr Arg Lys Tyr Val Asp Glu
            325                 330                 335

Gly Leu Glu Gly Ile Ile Leu Lys Asn Ile Gly Ala Phe Trp Glu Asn
        340                 345                 350

Thr Arg Ser Lys Asn Leu Tyr Lys Phe Lys Glu Val Ile Thr Ile Asp
        355                 360                 365

Leu Arg Ile Val Asp Ile Tyr Glu His Ser Lys Gln Pro Gly Lys Ala
```

```
        370              375              380
Gly Gly Phe Tyr Leu Glu Ser Glu Cys Gly Leu Ile Lys Val Lys Ala
385              390              395              400

Gly Ser Gly Leu Lys Asp Lys Pro Gly Lys Asp Ala His Glu Leu Asp
            405              410              415

Arg Thr Arg Ile Trp Glu Asn Lys Asn Asp Tyr Ile Gly Gly Val Leu
            420              425              430

Glu Ser Glu Cys Asn Gly Trp Leu Ala Ala Glu Gly Arg Thr Asp Tyr
            435              440              445

Val Lys Leu Phe Leu Pro Ile Ala Ile Lys Met Arg Arg Asp Lys Asp
            450              455              460

Val Ala Asn Thr Phe Ala Asp Ile Trp Gly Asp Phe His Glu Val Thr
465              470              475              480

Gly Leu

<210> SEQ ID NO 7
<211> LENGTH: 483
<212> TYPE: PRT
<213> ORGANISM: Artificial Sequence
<220> FEATURE:
<223> OTHER INFORMATION: Wild-type Enterobacteria phage CC31 DNA ligase
      protein sequence (when fused to CBD)

<400> SEQUENCE: 7

Gly Ser Ile Leu Asp Ile Ile Asn Glu Ile Ala Ser Ile Gly Ser Thr
1               5                10               15

Lys Glu Lys Glu Ala Ile Ile Arg Arg His Lys Asp Asn Glu Leu Leu
            20               25               30

Lys Arg Val Phe Arg Met Thr Tyr Asp Gly Lys Leu Gln Tyr Tyr Ile
        35               40               45

Lys Lys Trp Asp Thr Arg Pro Lys Gly Asp Ile His Leu Thr Leu Glu
    50               55               60

Asp Met Leu Tyr Leu Leu Glu Glu Lys Leu Ala Lys Arg Val Val Thr
65               70               75               80

Gly Asn Ala Ala Lys Glu Lys Leu Glu Ile Ala Leu Ser Gln Thr Ser
            85               90               95

Asp Ala Asp Ala Glu Val Val Lys Lys Val Leu Leu Arg Asp Leu Arg
            100              105              110

Cys Gly Ala Ser Arg Ser Ile Ala Asn Lys Val Trp Lys Asn Leu Ile
        115              120              125

Pro Glu Gln Pro Gln Met Leu Ala Ser Ser Tyr Asp Glu Lys Gly Ile
    130              135              140

Glu Lys Asn Ile Lys Phe Pro Ala Phe Ala Gln Leu Lys Ala Asp Gly
145              150              155              160

Ala Arg Ala Phe Ala Glu Val Arg Gly Asp Glu Leu Asp Asp Val Lys
            165              170              175

Ile Leu Ser Arg Ala Gly Asn Glu Tyr Leu Gly Leu Asp Leu Leu Lys
            180              185              190

Gln Gln Leu Ile Glu Met Thr Lys Glu Ala Arg Glu Arg His Pro Gly
        195              200              205

Gly Val Met Ile Asp Gly Glu Leu Val Tyr His Ala Ser Thr Leu Pro
    210              215              220

Ala Gly Pro Leu Asp Asp Ile Phe Gly Asp Leu Pro Glu Leu Ser Lys
225              230              235              240

Ala Lys Glu Phe Lys Glu Glu Ser Arg Thr Met Ser Asn Gly Leu Ala
```

-continued

```
                    245               250               255

Asn Lys Ser Leu Lys Gly Thr Ile Ser Ala Lys Glu Ala Ala Gly Met
            260               265               270

Lys Phe Gln Val Trp Asp Tyr Val Pro Leu Asp Val Val Tyr Ser Glu
            275               280               285

Gly Lys Gln Ser Gly Phe Ala Tyr Asp Val Arg Phe Arg Ala Leu Glu
            290               295               300

Leu Met Val Gln Gly Tyr Ser Gln Met Ile Leu Ile Glu Asn His Ile
305               310               315               320

Val His Asn Leu Asp Glu Ala Lys Val Ile Tyr Arg Lys Tyr Val Asp
                325               330               335

Glu Gly Leu Glu Gly Ile Ile Leu Lys Asn Ile Gly Ala Phe Trp Glu
            340               345               350

Asn Thr Arg Ser Lys Asn Leu Tyr Lys Phe Lys Glu Val Ile Thr Ile
            355               360               365

Asp Leu Arg Ile Val Asp Ile Tyr Glu His Ser Lys Gln Pro Gly Lys
            370               375               380

Ala Gly Gly Phe Tyr Leu Glu Ser Glu Cys Gly Leu Ile Lys Val Lys
385               390               395               400

Ala Gly Ser Gly Leu Lys Asp Lys Pro Gly Lys Asp Ala His Glu Leu
                405               410               415

Asp Arg Thr Arg Ile Trp Glu Asn Lys Asn Asp Tyr Ile Gly Gly Val
                420               425               430

Leu Glu Ser Glu Cys Asn Gly Trp Leu Ala Ala Glu Gly Arg Thr Asp
            435               440               445

Tyr Val Lys Leu Phe Leu Pro Ile Ala Ile Lys Met Arg Arg Asp Lys
            450               455               460

Asp Val Ala Asn Thr Phe Ala Asp Ile Trp Gly Asp Phe His Glu Val
465               470               475               480

Thr Gly Leu

<210> SEQ ID NO 8
<211> LENGTH: 497
<212> TYPE: PRT
<213> ORGANISM: Unknown
<220> FEATURE:
<223> OTHER INFORMATION: Description of Unknown:
      Shigella phage Shf125875

<400> SEQUENCE: 8

Met Ile Leu Asp Ile Leu Asn Gln Ile Ala Ala Ile Gly Ser Thr Lys
1               5                10               15

Thr Lys Gln Glu Ile Leu Lys Lys Asn Lys Asp Asn Lys Leu Leu Glu
            20               25               30

Arg Val Tyr Arg Leu Thr Tyr Ala Arg Gly Ile Gln Tyr Tyr Ile Lys
            35               40               45

Lys Trp Pro Gly Pro Gly Glu Arg Ser Gln Ala Tyr Gly Leu Leu Glu
            50               55               60

Leu Asp Asp Met Leu Asp Phe Ile Glu Phe Thr Leu Ala Thr Arg Lys
65               70               75               80

Leu Thr Gly Asn Ala Ala Ile Lys Glu Leu Met Gly Tyr Ile Ala Asp
                85               90               95

Gly Lys Pro Asp Asp Val Glu Val Leu Arg Arg Val Met Met Arg Asp
            100               105               110

Leu Glu Val Gly Ala Ser Val Ser Ile Ala Asn Lys Val Trp Pro Gly
```

-continued

```
            115                 120                 125

Leu Ile Gln Leu Gln Pro Gln Met Leu Ala Ser Ala Tyr Asp Glu Lys
    130                 135                 140

Leu Ile Thr Lys Asn Ile Lys Trp Pro Ala Phe Ala Gln Leu Lys Ala
145                 150                 155                 160

Asp Gly Ala Arg Cys Phe Ala Glu Val Arg Asp Asp Gly Val Gln Phe
                165                 170                 175

Phe Ser Arg Ala Gly Asn Glu Tyr His Gly Leu Thr Leu Leu Ala Asp
                180                 185                 190

Glu Leu Met Glu Met Thr Lys Glu Ala Arg Glu Arg His Pro Asn Gly
                195                 200                 205

Val Leu Ile Asp Gly Glu Leu Val Tyr His Ser Phe Asp Ile Lys Lys
    210                 215                 220

Ala Val Ser Ser Gly Asn Asp Leu Ser Phe Leu Phe Gly Asp Asn Glu
225                 230                 235                 240

Glu Ser Glu Glu Val Gln Val Ala Asp Arg Ser Thr Ser Asn Gly Leu
                245                 250                 255

Ala Asn Lys Ser Leu Gln Gly Thr Ile Ser Pro Lys Glu Ala Glu Gly
                260                 265                 270

Met Val Leu Gln Ala Trp Asp Tyr Val Pro Leu Asp Glu Val Tyr Ser
    275                 280                 285

Asp Gly Lys Ile Lys Gly Gln Lys Tyr Asp Val Arg Phe Ala Ala Leu
    290                 295                 300

Glu Asn Met Ala Glu Gly Phe Lys Arg Ile Glu Pro Ile Glu Asn Gln
305                 310                 315                 320

Leu Val His Asn Leu Asp Glu Ala Lys Val Val Tyr Lys Lys Tyr Val
                325                 330                 335

Asp Gln Gly Leu Glu Gly Ile Ile Leu Lys Asn Arg Asp Ser Tyr Trp
                340                 345                 350

Glu Asn Lys Arg Ser Lys Asn Leu Ile Lys Phe Lys Glu Val Ile Asp
                355                 360                 365

Ile Ala Leu Glu Val Val Gly Tyr Tyr Glu His Ser Lys Asp Pro Asn
    370                 375                 380

Lys Leu Gly Gly Val Glu Leu Val Ser Arg Cys Arg Arg Ile Thr Thr
385                 390                 395                 400

Asp Cys Gly Ser Gly Phe Lys Asp Thr Thr His Lys Thr Val Asp Gly
                405                 410                 415

Val Lys Val Leu Ile Pro Leu Asp Glu Arg His Asp Leu Asp Arg Glu
                420                 425                 430

Arg Leu Met Ala Glu Ala Arg Glu Gly Lys Leu Ile Gly Arg Ile Ala
    435                 440                 445

Asp Cys Glu Cys Asn Gly Trp Val His Ser Lys Gly Arg Glu Gly Thr
    450                 455                 460

Val Gly Ile Phe Leu Pro Ile Ile Lys Gly Phe Arg Phe Asp Lys Thr
465                 470                 475                 480

Glu Ala Asp Ser Phe Glu Asp Val Phe Gly Pro Trp Ser Gln Thr Gly
                485                 490                 495

Leu
```

<210> SEQ ID NO 9
<211> LENGTH: 498
<212> TYPE: PRT
<213> ORGANISM: Artificial Sequence
<220> FEATURE:

-continued

<223> OTHER INFORMATION: Wild-type Shigella phage Shf125875 DNA ligase
        protein sequence (when fused to CBD)

<400> SEQUENCE: 9

Gly Ser Ile Leu Asp Ile Leu Asn Gln Ile Ala Ala Ile Gly Ser Thr
1               5                   10                  15

Lys Thr Lys Gln Glu Ile Leu Lys Lys Asn Lys Asp Asn Lys Leu Leu
            20                  25                  30

Glu Arg Val Tyr Arg Leu Thr Tyr Ala Arg Gly Ile Gln Tyr Tyr Ile
            35                  40                  45

Lys Lys Trp Pro Gly Pro Gly Glu Arg Ser Gln Ala Tyr Gly Leu Leu
        50                  55                  60

Glu Leu Asp Asp Met Leu Asp Phe Ile Glu Phe Thr Leu Ala Thr Arg
65                  70                  75                  80

Lys Leu Thr Gly Asn Ala Ala Ile Lys Glu Leu Met Gly Tyr Ile Ala
                85                  90                  95

Asp Gly Lys Pro Asp Asp Val Glu Val Leu Arg Arg Val Met Met Arg
            100                 105                 110

Asp Leu Glu Val Gly Ala Ser Val Ser Ile Ala Asn Lys Val Trp Pro
        115                 120                 125

Gly Leu Ile Gln Leu Gln Pro Gln Met Leu Ala Ser Ala Tyr Asp Glu
        130                 135                 140

Lys Leu Ile Thr Lys Asn Ile Lys Trp Pro Ala Phe Ala Gln Leu Lys
145                 150                 155                 160

Ala Asp Gly Ala Arg Cys Phe Ala Glu Val Arg Asp Asp Gly Val Gln
                165                 170                 175

Phe Phe Ser Arg Ala Gly Asn Glu Tyr His Gly Leu Thr Leu Leu Ala
            180                 185                 190

Asp Glu Leu Met Glu Met Thr Lys Glu Ala Arg Glu Arg His Pro Asn
            195                 200                 205

Gly Val Leu Ile Asp Gly Glu Leu Val Tyr His Ser Phe Asp Ile Lys
        210                 215                 220

Lys Ala Val Ser Ser Gly Asn Asp Leu Ser Phe Leu Phe Gly Asp Asn
225                 230                 235                 240

Glu Glu Ser Glu Glu Val Gln Val Ala Asp Arg Ser Thr Ser Asn Gly
                245                 250                 255

Leu Ala Asn Lys Ser Leu Gln Gly Thr Ile Ser Pro Lys Glu Ala Glu
            260                 265                 270

Gly Met Val Leu Gln Ala Trp Asp Tyr Val Pro Leu Asp Glu Val Tyr
        275                 280                 285

Ser Asp Gly Lys Ile Lys Gly Gln Lys Tyr Asp Val Arg Phe Ala Ala
        290                 295                 300

Leu Glu Asn Met Ala Glu Gly Phe Lys Arg Ile Glu Pro Ile Glu Asn
305                 310                 315                 320

Gln Leu Val His Asn Leu Asp Glu Ala Lys Val Val Tyr Lys Lys Tyr
                325                 330                 335

Val Asp Gln Gly Leu Glu Gly Ile Ile Leu Lys Asn Arg Asp Ser Tyr
            340                 345                 350

Trp Glu Asn Lys Arg Ser Lys Asn Leu Ile Lys Phe Lys Glu Val Ile
            355                 360                 365

Asp Ile Ala Leu Glu Val Val Gly Tyr Tyr Glu His Ser Lys Asp Pro
        370                 375                 380

Asn Lys Leu Gly Gly Val Glu Leu Val Ser Arg Cys Arg Arg Ile Thr
385                 390                 395                 400

```
Thr Asp Cys Gly Ser Gly Phe Lys Asp Thr Thr His Lys Thr Val Asp
                405             410             415

Gly Val Lys Val Leu Ile Pro Leu Asp Glu Arg His Asp Leu Asp Arg
                420             425             430

Glu Arg Leu Met Ala Glu Ala Arg Glu Gly Lys Leu Ile Gly Arg Ile
                435             440             445

Ala Asp Cys Glu Cys Asn Gly Trp Val His Ser Lys Gly Arg Glu Gly
                450             455             460

Thr Val Gly Ile Phe Leu Pro Ile Ile Lys Gly Phe Arg Phe Asp Lys
    465             470             475             480

Thr Glu Ala Asp Ser Phe Glu Asp Val Phe Gly Pro Trp Ser Gln Thr
                485             490             495

Gly Leu

<210> SEQ ID NO 10
<211> LENGTH: 487
<212> TYPE: PRT
<213> ORGANISM: Artificial Sequence
<220> FEATURE:
<223> OTHER INFORMATION: Mutant ligase (T4 backbone) protein sequence

<400> SEQUENCE: 10

Met Ile Leu Lys Ile Leu Asn Glu Ile Ala Ser Ile Gly Ser Thr Lys
1               5               10              15

Gln Lys Gln Ala Ile Leu Glu Lys Asn Lys Asp Asn Glu Leu Leu Lys
                20              25              30

Arg Val Tyr Arg Leu Thr Tyr Ser Arg Gly Leu Gln Tyr Tyr Ile Lys
                35              40              45

Lys Trp Pro Lys Pro Gly Ile Ala Thr Gln Ser Phe Gly Met Leu Thr
    50              55              60

Leu Thr Asp Met Leu Asp Phe Ile Glu Phe Thr Leu Ala Thr Arg Lys
65              70              75              80

Leu Thr Gly Asn Ala Ala Ile Glu Glu Leu Thr Gly Tyr Ile Thr Asp
                85              90              95

Gly Lys Lys Asp Asp Val Glu Val Leu Arg Arg Val Met Met Arg Asp
                100             105             110

Leu Glu Cys Gly Ala Ser Val Ser Ile Ala Asn Lys Val Trp Pro Gly
                115             120             125

Leu Ile Pro Glu Gln Pro Gln Met Leu Ala Ser Ser Tyr Asp Glu Lys
    130             135             140

Gly Ile Asn Lys Asn Ile Lys Phe Pro Ala Phe Ala Gln Leu Lys Ala
145             150             155             160

Asp Gly Ala Arg Cys Phe Ala Glu Val Arg Gly Asp Glu Leu Asp Asp
                165             170             175

Val Arg Leu Leu Ser Arg Ala Gly Asn Glu Tyr Leu Gly Leu Asp Leu
                180             185             190

Leu Lys Glu Glu Leu Ile Lys Met Thr Ala Glu Ala Arg Gln Ile His
                195             200             205

Pro Glu Gly Val Leu Ile Asp Gly Glu Leu Val Tyr His Glu Gln Val
    210             215             220

Lys Lys Glu Pro Glu Gly Leu Asp Phe Leu Phe Asp Ala Tyr Pro Glu
225             230             235             240

Asn Ser Lys Ala Lys Glu Phe Ala Glu Val Ala Glu Ser Arg Thr Ala
                245             250             255
```

-continued

```
Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
            275                 280                 285

Glu Ile Tyr Ser Leu Pro Ala Phe Arg Leu Lys Tyr Asp Val Arg Phe
            290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
            325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Arg
            355                 360                 365

Val Ile Asp Val Asp Leu Lys Ile Val Gly Ile Tyr Pro His Arg Lys
            370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
            405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
            435                 440                 445

Gly Arg Thr Asp Tyr Val Lys Leu Phe Leu Pro Ile Ala Ile Arg Leu
            450                 455                 460

Arg Glu Asp Lys Thr Lys Ala Asn Thr Phe Glu Asp Val Phe Gly Asp
465                 470                 475                 480

Phe His Glu Val Thr Gly Leu
            485
```

```
<210> SEQ ID NO 11
<211> LENGTH: 487
<212> TYPE: PRT
<213> ORGANISM: Artificial Sequence
<220> FEATURE:
<223> OTHER INFORMATION: Mutant ligase (T4 backbone) protein sequence

<400> SEQUENCE: 11

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
            50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
            85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
            115                 120                 125
```

-continued

```
Leu Ile Pro Glu Gln Pro Gln Met Leu Ala Ser Ser Tyr Asp Glu Lys
    130             135                 140

Gly Ile Asn Lys Asn Ile Lys Phe Pro Ala Phe Ala Gln Leu Lys Ala
145             150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
                180                 185                 190

Leu Lys Glu Glu Leu Ile Lys Met Thr Ala Glu Ala Arg Gln Ile His
            195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
                260                 265                 270

Glu Ala Gln Cys Met Lys Phe Gln Val Trp Asp Tyr Val Pro Leu Val
            275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
                340                 345                 350

Gly Leu Trp Glu Asn Ala Arg Ser Lys Asn Leu Tyr Lys Phe Lys Gly
            355                 360                 365

Val Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
                420                 425                 430

Ile Gly Lys Ile Leu Glu Cys Glu Cys Asn Gly Trp Leu Lys Ser Asp
            435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485
```

<210> SEQ ID NO 12
<211> LENGTH: 487
<212> TYPE: PRT
<213> ORGANISM: Artificial Sequence
<220> FEATURE:
<223> OTHER INFORMATION: Mutant ligase (T4 backbone) protein sequence

<400> SEQUENCE: 12

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
        50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
        130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
            195                 200                 205

Pro Glu Gly Val Leu Ile Asp Gly Glu Leu Val Tyr His Glu Gln Val
        210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
                260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
        290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Lys
            355                 360                 365

Val Ile Asp Val Asp Leu Lys Ile Val Gly Ile Tyr Pro His Arg Lys
        370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
```

-continued

```
              420             425             430

Ile Gly Lys Ile Leu Glu Cys Glu Cys Asn Gly Trp Leu Lys Ser Asp
        435             440             445

Gly Arg Thr Asp Tyr Val Lys Leu Phe Leu Pro Ile Ala Ile Arg Leu
        450             455             460

Arg Glu Asp Lys Thr Lys Ala Asn Thr Phe Glu Asp Val Phe Gly Asp
465             470             475             480

Phe His Glu Val Thr Gly Leu
                485

<210> SEQ ID NO 13
<211> LENGTH: 487
<212> TYPE: PRT
<213> ORGANISM: Artificial Sequence
<220> FEATURE:
<223> OTHER INFORMATION: Mutant ligase (T4 backbone) protein sequence

<400> SEQUENCE: 13

Met Ile Leu Lys Ile Leu Asn Glu Ile Ala Ser Ile Gly Ser Thr Lys
1               5               10              15

Gln Lys Gln Ala Ile Leu Glu Lys Asn Lys Asp Asn Glu Leu Leu Lys
                20              25              30

Arg Val Tyr Arg Leu Thr Tyr Ser Arg Gly Leu Gln Tyr Tyr Ile Lys
        35              40              45

Lys Trp Pro Lys Pro Gly Ile Ala Thr Gln Ser Phe Gly Met Leu Thr
        50              55              60

Leu Thr Asp Met Leu Asp Phe Ile Glu Phe Thr Leu Ala Thr Arg Lys
65              70              75              80

Leu Thr Gly Asn Ala Ala Ile Glu Glu Leu Thr Gly Tyr Ile Thr Asp
                85              90              95

Gly Lys Lys Asp Asp Val Glu Val Leu Arg Arg Val Met Met Arg Asp
                100             105             110

Leu Glu Cys Gly Ala Ser Val Ser Ile Ala Asn Lys Val Trp Pro Gly
        115             120             125

Leu Ile Pro Glu Gln Pro Gln Met Leu Ala Ser Ser Tyr Asp Glu Lys
        130             135             140

Gly Ile Asn Lys Asn Ile Lys Phe Pro Ala Phe Ala Gln Leu Lys Ala
145             150             155             160

Asp Gly Ala Arg Cys Phe Ala Glu Val Arg Gly Asp Glu Leu Asp Asp
                165             170             175

Val Arg Leu Leu Ser Arg Ala Gly Asn Glu Tyr Leu Gly Leu Asp Leu
                180             185             190

Leu Lys Glu Glu Leu Ile Lys Met Thr Ala Glu Ala Arg Gln Ile His
        195             200             205

Pro Glu Gly Val Leu Ile Asp Gly Glu Leu Val Tyr His Glu Gln Val
        210             215             220

Lys Lys Glu Pro Glu Gly Leu Asp Phe Leu Phe Asp Ala Tyr Pro Glu
225             230             235             240

Asn Ser Lys Ala Lys Glu Phe Ala Glu Val Ala Glu Ser Arg Thr Ala
                245             250             255

Ser Asn Gly Ile Ala Asn Lys Ser Leu Lys Gly Thr Ile Ser Glu Lys
                260             265             270

Glu Ala Gln Cys Met Lys Phe Gln Val Trp Asp Tyr Val Pro Leu Val
        275             280             285

Glu Ile Tyr Ser Leu Pro Ala Phe Arg Leu Lys Tyr Asp Val Arg Phe
```

-continued

```
            290                 295                 300
Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
                340                 345                 350

Gly Leu Trp Glu Asn Ala Arg Ser Lys Asn Leu Tyr Lys Phe Lys Glu
                355                 360                 365

Val Ile Leu Val Asp Leu Lys Ile Val Gly Ile Tyr Pro His Arg Lys
            370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
                420                 425                 430

Ile Gly Lys Ile Leu Glu Cys Glu Cys Asn Gly Trp Leu Lys Ser Asp
                435                 440                 445

Gly Arg Thr Asp Tyr Val Lys Leu Phe Leu Pro Ile Ala Ile Arg Leu
            450                 455                 460

Arg Glu Asp Lys Thr Lys Ala Asn Thr Phe Glu Asp Val Phe Gly Asp
465                 470                 475                 480

Phe His Glu Val Thr Gly Leu
                485
```

```
<210> SEQ ID NO 14
<211> LENGTH: 487
<212> TYPE: PRT
<213> ORGANISM: Artificial Sequence
<220> FEATURE:
<223> OTHER INFORMATION: Mutant ligase (T4 backbone) protein sequence

<400> SEQUENCE: 14
```

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
                20                  25                  30

Arg Val Tyr Arg Leu Thr Tyr Ser Arg Gly Leu Gln Tyr Tyr Ile Lys
                35                  40                  45

Lys Trp Pro Lys Pro Gly Ile Ala Thr Gln Ser Phe Gly Met Leu Thr
            50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
                100                 105                 110

Leu Glu Cys Gly Ala Ser Val Ser Ile Ala Asn Lys Val Trp Pro Gly
                115                 120                 125

Leu Ile Pro Glu Gln Pro Gln Met Leu Ala Ser Ser Tyr Asp Glu Lys
            130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
```

-continued

```
                165              170              175
Val Arg Leu Leu Ser Arg Ala Gly Asn Glu Tyr Leu Gly Leu Asp Leu
          180              185              190

Leu Lys Glu Glu Leu Ile Lys Met Thr Ala Glu Ala Arg Gln Ile His
          195              200              205

Pro Glu Gly Val Leu Ile Asp Gly Glu Leu Val Tyr His Glu Gln Val
210              215              220

Lys Lys Glu Pro Glu Gly Leu Asp Phe Leu Phe Asp Ala Tyr Pro Glu
225              230              235              240

Asn Ser Lys Ala Lys Glu Phe Ala Glu Val Ala Glu Ser Arg Thr Ala
          245              250              255

Ser Asn Gly Ile Ala Asn Lys Ser Leu Lys Gly Thr Ile Ser Glu Lys
          260              265              270

Glu Ala Gln Cys Met Lys Phe Gln Val Trp Asp Tyr Val Pro Leu Val
          275              280              285

Glu Ile Tyr Ser Leu Pro Ala Phe Arg Leu Lys Tyr Asp Val Arg Phe
290              295              300

Ser Lys Leu Glu Gln Met Thr Ser Gly Tyr Asp Lys Val Ile Leu Ile
305              310              315              320

Glu Asn Gln Val Val Asn Asn Leu Asp Glu Ala Lys Val Ile Tyr Lys
          325              330              335

Lys Tyr Ile Asp Gln Gly Leu Glu Gly Ile Ile Leu Lys Asn Ile Asp
          340              345              350

Gly Leu Trp Glu Asn Ala Arg Ser Lys Asn Leu Tyr Lys Phe Lys Glu
          355              360              365

Val Ile Lys Val Asp Leu Lys Ile Val Gly Ile Tyr Pro His Arg Lys
          370              375              380

Asp Pro Thr Lys Ala Gly Gly Phe Ile Leu Glu Ser Glu Cys Gly Lys
385              390              395              400

Ile Lys Val Asn Ala Gly Ser Gly Leu Lys Asp Lys Ala Gly Val Lys
          405              410              415

Ser His Glu Leu Asp Arg Thr Arg Ile Met Glu Asn Gln Asn Tyr Tyr
          420              425              430

Ile Gly Lys Ile Leu Glu Cys Glu Cys Asn Gly Trp Leu Lys Ser Asp
          435              440              445

Gly Arg Thr Asp Tyr Val Lys Leu Phe Leu Pro Ile Ala Ile Arg Leu
          450              455              460

Arg Glu Asp Lys Thr Lys Ala Asn Thr Phe Glu Asp Val Phe Gly Asp
465              470              475              480

Phe His Glu Val Thr Gly Leu
                485
```

```
<210> SEQ ID NO 15
<211> LENGTH: 487
<212> TYPE: PRT
<213> ORGANISM: Artificial Sequence
<220> FEATURE:
<223> OTHER INFORMATION: Mutant ligase (T4 backbone) protein sequence

<400> SEQUENCE: 15

Met Ile Leu Lys Ile Leu Asn Glu Ile Ala Ser Ile Gly Ser Thr Lys
1               5               10              15

Gln Lys Gln Ala Ile Leu Glu Lys Asn Lys Asp Asn Glu Leu Leu Lys
          20              25              30

Arg Val Tyr Arg Leu Thr Tyr Ser Arg Gly Leu Gln Tyr Tyr Ile Lys
```

-continued

```
                 35                      40                      45
Lys Trp Pro Lys Pro Gly Ile Ala Thr Gln Ser Phe Gly Met Leu Thr
     50                      55                      60
Leu Thr Asp Met Leu Asp Phe Ile Glu Phe Thr Leu Ala Thr Arg Lys
65                      70                      75                      80
Leu Thr Gly Asn Ala Ala Ile Glu Glu Leu Thr Gly Tyr Ile Thr Asp
                 85                      90                      95
Gly Lys Lys Asp Asp Val Glu Val Leu Arg Arg Val Met Met Arg Asp
                 100                     105                     110
Leu Glu Cys Gly Ala Ser Val Ser Ile Ala Asn Lys Val Trp Pro Gly
                 115                     120                     125
Leu Ile Pro Glu Gln Pro Gln Met Leu Ala Ser Ser Tyr Asp Glu Lys
             130                     135                     140
Gly Ile Asn Lys Asn Ile Lys Phe Pro Ala Phe Ala Gln Leu Lys Ala
145                     150                     155                     160
Asp Gly Ala Arg Cys Phe Ala Glu Val Arg Gly Asp Glu Leu Asp Asp
                 165                     170                     175
Val Arg Leu Leu Ser Arg Ala Gly Asn Glu Tyr Leu Gly Leu Asp Leu
             180                     185                     190
Leu Lys Glu Glu Leu Ile Lys Met Thr Ala Glu Ala Arg Gln Ile His
             195                     200                     205
Pro Glu Gly Val Leu Ile Asp Gly Glu Leu Val Tyr His Glu Gln Val
     210                     215                     220
Lys Lys Glu Pro Glu Gly Leu Asp Phe Leu Phe Asp Ala Tyr Pro Glu
225                     230                     235                     240
Asn Ser Lys Ala Lys Glu Phe Ala Glu Val Ala Glu Ser Arg Thr Ala
                 245                     250                     255
Ser Asn Gly Ile Ala Asn Lys Ser Leu Lys Gly Thr Ile Ser Glu Lys
                 260                     265                     270
Glu Ala Gln Cys Met Lys Phe Gln Val Trp Asp Tyr Val Pro Leu Val
                 275                     280                     285
Glu Ile Tyr Ser Leu Pro Ala Phe Arg Leu Lys Tyr Asp Val Arg Phe
     290                     295                     300
Ser Lys Leu Glu Gln Met Thr Ser Gly Tyr Asp Lys Val Ile Leu Ile
305                     310                     315                     320
Glu Asn Gln Val Val Asn Asn Leu Asp Glu Ala Lys Val Ile Tyr Lys
                 325                     330                     335
Lys Tyr Ile Asp Gln Gly Leu Glu Gly Ile Ile Leu Lys Asn Ile Asp
                 340                     345                     350
Gly Leu Trp Glu Asn Ala Arg Ser Lys Asn Leu Tyr Lys Phe Lys Glu
             355                     360                     365
Val Ile Gln Val Asp Leu Lys Ile Val Gly Ile Tyr Pro His Arg Lys
     370                     375                     380
Asp Pro Thr Lys Ala Gly Gly Phe Ile Leu Glu Ser Glu Cys Gly Lys
385                     390                     395                     400
Ile Lys Val Asn Ala Gly Ser Gly Leu Lys Asp Lys Ala Gly Val Lys
                 405                     410                     415
Ser His Glu Leu Asp Arg Thr Arg Ile Met Glu Asn Gln Asn Tyr Tyr
             420                     425                     430
Ile Gly Lys Ile Leu Glu Cys Glu Cys Asn Gly Trp Leu Lys Ser Asp
             435                     440                     445
Gly Arg Thr Asp Tyr Val Lys Leu Phe Leu Pro Ile Ala Ile Arg Leu
     450                     455                     460
```

-continued

```
Arg Glu Asp Lys Thr Lys Ala Asn Thr Phe Glu Asp Val Phe Gly Asp
465             470             475             480

Phe His Glu Val Thr Gly Leu
                485

<210> SEQ ID NO 16
<211> LENGTH: 487
<212> TYPE: PRT
<213> ORGANISM: Artificial Sequence
<220> FEATURE:
<223> OTHER INFORMATION: Mutant ligase (T4 backbone) protein sequence

<400> SEQUENCE: 16

Met Ile Leu Lys Ile Leu Asn Glu Ile Ala Ser Ile Gly Ser Thr Lys
1               5               10              15

Gln Lys Gln Ala Ile Leu Glu Lys Asn Lys Asp Asn Glu Leu Leu Lys
            20              25              30

Arg Val Tyr Arg Leu Thr Tyr Ser Arg Gly Leu Gln Tyr Tyr Ile Lys
        35              40              45

Lys Trp Pro Lys Pro Gly Ile Ala Thr Gln Ser Phe Gly Met Leu Thr
    50              55              60

Leu Thr Asp Met Leu Asp Phe Ile Glu Phe Thr Leu Ala Thr Arg Lys
65              70              75              80

Leu Thr Gly Asn Ala Ala Ile Glu Glu Leu Thr Gly Tyr Ile Thr Asp
            85              90              95

Gly Lys Lys Asp Asp Val Glu Val Leu Arg Arg Val Met Met Arg Asp
            100             105             110

Leu Glu Cys Gly Ala Ser Val Ser Ile Ala Asn Lys Val Trp Pro Gly
        115             120             125

Leu Ile Pro Glu Gln Pro Gln Met Leu Ala Ser Ser Tyr Asp Glu Lys
    130             135             140

Gly Ile Asn Lys Asn Ile Lys Phe Pro Ala Phe Ala Gln Leu Lys Ala
145             150             155             160

Asp Gly Ala Arg Cys Phe Ala Glu Val Arg Gly Asp Glu Leu Asp Asp
            165             170             175

Val Arg Leu Leu Ser Arg Ala Gly Asn Glu Tyr Leu Gly Leu Asp Leu
        180             185             190

Leu Lys Glu Glu Leu Ile Lys Met Thr Ala Glu Ala Arg Gln Ile His
        195             200             205

Pro Glu Gly Val Leu Ile Asp Gly Glu Leu Val Tyr His Glu Gln Val
    210             215             220

Lys Lys Glu Pro Glu Gly Leu Asp Phe Leu Phe Asp Ala Tyr Pro Glu
225             230             235             240

Asn Ser Lys Ala Lys Glu Phe Ala Glu Val Ala Glu Ser Arg Thr Ala
            245             250             255

Ser Asn Gly Ile Ala Asn Lys Ser Leu Lys Gly Thr Ile Ser Glu Lys
            260             265             270

Glu Ala Gln Cys Met Lys Phe Gln Val Trp Asp Tyr Val Pro Leu Val
        275             280             285

Glu Ile Tyr Ser Leu Pro Ala Phe Arg Leu Lys Tyr Asp Val Arg Phe
        290             295             300

Ser Lys Leu Glu Gln Met Thr Ser Gly Tyr Asp Lys Val Ile Leu Ile
305             310             315             320

Glu Asn Gln Val Val Asn Asn Leu Asp Glu Ala Lys Val Ile Tyr Lys
            325             330             335
```

-continued

```
Lys Tyr Ile Asp Gln Gly Leu Glu Gly Ile Ile Leu Lys Asn Ile Asp
            340             345             350

Gly Leu Trp Glu Asn Ala Arg Ser Lys Asn Leu Tyr Lys Phe Lys Glu
            355             360             365

Val Ile Val Val Asp Leu Lys Ile Val Gly Ile Tyr Pro His Arg Lys
            370             375             380

Asp Pro Thr Lys Ala Gly Gly Phe Ile Leu Glu Ser Glu Cys Gly Lys
385             390             395             400

Ile Lys Val Asn Ala Gly Ser Gly Leu Lys Asp Lys Ala Gly Val Lys
            405             410             415

Ser His Glu Leu Asp Arg Thr Arg Ile Met Glu Asn Gln Asn Tyr Tyr
            420             425             430

Ile Gly Lys Ile Leu Glu Cys Glu Cys Asn Gly Trp Leu Lys Ser Asp
            435             440             445

Gly Arg Thr Asp Tyr Val Lys Leu Phe Leu Pro Ile Ala Ile Arg Leu
            450             455             460

Arg Glu Asp Lys Thr Lys Ala Asn Thr Phe Glu Asp Val Phe Gly Asp
465             470             475             480

Phe His Glu Val Thr Gly Leu
            485
```

```
<210> SEQ ID NO 17
<211> LENGTH: 487
<212> TYPE: PRT
<213> ORGANISM: Artificial Sequence
<220> FEATURE:
<223> OTHER INFORMATION: Mutant ligase (T4 backbone) protein sequence

<400> SEQUENCE: 17
```

```
Met Ile Leu Lys Ile Leu Asn Glu Ile Ala Ser Ile Gly Ser Thr Lys
1               5               10              15

Gln Lys Gln Ala Ile Leu Glu Lys Asn Lys Asp Asn Glu Leu Leu Lys
            20              25              30

Arg Val Tyr Arg Leu Thr Tyr Ser Arg Gly Leu Gln Tyr Tyr Ile Lys
            35              40              45

Lys Trp Pro Lys Pro Gly Ile Ala Thr Gln Ser Phe Gly Met Leu Thr
            50              55              60

Leu Thr Asp Met Leu Asp Phe Ile Glu Phe Thr Leu Ala Thr Arg Lys
65              70              75              80

Leu Thr Gly Asn Ala Ala Ile Glu Glu Leu Thr Gly Tyr Ile Thr Asp
            85              90              95

Gly Lys Lys Asp Asp Val Glu Val Leu Arg Arg Val Met Met Arg Asp
            100             105             110

Leu Glu Cys Gly Ala Ser Val Ser Ile Ala Asn Lys Val Trp Pro Gly
            115             120             125

Leu Ile Pro Glu Gln Pro Gln Met Leu Ala Ser Ser Tyr Asp Glu Lys
            130             135             140

Gly Ile Asn Lys Asn Ile Lys Phe Pro Ala Phe Ala Gln Leu Lys Ala
145             150             155             160

Asp Gly Ala Arg Cys Phe Ala Glu Val Arg Gly Asp Glu Leu Asp Asp
            165             170             175

Val Arg Leu Leu Ser Arg Ala Gly Asn Glu Tyr Leu Gly Leu Asp Leu
            180             185             190

Leu Lys Glu Glu Leu Ile Lys Met Thr Ala Glu Ala Arg Gln Ile His
            195             200             205
```

-continued

```
Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
                260                 265                 270

Glu Ala Gln Cys Met Lys Phe Gln Val Trp Asp Tyr Val Pro Leu Val
            275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
                340                 345                 350

Gly Leu Trp Glu Asn Ala Arg Ser Lys Asn Leu Tyr Lys Phe Lys Glu
            355                 360                 365

Val Ile Arg Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
            435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485
```

```
<210> SEQ ID NO 18
<211> LENGTH: 487
<212> TYPE: PRT
<213> ORGANISM: Artificial Sequence
<220> FEATURE:
<223> OTHER INFORMATION: Mutant ligase (T4 backbone) protein sequence

<400> SEQUENCE: 18

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
                20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80
```

-continued

```
Leu Thr Gly Asn Ala Ala Ile Glu Glu Leu Thr Gly Tyr Ile Thr Asp
            85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
            130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
                180                 185                 190

Leu Lys Glu Glu Leu Ile Lys Met Thr Ala Glu Ala Arg Gln Ile His
            195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
                260                 265                 270

Glu Ala Gln Cys Met Lys Phe Gln Val Trp Asp Tyr Val Pro Leu Val
            275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
            355                 360                 365

Ala Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
            435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485
```

-continued

<210> SEQ ID NO 19
<211> LENGTH: 487
<212> TYPE: PRT
<213> ORGANISM: Artificial Sequence
<220> FEATURE:
<223> OTHER INFORMATION: Mutant ligase (T4 backbone) protein sequence

<400> SEQUENCE: 19

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
                20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
        50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
        130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
            195                 200                 205

Pro Glu Gly Val Leu Ile Asp Gly Glu Leu Val Tyr His Glu Gln Val
        210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
                260                 265                 270

Glu Ala Gln Cys Met Lys Phe Gln Val Trp Asp Tyr Val Pro Leu Val
            275                 280                 285

Glu Ile Tyr Ser Leu Pro Ala Phe Arg Leu Lys Tyr Asp Val Arg Phe
        290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
        355                 360                 365

-continued

```
Lys Ile Asp Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
            420                 425                 430

Ile Gly Lys Ile Leu Glu Cys Glu Cys Asn Gly Trp Leu Lys Ser Asp
            435                 440                 445

Gly Arg Thr Asp Tyr Val Lys Leu Phe Leu Pro Ile Ala Ile Arg Leu
    450                 455                 460

Arg Glu Asp Lys Thr Lys Ala Asn Thr Phe Glu Asp Val Phe Gly Asp
465                 470                 475                 480

Phe His Glu Val Thr Gly Leu
                485
```

```
<210> SEQ ID NO 20
<211> LENGTH: 487
<212> TYPE: PRT
<213> ORGANISM: Artificial Sequence
<220> FEATURE:
<223> OTHER INFORMATION: Mutant ligase (T4 backbone) protein sequence

<400> SEQUENCE: 20
```

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
                100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
            195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240
```

-continued

```
Asn Ser Lys Ala Lys Glu Phe Ala Glu Val Ala Glu Ser Arg Thr Ala
            245             250             255

Ser Asn Gly Ile Ala Asn Lys Ser Leu Lys Gly Thr Ile Ser Glu Lys
            260             265             270

Glu Ala Gln Cys Met Lys Phe Gln Val Trp Asp Tyr Val Pro Leu Val
            275             280             285

Glu Ile Tyr Ser Leu Pro Ala Phe Arg Leu Lys Tyr Asp Val Arg Phe
        290             295             300

Ser Lys Leu Glu Gln Met Thr Ser Gly Tyr Asp Lys Val Ile Leu Ile
305             310             315             320

Glu Asn Gln Val Val Asn Asn Leu Asp Glu Ala Lys Val Ile Tyr Lys
            325             330             335

Lys Tyr Ile Asp Gln Gly Leu Glu Gly Ile Ile Leu Lys Asn Ile Asp
            340             345             350

Gly Leu Trp Glu Asn Ala Arg Ser Lys Asn Leu Tyr Lys Phe Lys Arg
            355             360             365

Val Ile Val Val Asp Leu Lys Ile Val Gly Ile Tyr Pro His Arg Lys
        370             375             380

Asp Pro Thr Lys Ala Gly Gly Phe Ile Leu Glu Ser Glu Cys Gly Lys
385             390             395             400

Ile Lys Val Asn Ala Gly Ser Gly Leu Lys Asp Lys Ala Gly Val Lys
            405             410             415

Ser His Glu Leu Asp Arg Thr Arg Ile Met Glu Asn Gln Asn Tyr Tyr
            420             425             430

Ile Gly Lys Ile Leu Glu Cys Glu Cys Asn Gly Trp Leu Lys Ser Asp
            435             440             445

Gly Arg Thr Asp Tyr Val Lys Leu Phe Leu Pro Ile Ala Ile Arg Leu
        450             455             460

Arg Glu Asp Lys Thr Lys Ala Asn Thr Phe Glu Asp Val Phe Gly Asp
465             470             475             480

Phe His Glu Val Thr Gly Leu
                485
```

```
<210> SEQ ID NO 21
<211> LENGTH: 487
<212> TYPE: PRT
<213> ORGANISM: Artificial Sequence
<220> FEATURE:
<223> OTHER INFORMATION: Mutant ligase (T4 backbone) protein sequence

<400> SEQUENCE: 21

Met Ile Leu Lys Ile Leu Asn Glu Ile Ala Ser Ile Gly Ser Thr Lys
1               5               10              15

Gln Lys Gln Ala Ile Leu Glu Lys Asn Lys Asp Asn Glu Leu Leu Lys
            20              25              30

Arg Val Tyr Arg Leu Thr Tyr Ser Arg Gly Leu Gln Tyr Tyr Ile Lys
            35              40              45

Lys Trp Pro Lys Pro Gly Ile Ala Thr Gln Ser Phe Gly Met Leu Thr
        50              55              60

Leu Thr Asp Met Leu Asp Phe Ile Glu Phe Thr Leu Ala Thr Arg Lys
65              70              75              80

Leu Thr Gly Asn Ala Ala Ile Glu Glu Leu Thr Gly Tyr Ile Thr Asp
            85              90              95

Gly Lys Lys Asp Asp Val Glu Val Leu Arg Arg Val Met Met Arg Asp
            100             105             110
```

```
Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
        130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
                180                 185                 190

Leu Lys Glu Glu Leu Ile Lys Met Thr Ala Glu Ala Arg Gln Ile His
                195                 200                 205

Pro Glu Gly Val Leu Ile Asp Gly Glu Leu Val Tyr His Glu Gln Val
        210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
                260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
        290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
                340                 345                 350

Gly Leu Trp Glu Asn Ala Arg Ser Lys Asn Leu Tyr Lys Phe Lys Lys
        355                 360                 365

Val Ile Glu Val Asp Leu Lys Ile Val Gly Ile Tyr Pro His Arg Lys
        370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
                420                 425                 430

Ile Gly Lys Ile Leu Glu Cys Glu Cys Asn Gly Trp Leu Lys Ser Asp
                435                 440                 445

Gly Arg Thr Asp Tyr Val Lys Leu Phe Leu Pro Ile Ala Ile Arg Leu
        450                 455                 460

Arg Glu Asp Lys Thr Lys Ala Asn Thr Phe Glu Asp Val Phe Gly Asp
465                 470                 475                 480

Phe His Glu Val Thr Gly Leu
                485
```

<210> SEQ ID NO 22
<211> LENGTH: 487
<212> TYPE: PRT
<213> ORGANISM: Artificial Sequence
<220> FEATURE:
<223> OTHER INFORMATION: Mutant ligase (T4 backbone) protein sequence

<400> SEQUENCE: 22

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
                20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
        50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
                100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
        130                 135                 140

Gly Ile Asn Lys Asn Ile Lys Phe Pro Ala Phe Ala Gln Leu Lys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
            195                 200                 205

Pro Glu Gly Val Leu Ile Asp Gly Glu Leu Val Tyr His Glu Gln Val
        210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
            245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
            325                 330                 335

Lys Tyr Ile Asp Gln Gly Leu Glu Gly Ile Ile Leu Lys Asn Ile Asp
        340                 345                 350

Gly Leu Trp Glu Asn Ala Arg Ser Lys Asn Leu Tyr Lys Phe Lys Lys
        355                 360                 365

Val Ile His Val Asp Leu Lys Ile Val Gly Ile Tyr Pro His Arg Lys
    370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys

-continued

```
                    405               410               415

Ser His Glu Leu Asp Arg Thr Arg Ile Met Glu Asn Gln Asn Tyr Tyr
            420               425               430

Ile Gly Lys Ile Leu Glu Cys Glu Cys Asn Gly Trp Leu Lys Ser Asp
        435               440               445

Gly Arg Thr Asp Tyr Val Lys Leu Phe Leu Pro Ile Ala Ile Arg Leu
    450               455               460

Arg Glu Asp Lys Thr Lys Ala Asn Thr Phe Glu Asp Val Phe Gly Asp
465               470               475               480

Phe His Glu Val Thr Gly Leu
                485
```

<210> SEQ ID NO 23
<211> LENGTH: 482
<212> TYPE: PRT
<213> ORGANISM: Artificial Sequence
<220> FEATURE:
<223> OTHER INFORMATION: Mutant ligase (Enterobacteria phage CC31
      backbone - clone A4) protein sequence

<400> SEQUENCE: 23

```
Met Ile Leu Asp Ile Ile Asn Glu Ile Ala Ser Ile Gly Ser Thr Lys
1               5                 10                15

Glu Lys Glu Ala Ile Ile Arg Arg His Lys Asp Asn Glu Leu Leu Lys
            20                25                30

Arg Val Phe Arg Met Thr Tyr Asp Gly Lys Leu Gln Tyr Tyr Ile Lys
        35                40                45

Lys Trp Asp Thr Arg Pro Lys Gly Asp Ile His Leu Thr Leu Glu Asp
    50                55                60

Met Leu Tyr Leu Leu Glu Glu Lys Leu Ala Lys Arg Val Val Thr Gly
65                70                75                80

Asn Ala Ala Lys Glu Lys Leu Glu Ile Ala Leu Ser Gln Thr Ser Asp
            85                90                95

Ala Asp Ala Glu Val Val Lys Lys Val Leu Leu Arg Asp Leu Arg Cys
            100               105               110

Gly Ala Ser Arg Ser Ile Ala Asn Lys Val Trp Lys Asn Leu Ile Pro
        115               120               125

Glu Gln Pro Gln Met Leu Ala Ser Ser Tyr Asp Glu Lys Gly Ile Glu
    130               135               140

Lys Asn Ile Lys Phe Pro Ala Phe Ala Gln Leu Lys Ala Asp Gly Ala
145               150               155               160

Arg Ala Phe Ala Glu Val Arg Gly Asp Glu Leu Asp Asp Val Lys Ile
            165               170               175

Leu Ser Arg Ala Gly Asn Glu Tyr Leu Gly Leu Asp Leu Leu Lys Gln
            180               185               190

Gln Leu Ile Glu Met Thr Lys Glu Ala Arg Glu Arg His Pro Gly Gly
        195               200               205

Val Met Ile Asp Gly Glu Leu Val Tyr His Ala Ser Thr Leu Pro Ala
    210               215               220

Gly Pro Leu Asp Asp Ile Phe Gly Asp Leu Pro Glu Leu Ser Lys Ala
225               230               235               240

Lys Glu Phe Lys Glu Glu Ser Arg Thr Met Ser Asn Gly Leu Ala Asn
            245               250               255

Lys Ser Leu Lys Gly Thr Ile Ser Ala Lys Glu Ala Ala Gly Met Lys
        260               265               270
```

```
Phe Gln Val Trp Asp Tyr Val Pro Leu Asp Val Val Tyr Ser Glu Gly
        275             280             285

Lys Gln Ser Gly Phe Ala Tyr Asp Val Arg Phe Arg Ala Leu Glu Leu
        290             295             300

Met Val Gln Gly Tyr Ser Gln Met Ile Leu Ile Glu Asn His Ile Val
305             310             315             320

His Asn Leu Asp Glu Ala Lys Val Ile Tyr Arg Lys Tyr Val Asp Glu
                325             330             335

Gly Leu Glu Gly Ile Ile Leu Lys Asn Ile Gly Ala Phe Trp Glu Asn
            340             345             350

Thr Arg Ser Lys Asn Leu Tyr Lys Phe Lys Arg Val Ile Val Ile Asp
        355             360             365

Leu Arg Ile Val Asp Ile Tyr Glu His Ser Lys Gln Pro Gly Lys Ala
        370             375             380

Gly Gly Phe Tyr Leu Glu Ser Glu Cys Gly Leu Ile Lys Val Lys Ala
385             390             395             400

Gly Ser Gly Leu Lys Asp Lys Pro Gly Lys Asp Ala His Glu Leu Asp
                405             410             415

Arg Thr Arg Ile Trp Glu Asn Lys Asn Asp Tyr Ile Gly Gly Val Leu
            420             425             430

Glu Ser Glu Cys Asn Gly Trp Leu Ala Ala Glu Gly Arg Thr Asp Tyr
            435             440             445

Val Lys Leu Phe Leu Pro Ile Ala Ile Lys Met Arg Arg Asp Lys Asp
        450             455             460

Val Ala Asn Thr Phe Ala Asp Ile Trp Gly Asp Phe His Glu Val Thr
465             470             475             480

Gly Leu
```

```
<210> SEQ ID NO 24
<211> LENGTH: 482
<212> TYPE: PRT
<213> ORGANISM: Artificial Sequence
<220> FEATURE:
<223> OTHER INFORMATION: Mutant ligase (Enterobacteria phage CC31
      backbone) protein sequence

<400> SEQUENCE: 24
```

```
Met Ile Leu Asp Ile Ile Asn Glu Ile Ala Ser Ile Gly Ser Thr Lys
1               5               10              15

Glu Lys Glu Ala Ile Ile Arg Arg His Lys Asp Asn Glu Leu Leu Lys
            20              25              30

Arg Val Phe Arg Met Thr Tyr Asp Gly Lys Leu Gln Tyr Tyr Ile Lys
        35              40              45

Lys Trp Asp Thr Arg Pro Lys Gly Asp Ile His Leu Thr Leu Glu Asp
        50              55              60

Met Leu Tyr Leu Leu Glu Glu Lys Leu Ala Lys Arg Val Val Thr Gly
65              70              75              80

Asn Ala Ala Lys Glu Lys Leu Glu Ile Ala Leu Ser Gln Thr Ser Asp
                85              90              95

Ala Asp Ala Glu Val Val Lys Lys Val Leu Leu Arg Asp Leu Arg Cys
            100             105             110

Gly Ala Ser Arg Ser Ile Ala Asn Lys Val Trp Lys Asn Leu Ile Pro
            115             120             125

Glu Gln Pro Gln Met Leu Ala Ser Ser Tyr Asp Glu Lys Gly Ile Glu
        130             135             140
```

-continued

```
Lys Asn Ile Lys Phe Pro Ala Phe Ala Gln Leu Lys Ala Asp Gly Ala
145                 150                 155                 160

Arg Ala Phe Ala Glu Val Arg Gly Asp Glu Leu Asp Asp Val Lys Ile
                165                 170                 175

Leu Ser Arg Ala Gly Asn Glu Tyr Leu Gly Leu Asp Leu Leu Lys Gln
            180                 185                 190

Gln Leu Ile Glu Met Thr Lys Glu Ala Arg Glu Arg His Pro Gly Gly
            195                 200                 205

Val Met Ile Asp Gly Glu Leu Val Tyr His Ala Ser Thr Leu Pro Ala
        210                 215                 220

Gly Pro Leu Asp Asp Ile Phe Gly Asp Leu Pro Glu Leu Ser Lys Ala
225                 230                 235                 240

Lys Glu Phe Lys Glu Glu Ser Arg Thr Met Ser Asn Gly Leu Ala Asn
                245                 250                 255

Lys Ser Leu Lys Gly Thr Ile Ser Ala Lys Glu Ala Ala Gly Met Lys
            260                 265                 270

Phe Gln Val Trp Asp Tyr Val Pro Leu Asp Val Val Tyr Ser Glu Gly
            275                 280                 285

Lys Gln Ser Gly Phe Ala Tyr Asp Val Arg Phe Arg Ala Leu Glu Leu
        290                 295                 300

Met Val Gln Gly Tyr Ser Gln Met Ile Leu Ile Glu Asn His Ile Val
305                 310                 315                 320

His Asn Leu Asp Glu Ala Lys Val Ile Tyr Arg Lys Tyr Val Asp Glu
                325                 330                 335

Gly Leu Glu Gly Ile Ile Leu Lys Asn Ile Gly Ala Phe Trp Glu Asn
            340                 345                 350

Thr Arg Ser Lys Asn Leu Tyr Lys Phe Lys Lys Val Ile Lys Ile Asp
            355                 360                 365

Leu Arg Ile Val Asp Ile Tyr Glu His Ser Lys Gln Pro Gly Lys Ala
        370                 375                 380

Gly Gly Phe Tyr Leu Glu Ser Glu Cys Gly Leu Ile Lys Val Lys Ala
385                 390                 395                 400

Gly Ser Gly Leu Lys Asp Lys Pro Gly Lys Asp Ala His Glu Leu Asp
                405                 410                 415

Arg Thr Arg Ile Trp Glu Asn Lys Asn Asp Tyr Ile Gly Gly Val Leu
            420                 425                 430

Glu Ser Glu Cys Asn Gly Trp Leu Ala Ala Glu Gly Arg Thr Asp Tyr
            435                 440                 445

Val Lys Leu Phe Leu Pro Ile Ala Ile Lys Met Arg Arg Asp Lys Asp
        450                 455                 460

Val Ala Asn Thr Phe Ala Asp Ile Trp Gly Asp Phe His Glu Val Thr
465                 470                 475                 480

Gly Leu
```

<210> SEQ ID NO 25
<211> LENGTH: 482
<212> TYPE: PRT
<213> ORGANISM: Artificial Sequence
<220> FEATURE:
<223> OTHER INFORMATION: Mutant ligase (Enterobacteria phage CC31
      backbone) protein sequence

<400> SEQUENCE: 25

```
Met Ile Leu Asp Ile Ile Asn Glu Ile Ala Ser Ile Gly Ser Thr Lys
1               5                   10                  15
```

```
Glu Lys Glu Ala Ile Ile Arg Arg His Lys Asp Asn Glu Leu Leu Lys
            20                  25                  30

Arg Val Phe Arg Met Thr Tyr Asp Gly Lys Leu Gln Tyr Tyr Ile Lys
            35                  40                  45

Lys Trp Asp Thr Arg Pro Lys Gly Asp Ile His Leu Thr Leu Glu Asp
            50                  55                  60

Met Leu Tyr Leu Leu Glu Glu Lys Leu Ala Lys Arg Val Val Thr Gly
65                  70                  75                  80

Asn Ala Ala Lys Glu Lys Leu Glu Ile Ala Leu Ser Gln Thr Ser Asp
                85                  90                  95

Ala Asp Ala Glu Val Val Lys Lys Val Leu Leu Arg Asp Leu Arg Cys
            100                 105                 110

Gly Ala Ser Arg Ser Ile Ala Asn Lys Val Trp Lys Asn Leu Ile Pro
            115                 120                 125

Glu Gln Pro Gln Met Leu Ala Ser Ser Tyr Asp Glu Lys Gly Ile Glu
            130                 135                 140

Lys Asn Ile Lys Phe Pro Ala Phe Ala Gln Leu Lys Ala Asp Gly Ala
145                 150                 155                 160

Arg Ala Phe Ala Glu Val Arg Gly Asp Glu Leu Asp Asp Val Lys Ile
                165                 170                 175

Leu Ser Arg Ala Gly Asn Glu Tyr Leu Gly Leu Asp Leu Leu Lys Gln
                180                 185                 190

Gln Leu Ile Glu Met Thr Lys Glu Ala Arg Glu Arg His Pro Gly Gly
            195                 200                 205

Val Met Ile Asp Gly Glu Leu Val Tyr His Ala Ser Thr Leu Pro Ala
            210                 215                 220

Gly Pro Leu Asp Asp Ile Phe Gly Asp Leu Pro Glu Leu Ser Lys Ala
225                 230                 235                 240

Lys Glu Phe Lys Glu Glu Ser Arg Thr Met Ser Asn Gly Leu Ala Asn
                245                 250                 255

Lys Ser Leu Lys Gly Thr Ile Ser Ala Lys Glu Ala Ala Gly Met Lys
            260                 265                 270

Phe Gln Val Trp Asp Tyr Val Pro Leu Asp Val Val Tyr Ser Glu Gly
            275                 280                 285

Lys Gln Ser Gly Phe Ala Tyr Asp Val Arg Phe Arg Ala Leu Glu Leu
            290                 295                 300

Met Val Gln Gly Tyr Ser Gln Met Ile Leu Ile Glu Asn His Ile Val
305                 310                 315                 320

His Asn Leu Asp Glu Ala Lys Val Ile Tyr Arg Lys Tyr Val Asp Glu
                325                 330                 335

Gly Leu Glu Gly Ile Ile Leu Lys Asn Ile Gly Ala Phe Trp Glu Asn
                340                 345                 350

Thr Arg Ser Lys Asn Leu Tyr Lys Phe Lys Gly Val Ile Phe Ile Asp
            355                 360                 365

Leu Arg Ile Val Asp Ile Tyr Glu His Ser Lys Gln Pro Gly Lys Ala
            370                 375                 380

Gly Gly Phe Tyr Leu Glu Ser Glu Cys Gly Leu Ile Lys Val Lys Ala
385                 390                 395                 400

Gly Ser Gly Leu Lys Asp Lys Pro Gly Lys Asp Ala His Glu Leu Asp
                405                 410                 415

Arg Thr Arg Ile Trp Glu Asn Lys Asn Asp Tyr Ile Gly Gly Val Leu
            420                 425                 430

Glu Ser Glu Cys Asn Gly Trp Leu Ala Ala Glu Gly Arg Thr Asp Tyr
```

-continued

```
              435              440              445

Val Lys Leu Phe Leu Pro Ile Ala Ile Lys Met Arg Arg Asp Lys Asp
    450              455              460

Val Ala Asn Thr Phe Ala Asp Ile Trp Gly Asp Phe His Glu Val Thr
465              470              475              480

Gly Leu

<210> SEQ ID NO 26
<211> LENGTH: 482
<212> TYPE: PRT
<213> ORGANISM: Artificial Sequence
<220> FEATURE:
<223> OTHER INFORMATION: Mutant ligase (Enterobacteria phage CC31
      backbone) protein sequence

<400> SEQUENCE: 26

Met Ile Leu Asp Ile Ile Asn Glu Ile Ala Ser Ile Gly Ser Thr Lys
1               5               10              15

Glu Lys Glu Ala Ile Ile Arg Arg His Lys Asp Asn Glu Leu Leu Lys
            20              25              30

Arg Val Phe Arg Met Thr Tyr Asp Gly Lys Leu Gln Tyr Tyr Ile Lys
        35              40              45

Lys Trp Asp Thr Arg Pro Lys Gly Asp Ile His Leu Thr Leu Glu Asp
    50              55              60

Met Leu Tyr Leu Leu Glu Glu Lys Leu Ala Lys Arg Val Val Thr Gly
65              70              75              80

Asn Ala Ala Lys Glu Lys Leu Glu Ile Ala Leu Ser Gln Thr Ser Asp
            85              90              95

Ala Asp Ala Glu Val Val Lys Lys Val Leu Leu Arg Asp Leu Arg Cys
            100             105             110

Gly Ala Ser Arg Ser Ile Ala Asn Lys Val Trp Lys Asn Leu Ile Pro
        115             120             125

Glu Gln Pro Gln Met Leu Ala Ser Ser Tyr Asp Glu Lys Gly Ile Glu
    130             135             140

Lys Asn Ile Lys Phe Pro Ala Phe Ala Gln Leu Lys Ala Asp Gly Ala
145             150             155             160

Arg Ala Phe Ala Glu Val Arg Gly Asp Glu Leu Asp Asp Val Lys Ile
            165             170             175

Leu Ser Arg Ala Gly Asn Glu Tyr Leu Gly Leu Asp Leu Leu Lys Gln
            180             185             190

Gln Leu Ile Glu Met Thr Lys Glu Ala Arg Glu Arg His Pro Gly Gly
        195             200             205

Val Met Ile Asp Gly Glu Leu Val Tyr His Ala Ser Thr Leu Pro Ala
    210             215             220

Gly Pro Leu Asp Asp Ile Phe Gly Asp Leu Pro Glu Leu Ser Lys Ala
225             230             235             240

Lys Glu Phe Lys Glu Glu Ser Arg Thr Met Ser Asn Gly Leu Ala Asn
            245             250             255

Lys Ser Leu Lys Gly Thr Ile Ser Ala Lys Glu Ala Ala Gly Met Lys
            260             265             270

Phe Gln Val Trp Asp Tyr Val Pro Leu Asp Val Val Tyr Ser Glu Gly
            275             280             285

Lys Gln Ser Gly Phe Ala Tyr Asp Val Arg Phe Arg Ala Leu Glu Leu
    290             295             300

Met Val Gln Gly Tyr Ser Gln Met Ile Leu Ile Glu Asn His Ile Val
```

-continued

```
                  305                    310                    315                    320

His Asn Leu Asp Glu Ala Lys Val Ile Tyr Arg Lys Tyr Val Asp Glu
                                  325                    330                    335

Gly Leu Glu Gly Ile Ile Leu Lys Asn Ile Gly Ala Phe Trp Glu Asn
                                  340                    345                    350

Thr Arg Ser Lys Asn Leu Tyr Lys Phe Lys Gly Val Ile Leu Ile Asp
                                  355                    360                    365

Leu Arg Ile Val Asp Ile Tyr Glu His Ser Lys Gln Pro Gly Lys Ala
                                  370                    375                    380

Gly Gly Phe Tyr Leu Glu Ser Glu Cys Gly Leu Ile Lys Val Lys Ala
                  385                    390                    395                    400

Gly Ser Gly Leu Lys Asp Lys Pro Gly Lys Asp Ala His Glu Leu Asp
                                  405                    410                    415

Arg Thr Arg Ile Trp Glu Asn Lys Asn Asp Tyr Ile Gly Gly Val Leu
                                  420                    425                    430

Glu Ser Glu Cys Asn Gly Trp Leu Ala Ala Glu Gly Arg Thr Asp Tyr
                                  435                    440                    445

Val Lys Leu Phe Leu Pro Ile Ala Ile Lys Met Arg Arg Asp Lys Asp
                                  450                    455                    460

Val Ala Asn Thr Phe Ala Asp Ile Trp Gly Asp Phe His Glu Val Thr
                  465                    470                    475                    480

Gly Leu

<210> SEQ ID NO 27
<211> LENGTH: 482
<212> TYPE: PRT
<213> ORGANISM: Artificial Sequence
<220> FEATURE:
<223> OTHER INFORMATION: Mutant ligase (Enterobacteria phage CC31
      backbone) protein sequence

<400> SEQUENCE: 27

Met Ile Leu Asp Ile Ile Asn Glu Ile Ala Ser Ile Gly Ser Thr Lys
1                   5                   10                  15

Glu Lys Glu Ala Ile Ile Arg Arg His Lys Asp Asn Glu Leu Leu Lys
                20                  25                  30

Arg Val Phe Arg Met Thr Tyr Asp Gly Lys Leu Gln Tyr Tyr Ile Lys
            35                  40                  45

Lys Trp Asp Thr Arg Pro Lys Gly Asp Ile His Leu Thr Leu Glu Asp
        50                  55                  60

Met Leu Tyr Leu Leu Glu Glu Lys Leu Ala Lys Arg Val Val Thr Gly
65                  70                  75                  80

Asn Ala Ala Lys Glu Lys Leu Glu Ile Ala Leu Ser Gln Thr Ser Asp
                85                  90                  95

Ala Asp Ala Glu Val Val Lys Lys Val Leu Leu Arg Asp Leu Arg Cys
            100                 105                 110

Gly Ala Ser Arg Ser Ile Ala Asn Lys Val Trp Lys Asn Leu Ile Pro
        115                 120                 125

Glu Gln Pro Gln Met Leu Ala Ser Ser Tyr Asp Glu Lys Gly Ile Glu
    130                 135                 140

Lys Asn Ile Lys Phe Pro Ala Phe Ala Gln Leu Lys Ala Asp Gly Ala
145                 150                 155                 160

Arg Ala Phe Ala Glu Val Arg Gly Asp Glu Leu Asp Asp Val Lys Ile
                165                 170                 175

Leu Ser Arg Ala Gly Asn Glu Tyr Leu Gly Leu Asp Leu Leu Lys Gln
```

-continued

```
              180             185             190
Gln Leu Ile Glu Met Thr Lys Glu Ala Arg Glu Arg His Pro Gly Gly
          195             200             205
Val Met Ile Asp Gly Glu Leu Val Tyr His Ala Ser Thr Leu Pro Ala
          210             215             220
Gly Pro Leu Asp Asp Ile Phe Gly Asp Leu Pro Glu Leu Ser Lys Ala
225             230             235             240
Lys Glu Phe Lys Glu Glu Ser Arg Thr Met Ser Asn Gly Leu Ala Asn
              245             250             255
Lys Ser Leu Lys Gly Thr Ile Ser Ala Lys Glu Ala Ala Gly Met Lys
              260             265             270
Phe Gln Val Trp Asp Tyr Val Pro Leu Asp Val Val Tyr Ser Glu Gly
          275             280             285
Lys Gln Ser Gly Phe Ala Tyr Asp Val Arg Phe Arg Ala Leu Glu Leu
          290             295             300
Met Val Gln Gly Tyr Ser Gln Met Ile Leu Ile Glu Asn His Ile Val
305             310             315             320
His Asn Leu Asp Glu Ala Lys Val Ile Tyr Arg Lys Tyr Val Asp Glu
              325             330             335
Gly Leu Glu Gly Ile Ile Leu Lys Asn Ile Gly Ala Phe Trp Glu Asn
              340             345             350
Thr Arg Ser Lys Asn Leu Tyr Lys Phe Lys Arg Val Ile Phe Ile Asp
          355             360             365
Leu Arg Ile Val Asp Ile Tyr Glu His Ser Lys Gln Pro Gly Lys Ala
          370             375             380
Gly Gly Phe Tyr Leu Glu Ser Glu Cys Gly Leu Ile Lys Val Lys Ala
385             390             395             400
Gly Ser Gly Leu Lys Asp Lys Pro Gly Lys Asp Ala His Glu Leu Asp
              405             410             415
Arg Thr Arg Ile Trp Glu Asn Lys Asn Asp Tyr Ile Gly Gly Val Leu
          420             425             430
Glu Ser Glu Cys Asn Gly Trp Leu Ala Ala Glu Gly Arg Thr Asp Tyr
          435             440             445
Val Lys Leu Phe Leu Pro Ile Ala Ile Lys Met Arg Arg Asp Lys Asp
          450             455             460
Val Ala Asn Thr Phe Ala Asp Ile Trp Gly Asp Phe His Glu Val Thr
465             470             475             480
Gly Leu
```

```
<210> SEQ ID NO 28
<211> LENGTH: 497
<212> TYPE: PRT
<213> ORGANISM: Artificial Sequence
<220> FEATURE:
<223> OTHER INFORMATION: Mutant ligase (Shigella phage Shf125875
      backbone) protein sequence

<400> SEQUENCE: 28

Met Ile Leu Asp Ile Leu Asn Gln Ile Ala Ala Ile Gly Ser Thr Lys
1               5               10              15
Thr Lys Gln Glu Ile Leu Lys Lys Asn Lys Asp Asn Lys Leu Leu Glu
              20              25              30
Arg Val Tyr Arg Leu Thr Tyr Ala Arg Gly Ile Gln Tyr Tyr Ile Lys
          35              40              45
Lys Trp Pro Gly Pro Gly Glu Arg Ser Gln Ala Tyr Gly Leu Leu Glu
```

-continued

```
        50              55              60

Leu Asp Asp Met Leu Asp Phe Ile Glu Phe Thr Leu Ala Thr Arg Lys
65              70              75              80

Leu Thr Gly Asn Ala Ala Ile Lys Glu Leu Met Gly Tyr Ile Ala Asp
                85              90              95

Gly Lys Pro Asp Asp Val Glu Val Leu Arg Arg Val Met Met Arg Asp
            100             105             110

Leu Glu Val Gly Ala Ser Val Ser Ile Ala Asn Lys Val Trp Pro Gly
        115             120             125

Leu Ile Gln Leu Gln Pro Gln Met Leu Ala Ser Ala Tyr Asp Glu Lys
        130             135             140

Leu Ile Thr Lys Asn Ile Lys Trp Pro Ala Phe Ala Gln Leu Lys Ala
145             150             155             160

Asp Gly Ala Arg Cys Phe Ala Glu Val Arg Asp Asp Gly Val Gln Phe
                165             170             175

Phe Ser Arg Ala Gly Asn Glu Tyr His Gly Leu Thr Leu Leu Ala Asp
            180             185             190

Glu Leu Met Glu Met Thr Lys Glu Ala Arg Glu Arg His Pro Asn Gly
            195             200             205

Val Leu Ile Asp Gly Glu Leu Val Tyr His Ser Phe Asp Ile Lys Lys
        210             215             220

Ala Val Ser Ser Gly Asn Asp Leu Ser Phe Leu Phe Gly Asp Asn Glu
225             230             235             240

Glu Ser Glu Glu Val Gln Val Ala Asp Arg Ser Thr Ser Asn Gly Leu
            245             250             255

Ala Asn Lys Ser Leu Gln Gly Thr Ile Ser Pro Lys Glu Ala Glu Gly
            260             265             270

Met Val Leu Gln Ala Trp Asp Tyr Val Pro Leu Asp Glu Val Tyr Ser
            275             280             285

Asp Gly Lys Ile Lys Gly Gln Lys Tyr Asp Val Arg Phe Ala Ala Leu
        290             295             300

Glu Asn Met Ala Glu Gly Phe Lys Arg Ile Glu Pro Ile Glu Asn Gln
305             310             315             320

Leu Val His Asn Leu Asp Glu Ala Lys Val Val Tyr Lys Lys Tyr Val
            325             330             335

Asp Gln Gly Leu Glu Gly Ile Ile Leu Lys Asn Arg Asp Ser Tyr Trp
            340             345             350

Glu Asn Lys Arg Ser Lys Asn Leu Ile Lys Phe Lys Arg Val Ile Val
            355             360             365

Ile Ala Leu Glu Val Val Gly Tyr Tyr Glu His Ser Lys Asp Pro Asn
        370             375             380

Lys Leu Gly Gly Val Glu Leu Val Ser Arg Cys Arg Arg Ile Thr Thr
385             390             395             400

Asp Cys Gly Ser Gly Phe Lys Asp Thr Thr His Lys Thr Val Asp Gly
            405             410             415

Val Lys Val Leu Ile Pro Leu Asp Glu Arg His Asp Leu Asp Arg Glu
            420             425             430

Arg Leu Met Ala Glu Ala Arg Glu Gly Lys Leu Ile Gly Arg Ile Ala
            435             440             445

Asp Cys Glu Cys Asn Gly Trp Val His Ser Lys Gly Arg Glu Gly Thr
        450             455             460

Val Gly Ile Phe Leu Pro Ile Ile Lys Gly Phe Arg Phe Asp Lys Thr
465             470             475             480
```

-continued

```
Glu Ala Asp Ser Phe Glu Asp Val Phe Gly Pro Trp Ser Gln Thr Gly
                485                 490                 495

Leu

<210> SEQ ID NO 29
<211> LENGTH: 298
<212> TYPE: PRT
<213> ORGANISM: Paramecium bursaria Chlorella virus 1
<220> FEATURE:
<223> OTHER INFORMATION: Paramecium bursaria Chlorella virus PBCV-1

<400> SEQUENCE: 29

Met Ala Ile Thr Lys Pro Leu Leu Ala Ala Thr Leu Glu Asn Ile Glu
1               5                   10                  15

Asp Val Gln Phe Pro Cys Leu Ala Thr Pro Lys Ile Asp Gly Ile Arg
                20                  25                  30

Ser Val Lys Gln Thr Gln Met Leu Ser Arg Thr Phe Lys Pro Ile Arg
            35                  40                  45

Asn Ser Val Met Asn Arg Leu Leu Thr Glu Leu Leu Pro Glu Gly Ser
        50                  55                  60

Asp Gly Glu Ile Ser Ile Glu Gly Ala Thr Phe Gln Asp Thr Thr Ser
65                  70                  75                  80

Ala Val Met Thr Gly His Lys Met Tyr Asn Ala Lys Phe Ser Tyr Tyr
                85                  90                  95

Trp Phe Asp Tyr Val Thr Asp Asp Pro Leu Lys Lys Tyr Ile Asp Arg
                100                 105                 110

Val Glu Asp Met Lys Asn Tyr Ile Thr Val His Pro His Ile Leu Glu
            115                 120                 125

His Ala Gln Val Lys Ile Ile Pro Leu Ile Pro Val Glu Ile Asn Asn
        130                 135                 140

Ile Thr Glu Leu Leu Gln Tyr Glu Arg Asp Val Leu Ser Lys Gly Phe
145                 150                 155                 160

Glu Gly Val Met Ile Arg Lys Pro Asp Gly Lys Tyr Lys Phe Gly Arg
                165                 170                 175

Ser Thr Leu Lys Glu Gly Ile Leu Leu Lys Met Lys Gln Phe Lys Asp
            180                 185                 190

Ala Glu Ala Thr Ile Ile Ser Met Thr Ala Leu Phe Lys Asn Thr Asn
            195                 200                 205

Thr Lys Thr Lys Asp Asn Phe Gly Tyr Ser Lys Arg Ser Thr His Lys
        210                 215                 220

Ser Gly Lys Val Glu Glu Asp Val Met Gly Ser Ile Glu Val Asp Tyr
225                 230                 235                 240

Asp Gly Val Val Phe Ser Ile Gly Thr Gly Phe Asp Ala Asp Gln Arg
                245                 250                 255

Arg Asp Phe Trp Gln Asn Lys Glu Ser Tyr Ile Gly Lys Met Val Lys
                260                 265                 270

Phe Lys Tyr Phe Glu Met Gly Ser Lys Asp Cys Pro Arg Phe Pro Val
            275                 280                 285

Phe Ile Gly Ile Arg His Glu Glu Asp Arg
    290                 295

<210> SEQ ID NO 30
<211> LENGTH: 23
<212> TYPE: DNA
<213> ORGANISM: Artificial Sequence
<220> FEATURE:
```

-continued

<223> OTHER INFORMATION: Example 5, 8 and 9 template oligonucleotide
      sequence

<400> SEQUENCE: 30
tttggtgcga agcagactga ggc                                                    23

<210> SEQ ID NO 31
<211> LENGTH: 23
<212> TYPE: DNA
<213> ORGANISM: Artificial Sequence
<220> FEATURE:
<223> OTHER INFORMATION: Example 5 template oligonucleotide sequence

<400> SEQUENCE: 31
tttggtgcga agcagagtga ggc                                                    23

<210> SEQ ID NO 32
<211> LENGTH: 23
<212> TYPE: DNA
<213> ORGANISM: Artificial Sequence
<220> FEATURE:
<223> OTHER INFORMATION: Example 5 template oligonucleotide sequence

<400> SEQUENCE: 32
tttggtgcga agcagattga ggc                                                    23

<210> SEQ ID NO 33
<211> LENGTH: 23
<212> TYPE: DNA
<213> ORGANISM: Artificial Sequence
<220> FEATURE:
<223> OTHER INFORMATION: Example 5 template oligonucleotide sequence

<400> SEQUENCE: 33
tttggtgcga agcagaatga ggc                                                    23

<210> SEQ ID NO 34
<211> LENGTH: 23
<212> TYPE: DNA
<213> ORGANISM: Artificial Sequence
<220> FEATURE:
<223> OTHER INFORMATION: Example 5 template oligonucleotide sequence

<400> SEQUENCE: 34
tttggtgcga agcagtctga ggc                                                    23

<210> SEQ ID NO 35
<211> LENGTH: 23
<212> TYPE: DNA
<213> ORGANISM: Artificial Sequence
<220> FEATURE:
<223> OTHER INFORMATION: Example 5 template oligonucleotide sequence

<400> SEQUENCE: 35
tttggtgcga agcagtgtga ggc                                                    23

<210> SEQ ID NO 36
<211> LENGTH: 23
<212> TYPE: DNA
<213> ORGANISM: Artificial Sequence
<220> FEATURE:
<223> OTHER INFORMATION: Example 5 template oligonucleotide sequence

<400> SEQUENCE: 36
tttggtgcga agcagtttga ggc                                                    23

-continued

```
<210> SEQ ID NO 37
<211> LENGTH: 23
<212> TYPE: DNA
<213> ORGANISM: Artificial Sequence
<220> FEATURE:
<223> OTHER INFORMATION: Example 5 template oligonucleotide sequence

<400> SEQUENCE: 37
tttggtgcga agcagtatga ggc                                                                              23

<210> SEQ ID NO 38
<211> LENGTH: 23
<212> TYPE: DNA
<213> ORGANISM: Artificial Sequence
<220> FEATURE:
<223> OTHER INFORMATION: Example 5 template oligonucleotide sequence

<400> SEQUENCE: 38
tttggtgcga agcagcctga ggc                                                                              23

<210> SEQ ID NO 39
<211> LENGTH: 23
<212> TYPE: DNA
<213> ORGANISM: Artificial Sequence
<220> FEATURE:
<223> OTHER INFORMATION: Example 5 template oligonucleotide sequence

<400> SEQUENCE: 39
tttggtgcga agcagcgtga ggc                                                                              23

<210> SEQ ID NO 40
<211> LENGTH: 23
<212> TYPE: DNA
<213> ORGANISM: Artificial Sequence
<220> FEATURE:
<223> OTHER INFORMATION: Example 5 template oligonucleotide sequence

<400> SEQUENCE: 40
tttggtgcga agcagcttga ggc                                                                              23

<210> SEQ ID NO 41
<211> LENGTH: 23
<212> TYPE: DNA
<213> ORGANISM: Artificial Sequence
<220> FEATURE:
<223> OTHER INFORMATION: Example 5 template oligonucleotide sequence

<400> SEQUENCE: 41
tttggtgcga agcagcatga ggc                                                                              23

<210> SEQ ID NO 42
<211> LENGTH: 23
<212> TYPE: DNA
<213> ORGANISM: Artificial Sequence
<220> FEATURE:
<223> OTHER INFORMATION: Example 5 template oligonucleotide sequence

<400> SEQUENCE: 42
tttggtgcga agcaggctga ggc                                                                              23

<210> SEQ ID NO 43
<211> LENGTH: 23
<212> TYPE: DNA
<213> ORGANISM: Artificial Sequence
<220> FEATURE:
<223> OTHER INFORMATION: Example 5 template oligonucleotide sequence
```

```
<400> SEQUENCE: 43
tttggtgcga agcagggtga ggc                                              23

<210> SEQ ID NO 44
<211> LENGTH: 23
<212> TYPE: DNA
<213> ORGANISM: Artificial Sequence
<220> FEATURE:
<223> OTHER INFORMATION: Example 5 template oligonucleotide sequence

<400> SEQUENCE: 44
tttggtgcga agcaggttga ggc                                              23

<210> SEQ ID NO 45
<211> LENGTH: 23
<212> TYPE: DNA
<213> ORGANISM: Artificial Sequence
<220> FEATURE:
<223> OTHER INFORMATION: Example 5 template oligonucleotide sequence

<400> SEQUENCE: 45
tttggtgcga agcaggatga ggc                                              23

<210> SEQ ID NO 46
<211> LENGTH: 20
<212> TYPE: DNA
<213> ORGANISM: Artificial Sequence
<220> FEATURE:
<223> OTHER INFORMATION: Example 14 "20 mer" oligonucleotide sequence

<400> SEQUENCE: 46
gccucagtct gcttcgcacc                                                  20

<210> SEQ ID NO 47
<211> LENGTH: 36
<212> TYPE: DNA
<213> ORGANISM: Artificial Sequence
<220> FEATURE:
<223> OTHER INFORMATION: Example 7 template oligonucleotide sequence

<400> SEQUENCE: 47
tttggtgcga agcagaaggt aagccgaggt ttggcc                                36

<210> SEQ ID NO 48
<211> LENGTH: 298
<212> TYPE: PRT
<213> ORGANISM: Paramecium bursaria Chlorella virus 1
<220> FEATURE:
<223> OTHER INFORMATION: Paramecium bursaria Chlorella virus NE-JV-4

<400> SEQUENCE: 48

Met Ala Ile Thr Lys Pro Leu Leu Ala Ala Thr Leu Glu Asn Ile Glu
1               5                   10                  15

Asp Val Gln Phe Pro Cys Leu Ala Thr Pro Lys Ile Asp Gly Ile Arg
            20                  25                  30

Ser Val Lys Gln Thr Gln Met Leu Ser Arg Thr Phe Lys Pro Ile Arg
        35                  40                  45

Asn Ser Val Met Asn Arg Leu Leu Thr Glu Leu Leu Pro Glu Gly Ser
    50                  55                  60

Asp Gly Glu Ile Ser Ile Glu Gly Ala Thr Phe Gln Asp Thr Thr Ser
65                  70                  75                  80

Ala Val Met Thr Gly His Lys Met Tyr Asn Ala Lys Phe Ser Tyr Tyr
```

-continued

```
                85              90              95

Trp Phe Asp Tyr Val Thr Asp Asp Pro Leu Lys Lys Tyr Ser Asp Arg
            100             105             110

Val Glu Asp Met Lys Asn Tyr Ile Thr Ala His Pro His Ile Leu Asp
            115             120             125

His Glu Gln Val Lys Ile Ile Pro Leu Ile Pro Val Glu Ile Asn Asn
        130             135             140

Ile Thr Glu Leu Leu Gln Tyr Glu Arg Asp Val Leu Ser Lys Gly Phe
145             150             155             160

Glu Gly Val Met Ile Arg Lys Pro Asp Gly Lys Tyr Lys Phe Gly Arg
                165             170             175

Ser Thr Leu Lys Glu Gly Ile Leu Leu Lys Met Lys Gln Phe Lys Asp
            180             185             190

Ala Glu Ala Thr Ile Ile Ser Met Thr Ala Leu Phe Lys Asn Thr Asn
            195             200             205

Thr Lys Thr Lys Asp Asn Phe Gly Tyr Ser Lys Arg Ser Thr His Lys
        210             215             220

Asn Gly Lys Val Glu Glu Asp Val Met Gly Ser Ile Glu Val Asp Tyr
225             230             235             240

Asp Gly Val Val Phe Ser Ile Gly Thr Gly Phe Asp Ala Asp Gln Arg
                245             250             255

Arg Asp Phe Trp Gln Asn Lys Glu Ser Tyr Ile Gly Lys Met Val Lys
            260             265             270

Phe Lys Tyr Phe Glu Met Gly Ser Lys Asp Cys Pro Arg Phe Pro Val
            275             280             285

Phe Ile Gly Ile Arg His Glu Glu Asp His
        290             295
```

```
<210> SEQ ID NO 49
<211> LENGTH: 298
<212> TYPE: PRT
<213> ORGANISM: Paramecium bursaria Chlorella virus 1
<220> FEATURE:
<223> OTHER INFORMATION: Paramecium bursaria Chlorella virus NYs1

<400> SEQUENCE: 49

Met Thr Ile Ala Lys Pro Leu Leu Ala Ala Thr Leu Glu Asn Leu Asp
1               5               10              15

Asp Val Lys Phe Pro Cys Leu Val Thr Pro Lys Ile Asp Gly Ile Arg
            20              25              30

Ser Leu Lys Gln Gln His Met Leu Ser Arg Thr Phe Lys Pro Ile Arg
        35              40              45

Asn Ser Val Met Asn Lys Leu Leu Ser Glu Leu Leu Pro Glu Gly Ala
        50              55              60

Asp Gly Glu Ile Cys Ile Glu Asp Ser Thr Phe Gln Ala Thr Thr Ser
65              70              75              80

Ala Val Met Thr Gly His Lys Val Tyr Asp Glu Lys Phe Ser Tyr Tyr
                85              90              95

Trp Phe Asp Tyr Val Val Asp Asp Pro Leu Lys Ser Tyr Thr Asp Arg
            100             105             110

Val Asn Asp Met Lys Lys Tyr Val Asp Asp His Pro His Ile Leu Glu
            115             120             125

His Glu Gln Val Lys Ile Ile Pro Leu Ile Pro Val Glu Ile Asn Asn
        130             135             140

Ile Asp Glu Leu Ser Gln Tyr Glu Arg Asp Val Leu Ala Lys Gly Phe
```

-continued

```
145                  150                  155                  160

Glu Gly Val Met Ile Arg Arg Pro Asp Gly Lys Tyr Lys Phe Gly Arg
                165                  170                  175

Ser Thr Leu Lys Glu Gly Ile Leu Leu Lys Met Lys Gln Phe Lys Asp
                180                  185                  190

Ala Glu Ala Thr Ile Ile Ser Met Ser Pro Arg Leu Lys Asn Thr Asn
                195                  200                  205

Ala Lys Ser Lys Asp Asn Leu Gly Tyr Ser Lys Arg Ser Thr His Lys
        210                  215                  220

Ser Gly Lys Val Glu Glu Glu Thr Met Gly Ser Ile Glu Val Asp Tyr
225                  230                  235                  240

Asp Gly Val Val Phe Ser Ile Gly Thr Gly Phe Asp Asp Glu Gln Arg
                245                  250                  255

Lys His Phe Trp Glu Asn Lys Asp Ser Tyr Ile Gly Lys Leu Leu Lys
                260                  265                  270

Phe Lys Tyr Phe Glu Met Gly Ser Lys Asp Ala Pro Arg Phe Pro Val
                275                  280                  285

Phe Ile Gly Ile Arg His Glu Glu Asp Cys
        290                  295

<210> SEQ ID NO 50
<211> LENGTH: 301
<212> TYPE: PRT
<213> ORGANISM: Paramecium bursaria Chlorella virus 1
<220> FEATURE:
<223> OTHER INFORMATION: Paramecium bursaria Chlorella virus NE-JV-1

<400> SEQUENCE: 50

Met Thr Ala Ile Gln Lys Pro Leu Leu Ala Ala Ser Phe Lys Lys Leu
1               5                   10                  15

Thr Val Ala Asp Val Lys Tyr Pro Val Phe Ala Thr Pro Lys Leu Asp
                20                  25                  30

Gly Ile Arg Ala Leu Lys Ile Asp Gly Ala Phe Val Ser Arg Thr Phe
        35                  40                  45

Lys Pro Ile Arg Asn Arg Ala Ile Ala Asp Ala Leu Gln Asp Leu Leu
        50                  55                  60

Pro Asn Gly Ser Asp Gly Glu Ile Leu Ser Gly Ser Thr Phe Gln Asp
65                  70                  75                  80

Ala Ser Ser Ala Val Met Thr Ala Lys Ala Gly Ile Gly Ala Asn Thr
                85                  90                  95

Ile Phe Tyr Trp Phe Asp Tyr Val Lys Asp Asp Pro Asn Lys Pro Tyr
                100                 105                 110

Leu Asp Arg Met Thr Asp Met Glu Asn Tyr Leu Lys Glu Arg Pro Glu
        115                 120                 125

Ile Leu Asn Asp Asp Arg Ile Lys Ile Val Pro Leu Ile Pro Lys Lys
        130                 135                 140

Ile Glu Thr Lys Asp Glu Leu Asp Thr Phe Glu Lys Ile Cys Leu Asp
145                 150                 155                 160

Gln Gly Phe Glu Gly Val Met Ile Arg Ser Gly Ala Gly Lys Tyr Lys
                165                 170                 175

Phe Gly Arg Ser Thr Glu Lys Glu Gly Ile Leu Ile Lys Ile Lys Gln
                180                 185                 190

Phe Glu Asp Asp Glu Ala Val Val Ile Gly Phe Thr Pro Met Gln Thr
                195                 200                 205

Asn Thr Asn Asp Lys Ser Met Asn Glu Leu Gly Asp Met Lys Arg Ser
```

```
            210             215             220
Ser His Lys Asp Gly Lys Val Asn Leu Asp Thr Leu Gly Ala Leu Glu
225             230             235             240

Val Asp Trp Asn Gly Ile Thr Phe Ser Ile Gly Thr Gly Phe Asp His
            245             250             255

Ala Leu Arg Asp Lys Leu Trp Ser Glu Arg Asp Lys Leu Ile Gly Lys
            260             265             270

Ile Val Lys Phe Lys Tyr Phe Ala Gln Gly Val Lys Thr Ala Pro Arg
            275             280             285

Phe Pro Val Phe Ile Gly Phe Arg Asp Pro Asp Asp Met
            290             295             300
```

<210> SEQ ID NO 51
<211> LENGTH: 300
<212> TYPE: PRT
<213> ORGANISM: Acanthocystis turfacea Chlorella virus 1
<220> FEATURE:
<223> OTHER INFORMATION: Acanthocystis turfacea Chlorella virus Canal-1

<400> SEQUENCE: 51

```
Met Ala Ile Gln Lys Pro Leu Leu Ala Ala Ser Leu Lys Lys Met Ser
1               5               10              15

Val Gly Asp Leu Thr Phe Pro Val Phe Ala Thr Pro Lys Leu Asp Gly
            20              25              30

Ile Arg Ala Leu Lys Val Gly Gly Thr Ile Val Ser Arg Thr Phe Lys
            35              40              45

Pro Val Arg Asn Ser Ala Ile Ser Glu Val Leu Ala Ser Ile Leu Pro
    50              55              60

Asp Gly Ser Asp Gly Glu Ile Leu Ser Gly Lys Thr Phe Gln Glu Ser
65              70              75              80

Thr Ser Thr Val Met Thr Ala Asp Ala Gly Leu Gly Ser Gly Thr Met
            85              90              95

Phe Phe Trp Phe Asp Tyr Val Lys Asp Asp Pro Asn Lys Gly Tyr Leu
            100             105             110

Asp Arg Ile Ala Asp Met Lys Ser Phe Thr Asp Arg His Pro Glu Ile
            115             120             125

Leu Lys Asp Lys Arg Val Thr Ile Val Pro Leu Phe Pro Lys Lys Ile
    130             135             140

Asp Thr Thr Glu Glu Leu His Glu Phe Glu Lys Trp Cys Leu Asp Gln
145             150             155             160

Gly Phe Glu Gly Val Met Val Arg Asn Ala Gly Gly Lys Tyr Lys Phe
            165             170             175

Gly Arg Ser Thr Glu Lys Glu Gln Ile Leu Val Lys Ile Lys Gln Phe
            180             185             190

Glu Asp Asp Glu Ala Val Val Ile Gly Val Ser Ala Leu Gln Thr Asn
            195             200             205

Thr Asn Asp Lys Lys Leu Asn Gln Leu Gly Glu Met Arg Arg Thr Ser
    210             215             220

His Gln Asp Gly Lys Val Glu Leu Glu Met Leu Gly Ala Leu Asp Val
225             230             235             240

Asp Trp Asn Gly Ile Arg Phe Ser Ile Gly Thr Gly Phe Asp Arg Asp
            245             250             255

Thr Arg Val Asp Leu Trp Lys Arg Arg Glu Gly Val Ile Gly Lys Ile
            260             265             270

Val Lys Phe Lys Tyr Phe Ser Gln Gly Ile Lys Thr Ala Pro Arg Phe
```

-continued

```
            275                 280                 285

Pro Val Phe Leu Gly Phe Arg Asp Lys Asp Asp Met
    290                 295                 300

<210> SEQ ID NO 52
<211> LENGTH: 300
<212> TYPE: PRT
<213> ORGANISM: Acanthocystis turfacea Chlorella virus 1
<220> FEATURE:
<223> OTHER INFORMATION: Acanthocystis turfacea Chlorella virus Br0604L

<400> SEQUENCE: 52

Met Ala Ile Gln Lys Pro Leu Leu Ala Ala Ser Leu Lys Lys Leu Ser
1               5                   10                  15

Val Asp Asp Leu Thr Phe Pro Val Tyr Ala Thr Pro Lys Leu Asp Gly
            20                  25                  30

Ile Arg Ala Leu Lys Ile Asp Gly Thr Leu Val Ser Arg Thr Phe Lys
            35                  40                  45

Pro Ile Arg Asn Thr Thr Ile Ser Lys Val Leu Thr Ser Leu Leu Pro
    50                  55                  60

Asp Gly Ser Asp Gly Glu Ile Leu Ser Gly Lys Thr Phe Gln Asp Ser
65                  70                  75                  80

Thr Ser Thr Val Met Ser Ala Asp Ala Gly Ile Gly Ser Gly Thr Thr
                85                  90                  95

Phe Phe Trp Phe Asp Tyr Val Lys Asp Asp Pro Asn Lys Gly Tyr Leu
                100                 105                 110

Asp Arg Ile Ala Asp Ile Lys Lys Phe Ile Asp Cys Arg Pro Glu Ile
                115                 120                 125

Leu Lys Asp Ser Arg Val Ile Ile Val Pro Leu Phe Pro Lys Lys Ile
    130                 135                 140

Asp Thr Ala Glu Glu Leu Asn Val Phe Glu Lys Trp Cys Leu Asp Gln
145                 150                 155                 160

Gly Phe Glu Gly Val Met Val Arg Asn Ala Gly Gly Lys Tyr Lys Phe
                165                 170                 175

Gly Arg Ser Thr Glu Lys Glu Gln Ile Leu Val Lys Ile Lys Gln Phe
                180                 185                 190

Glu Asp Asp Glu Ala Val Val Ile Gly Val Ser Ala Leu Gln Thr Asn
                195                 200                 205

Thr Asn Asp Lys Lys Val Asn Glu Leu Gly Glu Met Arg Arg Thr Ser
    210                 215                 220

His Gln Asp Gly Lys Val Asp Leu Asp Met Leu Gly Ala Leu Asp Val
225                 230                 235                 240

Asp Trp Asn Gly Ile Arg Phe Gly Ile Gly Thr Gly Phe Asp Lys Asp
                245                 250                 255

Thr Arg Glu Asp Leu Trp Lys Arg Arg Asp Ser Ile Ile Gly Lys Ile
                260                 265                 270

Val Lys Phe Lys Tyr Phe Ser Gln Gly Val Lys Thr Ala Pro Arg Phe
    275                 280                 285

Pro Val Phe Leu Gly Phe Arg Asp Lys Asn Asp Met
    290                 295                 300

<210> SEQ ID NO 53
<211> LENGTH: 300
<212> TYPE: PRT
<213> ORGANISM: Acanthocystis turfacea Chlorella virus 1
<220> FEATURE:
<223> OTHER INFORMATION: Acanthocystis turfacea Chlorella virus NE-JV-2
```

-continued

<400> SEQUENCE: 53

```
Met Ala Ile Gln Lys Pro Leu Leu Ala Ala Ser Leu Lys Lys Leu Ser
1               5                   10                  15

Val Asp Asp Leu Thr Phe Pro Val Tyr Ala Thr Pro Lys Leu Asp Gly
            20                  25                  30

Ile Arg Ala Leu Lys Ile Asp Gly Thr Ile Val Ser Arg Thr Phe Lys
        35                  40                  45

Pro Ile Arg Asn Thr Thr Ile Ser Asn Val Leu Met Ser Leu Leu Pro
    50                  55                  60

Asp Gly Ser Asp Gly Glu Ile Leu Ser Gly Lys Thr Phe Gln Asp Ser
65                  70                  75                  80

Thr Ser Thr Val Met Ser Ala Asp Ala Gly Ile Gly Ser Gly Thr Thr
                85                  90                  95

Phe Phe Trp Phe Asp Tyr Val Lys Asp Asp Pro Asp Lys Gly Tyr Leu
            100                 105                 110

Asp Arg Ile Ala Asp Met Lys Lys Phe Val Asp Ser His Pro Glu Ile
            115                 120                 125

Leu Lys Asp Arg Arg Val Thr Ile Val Pro Leu Ile Pro Lys Lys Ile
        130                 135                 140

Asp Thr Val Glu Glu Leu Asn Val Phe Glu Gln Trp Cys Leu Asp Gln
145                 150                 155                 160

Gly Phe Glu Gly Val Met Val Arg Asn Ala Gly Gly Lys Tyr Lys Phe
                165                 170                 175

Gly Arg Ser Thr Glu Lys Glu Gln Ile Leu Val Lys Ile Lys Gln Phe
            180                 185                 190

Glu Asp Asp Glu Ala Val Val Ile Gly Val Ser Ala Leu Gln Thr Asn
            195                 200                 205

Val Asn Asp Lys Lys Met Asn Glu Leu Gly Asp Met Arg Arg Thr Ser
    210                 215                 220

His Lys Asp Gly Lys Ile Asp Leu Glu Met Leu Gly Ala Leu Asp Val
225                 230                 235                 240

Glu Trp Asn Gly Ile Arg Phe Gly Ile Gly Thr Gly Phe Asp Lys Asp
                245                 250                 255

Thr Arg Glu Asp Leu Trp Lys Lys Arg Asp Ser Ile Ile Gly Lys Val
            260                 265                 270

Val Lys Phe Lys Tyr Phe Ser Gln Gly Ile Lys Thr Ala Pro Arg Phe
        275                 280                 285

Pro Val Phe Leu Gly Phe Arg Asp Glu Asn Asp Met
    290                 295                 300
```

<210> SEQ ID NO 54
<211> LENGTH: 300
<212> TYPE: PRT
<213> ORGANISM: Acanthocystis turfacea Chlorella virus 1
<220> FEATURE:
<223> OTHER INFORMATION: Acanthocystis turfacea Chlorella virus
      TN603.4.2

<400> SEQUENCE: 54

```
Met Ala Ile Gln Lys Pro Leu Leu Ala Ala Ser Leu Lys Lys Met Ser
1               5                   10                  15

Val Asp Asn Leu Thr Phe Pro Val Tyr Ala Thr Pro Lys Leu Asp Gly
            20                  25                  30

Ile Arg Ala Leu Lys Ile Asp Gly Thr Leu Val Ser Arg Thr Phe Lys
        35                  40                  45
```

-continued

```
Pro Ile Arg Asn Thr Thr Ile Ser Lys Val Leu Ala Ser Leu Leu Pro
    50                  55                  60

Asp Gly Ser Asp Gly Glu Ile Leu Ser Gly Lys Thr Phe Gln Asp Ser
65                  70                  75                  80

Thr Ser Thr Val Met Thr Thr Asp Ala Gly Ile Gly Ser Asp Thr Thr
                85                  90                  95

Phe Phe Trp Phe Asp Tyr Val Lys Asp Asp Pro Asp Lys Gly Tyr Leu
            100                 105                 110

Asp Arg Ile Ala Asp Met Lys Thr Phe Val Asp Gln His Pro Glu Ile
        115                 120                 125

Leu Lys Asp Ser Cys Val Thr Ile Val Pro Leu Phe Pro Lys Lys Ile
        130                 135                 140

Asp Thr Pro Glu Glu Leu His Val Phe Glu Lys Trp Cys Leu Asp Gln
145                 150                 155                 160

Gly Phe Glu Gly Val Met Val Arg Thr Ala Gly Gly Lys Tyr Lys Phe
                165                 170                 175

Gly Arg Ser Thr Glu Lys Glu Gln Ile Leu Val Lys Ile Lys Gln Phe
            180                 185                 190

Glu Asp Asp Glu Ala Val Val Ile Gly Val Ser Ala Leu Gln Thr Asn
        195                 200                 205

Thr Asn Asp Lys Lys Leu Asn Gln Leu Gly Glu Met Arg Arg Thr Ser
    210                 215                 220

His Gln Asp Gly Lys Val Asp Leu Asp Met Leu Gly Ala Leu Asp Val
225                 230                 235                 240

Asp Trp Asn Gly Ile Arg Phe Ser Ile Gly Thr Gly Phe Asp Lys Asp
                245                 250                 255

Thr Arg Glu Asp Leu Trp Lys Gln Arg Asp Ser Ile Val Gly Lys Val
            260                 265                 270

Val Lys Phe Lys Tyr Phe Ser Gln Gly Ile Lys Thr Ala Pro Arg Phe
        275                 280                 285

Pro Val Phe Leu Gly Phe Arg Asp Glu Asn Asp Met
    290                 295                 300
```

```
<210> SEQ ID NO 55
<211> LENGTH: 300
<212> TYPE: PRT
<213> ORGANISM: Acanthocystis turfacea Chlorella virus 1
<220> FEATURE:
<223> OTHER INFORMATION: Acanthocystis turfacea Chlorella virus GM0701.1

<400> SEQUENCE: 55
```

```
Met Ala Ile Gln Lys Pro Leu Leu Ala Ala Ser Leu Lys Lys Met Ser
1                   5                   10                  15

Val Asp Asp Leu Thr Phe Pro Val Tyr Thr Thr Pro Lys Leu Asp Gly
                20                  25                  30

Ile Arg Ala Leu Lys Ile Asp Gly Thr Leu Val Ser Arg Thr Phe Lys
            35                  40                  45

Pro Val Arg Asn Ser Ala Ile Ser Glu Val Leu Ala Ser Leu Leu Pro
    50                  55                  60

Asp Gly Ser Asp Gly Glu Ile Leu Ser Gly Lys Thr Phe Gln Asp Ser
65                  70                  75                  80

Thr Ser Thr Val Met Thr Thr Asp Ala Gly Ile Gly Ser Asp Thr Thr
                85                  90                  95

Phe Phe Trp Phe Asp Tyr Val Lys Asp Asp Pro Asn Lys Gly Tyr Leu
            100                 105                 110
```

-continued

```
Asp Arg Ile Ala Asp Met Lys Thr Phe Ile Asp Gln His Pro Glu Met
        115                 120                 125

Leu Lys Asp Asn His Val Thr Ile Val Pro Leu Ile Pro Lys Lys Ile
    130                 135                 140

Asp Thr Val Glu Glu Leu Asn Ile Phe Glu Lys Trp Cys Leu Asp Gln
145                 150                 155                 160

Gly Phe Glu Gly Val Met Val Arg Asn Ala Gly Gly Lys Tyr Lys Phe
                165                 170                 175

Gly Arg Ser Thr Glu Lys Glu Gln Ile Leu Val Lys Ile Lys Gln Phe
                180                 185                 190

Glu Asp Asp Glu Ala Val Val Ile Gly Val Ser Ala Leu Gln Thr Asn
                195                 200                 205

Thr Asn Asp Lys Lys Leu Asn Gln Leu Gly Glu Met Arg Arg Thr Ser
    210                 215                 220

His Gln Asp Gly Lys Ile Asp Leu Glu Met Leu Gly Ala Leu Asp Val
225                 230                 235                 240

Asp Trp Asn Gly Ile Arg Phe Ser Ile Gly Thr Gly Phe Asp Arg Asp
                245                 250                 255

Thr Arg Val Asp Leu Trp Lys Arg Arg Asp Gly Ile Val Gly Arg Thr
                260                 265                 270

Ile Lys Phe Lys Tyr Phe Gly Gln Gly Ile Lys Thr Ala Pro Arg Phe
                275                 280                 285

Pro Val Phe Leu Gly Phe Arg Asp Lys Asp Asp Met
    290                 295                 300
```

```
<210> SEQ ID NO 56
<211> LENGTH: 287
<212> TYPE: PRT
<213> ORGANISM: Unknown
<220> FEATURE:
<223> OTHER INFORMATION: Description of Unknown:
      Synechococcus phage S-CRM01

<400> SEQUENCE: 56
```

```
Met Leu Ala Gly Asn Phe Asp Pro Lys Lys Ala Lys Phe Pro Tyr Cys
1                 5                 10                 15

Ala Thr Pro Lys Ile Asp Gly Ile Arg Phe Leu Met Val Asn Gly Arg
                20                 25                 30

Ala Leu Ser Arg Thr Phe Lys Pro Ile Arg Asn Glu Tyr Ile Gln Lys
                35                 40                 45

Leu Leu Ser Lys His Leu Pro Asp Gly Ile Asp Gly Glu Leu Thr Cys
    50                 55                 60

Gly Asp Thr Phe Gln Ser Ser Thr Ser Ala Ile Met Arg Ile Ala Gly
65                 70                 75                 80

Glu Pro Asp Phe Lys Ala Trp Ile Phe Asp Tyr Val Asp Pro Asp Ser
                85                 90                 95

Thr Ser Ile Leu Pro Phe Ile Glu Arg Phe Asp Gln Ile Ser Asp Ile
                100                 105                 110

Ile Tyr Asn Gly Pro Ile Pro Phe Lys His Gln Val Leu Gly Gln Ser
    115                 120                 125

Ile Leu Tyr Asn Ile Asp Asp Leu Asn Arg Tyr Glu Glu Ala Cys Leu
    130                 135                 140

Asn Glu Gly Tyr Glu Gly Val Met Leu Arg Asp Pro Tyr Gly Thr Tyr
145                 150                 155                 160

Lys Phe Gly Arg Ser Ser Thr Asn Glu Gly Ile Leu Leu Lys Val Lys
```

-continued

```
                165             170             175
Arg Phe Glu Asp Ala Glu Ala Thr Val Ile Arg Ile Asp Glu Lys Met
            180             185             190
Ser Asn Gln Asn Ile Ala Glu Lys Asp Asn Phe Gly Arg Thr Lys Arg
            195             200             205
Ser Ser Cys Leu Asp Gly Met Val Pro Met Glu Thr Thr Gly Ala Leu
            210             215             220
Phe Val Arg Asn Ser Asp Gly Leu Glu Phe Ser Ile Gly Ser Gly Leu
225             230             235             240
Asn Asp Glu Met Arg Asp Glu Ile Trp Lys Asn Lys Ser Ser Tyr Ile
            245             250             255
Gly Lys Leu Val Lys Tyr Lys Tyr Phe Pro Gln Gly Val Lys Asp Leu
            260             265             270
Pro Arg His Pro Val Phe Leu Gly Phe Arg Asp Pro Asp Asp Met
            275             280             285

<210> SEQ ID NO 57
<211> LENGTH: 322
<212> TYPE: PRT
<213> ORGANISM: Unknown
<220> FEATURE:
<223> OTHER INFORMATION: Description of Unknown:
      marine sediment metagenome

<400> SEQUENCE: 57

Met Asp Ala His Glu Leu Met Lys Leu Asn Glu Tyr Ala Glu Arg Gln
1               5               10              15
Asn Gln Lys Gln Lys Lys Gln Ile Thr Lys Pro Met Leu Ala Ala Ser
            20              25              30
Leu Lys Asp Ile Thr Gln Leu Asp Tyr Ser Lys Gly Tyr Leu Ala Thr
            35              40              45
Gln Lys Leu Asp Gly Ile Arg Ala Leu Met Ile Asp Gly Lys Leu Val
            50              55              60
Ser Arg Thr Phe Lys Pro Ile Arg Asn Asn His Ile Arg Glu Met Leu
65              70              75              80
Glu Asp Val Leu Pro Asp Gly Ala Asp Gly Glu Ile Val Cys Pro Gly
            85              90              95
Ala Phe Gln Ala Thr Ser Ser Gly Val Met Ser Ala Asn Gly Glu Pro
            100             105             110
Glu Phe Ile Tyr Tyr Met Phe Asp Tyr Val Lys Asp Asp Ile Thr Lys
            115             120             125
Glu Tyr Trp Arg Arg Thr Gln Asp Met Val Gln Trp Leu Ile Asn Gln
            130             135             140
Gly Pro Thr Arg Thr Pro Gly Leu Ser Lys Leu Lys Leu Leu Val Pro
145             150             155             160
Thr Leu Ile Lys Asn Tyr Asp His Leu Lys Thr Tyr Glu Thr Glu Cys
            165             170             175
Ile Asp Lys Gly Phe Glu Gly Val Ile Leu Arg Thr Pro Asp Ser Pro
            180             185             190
Tyr Lys Cys Gly Arg Ser Thr Ala Lys Gln Glu Trp Leu Leu Lys Leu
            195             200             205
Lys Arg Phe Ala Asp Asp Glu Ala Val Val Ile Gly Phe Thr Glu Lys
            210             215             220
Met His Asn Asp Asn Glu Ala Thr Lys Asp Lys Phe Gly His Thr Val
225             230             235             240
```

Arg Ser Ser His Lys Glu Asn Lys Arg Pro Ala Gly Thr Leu Gly Ser
                245                 250                 255

Leu Ile Val Arg Asp Ile Lys Thr Glu Ile Glu Phe Glu Ile Gly Thr
            260                 265                 270

Gly Phe Asp Asp Glu Leu Arg Gln Lys Ile Trp Asp Ala Arg Pro Glu
            275                 280                 285

Trp Asp Gly Leu Cys Val Lys Tyr Lys His Phe Ala Ile Ser Gly Val
        290                 295                 300

Lys Glu Lys Pro Arg Phe Pro Ser Phe Ile Gly Val Arg Asp Val Glu
305                 310                 315                 320

Asp Met

<210> SEQ ID NO 58
<211> LENGTH: 691
<212> TYPE: PRT
<213> ORGANISM: Mycobacterium tuberculosis
<220> FEATURE:
<223> OTHER INFORMATION: Mycobacterium tuberculosis (strain ATCC
      25618/H37Rv)

<400> SEQUENCE: 58

Met Ser Ser Pro Asp Ala Asp Gln Thr Ala Pro Glu Val Leu Arg Gln
1               5                   10                  15

Trp Gln Ala Leu Ala Glu Glu Val Arg Glu His Gln Phe Arg Tyr Tyr
            20                  25                  30

Val Arg Asp Ala Pro Ile Ile Ser Asp Ala Glu Phe Asp Glu Leu Leu
        35                  40                  45

Arg Arg Leu Glu Ala Leu Glu Glu Gln His Pro Glu Leu Arg Thr Pro
        50                  55                  60

Asp Ser Pro Thr Gln Leu Val Gly Gly Ala Gly Phe Ala Thr Asp Phe
65                  70                  75                  80

Glu Pro Val Asp His Leu Glu Arg Met Leu Ser Leu Asp Asn Ala Phe
                85                  90                  95

Thr Ala Asp Glu Leu Ala Ala Trp Ala Gly Arg Ile His Ala Glu Val
            100                 105                 110

Gly Asp Ala Ala His Tyr Leu Cys Glu Leu Lys Ile Asp Gly Val Ala
        115                 120                 125

Leu Ser Leu Val Tyr Arg Glu Gly Arg Leu Thr Arg Ala Ser Thr Arg
        130                 135                 140

Gly Asp Gly Arg Thr Gly Glu Asp Val Thr Leu Asn Ala Arg Thr Ile
145                 150                 155                 160

Ala Asp Val Pro Glu Arg Leu Thr Pro Gly Asp Asp Tyr Pro Val Pro
                165                 170                 175

Glu Val Leu Glu Val Arg Gly Glu Val Phe Phe Arg Leu Asp Asp Phe
            180                 185                 190

Gln Ala Leu Asn Ala Ser Leu Val Glu Glu Gly Lys Ala Pro Phe Ala
        195                 200                 205

Asn Pro Arg Asn Ser Ala Ala Gly Ser Leu Arg Gln Lys Asp Pro Ala
    210                 215                 220

Val Thr Ala Arg Arg Arg Leu Arg Met Ile Cys His Gly Leu Gly His
225                 230                 235                 240

Val Glu Gly Phe Arg Pro Ala Thr Leu His Gln Ala Tyr Leu Ala Leu
            245                 250                 255

Arg Ala Trp Gly Leu Pro Val Ser Glu His Thr Thr Leu Ala Thr Asp
        260                 265                 270

-continued

```
Leu Ala Gly Val Arg Glu Arg Ile Asp Tyr Trp Gly Glu His Arg His
        275             280             285

Glu Val Asp His Glu Ile Asp Gly Val Val Val Lys Val Asp Glu Val
        290             295             300

Ala Leu Gln Arg Arg Leu Gly Ser Thr Ser Arg Ala Pro Arg Trp Ala
305             310             315             320

Ile Ala Tyr Lys Tyr Pro Pro Glu Glu Ala Gln Thr Lys Leu Leu Asp
                325             330             335

Ile Arg Val Asn Val Gly Arg Thr Gly Arg Ile Thr Pro Phe Ala Phe
            340             345             350

Met Thr Pro Val Lys Val Ala Gly Ser Thr Val Gly Gln Ala Thr Leu
        355             360             365

His Asn Ala Ser Glu Ile Lys Arg Lys Gly Val Leu Ile Gly Asp Thr
    370             375             380

Val Val Ile Arg Lys Ala Gly Asp Val Ile Pro Glu Val Leu Gly Pro
385             390             395             400

Val Val Glu Leu Arg Asp Gly Ser Glu Arg Glu Phe Ile Met Pro Thr
            405             410             415

Thr Cys Pro Glu Cys Gly Ser Pro Leu Ala Pro Glu Lys Glu Gly Asp
            420             425             430

Ala Asp Ile Arg Cys Pro Asn Ala Arg Gly Cys Pro Gly Gln Leu Arg
            435             440             445

Glu Arg Val Phe His Val Ala Ser Arg Asn Gly Leu Asp Ile Glu Val
        450             455             460

Leu Gly Tyr Glu Ala Gly Val Ala Leu Leu Gln Ala Lys Val Ile Ala
465             470             475             480

Asp Glu Gly Glu Leu Phe Ala Leu Thr Glu Arg Asp Leu Leu Arg Thr
            485             490             495

Asp Leu Phe Arg Thr Lys Ala Gly Glu Leu Ser Ala Asn Gly Lys Arg
            500             505             510

Leu Leu Val Asn Leu Asp Lys Ala Lys Ala Ala Pro Leu Trp Arg Val
        515             520             525

Leu Val Ala Leu Ser Ile Arg His Val Gly Pro Thr Ala Ala Arg Ala
        530             535             540

Leu Ala Thr Glu Phe Gly Ser Leu Asp Ala Ile Ala Ala Ala Ser Thr
545             550             555             560

Asp Gln Leu Ala Ala Val Glu Gly Val Gly Pro Thr Ile Ala Ala Ala
            565             570             575

Val Thr Glu Trp Phe Ala Val Asp Trp His Arg Glu Ile Val Asp Lys
            580             585             590

Trp Arg Ala Ala Gly Val Arg Met Val Asp Glu Arg Asp Glu Ser Val
        595             600             605

Pro Arg Thr Leu Ala Gly Leu Thr Ile Val Val Thr Gly Ser Leu Thr
        610             615             620

Gly Phe Ser Arg Asp Asp Ala Lys Glu Ala Ile Val Ala Arg Gly Gly
625             630             635             640

Lys Ala Ala Gly Ser Val Ser Lys Lys Thr Asn Tyr Val Val Ala Gly
                645             650             655

Asp Ser Pro Gly Ser Lys Tyr Asp Lys Ala Val Glu Leu Gly Val Pro
            660             665             670

Ile Leu Asp Glu Asp Gly Phe Arg Arg Leu Leu Ala Asp Gly Pro Ala
        675             680             685

Ser Arg Thr
```

-continued

690

<210> SEQ ID NO 59
<211> LENGTH: 676
<212> TYPE: PRT
<213> ORGANISM: Enterococcus faecalis
<220> FEATURE:
<223> OTHER INFORMATION: Enterococcus faecalis (strain ATCC 700802/V583)

<400> SEQUENCE: 59

```
Met Glu Gln Gln Pro Leu Thr Leu Thr Ala Ala Thr Thr Arg Ala Gln
1               5                   10                  15

Glu Leu Arg Lys Gln Leu Asn Gln Tyr Ser His Glu Tyr Tyr Val Lys
                20                  25                  30

Asp Gln Pro Ser Val Glu Asp Tyr Val Tyr Asp Arg Leu Tyr Lys Glu
            35                  40                  45

Leu Val Asp Ile Glu Thr Glu Phe Pro Asp Leu Ile Thr Pro Asp Ser
        50                  55                  60

Pro Thr Gln Arg Val Gly Gly Lys Val Leu Ser Gly Phe Glu Lys Ala
65                  70                  75                  80

Pro His Asp Ile Pro Met Tyr Ser Leu Asn Asp Gly Phe Ser Lys Glu
                85                  90                  95

Asp Ile Phe Ala Phe Asp Glu Arg Val Arg Lys Ala Ile Gly Lys Pro
            100                 105                 110

Val Ala Tyr Cys Cys Glu Leu Lys Ile Asp Gly Leu Ala Ile Ser Leu
        115                 120                 125

Arg Tyr Glu Asn Gly Val Phe Val Arg Gly Ala Thr Arg Gly Asp Gly
        130                 135                 140

Thr Val Gly Glu Asn Ile Thr Glu Asn Leu Arg Thr Val Arg Ser Val
145                 150                 155                 160

Pro Met Arg Leu Thr Glu Pro Ile Ser Val Glu Val Arg Gly Glu Cys
                165                 170                 175

Tyr Met Pro Lys Gln Ser Phe Val Ala Leu Asn Glu Glu Arg Glu Glu
            180                 185                 190

Asn Gly Gln Asp Ile Phe Ala Asn Pro Arg Asn Ala Ala Ala Gly Ser
        195                 200                 205

Leu Arg Gln Leu Asp Thr Lys Ile Val Ala Lys Arg Asn Leu Asn Thr
        210                 215                 220

Phe Leu Tyr Thr Val Ala Asp Phe Gly Pro Met Lys Ala Lys Thr Gln
225                 230                 235                 240

Phe Glu Ala Leu Glu Glu Leu Ser Ala Ile Gly Phe Arg Thr Asn Pro
                245                 250                 255

Glu Arg Gln Leu Cys Gln Ser Ile Asp Glu Val Trp Ala Tyr Ile Glu
            260                 265                 270

Glu Tyr His Glu Lys Arg Ser Thr Leu Pro Tyr Glu Ile Asp Gly Ile
        275                 280                 285

Val Ile Lys Val Asn Glu Phe Ala Leu Gln Asp Glu Leu Gly Phe Thr
        290                 295                 300

Val Lys Ala Pro Arg Trp Ala Ile Ala Tyr Lys Phe Pro Pro Glu Glu
305                 310                 315                 320

Ala Glu Thr Val Val Glu Asp Ile Glu Trp Thr Ile Gly Arg Thr Gly
                325                 330                 335

Val Val Thr Pro Thr Ala Val Met Ala Pro Val Arg Val Ala Gly Thr
            340                 345                 350

Thr Val Ser Arg Ala Ser Leu His Asn Ala Asp Phe Ile Gln Met Lys
```

-continued

```
                355                    360                    365

Asp Ile Arg Leu Asn Asp His Val Ile Ile Tyr Lys Ala Gly Asp Ile
    370                    375                    380

Ile Pro Glu Val Ala Gln Val Leu Val Glu Lys Arg Ala Ala Asp Ser
385                    390                    395                    400

Gln Pro Tyr Glu Met Pro Thr His Cys Pro Ile Cys His Ser Glu Leu
                405                    410                    415

Val His Leu Asp Glu Glu Val Ala Leu Arg Cys Ile Asn Pro Lys Cys
                420                    425                    430

Pro Ala Gln Ile Lys Glu Gly Leu Asn His Phe Val Ser Arg Asn Ala
                435                    440                    445

Met Asn Ile Asp Gly Leu Gly Pro Arg Val Leu Ala Gln Met Tyr Asp
    450                    455                    460

Lys Gly Leu Val Lys Asp Val Ala Asp Leu Tyr Phe Leu Thr Glu Glu
465                    470                    475                    480

Gln Leu Met Thr Leu Asp Lys Ile Lys Glu Lys Ser Ala Asn Asn Ile
                485                    490                    495

Tyr Thr Ala Ile Gln Gly Ser Lys Glu Asn Ser Val Glu Arg Leu Ile
                500                    505                    510

Phe Gly Leu Gly Ile Arg His Val Gly Ala Lys Ala Ala Lys Ile Leu
                515                    520                    525

Ala Glu His Phe Gly Asp Leu Pro Thr Leu Ser Arg Ala Thr Ala Glu
    530                    535                    540

Glu Ile Val Ala Leu Asp Ser Ile Gly Glu Thr Ile Ala Asp Ser Val
545                    550                    555                    560

Val Thr Tyr Phe Glu Asn Glu Glu Val His Glu Leu Met Ala Glu Leu
                565                    570                    575

Glu Lys Ala Gln Val Asn Leu Thr Tyr Lys Gly Leu Arg Thr Glu Gln
                580                    585                    590

Leu Ala Glu Val Glu Ser Pro Phe Lys Asp Lys Thr Val Val Leu Thr
                595                    600                    605

Gly Lys Leu Ala Gln Tyr Thr Arg Glu Glu Ala Lys Glu Lys Ile Glu
    610                    615                    620

Asn Leu Gly Gly Lys Val Thr Gly Ser Val Ser Lys Lys Thr Asp Ile
625                    630                    635                    640

Val Val Ala Gly Glu Asp Ala Gly Ser Lys Leu Thr Lys Ala Glu Ser
                645                    650                    655

Leu Gly Val Thr Val Trp Asn Glu Gln Glu Met Val Asp Ala Leu Asp
                660                    665                    670

Ala Ser His Phe
        675
```

```
<210> SEQ ID NO 60
<211> LENGTH: 670
<212> TYPE: PRT
<213> ORGANISM: Haemophilus influenzae
<220> FEATURE:
<223> OTHER INFORMATION: Haemophilus influenzae (strain ATCC 51907/DSM
      11121/ KW20/Rd)

<400> SEQUENCE: 60

Met Thr Asn Ile Gln Thr Gln Leu Asp Asn Leu Arg Lys Thr Leu Arg
1               5                   10                  15

Gln Tyr Glu Tyr Glu Tyr His Val Leu Asp Asn Pro Ser Val Pro Asp
            20                  25                  30
```

Ser Glu Tyr Asp Arg Leu Phe His Gln Leu Lys Ala Leu Glu Leu Glu
        35                      40                      45

His Pro Glu Phe Leu Thr Ser Asp Ser Pro Thr Gln Arg Val Gly Ala
        50                      55                      60

Lys Pro Leu Ser Gly Phe Ser Gln Ile Arg His Glu Ile Pro Met Leu
65                      70                      75                      80

Ser Leu Asp Asn Ala Phe Ser Asp Ala Glu Phe Asn Ala Phe Val Lys
                        85                      90                      95

Arg Ile Glu Asp Arg Leu Ile Leu Leu Pro Lys Pro Leu Thr Phe Cys
                100                     105                     110

Cys Glu Pro Lys Leu Asp Gly Leu Ala Val Ser Ile Leu Tyr Val Asn
                115                     120                     125

Gly Glu Leu Thr Gln Ala Ala Thr Arg Gly Asp Gly Thr Thr Gly Glu
        130                     135                     140

Asp Ile Thr Ala Asn Ile Arg Thr Ile Arg Asn Val Pro Leu Gln Leu
145                     150                     155                     160

Leu Thr Asp Asn Pro Pro Ala Arg Leu Glu Val Arg Gly Glu Val Phe
                        165                     170                     175

Met Pro His Ala Gly Phe Glu Arg Leu Asn Lys Tyr Ala Leu Glu His
                180                     185                     190

Asn Glu Lys Thr Phe Ala Asn Pro Arg Asn Ala Ala Ala Gly Ser Leu
                195                     200                     205

Arg Gln Leu Asp Pro Asn Ile Thr Ser Lys Arg Pro Leu Val Leu Asn
        210                     215                     220

Ala Tyr Gly Ile Gly Ile Ala Glu Gly Val Asp Leu Pro Thr Thr His
225                     230                     235                     240

Tyr Ala Arg Leu Gln Trp Leu Lys Ser Ile Gly Ile Pro Val Asn Pro
                245                     250                     255

Glu Ile Arg Leu Cys Asn Gly Ala Asp Glu Val Leu Gly Phe Tyr Arg
                260                     265                     270

Asp Ile Gln Asn Lys Arg Ser Ser Leu Gly Tyr Asp Ile Asp Gly Thr
                275                     280                     285

Val Leu Lys Ile Asn Asp Ile Ala Leu Gln Asn Glu Leu Gly Phe Ile
        290                     295                     300

Ser Lys Ala Pro Arg Trp Ala Ile Ala Tyr Lys Phe Pro Ala Gln Glu
305                     310                     315                     320

Glu Leu Thr Leu Leu Asn Asp Val Glu Phe Gln Val Gly Arg Thr Gly
                        325                     330                     335

Ala Ile Thr Pro Val Ala Lys Leu Glu Pro Val Phe Val Ala Gly Val
                340                     345                     350

Thr Val Ser Asn Ala Thr Leu His Asn Gly Asp Glu Ile Glu Arg Leu
                355                     360                     365

Asn Ile Ala Ile Gly Asp Thr Val Val Ile Arg Arg Ala Gly Asp Val
        370                     375                     380

Ile Pro Gln Ile Ile Gly Val Leu His Glu Arg Arg Pro Asp Asn Ala
385                     390                     395                     400

Lys Pro Ile Ile Phe Pro Thr Asn Cys Pro Val Cys Asp Ser Gln Ile
                        405                     410                     415

Ile Arg Ile Glu Gly Glu Ala Val Ala Arg Cys Thr Gly Gly Leu Phe
                420                     425                     430

Cys Ala Ala Gln Arg Lys Glu Ala Leu Lys His Phe Val Ser Arg Lys
        435                     440                     445

Ala Met Asp Ile Asp Gly Val Gly Gly Lys Leu Ile Glu Gln Leu Val

```
          450               455               460

Asp Arg Glu Leu Ile His Thr Pro Ala Asp Leu Phe Lys Leu Asp Leu
465               470               475               480

Thr Thr Leu Thr Arg Leu Glu Arg Met Gly Ala Lys Ser Ala Glu Asn
              485               490               495

Ala Leu Asn Ser Leu Glu Asn Ala Lys Ser Thr Thr Leu Ala Arg Phe
              500               505               510

Ile Phe Ala Leu Gly Ile Arg Glu Val Gly Glu Ala Thr Ala Leu Asn
              515               520               525

Leu Ala Asn His Phe Lys Thr Leu Asp Ala Leu Lys Asp Ala Asn Leu
              530               535               540

Glu Glu Leu Gln Gln Val Pro Asp Val Gly Glu Val Val Ala Asn Arg
545               550               555               560

Ile Phe Ile Phe Trp Arg Glu Ala His Asn Val Ala Val Val Glu Asp
              565               570               575

Leu Ile Ala Gln Gly Val His Trp Glu Thr Val Glu Val Lys Glu Ala
              580               585               590

Ser Glu Asn Leu Phe Lys Asp Lys Thr Val Val Leu Thr Gly Thr Leu
              595               600               605

Thr Gln Met Gly Arg Asn Glu Ala Lys Ala Leu Leu Gln Gln Leu Gly
              610               615               620

Ala Lys Val Ser Gly Ser Val Ser Ser Lys Thr Asp Phe Val Ile Ala
625               630               635               640

Gly Asp Ala Ala Gly Ser Lys Leu Ala Lys Ala Gln Glu Leu Asn Ile
              645               650               655

Thr Val Leu Thr Glu Glu Glu Phe Leu Ala Gln Ile Thr Arg
              660               665               670

<210> SEQ ID NO 61
<211> LENGTH: 667
<212> TYPE: PRT
<213> ORGANISM: Staphylococcus aureus

<400> SEQUENCE: 61

Met Ala Asp Leu Ser Ser Arg Val Asn Glu Leu His Asp Leu Leu Asn
1               5               10               15

Gln Tyr Ser Tyr Glu Tyr Tyr Val Glu Asp Asn Pro Ser Val Pro Asp
              20               25               30

Ser Glu Tyr Asp Lys Leu Leu His Glu Leu Ile Lys Ile Glu Glu Glu
              35               40               45

His Pro Glu Tyr Lys Thr Val Asp Ser Pro Thr Val Arg Val Gly Gly
              50               55               60

Glu Ala Gln Ala Ser Phe Asn Lys Val Asn His Asp Thr Pro Met Leu
65               70               75               80

Ser Leu Gly Asn Ala Phe Asn Glu Asp Asp Leu Arg Lys Phe Asp Gln
              85               90               95

Arg Ile Arg Glu Gln Ile Gly Asn Val Glu Tyr Met Cys Glu Leu Lys
              100               105               110

Ile Asp Gly Leu Ala Val Ser Leu Lys Tyr Val Asp Gly Tyr Phe Val
              115               120               125

Gln Gly Leu Thr Arg Gly Asp Gly Thr Thr Gly Glu Asp Ile Thr Glu
              130               135               140

Asn Leu Lys Thr Ile His Ala Ile Pro Leu Lys Met Lys Glu Pro Leu
145               150               155               160
```

-continued

```
Asn Val Glu Val Arg Gly Glu Ala Tyr Met Pro Arg Arg Ser Phe Leu
            165                 170                 175

Arg Leu Asn Glu Glu Lys Glu Lys Asn Asp Glu Gln Leu Phe Ala Asn
            180                 185                 190

Pro Arg Asn Ala Ala Ala Gly Ser Leu Arg Gln Leu Asp Ser Lys Leu
            195                 200                 205

Thr Ala Lys Arg Lys Leu Ser Val Phe Ile Tyr Ser Val Asn Asp Phe
    210                 215                 220

Thr Asp Phe Asn Ala Arg Ser Gln Ser Glu Ala Leu Asp Glu Leu Asp
225                 230                 235                 240

Lys Leu Gly Phe Thr Thr Asn Lys Asn Arg Ala Arg Val Asn Asn Ile
                245                 250                 255

Asp Gly Val Leu Glu Tyr Ile Glu Lys Trp Thr Ser Gln Arg Glu Ser
                260                 265                 270

Leu Pro Tyr Asp Ile Asp Gly Ile Val Ile Lys Val Asn Asp Leu Asp
                275                 280                 285

Gln Gln Asp Glu Met Gly Phe Thr Gln Lys Ser Pro Arg Trp Ala Ile
    290                 295                 300

Ala Tyr Lys Phe Pro Ala Glu Glu Val Val Thr Lys Leu Leu Asp Ile
305                 310                 315                 320

Glu Leu Ser Ile Gly Arg Thr Gly Val Val Thr Pro Thr Ala Ile Leu
                325                 330                 335

Glu Pro Val Lys Val Ala Gly Thr Thr Val Ser Arg Ala Ser Leu His
                340                 345                 350

Asn Glu Asp Leu Ile His Asp Arg Asp Ile Arg Ile Gly Asp Ser Val
                355                 360                 365

Val Val Lys Lys Ala Gly Asp Ile Ile Pro Glu Val Val Arg Ser Ile
    370                 375                 380

Pro Glu Arg Arg Pro Glu Asp Ala Val Thr Tyr His Met Pro Thr His
385                 390                 395                 400

Cys Pro Ser Cys Gly His Glu Leu Val Arg Ile Glu Gly Glu Val Ala
                405                 410                 415

Leu Arg Cys Ile Asn Pro Lys Cys Gln Ala Gln Leu Val Glu Gly Leu
                420                 425                 430

Ile His Phe Val Ser Arg Gln Ala Met Asn Ile Asp Gly Leu Gly Thr
                435                 440                 445

Lys Ile Ile Gln Gln Leu Tyr Gln Ser Glu Leu Ile Lys Asp Val Ala
    450                 455                 460

Asp Ile Phe Tyr Leu Thr Glu Glu Asp Leu Leu Pro Leu Asp Arg Met
465                 470                 475                 480

Gly Gln Lys Lys Val Asp Asn Leu Leu Ala Ala Ile Gln Gln Ala Lys
                485                 490                 495

Asp Asn Ser Leu Glu Asn Leu Leu Phe Gly Leu Gly Ile Arg His Leu
                500                 505                 510

Gly Val Lys Ala Ser Gln Val Leu Ala Glu Lys Tyr Glu Thr Ile Asp
                515                 520                 525

Arg Leu Leu Thr Val Thr Glu Ala Glu Leu Val Glu Ile His Asp Ile
            530                 535                 540

Gly Asp Lys Val Ala Gln Ser Val Val Thr Tyr Leu Glu Asn Glu Asp
545                 550                 555                 560

Ile Arg Ala Leu Ile Gln Lys Leu Lys Asp Lys His Val Asn Met Ile
                565                 570                 575

Tyr Lys Gly Ile Lys Thr Ser Asp Ile Glu Gly His Pro Glu Phe Ser
```

-continued

```
              580                585                590
Gly Lys Thr Ile Val Leu Thr Gly Lys Leu His Gln Met Thr Arg Asn
         595                600                605
Glu Ala Ser Lys Trp Leu Ala Ser Gln Gly Ala Lys Val Thr Ser Ser
      610                615                620
Val Thr Lys Asn Thr Asp Val Val Ile Ala Gly Glu Asp Ala Gly Ser
625                630                635                640
Lys Leu Thr Lys Ala Gln Ser Leu Gly Ile Glu Ile Trp Thr Glu Gln
               645                650                655
Gln Phe Val Asp Lys Gln Asn Glu Leu Asn Ser
          660                665
```

<210> SEQ ID NO 62
<211> LENGTH: 652
<212> TYPE: PRT
<213> ORGANISM: Streptococcus pneumoniae
<220> FEATURE:
<223> OTHER INFORMATION: Streptococcus pneumoniae (strain P1031)

<400> SEQUENCE: 62

```
Met Asn Lys Arg Met Asn Glu Leu Val Ala Leu Leu Asn Arg Tyr Ala
1                5                10                15
Thr Glu Tyr Tyr Thr Ser Asp Asn Pro Ser Val Ser Asp Ser Glu Tyr
               20                25                30
Asp Arg Leu Tyr Arg Glu Leu Val Glu Leu Glu Thr Ala Tyr Pro Glu
          35                40                45
Gln Val Leu Ala Asp Ser Pro Thr His Arg Val Gly Gly Lys Val Leu
      50                55                60
Asp Gly Phe Glu Lys Tyr Ser His Gln Tyr Pro Leu Tyr Ser Leu Gln
65                70                75                80
Asp Ala Phe Ser Arg Glu Glu Leu Asp Ala Phe Asp Ala Arg Val Arg
               85                90                95
Lys Glu Val Ala His Pro Thr Tyr Ile Cys Glu Leu Lys Ile Asp Gly
          100                105                110
Leu Ser Ile Ser Leu Thr Tyr Glu Lys Gly Ile Leu Val Ala Gly Val
          115                120                125
Thr Arg Gly Asp Gly Ser Ile Gly Glu Asn Ile Thr Glu Asn Leu Lys
      130                135                140
Arg Val Lys Asp Ile Pro Leu Thr Leu Pro Glu Glu Leu Asp Ile Thr
145                150                155                160
Val Arg Gly Glu Cys Tyr Met Pro Arg Ala Ser Phe Asp Gln Val Asn
               165                170                175
Gln Ala Arg Gln Glu Asn Gly Glu Pro Glu Phe Ala Asn Pro Arg Asn
          180                185                190
Ala Ala Ala Gly Thr Leu Arg Gln Leu Asp Thr Ala Val Val Ala Lys
          195                200                205
Arg Asn Leu Ala Thr Phe Leu Tyr Gln Glu Ala Ser Pro Ser Thr Arg
      210                215                220
Asp Ser Gln Glu Lys Gly Leu Lys Tyr Leu Glu Gln Leu Gly Phe Val
225                230                235                240
Val Asn Pro Lys Arg Ile Leu Ala Glu Asn Ile Asp Glu Ile Trp Asn
               245                250                255
Phe Ile Gln Glu Val Gly Gln Glu Arg Glu Asn Leu Pro Tyr Asp Ile
          260                265                270
Asp Gly Val Val Ile Lys Val Asn Asp Leu Ala Ser Gln Glu Glu Leu
```

-continued

```
              275                   280                   285
Gly Phe Thr Val Lys Ala Pro Lys Trp Ala Val Ala Tyr Lys Phe Pro
    290                   295                   300

Ala Glu Glu Lys Glu Ala Gln Leu Leu Ser Val Asp Trp Thr Val Gly
305                   310                   315                   320

Arg Thr Gly Val Val Thr Pro Thr Ala Asn Leu Thr Pro Val Gln Leu
                  325                   330                   335

Ala Gly Thr Thr Val Ser Arg Ala Thr Leu His Asn Val Asp Tyr Ile
                  340                   345                   350

Ala Glu Lys Asp Ile Arg Lys Asp Asp Thr Val Ile Val Tyr Lys Ala
                  355                   360                   365

Gly Asp Ile Ile Pro Ala Val Leu Arg Val Val Glu Ser Lys Arg Val
              370                   375                   380

Ser Glu Glu Lys Leu Asp Ile Pro Thr Asn Cys Pro Ser Cys Asn Ser
385                   390                   395                   400

Asp Leu Leu His Phe Glu Asp Glu Val Ala Leu Arg Cys Ile Asn Pro
                  405                   410                   415

Arg Cys Pro Ala Gln Ile Met Glu Gly Leu Ile His Phe Ala Ser Arg
                  420                   425                   430

Asp Ala Met Asn Ile Thr Gly Leu Gly Pro Ser Ile Val Glu Lys Leu
                  435                   440                   445

Phe Ala Ala Asn Leu Val Lys Asp Val Ala Asp Ile Tyr Arg Leu Gln
              450                   455                   460

Glu Glu Asp Phe Leu Leu Leu Glu Gly Val Lys Glu Lys Ser Ala Ala
465                   470                   475                   480

Lys Leu Tyr Gln Ala Ile Gln Ala Ser Lys Glu Asn Ser Ala Glu Lys
                  485                   490                   495

Leu Leu Phe Gly Leu Gly Ile Arg His Val Gly Ser Lys Ala Ser Gln
                  500                   505                   510

Leu Leu Leu Gln Tyr Phe His Ser Ile Glu Asn Leu Tyr Gln Ala Asp
                  515                   520                   525

Ser Glu Glu Val Ala Ser Ile Glu Ser Leu Gly Gly Val Ile Ala Lys
              530                   535                   540

Ser Leu Gln Thr Tyr Phe Ala Thr Glu Gly Ser Glu Ile Leu Leu Arg
545                   550                   555                   560

Glu Leu Lys Glu Thr Gly Val Asn Leu Asp Tyr Lys Gly Gln Thr Val
                  565                   570                   575

Val Ala Asp Ala Ala Leu Ser Gly Leu Thr Val Val Leu Thr Gly Lys
                  580                   585                   590

Leu Glu Arg Leu Lys Arg Ser Glu Ala Lys Ser Lys Leu Glu Ser Leu
                  595                   600                   605

Gly Ala Lys Val Thr Gly Ser Val Ser Lys Lys Thr Asp Leu Val Val
              610                   615                   620

Val Gly Ala Asp Ala Gly Ser Lys Leu Gln Lys Ala Gln Glu Leu Gly
625                   630                   635                   640

Ile Gln Val Arg Asp Glu Ala Trp Leu Glu Ser Leu
                  645                   650
```

<210> SEQ ID NO 63
<211> LENGTH: 374
<212> TYPE: PRT
<213> ORGANISM: Unknown
<220> FEATURE:
<223> OTHER INFORMATION: Description of Unknown:
      Wild-type Enterobacteria phage T4 RNA ligase 1 protein -continued

```
        sequence - 'Rnl1'

<400> SEQUENCE: 63

Met Gln Glu Leu Phe Asn Asn Leu Met Glu Leu Cys Lys Asp Ser Gln
1               5                   10                  15

Arg Lys Phe Phe Tyr Ser Asp Asp Val Ser Ala Ser Gly Arg Thr Tyr
                20                  25                  30

Arg Ile Phe Ser Tyr Asn Tyr Ala Ser Tyr Ser Asp Trp Leu Leu Pro
                35                  40                  45

Asp Ala Leu Glu Cys Arg Gly Ile Met Phe Glu Met Asp Gly Glu Lys
        50                  55                  60

Pro Val Arg Ile Ala Ser Arg Pro Met Glu Lys Phe Phe Asn Leu Asn
65                  70                  75                  80

Glu Asn Pro Phe Thr Met Asn Ile Asp Leu Asn Asp Val Asp Tyr Ile
                85                  90                  95

Leu Thr Lys Glu Asp Gly Ser Leu Val Ser Thr Tyr Leu Asp Gly Asp
                100                 105                 110

Glu Ile Leu Phe Lys Ser Lys Gly Ser Ile Lys Ser Glu Gln Ala Leu
            115                 120                 125

Met Ala Asn Gly Ile Leu Met Asn Ile Asn His His Arg Leu Arg Asp
        130                 135                 140

Arg Leu Lys Glu Leu Ala Glu Asp Gly Phe Thr Ala Asn Phe Glu Phe
145                 150                 155                 160

Val Ala Pro Thr Asn Arg Ile Val Leu Ala Tyr Gln Glu Met Lys Ile
                165                 170                 175

Ile Leu Leu Asn Val Arg Glu Asn Glu Thr Gly Glu Tyr Ile Ser Tyr
            180                 185                 190

Asp Asp Ile Tyr Lys Asp Ala Thr Leu Arg Pro Tyr Leu Val Glu Arg
            195                 200                 205

Tyr Glu Ile Asp Ser Pro Lys Trp Ile Glu Glu Ala Lys Asn Ala Glu
        210                 215                 220

Asn Ile Glu Gly Tyr Val Ala Val Met Lys Asp Gly Ser His Phe Lys
225                 230                 235                 240

Ile Lys Ser Asp Trp Tyr Val Ser Leu His Ser Thr Lys Ser Ser Leu
                245                 250                 255

Asp Asn Pro Glu Lys Leu Phe Lys Thr Ile Ile Asp Gly Ala Ser Asp
                260                 265                 270

Asp Leu Lys Ala Met Tyr Ala Asp Asp Glu Tyr Ser Tyr Arg Lys Ile
            275                 280                 285

Glu Ala Phe Glu Thr Thr Tyr Leu Lys Tyr Leu Asp Arg Ala Leu Phe
        290                 295                 300

Leu Val Leu Asp Cys His Asn Lys His Cys Gly Lys Asp Arg Lys Thr
305                 310                 315                 320

Tyr Ala Met Glu Ala Gln Gly Val Ala Lys Gly Ala Gly Met Asp His
            325                 330                 335

Leu Phe Gly Ile Ile Met Ser Leu Tyr Gln Gly Tyr Asp Ser Gln Glu
            340                 345                 350

Lys Val Met Cys Glu Ile Glu Gln Asn Phe Leu Lys Asn Tyr Lys Lys
            355                 360                 365

Phe Ile Pro Glu Gly Tyr
    370

<210> SEQ ID NO 64
<211> LENGTH: 334
```

-continued

<212> TYPE: PRT
<213> ORGANISM: Unknown
<220> FEATURE:
<223> OTHER INFORMATION: Description of Unknown:
      Wild-type Enterobacteria phage T4 RNA ligase 2 protein
      sequence - 'Rnl2'

<400> SEQUENCE: 64

Met Phe Lys Lys Tyr Ser Ser Leu Glu Asn His Tyr Asn Ser Lys Phe
1               5                   10                  15

Ile Glu Lys Leu Tyr Ser Leu Gly Leu Thr Gly Gly Glu Trp Val Ala
            20                  25                  30

Arg Glu Lys Ile His Gly Thr Asn Phe Ser Leu Ile Ile Glu Arg Asp
        35                  40                  45

Lys Val Thr Cys Ala Lys Arg Thr Gly Pro Ile Leu Pro Ala Glu Asp
    50                  55                  60

Phe Phe Gly Tyr Glu Ile Ile Leu Lys Asn Tyr Ala Asp Ser Ile Lys
65                  70                  75                  80

Ala Val Gln Asp Ile Met Glu Thr Ser Ala Val Val Ser Tyr Gln Val
                85                  90                  95

Phe Gly Glu Phe Ala Gly Pro Gly Ile Gln Lys Asn Val Asp Tyr Cys
                100                 105                 110

Asp Lys Asp Phe Tyr Val Phe Asp Ile Ile Val Thr Thr Glu Ser Gly
            115                 120                 125

Asp Val Thr Tyr Val Asp Asp Tyr Met Met Glu Ser Phe Cys Asn Thr
    130                 135                 140

Phe Lys Phe Lys Met Ala Pro Leu Leu Gly Arg Gly Lys Phe Glu Glu
145                 150                 155                 160

Leu Ile Lys Leu Pro Asn Asp Leu Asp Ser Val Val Gln Asp Tyr Asn
                165                 170                 175

Phe Thr Val Asp His Ala Gly Leu Val Asp Ala Asn Lys Cys Val Trp
                180                 185                 190

Asn Ala Glu Ala Lys Gly Glu Val Phe Thr Ala Glu Gly Tyr Val Leu
            195                 200                 205

Lys Pro Cys Tyr Pro Ser Trp Leu Arg Asn Gly Asn Arg Val Ala Ile
    210                 215                 220

Lys Cys Lys Asn Ser Lys Phe Ser Glu Lys Lys Lys Ser Asp Lys Pro
225                 230                 235                 240

Ile Lys Ala Lys Val Glu Leu Ser Glu Ala Asp Asn Lys Leu Val Gly
                245                 250                 255

Ile Leu Ala Cys Tyr Val Thr Leu Asn Arg Val Asn Asn Val Ile Ser
                260                 265                 270

Lys Ile Gly Glu Ile Gly Pro Lys Asp Phe Gly Lys Val Met Gly Leu
            275                 280                 285

Thr Val Gln Asp Ile Leu Glu Glu Thr Ser Arg Glu Gly Ile Thr Leu
    290                 295                 300

Thr Gln Ala Asp Asn Pro Ser Leu Ile Lys Lys Glu Leu Val Lys Met
305                 310                 315                 320

Val Gln Asp Val Leu Arg Pro Ala Trp Ile Glu Leu Val Ser
                325                 330

<210> SEQ ID NO 65
<211> LENGTH: 389
<212> TYPE: PRT
<213> ORGANISM: Unknown
<220> FEATURE:
<223> OTHER INFORMATION: Description of Unknown:

-continued

```
        Wild-type Aeromonas virus Aeh1 ligase protein sequence - 'RNA3'

<400> SEQUENCE: 65

Met Gln Ser Ile Lys Glu Leu Tyr Gln Asn Leu Ile Asn Leu Cys Val
1               5                   10                  15

Asp Asp Asn Thr Lys Phe Tyr Phe Ala Glu Thr Val Thr Ser Leu Gly
            20                  25                  30

Thr Lys Val Arg Ile Phe Asp Tyr His Val Ala Gly Tyr Asn Asp Trp
            35                  40                  45

Ile Arg Pro Asp Ala Met Ala Ser Arg Gly Ile Met Phe Glu Met Asn
    50                  55                  60

Gly Glu Ile Pro Val Arg Ile Met Ser Arg Pro Met Asp Lys Phe Phe
65                  70                  75                  80

Asn Tyr Ser Glu Val Ile Gly Trp Glu Lys Leu Glu Thr Ala Gly Asn
                85                  90                  95

Met Lys Met Pro Asp Leu Asn Lys Ile Ala Tyr Val Ile Asp Lys Arg
            100                 105                 110

Asp Gly Ser Leu Ile Ser Thr Tyr Leu Asp Ile Ser Gly Glu Ile Lys
            115                 120                 125

Asn Leu Leu Leu Lys Ser Lys Ala Ser Ile Arg Ser Asn Gln Ala Asn
    130                 135                 140

Asp Ala Ser Val Trp Leu Tyr Gln Glu Asp His Lys Asp Leu Leu Glu
145                 150                 155                 160

Phe Cys Thr Ala Tyr Ala Glu Asn Gly Phe Thr Val Asn Met Glu Trp
                165                 170                 175

Thr Ala Pro His Asn Gln Ile Val Leu Cys Tyr Asn Glu His Gln Leu
            180                 185                 190

Arg Ile Leu Asn Ile Arg His Asn Glu Thr Gly Glu Tyr Val Asp Phe
            195                 200                 205

Gly Glu Leu Gln Lys Asp Pro Thr Phe Val Lys Tyr Ala Ala Asp Phe
    210                 215                 220

Phe Glu Val Pro Gly Asp Gly Lys Ala Trp Ile Asp Glu Val Tyr Gln
225                 230                 235                 240

Met Thr Gly Ile Glu Gly Phe Val Val Val Met Glu Asp Tyr Gln Met
                245                 250                 255

Phe Lys Leu Lys Thr Asp Trp Tyr Val Ala Leu His His Thr Lys Asp
            260                 265                 270

Ser Ile Asn Asn Ser Glu Arg Leu Ile Tyr Ala Cys Ala Glu Asn Cys
            275                 280                 285

Thr Asp Asp Leu Arg Gln Met Phe Arg Asp Asp Glu Asn Ser Leu Gln
    290                 295                 300

Lys Ile Glu Ile Phe Asp Asn His Phe Arg Asp Val Val Met Asp Ala
305                 310                 315                 320

Met Lys Lys Leu Thr Glu Ala Tyr Glu Lys Tyr Arg Gly Met Glu Arg
                325                 330                 335

Arg Asp Tyr Ala Ile Asn Met Asn Asn Asp Phe Lys Asn Glu Arg His
            340                 345                 350

Trp Phe Asn Ile Ala Met Gln Met Phe Ala Gln Arg Pro Asp Phe Ser
            355                 360                 365

Met Thr Asp Glu Ile Val Ala Val Ile Lys Lys Tyr Pro Lys Thr Phe
    370                 375                 380

Ile Pro Lys Gly Tyr
385
```

-continued

```
<210> SEQ ID NO 66
<211> LENGTH: 383
<212> TYPE: PRT
<213> ORGANISM: Unknown
<220> FEATURE:
<223> OTHER INFORMATION: Description of Unknown:
      Wild-type Klebsiella phage JD18 ligase protein sequence -
      'RNA6'

<400> SEQUENCE: 66

Met Leu Glu Leu Tyr Lys Asn Leu Met Asn Leu Cys Glu Ser Ser Glu
1               5                   10                  15

Val Ala Lys Phe Phe Tyr Lys Asp Phe Thr Gly Pro Met Asp Gly Lys
                20                  25                  30

Phe Arg Val Phe Ser Tyr His Tyr Ala Ser Tyr Ser Glu Trp Leu Lys
            35                  40                  45

Pro Asp Ala Leu Glu Cys Arg Gly Ile Met Phe Glu Met Asp Gly Asp
        50                  55                  60

Thr Pro Ile Arg Ile Ala Ser Arg Pro Met Glu Lys Phe Phe Asn Leu
65                  70                  75                  80

Asn Glu Asn Pro Met Thr Met Gly Ile Asp Ile Ser Asp Val Glu Tyr
                85                  90                  95

Ile Met Asp Lys Ala Asp Gly Ser Leu Val Ser Ser Tyr Val Asp Asp
                100                 105                 110

Gly Tyr Leu Tyr Leu Lys Ser Lys Thr Ser Leu Tyr Ser Asp Gln Ala
            115                 120                 125

Arg Gln Ala Ser Ala Leu Leu Asn Ser Glu Glu Tyr Ser Ser Leu His
        130                 135                 140

Gln Val Ile Leu Glu Leu Ala Leu Asp Gly Tyr Thr Val Asn Met Glu
145                 150                 155                 160

Phe Val Ser Pro Asn Asn Arg Val Val Leu Ala Tyr Gln Glu Pro Gln
                165                 170                 175

Leu Phe Val Leu Asn Val Arg Asn Asn Thr Thr Gly Glu Tyr Ile Lys
            180                 185                 190

Tyr Asp Asp Leu Tyr Ala Asn Ala Lys Ile Arg Pro Tyr Leu Ile Asn
            195                 200                 205

Ala Tyr Gly Ile Ser Asp Pro Thr Thr Trp Val Glu Gly Val Arg Ala
        210                 215                 220

Leu Glu Gly Val Glu Gly Tyr Ile Ala Val Leu Asn Thr Gly Gln Arg
225                 230                 235                 240

Phe Lys Val Lys Thr Glu Trp Tyr Ser Ala Leu His His Thr Lys Asp
                245                 250                 255

Ser Ile Thr Ser Asn Glu Arg Leu Phe Ala Ser Val Val Ser Ala Asn
                260                 265                 270

Ser Asp Asp Leu Arg Ser Leu Phe Ala Gly Asp Glu Tyr Ala Ile Lys
        275                 280                 285

Lys Ile Ser Ala Phe Glu Gln Ala Tyr Leu Asp Tyr Leu Gly Lys Ser
        290                 295                 300

Leu Glu Leu Cys Gln Ser Phe Tyr Asp Glu Tyr Arg Gly Arg Ala Arg
305                 310                 315                 320

Lys Asp Tyr Ala Ile Ala Ala Gln Lys Ala Thr Val Asn Gln Arg His
            325                 330                 335

Leu Phe Gly Val Ile Met Asn Met Tyr Glu Gly Thr Val Asp Val Asp
            340                 345                 350

Lys Leu Leu Lys Asp Leu Glu Arg Val Phe Leu Lys Tyr Trp Ala Gly
```

-continued

```
                355                 360                 365
      Tyr Val Pro Lys Glu Tyr Glu Lys Glu Ile Glu Ile Ser Glu Glu
          370                 375                 380

<210> SEQ ID NO 67
<211> LENGTH: 384
<212> TYPE: PRT
<213> ORGANISM: Unknown
<220> FEATURE:
<223> OTHER INFORMATION: Description of Unknown:
      Wild-type Stenotrophomonas phage IME13 ligase protein sequence
      - 'RNA8'

<400> SEQUENCE: 67

Met Ser Arg Thr Ile Glu Leu Phe Asn Asn Leu Met Ser Val Val Glu
1               5                   10                  15

Lys Ser Glu Lys Gly Asn Phe Tyr Phe Lys Asp Val Ile Thr Ser Met
            20                  25                  30

Gly Thr Lys Ala Arg Ile Phe Ser Tyr Phe Ile Ala Ser Tyr Thr Asp
            35                  40                  45

Trp Leu Gln Asp Asp Ala Leu Glu Cys Arg Gly Ile Met Phe Glu Leu
        50                  55                  60

Asn Asp Lys Asn Glu Pro Val Arg Ile Met Ala Arg Pro Met Gln Lys
65                  70                  75                  80

Phe Phe Asn Leu Lys Glu Asn Pro Met Thr Ile Gly Leu Asp Leu Thr
                85                  90                  95

Lys Met Ile Gly Leu Met Glu Lys Ala Asp Gly Ser Leu Ile Ser Ser
            100                 105                 110

Tyr His Asp Gln Gly Tyr Val Tyr Leu Lys Ser Lys Ala Ala Ile Phe
        115                 120                 125

Ser Asp Gln Ala Asn Lys Ala Met Ala Leu Leu Asn Ser Pro Ala Tyr
        130                 135                 140

Glu Lys Leu Arg Asp Ala Ile Val Arg Ala Gly Ser Asp Phe Thr Phe
145                 150                 155                 160

Asn Met Glu Tyr Val Gly Pro Ser Asn Arg Val Val Leu Pro Tyr Glu
                165                 170                 175

Glu Glu Glu Leu Ile Val Leu Asn Val Arg His Asn Glu Thr Gly Gln
                180                 185                 190

Tyr Val Glu Phe Ser Thr Leu Leu Asp Asp Pro Leu Ile Arg His Arg
        195                 200                 205

Met Ile Gly Val Tyr Pro Cys Pro Asp Trp Ser Lys Val Thr Pro Glu
        210                 215                 220

Glu Trp Glu Ala Ala Thr Arg Ala Glu Thr Asp Ile Glu Gly Val Ile
225                 230                 235                 240

Gly Ile Met Pro Asp Gly Gln Leu Phe Lys Leu Lys Thr Asp Trp Tyr
                245                 250                 255

Ser Ser Leu His Arg Thr Lys Asp Ser Ile Asn Asn Asn Lys Ala Leu
            260                 265                 270

Phe Gln Ser Ile Lys Glu Arg Ala Ser Asp Asp Leu Arg Gly Met Phe
        275                 280                 285

Ser Asp Asp Asn Ala Ala Leu Ala Lys Ile Glu Ala Phe Glu Ser Ala
        290                 295                 300

Tyr Ile Asp Thr Val Ala Lys Tyr His Lys Ile Cys Ala Glu Val Phe
305                 310                 315                 320

Leu Arg Phe Ala Arg Phe Leu Ile Val Glu Val Phe Ala Ile Glu Ala
                325                 330                 335
```

```
Gln Ala Arg Met Lys Asp Cys Arg Tyr Leu Phe Ser Ile Val Met Gln
            340                 345                 350

Gln Tyr Gly Arg Asp Trp Asp Gly Glu Leu Ala Val Glu Lys Ile Glu
            355                 360                 365

Glu His Ile Ile Lys Glu Tyr Ala Thr Tyr Val Pro Met Ala Tyr Arg
            370                 375                 380
```

<210> SEQ ID NO 68
<211> LENGTH: 394
<212> TYPE: PRT
<213> ORGANISM: Unknown
<220> FEATURE:
<223> OTHER INFORMATION: Description of Unknown:
      Wild-type Escherichia phage JSE ligase protein sequence -
      'RNA9'

<400> SEQUENCE: 68

```
Met Glu His Lys Leu Cys Gln Gln Lys Lys Thr Thr Lys Lys Val Leu
1               5                   10                  15

Ala Leu Phe Lys Asn Leu Met Ala Leu Cys Asp Gly Ser Asp Thr Phe
            20                  25                  30

Tyr Tyr Lys Asp Glu Ile Thr Ala Met Gln Thr Arg Met Arg Ile Phe
            35                  40                  45

Ser Tyr Leu Tyr Leu Ser Lys Pro Glu Met Trp Asn Lys Pro Asp Ala
        50                  55                  60

Leu Glu Cys Arg Gly Ile Met Phe Glu Ile Asp Asp Lys Asp Arg Pro
65                  70                  75                  80

Val Arg Ile Ala Ser Arg Pro Met Glu Lys Phe Phe Asn Leu Gly Glu
                85                  90                  95

Asn Asp Arg Ala Arg Phe Lys Pro Glu Asp Val Glu Met Val Met Asp
            100                 105                 110

Lys Met Asp Gly Ser Leu Val Ser Thr Tyr Ile Asp Asn Gly Tyr Val
            115                 120                 125

Gln Leu Lys Ser Lys Ala Ala Leu Tyr Ser Ser Gln Ala Glu Arg Ala
            130                 135                 140

Asn Gly Leu Leu Tyr Ser Glu Lys Tyr Ala Asp Leu Arg Ala Lys Ile
145                 150                 155                 160

Ala Asp Ile Gly Ser Asp Tyr Thr Phe Asn Phe Glu Tyr Thr Ala Pro
                165                 170                 175

Ser Asn Arg Ile Val Val Glu Tyr Ser Glu Pro Ser Leu Thr Leu Leu
            180                 185                 190

Asn Val Arg His Asn Val Thr Gly Glu Tyr Val Pro His Gln Met Leu
            195                 200                 205

Phe Ala Asp Ala Ile Leu Arg Pro His Leu Val Asn Ala Leu Gln Val
            210                 215                 220

Asp Ser Ala Arg Phe Ser Asn Ile Leu Asp Glu Val Arg Thr Ala Glu
225                 230                 235                 240

Gly Ile Glu Gly Ile Val Ala Arg Thr Lys Asp Gly Gln Met Phe Lys
                245                 250                 255

Val Lys Ser Glu Trp Tyr Ile Gly Val His Asn Ile Lys Asn Thr Ser
            260                 265                 270

Met Phe Pro Asn Asn Leu Ile Tyr Tyr Val Val Glu Ser Glu Thr Asp
            275                 280                 285

Asp Leu Arg Ala Ala Tyr Glu Gly Glu Pro Glu Ala Leu Glu Arg Ile
            290                 295                 300
```

-continued

Glu Leu Phe Glu Glu Ala Phe Arg Ser Ile Leu Arg Asn Ala Phe Thr
305                 310                 315                 320

Thr Ala Thr Glu Phe Tyr Asn Ala His Ala Gly Glu Asp Arg Lys Thr
                325                 330                 335

Tyr Ala Ser Asn Ala Thr Ile Glu Ser Arg Lys His Gly Asp Ala Gln
                340                 345                 350

Ser Tyr Ile Phe Met Cys Leu Met Ile Ala Phe Asp Gly Leu Asp Tyr
                355                 360                 365

Asp Arg Ile Leu Ala Ser Met Lys Thr Tyr Tyr Leu Arg Asn Tyr Lys
370                 375                 380

Lys Leu Ile Pro Ala Asp Lys Ile Asp Trp
385                 390

<210> SEQ ID NO 69
<211> LENGTH: 385
<212> TYPE: PRT
<213> ORGANISM: Unknown
<220> FEATURE:
<223> OTHER INFORMATION: Description of Unknown:
      Wild-type Acinetobacter phage Acj61 ligase protein sequence -
      'RNA16'

<400> SEQUENCE: 69

Met Lys Glu Leu Phe Asp Asn Leu Met Ala Leu Gln Asp Pro Asn Asp
1               5                   10                  15

Ile Ser Lys Phe Phe Tyr Lys Asp Val Val Thr Gln Pro Gly Thr Lys
                20                  25                  30

Cys Arg Ile Phe Ser Tyr Asn Tyr Ala Ala Tyr Ser Asp Trp Leu Leu
                35                  40                  45

Pro Gly Ala Leu Glu Ser Arg Gly Ile Met Phe Glu Leu Asp Ala Asp
        50                  55                  60

Asn Gln Pro Val Arg Val Met Ala Arg Pro Met Glu Lys Phe Phe Asn
65                  70                  75                  80

Leu Glu Glu Asn Pro Phe Thr Met Asp Leu Asp Leu Ser Gln Leu Glu
                85                  90                  95

Tyr Ala Met Thr Lys Ala Asp Gly Ser Leu Ile Ser Thr Tyr Val Asp
                100                 105                 110

Gln Gly Tyr Leu Tyr Thr Lys Ser Lys Gly Ser Ile Ser Ser Ser Gln
        115                 120                 125

Ala Ile Glu Ser Lys Gln Leu Leu Leu Asp Ile Asn Tyr Lys Pro Leu
        130                 135                 140

Ala Glu Arg Ala Leu Glu Leu Ala Lys Asp Gly Phe Thr Cys Asn Phe
145                 150                 155                 160

Glu Tyr Val Ala Pro Asn Asn Arg Ile Val Leu Asn Tyr Ala Lys Lys
                165                 170                 175

Asp Leu Ile Leu Leu Asn Val Arg His Asn Glu Thr Gly Glu Tyr Val
                180                 185                 190

Pro Met Ala Glu Leu Gln Lys Asp Pro Val Leu Arg Asn Tyr Leu Ile
        195                 200                 205

Asp Val Tyr Pro Pro Arg Glu Asp Ile Asp Thr Asn Glu Met Ile Lys
        210                 215                 220

Glu Ile Arg Glu Met Val Asp Ile Glu Gly Phe Val Phe Gln His Ala
225                 230                 235                 240

Ser Gly Leu Lys Phe Lys Leu Lys Thr Glu Trp Tyr Ser Asn Leu His
                245                 250                 255

Arg Val Lys Asp Thr Leu Asn Asn Ser Glu Ala Leu Phe Met Val Val

-continued

```
                260                 265                 270

Val Ala Gly Gly Ser Asp Asp Met Lys Ser Leu Phe Thr Asp Asp Leu
            275                 280                 285

Ser Arg Thr Lys Ile Glu Ser Phe Glu Thr Ala Phe Leu Asp Tyr Leu
            290                 295                 300

Lys Lys Thr Ser Asn Phe Val Phe Asp Leu Gln Arg Gln Leu Ile Gly
305                 310                 315                 320

Ser Asp Arg Lys Thr Tyr Ala Ile Glu Cys Gln Thr Ile Leu Arg Asn
                325                 330                 335

Thr Asp Gln Leu Glu Leu Phe Gly Val Met Met Glu Leu Tyr Lys Gly
            340                 345                 350

Ala Asp Gln Glu Gln Thr Ile Lys Asn Ile Asn Val Val Phe Met Lys
            355                 360                 365

Asn Tyr Lys Lys Tyr Val Pro Ala Gly Phe Glu Thr Leu Lys Asn Glu
    370                 375                 380

Tyr
385

<210> SEQ ID NO 70
<211> LENGTH: 381
<212> TYPE: PRT
<213> ORGANISM: Unknown
<220> FEATURE:
<223> OTHER INFORMATION: Description of Unknown:
      Wild-type Vibrio phage VH7D ligase protein sequence - 'RNA20'

<400> SEQUENCE: 70

Met Asn Val Gln Glu Leu Tyr Lys Asn Leu Met Ser Leu Ala Asp Asp
1                   5                   10                  15

Ala Glu Gly Lys Phe Phe Phe Ala Asp His Leu Ser Pro Leu Gly Glu
                20                  25                  30

Lys Phe Arg Val Phe Ser Tyr His Ile Ala Ser Tyr Ser Asp Trp Leu
            35                  40                  45

Leu Pro Gly Ala Leu Glu Ala Arg Gly Ile Met Phe Gln Leu Asp Asp
    50                  55                  60

Asn Asp Glu Met Ile Arg Ile Val Ser Arg Pro Met Glu Lys Phe Phe
65                  70                  75                  80

Asn Leu Asn Glu Asn Pro Phe Thr Met Glu Leu Asp Leu Thr Thr Thr
                85                  90                  95

Val Gln Leu Met Asp Lys Ala Asp Gly Ser Leu Ile Ser Thr Tyr Leu
            100                 105                 110

Ser Gly Glu Asn Phe Ala Leu Lys Ser Lys Thr Ser Ile Phe Ser Glu
            115                 120                 125

Gln Ala Val Ala Ala Asn Arg Tyr Ile Lys Lys Pro Glu Asn Arg Asp
    130                 135                 140

Leu Trp Glu Phe Cys Asp Asp Cys Thr Gln Ala Gly Leu Thr Val Asn
145                 150                 155                 160

Met Glu Trp Cys Ala Pro Asn Asn Arg Ile Val Leu Glu Tyr Pro Glu
                165                 170                 175

Ala Lys Leu Val Ile Leu Asn Ile Arg Asp Asn Glu Thr Gly Asp Tyr
            180                 185                 190

Val Ser Phe Asp Asp Ile Pro Gln Ser Ala Leu Met Arg Val Lys Gln
            195                 200                 205

Trp Leu Val Asp Glu Tyr Asp Pro Ala Thr Ala His Glu Pro Asp Phe
    210                 215                 220
```

-continued

```
Val Glu Lys Leu Arg Asp Thr Lys Gly Ile Glu Gly Met Ile Leu Arg
225                 230                 235                 240

Leu Ala Asn Gly Gln Ser Val Lys Ile Lys Thr Gln Trp Tyr Val Asp
                245                 250                 255

Leu His Ser Gln Lys Asp Ser Val Asn Val Pro Lys Lys Leu Val Thr
                260                 265                 270

Thr Ile Leu Asn Gly Asn His Asp Asp Leu Tyr Ala Leu Phe Ala Asp
                275                 280                 285

Asp Lys Pro Thr Ile Glu Arg Ile Arg Glu Phe Asp Ser His Val Thr
                290                 295                 300

Lys Thr Leu Thr Asn Ser Phe Asn Ala Val Arg Gln Phe Tyr Ala Arg
305                 310                 315                 320

Asn Arg His Leu Ala Arg Lys Asp Tyr Ala Ile Ala Gly Gln Lys Val
                325                 330                 335

Leu Lys Pro Trp Glu Phe Gly Val Ala Met Ile Ala Tyr Gln Lys Gln
                340                 345                 350

Thr Val Glu Gly Val Tyr Glu Ser Leu Val Thr Ala Tyr Leu Lys Arg
                355                 360                 365

Pro Glu Leu Ala Ile Pro Glu Lys Tyr Leu Asn Gly Val
                370                 375                 380

<210> SEQ ID NO 71
<211> LENGTH: 382
<212> TYPE: PRT
<213> ORGANISM: Unknown
<220> FEATURE:
<223> OTHER INFORMATION: Description of Unknown:
      Wild-type Escherichia phage JS98 ligase protein sequence -
      'RNA22'

<400> SEQUENCE: 71

Met Ile Glu Leu Tyr Asp Asn Leu Met Thr Leu Val Lys Asn Ser Thr
1                   5                   10                  15

Lys Ser Lys Phe Phe Phe Lys Asp Phe Gln Ser Ala Leu Gly Val Asn
                20                  25                  30

Tyr Arg Ile Phe Ser Tyr Asn Tyr Ala Ser Tyr Ser Asp Trp Leu Glu
                35                  40                  45

Asp Gly Ala Leu Glu Cys Arg Gly Ile Met Phe Glu Met Asp Glu Asn
                50                  55                  60

Gly Pro Val Arg Ile Ala Ala Arg Pro Met Gln Lys Phe Phe Asn Leu
65                  70                  75                  80

Asp Glu Asn Pro Leu Thr Ile Gly Leu Asp Leu Ser Gln Glu Asn Ile
                85                  90                  95

Asp Leu Val Met Ala Lys Glu Asp Gly Ser Leu Ile Ser Thr Phe Met
                100                 105                 110

Asp Arg Gln Tyr Leu Ser Val Lys Ser Lys Gly Ser Ile His Ser Ser
                115                 120                 125

Met Val His Asp Ser Leu Arg Phe Leu Arg Leu Pro Glu Asn Glu Ala
                130                 135                 140

Phe Ala Ala Arg Leu Glu Glu Ile Thr Lys Ala Gly Tyr Thr Cys Asn
145                 150                 155                 160

Leu Glu Tyr Val Ser Pro Thr Asn Arg Ile Val Leu Ala Tyr Gln Glu
                165                 170                 175

Thr Asn Leu Ile Leu Leu Asn Val Arg Asn Asn Glu Thr Gly Glu Tyr
                180                 185                 190

Ile Pro Tyr Ala Glu Leu Phe Lys Asp Gly Ala Leu Arg Lys His Leu
```

-continued

```
           195                     200                     205

Val Lys Ser Tyr Glu Leu Ser Glu Gly Asp Phe Val Asp Asn Ile Arg
    210                     215                     220

Lys Gln Glu Gly Ile Glu Gly Phe Ile Phe Val Leu Lys Asp Gly Thr
225                     230                     235                     240

Phe Phe Lys Leu Lys Thr Ala Trp Tyr Ser Ala Leu His His Thr Lys
                    245                     250                     255

Asp Ser Ile Asn Asn Asn Glu Arg Leu Phe Glu Val Val Ala Gly
                    260                     265                     270

Gly Thr Asp Asp Leu Arg Gly Leu Phe Ser Thr Asp Ser Phe Ala Ile
                    275                     280                     285

Glu Lys Ile Asn Ala Phe Glu Arg Ile His Leu Asp Tyr Leu Glu Gln
    290                     295                     300

Ser Leu Ala Leu Leu Glu Ala Ala Tyr Ser Gln Leu Lys Gly Arg Asp
305                     310                     315                     320

Arg Lys Asp Tyr Ala Val Thr Gly Gln Leu Ile Leu Lys Asp Phe Pro
                    325                     330                     335

Gly Leu Phe Ser Ile Leu Met Gln Ala Tyr Val Asp Gly Ile Asn Tyr
                    340                     345                     350

Asp Thr Val Met Asp Gln Ile Asn Ser Val Phe Leu Lys Asn His Lys
                    355                     360                     365

Ala Gln Ile Pro Glu Lys Tyr Leu Lys Glu Ile Val Val Glu
    370                     375                     380
```

<210> SEQ ID NO 72
<211> LENGTH: 386
<212> TYPE: PRT
<213> ORGANISM: Unknown
<220> FEATURE:
<223> OTHER INFORMATION: Description of Unknown:
      Wild-type Escherichia phage vB_EcoM_112 ligase protein sequence
      - 'RNA23'

<400> SEQUENCE: 72

```
Met Val Leu Tyr Ser Lys His Lys Arg Gly Tyr Thr Met Gln Glu Leu
1               5                   10                  15

Phe Asn Asn Leu Met Glu Leu Cys Lys Asp Ser Gln Arg Lys Phe Phe
                20                  25                  30

Tyr Ser Asp Asp Val Ser Ala Ser Gly Arg Thr Tyr Arg Ile Phe Ser
            35                  40                  45

Tyr Asn Tyr Ala Ser Tyr Ser Asp Trp Leu Leu Pro Asp Ala Leu Glu
    50                  55                  60

Cys Arg Gly Ile Met Phe Glu Met Asp Gly Glu Lys Pro Val Arg Ile
65                  70                  75                  80

Ala Ser Arg Pro Met Glu Lys Phe Phe Asn Leu Asn Glu Asn Pro Phe
                85                  90                  95

Thr Met Asn Ile Asp Leu Asn Asp Val Asp Tyr Ile Leu Thr Lys Glu
                100                 105                 110

Asp Gly Ser Leu Val Ser Thr Tyr Leu Asp Gly Asp Glu Ile Leu Phe
            115                 120                 125

Lys Ser Lys Gly Ser Ile Lys Ser Glu Gln Ala Leu Met Ala Asn Gly
    130                 135                 140

Ile Leu Met Asn Ile Asn His His Gln Leu Arg Asp Arg Leu Lys Glu
145                 150                 155                 160

Leu Ala Glu Asp Gly Phe Thr Ala Asn Phe Glu Phe Val Ala Pro Thr
                165                 170                 175
```

-continued

```
Asn Arg Ile Val Leu Ala Tyr Gln Glu Met Lys Ile Ile Leu Leu Asn
            180                 185                 190

Val Arg Glu Asn Glu Thr Gly Glu Tyr Ile Ser Tyr Asp Asp Ile Tyr
            195                 200                 205

Lys Asp Ala Ile Leu Arg Pro Tyr Leu Val Glu Arg Tyr Glu Ile Asp
            210                 215                 220

Ser Pro Lys Trp Val Glu Glu Ala Lys Asn Ala Glu Asn Ile Glu Gly
225                 230                 235                 240

Tyr Val Ala Val Met Lys Asp Gly Ser His Phe Lys Ile Lys Ser Asp
                245                 250                 255

Trp Tyr Val Ser Leu His Ser Thr Lys Ser Ser Leu Asp Asn Pro Glu
                260                 265                 270

Lys Leu Phe Lys Thr Ile Ile Asp Gly Ala Ser Asp Asp Leu Lys Ala
            275                 280                 285

Met Tyr Ala Asp Asp Glu Tyr Ser Tyr Arg Lys Ile Glu Ala Phe Glu
            290                 295                 300

Thr Thr Tyr Leu Lys Tyr Leu Asp Arg Ala Leu Phe Leu Val Leu Asp
305                 310                 315                 320

Cys His Asn Lys His Cys Gly Lys Asp Arg Lys Thr Tyr Ala Met Glu
                325                 330                 335

Ala Gln Gly Val Ala Lys Gly Ala Gly Met Asp His Leu Phe Gly Ile
                340                 345                 350

Ile Met Ser Leu Tyr Gln Gly Tyr Asp Ser Gln Glu Lys Val Met Cys
                355                 360                 365

Glu Ile Glu Gln Asn Phe Leu Lys Asn Tyr Lys Lys Phe Ile Pro Glu
            370                 375                 380

Gly Tyr
385
```

```
<210> SEQ ID NO 73
<211> LENGTH: 392
<212> TYPE: PRT
<213> ORGANISM: Unknown
<220> FEATURE:
<223> OTHER INFORMATION: Description of Unknown:
      Wild-type Aeromonas phage CC2 ligase protein sequence - 'RNA28'

<400> SEQUENCE: 73
```

```
Met Lys Glu Leu Tyr Asn Asn Leu Leu Lys Leu Thr Glu Glu His Gly
1               5                   10                  15

Asp Cys Phe Phe Phe Arg Asp His Trp Ser Ser Ile Gly Asn His Phe
            20                  25                  30

Arg Val Phe Ser Tyr His Ile Ala Gly Leu Thr Gln Trp Met Leu Pro
            35                  40                  45

Asp Ala Leu Glu Cys Arg Gly Ile Met Phe Glu Leu Ile Asn Gly Glu
            50                  55                  60

Pro Tyr Arg Ile Ala Ser Arg Pro Met Glu Lys Phe Phe Asn Leu Ala
65                  70                  75                  80

Glu Arg Gln Ala Trp Asn Leu Thr Asn Ser Gly Val Val Gly Leu Asp
                85                  90                  95

Lys Leu Glu Leu Asp Tyr Ser Asn Ile Asp Arg Tyr Glu Asp Lys Ala
            100                 105                 110

Asp Gly Ser Leu Met Ser Ser Tyr His Phe Ile Asp Pro Glu Asp Asp
            115                 120                 125

Asn Arg Ile Asn Tyr Met Leu Lys Ser Lys Thr Ser Ile Asn Ser Asp
```

-continued

```
        130              135              140
Gln Ala Asn Asp Ala Asn Arg Trp Leu Val Asn His Thr Asp Leu Leu
145              150              155              160

Asp Phe Ile Ile Asp Cys Glu Glu Ala Gly Tyr Thr Val Asn Leu Glu
                165              170              175

Trp Cys Ser Pro Lys Asn Gln Ile Val Ile Met Tyr Pro Glu Glu Ser
                180              185              190

Leu Lys Ile Leu Asn Val Arg His Arg Asp Thr Gly Glu Tyr Tyr Ser
            195              200              205

Asn Asn Ser Leu Ile Arg Ser Pro Val Phe Arg Lys Tyr Ala Val Asp
        210              215              220

Gln Phe Met Phe Glu Glu Gly Thr Asp Val Asn Thr Ala Ile Ser Asn
225              230              235              240

Met Tyr Asn Glu Thr Gly Ile Glu Gly Tyr Ile Leu Val Met Arg Asp
                245              250              255

Gly Ser Arg Val Lys Ile Lys Thr Thr Ser Tyr Val Ala Arg His Lys
                260              265              270

Leu Lys Asp Ser Ile Thr Asn Asn Lys Asp Leu Val Ile Ala Val Ala
            275              280              285

Gln Gly Val Ser Asp Asp Leu Arg Gln Leu Phe Leu Asp Asp Ser Leu
        290              295              300

Ser Leu Thr Lys Ile Gln Glu Phe Glu Asp His Val Val Ser Val Ala
305              310              315              320

Gly Ser Thr Tyr Thr Lys Ile Arg Glu Ala His Lys Ala Cys Ala Gly
                325              330              335

Met Glu Arg Arg Glu Tyr Ala Ile Ser Met Gln Asn Thr Phe Lys Gln
                340              345              350

Asp Arg Met Phe Phe Asn Ile Val Met Lys Met Phe Gln Ala Pro Asp
            355              360              365

Leu Glu Val Met Pro Glu Ile Met Ser Val Ile Ile Lys Tyr Pro Asp
        370              375              380

Glu Phe Val Pro Thr Lys Trp Lys
385              390

<210> SEQ ID NO 74
<211> LENGTH: 374
<212> TYPE: PRT
<213> ORGANISM: Unknown
<220> FEATURE:
<223> OTHER INFORMATION: Description of Unknown:
      Wild-type Enterobacteria phage RB69 ligase protein sequence -
      'RNA29'

<400> SEQUENCE: 74

Met Glu Lys Leu Tyr Tyr Asn Leu Leu Ser Leu Cys Lys Ser Ser Ser
1               5               10              15

Asp Arg Lys Phe Phe Tyr Ser Asp Asp Val Ser Pro Ile Gly Lys Lys
                20              25              30

Tyr Arg Ile Phe Ser Tyr Asn Phe Ala Ser Tyr Ser Asp Trp Leu Leu
            35              40              45

Pro Asp Ala Leu Glu Cys Arg Gly Ile Met Phe Glu Met Asp Gly Glu
        50              55              60

Thr Pro Leu Arg Ile Ala Ser Arg Pro Met Glu Lys Phe Phe Asn Leu
65              70              75              80

Asn Glu Asn Pro Phe Thr Leu Ser Ile Asp Leu Asn Asp Val Lys Tyr
                85              90              95
```

-continued

Leu Met Thr Lys Glu Asp Gly Ser Leu Val Ser Thr Tyr Leu Asp Gly
            100                     105                     110

Asn Met Val Arg Phe Lys Ser Lys Gly Ser Ile Lys Ser Asp Gln Ala
            115                     120                     125

Ala Ser Ala Thr Ser Ile Leu Leu Asp Ile Asn His Lys Asp Leu Ala
            130                     135                     140

Asp Arg Leu Leu Glu Leu Cys Asn Asp Gly Phe Thr Ala Asn Phe Glu
145                     150                     155                     160

Tyr Val Ala Pro Ser Asn Lys Ile Val Leu Thr Tyr Pro Glu Lys Arg
                        165                     170                     175

Leu Ile Leu Leu Asn Ile Arg Asp Asn Asn Thr Gly Lys Tyr Ile Glu
                180                     185                     190

Tyr Asp Asp Ile Tyr Leu Asp Pro Val Phe Arg Lys Tyr Leu Val Asp
                195                     200                     205

Arg Phe Glu Ala Pro Glu Gly Asp Trp Val Pro Gly Val Lys Ser Ser
            210                     215                     220

Thr Asn Ile Glu Gly Tyr Val Ala Val Met Lys Asp Gly Ser His Phe
225                     230                     235                     240

Lys Leu Lys Thr Asp Trp Tyr Val Ala Leu His Thr Thr Arg Asp Ser
                        245                     250                     255

Ile Ser Ser Pro Glu Lys Leu Phe Leu Ala Ile Met Asn Gly Ala Ser
                260                     265                     270

Asp Asp Leu Lys Ala Met Tyr Ala Asp Asp Glu Phe Ser Phe Lys Lys
                275                     280                     285

Val Glu Leu Phe Glu Lys Ala Tyr Leu Asp Phe Leu Asp Arg Ser Phe
            290                     295                     300

Tyr Ile Cys Leu Asp Ala Tyr Asp Lys His Lys Gly Lys Asp Arg Lys
305                     310                     315                     320

Thr Tyr Ala Ile Glu Ala Gln Ala Ile Cys Lys Gly Ala Gln Ser Pro
                        325                     330                     335

Trp Leu Phe Gly Ile Ile Met Asn Leu Tyr Gln Gly Gly Ser Lys Glu
                340                     345                     350

Gln Met Met Thr Ala Leu Glu Ser Val Phe Ile Lys Asn His Lys Asn
                355                     360                     365

Phe Ile Pro Glu Gly Tyr
        370

<210> SEQ ID NO 75
<211> LENGTH: 388
<212> TYPE: PRT
<213> ORGANISM: Unknown
<220> FEATURE:
<223> OTHER INFORMATION: Description of Unknown:
        Wild-type Acinetobacter phage Ac42 ligase protein sequence -
        'RNA31'

<400> SEQUENCE: 75

Met Asn Glu Leu Tyr Asn Asn Leu Met Thr Leu Ile Glu Pro Gly Lys
1                       5                       10                      15

Met Ser Arg Phe Phe Leu Arg Asp Ala Val Thr Pro Phe Gly Thr Arg
                20                      25                      30

Val Arg Met Phe Gly Tyr Asn Tyr Ala Ser Tyr Thr Asp Trp Leu Leu
                35                      40                      45

Pro Asp Ala Leu Glu Ala Arg Gly Ile Met Phe Glu Met Asp Glu Asn
        50                      55                      60

```
Asp Gln Pro Ile Arg Val Met Ala Arg Pro Met Glu Lys Phe Phe Asn
65                  70                  75                  80

Leu Gly Glu Asn Pro Phe Thr Ile Asp Leu Asp Leu Ser Thr Ile Glu
                85                  90                  95

Tyr Phe Met Asp Lys Ser Asp Gly Ser Leu Ile Ser Ser Tyr Val Asp
                100                 105                 110

Asn Asp Thr Leu Phe Met Lys Ser Lys Met Ser Ile Gly Ser Val Gln
                115                 120                 125

Ala Val Ala Ala Arg Gln Val Ile Gln Asp Tyr Val His Arg Asp Leu
                130                 135                 140

His Asp Arg Val Leu Glu Leu Ala Lys Asp Gly Phe Thr Cys Asn Phe
145                 150                 155                 160

Glu Tyr Val Ala Pro Asp Asn Arg Val Val Ile Leu Tyr Pro Glu Arg
                165                 170                 175

Ala Leu Val Leu Leu Asn Val Arg Asn Asn Glu Thr Gly Glu Tyr Val
                180                 185                 190

His Ile Glu Glu Leu Lys Arg Asp Pro Val Leu Arg Arg Tyr Leu Val
                195                 200                 205

Asn Asn Tyr Val Ile Asp Pro Glu Asn Phe Asp Gln Asp Thr Phe Val
                210                 215                 220

Asn Asp Ile Tyr Gln Met Val Asp Ile Glu Gly Tyr Val Phe Arg Leu
225                 230                 235                 240

Met Thr Gly Gln His Val Lys Ile Lys Thr Glu Trp Tyr Lys Met Leu
                245                 250                 255

His Tyr Ala Lys Asp Thr Ile Asn Asn Asn Glu Ala Leu Phe Ala Ile
                260                 265                 270

Thr Val Ala Ala Gln Leu Asp Asp Val Arg Ser Leu Tyr Ser Asp Asp
                275                 280                 285

Tyr Ala Leu Gly Lys Ile Asn Lys Phe Glu Glu Val Phe Leu Gly Phe
                290                 295                 300

Leu Asp Thr Arg Leu Pro Ile Leu Leu Asn Leu His Lys Glu Leu Asn
305                 310                 315                 320

Gly Ser Ser Arg Lys Asp Tyr Ala Ile Lys Ser Gln Thr Tyr Phe Lys
                325                 330                 335

Gln Ala Asn Glu Leu Tyr Leu Phe Gly Ile Phe Met Gln Met Phe Glu
                340                 345                 350

Gly Val Pro Pro Arg Glu Gln Leu Val Glu Lys Leu Ser Glu Ala Phe
                355                 360                 365

Met Lys Asn Tyr Lys Leu Phe Val Pro Pro Glu Tyr Asp Lys Val Val
                370                 375                 380

Glu Tyr Asp Asn
385
```

```
<210> SEQ ID NO 76
<211> LENGTH: 382
<212> TYPE: PRT
<213> ORGANISM: Unknown
<220> FEATURE:
<223> OTHER INFORMATION: Description of Unknown:
      Wild-type Pectobacterium phage CBB ligase protein sequence -
      'RNA33'

<400> SEQUENCE: 76
```

```
Met Arg Thr Lys Gln Ile Phe Asp Asp Leu Met Asn Leu Thr Ala Lys
1               5                   10                  15

Asn Asp Ala Phe Met Trp Lys Asp Phe Val Ser Pro Ala Gly Gly Leu
```

-continued

```
                20              25              30
Phe Arg Ile Phe Ser Tyr Arg Leu Ala Ser Tyr Ser Asp Phe Leu Glu
        35              40              45
Pro Asn Ala Leu Glu Cys Arg Gly Ser Met Phe Lys Val Asp Asp Glu
    50              55              60
Gly Asn Phe Val Gly Ile Ala Ser Arg Thr Pro Met Lys Phe Phe Asn
65              70              75              80
Ala Tyr Glu Asn Pro Phe Thr Met Tyr Asp Lys Asp Thr Leu Ser Ser
                85              90              95
Glu Ile Ala Val Val Met Asp Lys Leu Asp Gly Ser Ile Ile Ser Thr
            100             105             110
Phe Met Asp Val Asp Phe Val Val Arg Thr Lys Ser His Ala Ser Leu
        115             120             125
His Ser Asp His Ala Tyr Asn Ser Thr Ala Met Leu Ile Ala Asp Lys
    130             135             140
Glu Leu Tyr Asn Glu Val His Tyr Ala Glu Ser Met Gly Tyr Thr Val
145             150             155             160
Asn Met Glu Tyr Thr Ser Pro Glu Tyr Arg Ile Val Leu Pro Tyr Gln
                165             170             175
Glu Asp Asn Leu Thr Val Leu Asn Leu Arg His Arg Glu Thr Gly Glu
            180             185             190
Leu Leu Ile Gly Glu Arg Leu Lys Glu Phe Ser Lys Ile Leu Tyr Glu
            195             200             205
Arg Ser Val Phe Ala Lys His Gly Glu Ile Asp Ala Thr Phe Pro Met
    210             215             220
Lys Glu Thr Leu Lys Glu Ser Ile Asp Ala Val Arg Gly Met Ala Asp
225             230             235             240
Ile Glu Gly Tyr Val Leu Ile Leu Lys Asp Gly Arg Met Cys Lys Ile
                245             250             255
Lys Thr Asp Trp Tyr Cys Ala Leu His Phe Thr Lys Asp Ser Ile Asn
            260             265             270
Val Asp Ser Arg Leu Tyr Asp Ala Ile Ile Thr Gly Ala Ser Asp Asp
            275             280             285
Leu Lys Gln Met Phe Ser Thr Asp Leu Tyr Ala Met Lys Lys Ile Glu
    290             295             300
Lys Met Glu Gln Leu Ile Phe Ser Cys Tyr Asn Lys Leu Val His Asp
305             310             315             320
Val Glu Ser Phe Tyr Glu Glu Asn Lys His Leu Glu Arg Lys Glu Tyr
            325             330             335
Ala Leu Lys Val Gln Ser Thr Leu Pro Asn Glu Leu Gly Met Pro Gly
            340             345             350
Leu Ala Phe Ser Leu Tyr Ala Ser Lys Pro Val Asp Tyr Lys Gly Gln
            355             360             365
Met Leu Lys Tyr Met Lys Asp Val Leu Val Asn Phe Glu Val
    370             375             380
```

<210> SEQ ID NO 77
<211> LENGTH: 385
<212> TYPE: PRT
<213> ORGANISM: Unknown
<220> FEATURE:
<223> OTHER INFORMATION: Description of Unknown:
      Wild-type Aeromonas phage phiAS5 ligase protein sequence - 'RNA35'

<400> SEQUENCE: 77

```
Met Gln Ser Ile Lys Glu Leu Tyr Gln Asn Leu Val Asn Leu Cys Val
1               5                   10                  15

Asp Asp Asn Thr Lys Phe Phe Phe Ser Glu Thr Val Thr Ser Leu Gly
                20                  25                  30

Thr Lys Val Arg Ile Phe Asp Tyr His Val Ala Gly Tyr Asn Asp Trp
            35                  40                  45

Ile Arg Pro Asp Ala Met Ala Cys Arg Gly Ile Met Phe Glu Met Asn
        50                  55                  60

Gly Glu Ile Pro Val Arg Ile Met Ser Arg Pro Met Asp Lys Phe Phe
65                  70                  75                  80

Asn Tyr Ser Glu Val Ile Gly Trp Glu Lys Leu Glu Thr His Gly Asn
                85                  90                  95

Met Lys Met Pro Asp Leu Ser Lys Ile Lys Phe Val Ile Asp Lys Arg
            100                 105                 110

Asp Gly Ser Leu Ile Ser Thr Phe Met Asp Val Asp Asn Leu Leu Leu
        115                 120                 125

Lys Ser Lys Gly Ser Ile Arg Ser Asn Gln Ala Asn Asp Ala Ser Val
    130                 135                 140

Trp Leu Tyr Gln Asp Asp Gln Ala Asp Leu Leu Glu Phe Cys Arg Ala
145                 150                 155                 160

Tyr Ala Lys Glu Gly Phe Thr Val Asn Met Glu Trp Thr Ala Pro His
                165                 170                 175

Asn Gln Ile Val Leu Cys Tyr Thr Asp His Gln Leu Arg Ile Leu Asn
            180                 185                 190

Ile Arg His Asn Glu Thr Gly Glu Tyr Val Asp Phe Ala Glu Leu Gln
        195                 200                 205

Lys Asp Ser Val Phe Arg Lys Tyr Ala Ala Asp Phe Tyr Glu Val Pro
    210                 215                 220

Gln Asp Gly Ala Glu Trp Ile Lys Asn Val Tyr Gly Met Thr Gly Ile
225                 230                 235                 240

Glu Gly Tyr Val Val Val Met Glu Asp Tyr Gln Met Phe Lys Leu Lys
                245                 250                 255

Thr Asp Trp Tyr Val Ala Leu His His Thr Lys Asp Ser Ile Asn Asp
            260                 265                 270

Ser Lys Arg Leu Ile Ser Ala Cys Ala Glu Asn Ala Thr Asp Asp Leu
    275                 280                 285

Arg Gln Met Phe Arg Asp Asp Pro Asn Ser Leu Ala Lys Ile Glu Val
    290                 295                 300

Phe Asp Ala Lys Phe Arg Asp Val Val Ser Ser Ala Met Gln Ala Leu
305                 310                 315                 320

Thr Asn Ala Tyr Ser Lys Tyr Lys Ala Leu Glu Arg Arg Glu Tyr Ala
                325                 330                 335

Ile Ser Met Thr Asn Glu Phe Lys Asn Glu Arg His Trp Phe Asn Ile
            340                 345                 350

Ala Met Gln Met Phe Ser Thr Arg Pro Asp Phe Ser Leu Ala Asp Glu
            355                 360                 365

Ile Val Ala Val Ile Lys Lys Tyr Pro Glu Lys Phe Val Pro Gln Gly
    370                 375                 380

Tyr
385

<210> SEQ ID NO 78
<211> LENGTH: 376
<212> TYPE: PRT
```

-continued

<213> ORGANISM: Unknown
<220> FEATURE:
<223> OTHER INFORMATION: Description of Unknown:
      Wild-type Salmonella phage vB_SenMS16 ligase protein sequence -
      'RNA36'

<400> SEQUENCE: 78

Met Lys Glu Leu Phe Asp Asn Leu Met Asn Leu Cys Asn Asp Thr Asp
1               5                   10                  15

Glu Ser Arg Phe Phe Tyr Arg Asp Asp Ile Ser Pro Ser Gly Leu Lys
            20                  25                  30

Tyr Arg Ile Phe Ser Tyr Asn Tyr Ala Ser Tyr Ser Asp Trp Leu Leu
            35                  40                  45

Pro Asp Ala Leu Glu Cys Arg Gly Ile Met Phe Glu Met Ile Asp Gly
    50                  55                  60

Val Pro Val Arg Ile Ala Ser Arg Pro Met Glu Lys Phe Phe Asn Leu
65                  70                  75                  80

Asn Glu Thr Pro Phe Thr Met Asn Leu Asp Leu Ser Asn Ala Val His
                85                  90                  95

Met Met Lys Lys Glu Asp Gly Ser Leu Val Ser Ser Tyr Leu Asp Gly
            100                 105                 110

Asn Ile Leu Arg Phe Lys Ser Lys Ser Ser Leu Lys Ser Glu Gln Ala
            115                 120                 125

Tyr Leu Ser Ser Ala Met Leu Thr Ser Ile Thr His Glu Ala Leu Leu
    130                 135                 140

Trp Arg Leu Leu Glu Leu Ala Arg Asp Gly Phe Thr Ala Asn Phe Glu
145                 150                 155                 160

Tyr Val Ser Pro Glu Asn Arg Ile Val Leu Ala Tyr Gln Lys Lys Asp
                165                 170                 175

Leu Ile Leu Leu Asn Ile Arg Glu Asn Asp Thr Gly Ala Tyr Val Pro
            180                 185                 190

Tyr Asn Glu Ile Ala Lys Asp Pro Val Leu Arg Gln Tyr Leu Val Glu
            195                 200                 205

Ser Tyr Glu Ile Pro Glu Gly Asp Phe Val Ser Asp Ile Lys Ala Met
    210                 215                 220

Glu Gly Ile Glu Gly Tyr Val Phe Val Met Asp Asn Gly Leu Arg Phe
225                 230                 235                 240

Lys Leu Lys Thr Asp Trp Tyr Thr Ala Leu His His Thr Lys Asp Ser
            245                 250                 255

Ile Thr Lys Asn Asp Arg Leu Phe Glu Val Ile Val Asn Asn Ala Ser
            260                 265                 270

Asp Asp Leu Lys Gly Leu Phe Ser Asn Asp Ala Tyr Ser Leu Lys Lys
            275                 280                 285

Ile Asn Lys Phe Glu Glu Val Tyr Leu Asp Tyr Leu Arg Arg Ser Leu
    290                 295                 300

Ser Phe Ile Ser Thr Ser Tyr Gln Lys Leu Arg Gly Leu Asp Arg Lys
305                 310                 315                 320

Thr Tyr Ala Gly Glu Ala Lys Arg Leu Ala Asp Ala Glu Arg Leu Pro
            325                 330                 335

Phe Leu Phe Thr Ile Leu Met Leu Met Phe Asn Asp Ser Met Asp Tyr
            340                 345                 350

Asp Thr Thr Ile Lys Lys Val Asn Glu Leu Phe Met Lys Asn Tyr Lys
            355                 360                 365

Thr Phe Ile Pro Lys Glu Tyr Glu
    370                 375

<210> SEQ ID NO 79
<211> LENGTH: 381
<212> TYPE: PRT
<213> ORGANISM: Unknown
<220> FEATURE:
<223> OTHER INFORMATION: Description of Unknown:
    Wild-type Vibrio phage KVP40 ligase protein sequence - 'RNA39'

<400> SEQUENCE: 79

Met Thr Thr Gln Glu Leu Tyr Asn His Leu Met Thr Leu Thr Glu Asp
1               5                   10                  15

Ala Glu Gly Lys Phe Phe Phe Ala Asp His Ile Ser Pro Leu Gly Glu
                20                  25                  30

Lys Leu Arg Val Phe Ser Tyr His Ile Ala Ser Tyr Ser Asp Trp Leu
            35                  40                  45

Leu Pro Gly Ala Leu Glu Ala Arg Gly Ile Met Phe Gln Leu Asp Glu
        50                  55                  60

Gln Asp Lys Met Val Arg Ile Val Ser Arg Pro Met Glu Lys Phe Phe
65                  70                  75                  80

Asn Leu Asn Glu Asn Pro Phe Thr Met Asp Leu Asp Leu Thr Thr Thr
                85                  90                  95

Val Gln Leu Met Asp Lys Ala Asp Gly Ser Leu Ile Ser Thr Tyr Leu
                100                 105                 110

Thr Gly Glu Asn Phe Ala Leu Lys Ser Lys Thr Ser Ile Phe Ser Glu
            115                 120                 125

Gln Ala Val Ala Ala Asn Arg Tyr Ile Lys Leu Pro Glu Asn Arg Asp
        130                 135                 140

Leu Trp Glu Phe Cys Asp Asp Leu Thr Gln Ala Gly Cys Thr Val Asn
145                 150                 155                 160

Met Glu Trp Cys Ala Pro Asn Asn Arg Ile Val Leu Glu Tyr Pro Glu
                165                 170                 175

Ala Lys Leu Val Ile Leu Asn Ile Arg Asp Asn Glu Thr Gly Asp Tyr
                180                 185                 190

Val Ser Phe Asp Asp Ile Pro Leu Pro Ala Leu Met Arg Val Lys Lys
            195                 200                 205

Trp Leu Val Asp Glu Tyr Asp Pro Glu Thr Ala His Val Asp Asp Phe
        210                 215                 220

Val Glu Lys Leu Arg Ala Thr Lys Gly Ile Glu Gly Met Ile Leu Arg
225                 230                 235                 240

Leu Ala Asn Gly Gln Ser Val Lys Ile Lys Thr Gln Trp Tyr Val Asp
                245                 250                 255

Leu His Ser Gln Lys Asp Ser Val Asn Val Pro Lys Lys Leu Val Thr
                260                 265                 270

Thr Ile Leu Asn Asn Asn His Asp Asp Leu Tyr Ala Leu Phe Ala Asp
            275                 280                 285

Asp Lys Pro Thr Ile Asp Arg Ile Arg Glu Phe Asp Ser His Val Ser
        290                 295                 300

Lys Thr Val Ser Ala Ser Phe His Ala Val Ser Gln Phe Tyr Val Lys
305                 310                 315                 320

Asn Arg His Met Ser Arg Lys Asp Tyr Ala Ile Ala Gly Gln Lys Ala
                325                 330                 335

Leu Lys Pro Trp Glu Phe Gly Val Ala Met Ile Ala Tyr Gln Lys Lys
            340                 345                 350

Thr Val Glu Gly Val Tyr Glu Ala Leu Val Gly Ala Tyr Leu Lys Arg

-continued

```
        355                 360                 365

Pro Glu Leu Leu Ile Pro Glu Lys Tyr Leu Asn Glu Ala
    370                 375                 380

<210> SEQ ID NO 80
<211> LENGTH: 361
<212> TYPE: PRT
<213> ORGANISM: Unknown
<220> FEATURE:
<223> OTHER INFORMATION: Description of Unknown:
      Wild-type Campylobacter virus CP220 ligase protein sequence -
      'RNA49'

<400> SEQUENCE: 80

Met Asn Tyr Leu Glu Leu Lys Asn Met Ala Glu Asn Leu Lys Asp Ser
1               5                  10                  15

Asn Tyr Arg Ser Thr Lys Leu Asn Asn Phe Lys Phe Tyr Thr Tyr Ile
            20                  25                  30

Phe Ser Asp Tyr Lys Asn Phe Lys Glu Asn Asn Thr Phe Phe Ile Arg
            35                  40                  45

Gly Leu Met Ile Asp Ser Lys Ser Ile Leu Asn Lys Asp Thr Leu Ala
        50                  55                  60

Pro Gly Ile Ser Ile Pro Met Pro Lys Phe Phe Asn Ile Asn Glu Asn
65                  70                  75                  80

Glu Asp Trp Leu Leu Pro Asp Ser Thr Asn Leu Glu Asp Phe Thr Ile
                85                  90                  95

Val Thr Lys Tyr Asp Gly Ser Leu Met Ile Pro Tyr Glu Tyr Asp Gly
            100                 105                 110

Ile Lys Phe Arg Thr Lys Met Ser Ile Asp Asn Asp Gln Thr Lys Leu
            115                 120                 125

Ala Asn Lys Tyr Ile Lys Asn Asn Pro Asp Ile Leu Asp Leu Ile Lys
        130                 135                 140

Asn Asn Pro Asp Thr Gln Tyr Phe Phe Glu Leu Ile Ser Pro Leu Asn
145                 150                 155                 160

Arg Ile Val Val Asp Tyr Asn Lys Thr Glu Leu Lys Leu Ile Ala Glu
                165                 170                 175

Leu Asp Leu Arg Thr Leu Glu Phe Lys Ile His Glu Thr Asn Glu Phe
            180                 185                 190

Asn Phe Lys Asp Leu Asn Ile Lys Thr Leu Lys Asp Leu Lys Asp Tyr
            195                 200                 205

Ile Asn Thr Ile Ser Asn Tyr Glu Gly Val Ile Leu Gln His Lys Val
        210                 215                 220

Thr Lys Lys Val Tyr Lys Leu Lys Thr Gln Glu Tyr Leu Asp Leu His
225                 230                 235                 240

Asn Thr Met Thr Asn Leu Asp Leu Lys Val Ile Tyr Lys Met Ile Leu
                245                 250                 255

Glu Glu Thr Ile Asp Asp Val Leu Pro Lys Leu Ser Pro Glu Ala Val
            260                 265                 270

Ala Tyr Ile Asp Ser Val Ser Asn Ser Val Lys Val Lys Leu Asn Glu
            275                 280                 285

Ile Leu Asp Ser Ile Asp Ser Asn Tyr Ile Lys Thr Lys Asp Leu Glu
        290                 295                 300

Thr Pro Ala Leu Tyr Ile Lys Asp Leu Asn Ile Asp Pro Ile Ala Lys
305                 310                 315                 320

Asp Cys Leu Phe Lys Leu Cys Lys Asn Lys Leu Asn Leu Asp Asp Val
                325                 330                 335
```

-continued

```
Leu Asn Gln Val Lys Lys Ser Met Leu Lys Tyr Asn Lys Leu Arg Asp
        340                 345                 350

Ile Lys Val Phe Leu Lys Trp Ile His
        355             360

<210> SEQ ID NO 81
<211> LENGTH: 380
<212> TYPE: PRT
<213> ORGANISM: Unknown
<220> FEATURE:
<223> OTHER INFORMATION: Description of Unknown:
      Wild-type Pseudomonas phage phiPMW ligase protein sequence -
      'RNA59'

<400> SEQUENCE: 81

Met Lys Val Ile Glu Phe Leu Lys Asn Ala Pro Ser Ile Thr Asp Gly
1               5                   10                  15

Leu Ala Ser Leu His Leu Glu Leu Gly Ile Lys Ala Lys Ile Tyr Glu
        20                  25                  30

Asp Glu Gly Leu Ile Val Leu Asn Tyr Ser Gln Ile Asp Ser Pro Lys
        35                  40                  45

Thr His Pro Ile Val Gln Glu Cys Arg Gly Leu Ile Ile Asp Asn Asp
    50                  55                  60

Leu Thr Val Val Ala Arg Pro Phe Asp Arg Phe Phe Asn Tyr Gly Glu
65                  70                  75                  80

Ala Leu Asn Val Met Pro Glu Ile Asp Trp Glu Asn Ala Ser Ile Phe
                85                  90                  95

Glu Lys Val Asp Gly Ser Leu Ile Lys Ile Tyr Phe His Lys Gly Arg
        100                 105                 110

Trp Glu Val Ala Thr Arg Gly Thr Ala Phe Ala Glu Ser Glu Cys Met
        115                 120                 125

Gly His Gly Ile Thr Phe Lys Glu Leu Val Phe Asn Ala Leu Lys Val
    130                 135                 140

His Asp Asp Asp Gly Phe Gln Tyr Leu Met Asn Asn Ala Tyr Leu Phe
145                 150                 155                 160

Arg Asp Thr Thr Tyr Leu Phe Glu Leu Thr Cys Val Glu Asn Arg Val
                165                 170                 175

Val Arg His Tyr His Gly Tyr Asn Leu His Phe Leu Ala Ala Arg Asp
        180                 185                 190

Asn Val Ser Gly Asn Tyr Ser Glu Glu Cys Arg Asp Trp Leu Arg Ser
        195                 200                 205

Pro Asp Cys Ile Leu Tyr Gly Ile Val Lys His Pro Lys Arg Tyr Ala
    210                 215                 220

Leu Gly Ser Ala Asp Glu Ala Leu Gln Ala Ala Lys Glu Leu Lys Asn
225                 230                 235                 240

Leu Asp Glu Gly Phe Ile Val Tyr Gln Asn Ala Val Pro Ile Ala Lys
                245                 250                 255

Ile Lys Ser Pro Ala Tyr Val Ala Val His His Ile Arg Gly Glu Gly
        260                 265                 270

Leu Asn Pro Lys Arg Ile Met Glu Leu Val Leu Ser Gly Glu His Asp
        275                 280                 285

Glu Tyr Leu Ser Tyr Phe Pro Glu Asp Arg Pro Ile Ile Gln Pro Tyr
    290                 295                 300

Val Asp Ser Leu Leu Asp Met Leu Asn Ile Ile Ala Val Thr Tyr Pro
305                 310                 315                 320
```

-continued

Arg Leu Asn Gln Ala Thr Thr Pro Lys Ala Phe Ala Ala Ala Ile Lys
        325             330             335

His Ala Gly Ile Asp Lys Gln Lys Ala Ser Val Tyr Phe Met Ala Arg
        340             345             350

Arg Asp Asn Lys Asp Pro Val Gln Val Phe His Gly Met Lys Thr Thr
        355             360             365

Phe Lys Met Asp Met Leu Arg Lys Trp Met Met Val
370             375             380

<210> SEQ ID NO 82
<211> LENGTH: 317
<212> TYPE: PRT
<213> ORGANISM: Unknown
<220> FEATURE:
<223> OTHER INFORMATION: Description of Unknown:
      Wild-type Pseudomonas phage vB_PaeM_C2-10_Ab1 ligase protein
      sequence - 'RNA61'

<400> SEQUENCE: 82

Met Pro Asn Cys Arg Ile Glu Ile Arg Arg Ser Arg Met Glu Gly Asn
1               5               10              15

Leu Asn Ile Ala Met Tyr Lys Asp Leu Ile Ala Asn Lys Leu Val Thr
        20              25              30

Val Lys His Phe Asn Gly Met Ser Ile Ile Lys Tyr Ala Arg Lys Val
        35              40              45

Phe Tyr Glu Asn Leu Trp Asn Glu His Pro Leu Leu Leu Glu Ala Arg
        50              55              60

Gly His Val Phe Asp Gln His Ser Gly Asp Cys Ile Val Arg Pro Phe
65              70              75              80

Glu Lys Val Phe Asn Leu Gly Glu Asn Gly Ala Gly Ser Phe Leu His
        85              90              95

Pro Lys Phe Arg Val Arg Leu Ile Glu Lys Val Asn Gly Phe Met Phe
        100             105             110

Ser Val Thr Lys His Asn Gly Ser Leu Ile Phe Ser Thr Thr Gly Ser
        115             120             125

Leu Thr Ser Asp Tyr Val Ala Leu Gly Gln Lys Tyr Val Ser Asn Asn
        130             135             140

Pro Asp Asp Tyr Ile Ala Gly Phe Thr Tyr Asn Phe Glu Ile Cys Ser
145             150             155             160

Pro Asp Asp Pro His Ile Val Glu Glu Glu Gly Ala Tyr Leu Ile
        165             170             175

Gly Ile Arg Asp Ile Phe Thr Gly Gly Gln Leu Ser Glu Tyr Ile Leu
        180             185             190

Asp Ser His Ala Leu Gly Val Thr Asp His Ser Ser Val Lys Ile Leu
        195             200             205

Arg Pro Glu His Ile Glu Cys Ser Trp Glu His Ala Lys Gly Leu Leu
        210             215             220

Ser Ser Cys Glu Lys Glu Gly Tyr Met Val Gln Thr Gly Leu Gly Thr
225             230             235             240

Val Lys Cys Lys Ser Thr His Tyr Leu Gly Lys Lys Phe Ile Met Arg
        245             250             255

Met Gly Ser Lys Lys Val Asn Ser Met Tyr Gln Asp Pro Ala Gly Phe
        260             265             270

Lys Gln Thr Leu Asp Glu Glu Phe Tyr Pro Leu Val Asp Phe Leu Val
        275             280             285

Asn Glu Val Glu Glu Val Arg Phe Thr Glu Met Thr Asp Ala Gln Arg

-continued

```
       290              295              300
Arg Leu Leu Ile Glu Thr Tyr Phe Asp Met Ala Arg Ile
305              310              315

<210> SEQ ID NO 83
<211> LENGTH: 368
<212> TYPE: PRT
<213> ORGANISM: Unknown
<220> FEATURE:
<223> OTHER INFORMATION: Description of Unknown:
      Wild-type Butyrivibrio proteoclasticus ligase protein sequence
      - 'RNA82'

<400> SEQUENCE: 83

Met Lys Ser Arg Ile Leu Glu Phe Ile Lys Asn Asn Pro Asp Thr Trp
1               5                10               15

Glu Glu Lys Leu Asn Glu Lys Phe Ile Arg Thr Asn His Asn Gly Asp
            20               25               30

Leu Val Cys Phe Lys Tyr Ala Thr Glu Ala Asp Phe Ser Asp Pro Leu
        35               40               45

Val Cys Glu Ala Arg Gly Ile Ile Ile Asp Val Ala Gln Leu Val Val
    50               55               60

Val Cys Trp Pro Phe Asp Lys Phe Phe Asn Val Gln Glu Lys Tyr Ala
65               70               75               80

Ala Asp Ile Asp Trp Asn Ser Ala Arg Val Leu Glu Lys Ile Asp Gly
            85               90               95

Ser Met Ile Lys Leu Phe Trp Tyr Lys Gly Ala Trp Arg Phe Ala Thr
            100              105              110

Ser Ser Thr Cys Asp Ala Lys Asp Ala Ala Ile Pro Gly Tyr Asn Glu
        115              120              125

Leu Thr Tyr Ala Asp Ile Ile Ala Arg Ala Glu Asn Val Asn Glu Ile
        130              135              140

Pro Phe Glu Glu Leu Asn Lys Asp Tyr Thr Tyr Ile Phe Glu Leu Val
145              150              155              160

Ser Pro Leu Ser Gln Ile Val Val Arg Tyr Glu Met Thr Glu Leu Phe
            165              170              175

Phe Leu Thr Ala Arg Asn Asn Leu Thr Gly Glu Glu Leu Asp Thr Glu
            180              185              190

Leu Leu Gln Phe Arg Arg Pro Arg Ser Phe Ala Leu Lys Ser Met Asn
            195              200              205

Glu Cys Leu Asp Ala Ala Leu Ala Leu Asn Lys Gly Asp Glu Ile Glu
    210              215              220

Asp Glu Gly Phe Val Val Val Asp Glu Lys His Asn Arg Val Lys Ile
225              230              235              240

Lys Ser Pro Ala Tyr Val Ala Met His Arg Leu Ser Thr Asn Lys Val
            245              250              255

Phe Thr Val Lys Arg Met Ala Glu Phe Phe Cys Asn Gly Glu Asp Leu
            260              265              270

Ser Lys Leu Ala Lys Asp Phe Pro Ala Asn Ala His Ile Ile Lys Tyr
            275              280              285

Tyr Asp Trp Gln Phe Ala Glu Met Lys His Lys Ala Glu Asp Met Met
        290              295              300

Leu Tyr Ser Arg Arg Leu Tyr Glu Glu Tyr Asp His Asp Arg Lys Ala
305              310              315              320

Val Ala Met Thr Ile Lys Asp Ser Pro Tyr Ala Trp Ala Gly Phe Arg
            325              330              335
```

-continued

```
Ala Ile Gly Asn Asp Lys Asp Ile Thr Asp Ile Met Ala Val Leu Ala
            340                 345                 350

Pro Ala Asn Val Glu Lys Leu Ile Val Glu Tyr Pro Glu Ile Ser Asn
            355                 360                 365

<210> SEQ ID NO 84
<211> LENGTH: 10
<212> TYPE: RNA
<213> ORGANISM: Artificial Sequence
<220> FEATURE:
<223> OTHER INFORMATION: Example 15 and 16 primer oligonucleotide
      sequence

<400> SEQUENCE: 84
acuccucggu                                                             10

<210> SEQ ID NO 85
<211> LENGTH: 11
<212> TYPE: RNA
<213> ORGANISM: Artificial Sequence
<220> FEATURE:
<223> OTHER INFORMATION: Example 15 and 16 product oligonucleotide
      sequence

<400> SEQUENCE: 85
acuccucggu a                                                           11

<210> SEQ ID NO 86
<211> LENGTH: 10
<212> TYPE: DNA
<213> ORGANISM: Artificial Sequence
<220> FEATURE:
<223> OTHER INFORMATION: Example 17 primer oligonucleotide sequence

<400> SEQUENCE: 86
actcatcgat                                                             10

<210> SEQ ID NO 87
<211> LENGTH: 11
<212> TYPE: DNA
<213> ORGANISM: Artificial Sequence
<220> FEATURE:
<223> OTHER INFORMATION: Example 17 product oligonucleotide sequence

<400> SEQUENCE: 87
actcatcgat a                                                           11

<210> SEQ ID NO 88
<211> LENGTH: 384
<212> TYPE: PRT
<213> ORGANISM: Artificial Sequence
<220> FEATURE:
<223> OTHER INFORMATION: Mutant ligase (Stenotrophomonas phage IME13
      backbone) protein sequence

<400> SEQUENCE: 88

Met Ser Arg Thr Ile Glu Leu Phe Asn Asn Leu Met Ser Val Val Glu
1               5                   10                  15

Lys Ser Glu Lys Gly Asn Phe Tyr Phe Lys Asp Val Ile Thr Ser Met
            20                  25                  30

Gly Thr Lys Ala Arg Ile Phe Ser His Lys Ile Ala Ser Tyr Thr Asp
        35                  40                  45

Trp Leu Gln Asp Asp Ala Leu Glu Cys Arg Gly Ile Met Phe Glu Leu
    50                  55                  60
```

-continued

Asn Asp Lys Asn Glu Pro Val Arg Ile Met Ala Arg Pro Met Gln Lys
65                  70                  75                  80

Phe Phe Asn Leu Lys Glu Asn Pro Met Thr Ile Gly Leu Asp Leu Thr
                85                  90                  95

Lys Met Ile Gly Leu Met Glu Lys Ala Asp Gly Ser Leu Ile Ser Ser
            100                 105                 110

Tyr His Asp Gln Gly Tyr Val Tyr Leu Lys Ser Lys Thr Ser Ile Phe
            115                 120                 125

Ser Asp Gln Ala Asn Lys Ala Met Ala Leu Leu Asn Ser Pro Ala Tyr
        130                 135                 140

Glu Lys Leu Arg Asp Ala Ile Val Arg Ala Gly Ser Asp Phe Thr Phe
145                 150                 155                 160

Asn Met Glu Tyr Val Gly Pro Ser Asn Arg Val Val Leu Pro Tyr Glu
                165                 170                 175

Glu Glu Glu Leu Ile Val Leu Asn Val Arg His Asn Glu Thr Gly Gln
            180                 185                 190

Tyr Val Glu Phe Ser Thr Leu Leu Asp Asp Pro Leu Ile Arg His Arg
            195                 200                 205

Met Ile Gly Val Tyr Pro Cys Pro Asp Trp Ser Lys Val Thr Pro Glu
        210                 215                 220

Glu Trp Glu Ala Ala Thr Arg Ala Glu Thr Asp Ile Glu Gly Val Ile
225                 230                 235                 240

Gly Ile Met Pro Asp Gly Gln Leu Phe Lys Leu Lys Thr Asp Trp Tyr
                245                 250                 255

Ser Ser Leu Gly Arg Thr Lys Phe Ser Ile Asn Asn Asn Lys Ala Leu
            260                 265                 270

His Gln Ser Ile Lys Glu Arg Ala Ser Val Ala Leu Arg Gly Met Phe
            275                 280                 285

Ser Asp Asp Asn Ala Ala Leu Ala Lys Ile Glu Ala Phe Glu Ser Ala
        290                 295                 300

Tyr Ile Asp Thr Val Ala Lys Tyr His Lys Ile Cys Ala Glu Val Phe
305                 310                 315                 320

Leu Arg Phe Ala Arg Phe Leu Ile Val Glu Val Phe Ala Ile Glu Ala
                325                 330                 335

Gln Ala Arg Met Lys Asp Cys Arg Tyr Leu Phe Ser Ile Val Met Gln
            340                 345                 350

Gln Tyr Gly Arg Asp Trp Asp Gly Glu Leu Ala Val Glu Lys Ile Glu
            355                 360                 365

Glu His Ile Ile Lys Glu Tyr Ala Thr Tyr Val Pro Met Ala Tyr Arg
        370                 375                 380

<210> SEQ ID NO 89
<211> LENGTH: 384
<212> TYPE: PRT
<213> ORGANISM: Artificial Sequence
<220> FEATURE:
<223> OTHER INFORMATION: Mutant ligase (Stenotrophomonas phage IME13
      backbone) protein sequence

<400> SEQUENCE: 89

Met Ser Arg Thr Ile Glu Leu Phe Asn Asn Leu Met Ser Val Val Glu
1               5                   10                  15

Lys Ser Glu Lys Gly Asn Phe Tyr Phe Lys Asp Val Ile Thr Ser Met
            20                  25                  30

Gly Thr Lys Ala Arg Ile Phe Ser His Gln Ile Ala Ser Tyr Thr Asp

```
            35                  40                  45

Trp Leu Gln Asp Asp Ala Leu Glu Cys Arg Gly Ile Met Phe Glu Leu
    50                  55                  60

Asn Asp Lys Asn Glu Pro Val Arg Ile Met Ala Arg Pro Met Gln Lys
65                  70                  75                  80

Phe Phe Asn Leu Lys Glu Asn Pro Met Thr Ile Gly Leu Asp Leu Thr
                85                  90                  95

Lys Met Ile Gly Leu Met Glu Lys Ala Asp Gly Ser Leu Ile Ser Ser
            100                 105                 110

Tyr His Asp Gln Gly Tyr Val Tyr Leu Lys Ser Lys Thr Ser Ile Phe
            115                 120                 125

Ser Asp Gln Ala Asn Lys Ala Met Ala Leu Leu Asn Ser Pro Ala Tyr
    130                 135                 140

Glu Lys Leu Arg Asp Ala Ile Val Arg Ala Gly Ser Asp Phe Thr Phe
145                 150                 155                 160

Asn Met Glu Tyr Val Gly Pro Ser Asn Arg Val Val Leu Pro Tyr Glu
                165                 170                 175

Glu Glu Glu Leu Ile Val Leu Asn Val Arg His Asn Glu Thr Gly Gln
            180                 185                 190

Tyr Val Glu Phe Ser Thr Leu Leu Asp Asp Pro Leu Ile Arg His Arg
            195                 200                 205

Met Ile Gly Val Tyr Pro Cys Pro Asp Trp Ser Lys Val Thr Pro Glu
    210                 215                 220

Glu Trp Glu Ala Ala Thr Arg Ala Glu Thr Asp Ile Glu Gly Val Ile
225                 230                 235                 240

Gly Ile Met Pro Asp Gly Gln Leu Phe Lys Leu Lys Thr Asp Trp Tyr
                245                 250                 255

Ser Ser Leu Gly Arg Thr Lys Phe Ser Ile Asn Asn Asn Lys Ala Leu
            260                 265                 270

His Gln Ser Ile Lys Glu Arg Ala Ser Gly Ala Leu Arg Gly Met Phe
            275                 280                 285

Ser Asp Asp Asn Ala Ala Leu Ala Lys Ile Glu Ala Phe Glu Ser Ala
    290                 295                 300

Tyr Ile Asp Thr Val Ala Lys Tyr His Lys Ile Cys Ala Glu Val Phe
305                 310                 315                 320

Leu Arg Phe Ala Arg Phe Leu Ile Val Glu Val Phe Ala Ile Glu Ala
                325                 330                 335

Gln Ala Arg Met Lys Asp Cys Arg Tyr Leu Phe Ser Ile Val Met Gln
            340                 345                 350

Gln Tyr Gly Arg Asp Trp Asp Gly Glu Leu Ala Val Glu Lys Ile Glu
            355                 360                 365

Glu His Ile Ile Lys Glu Tyr Ala Thr Tyr Val Pro Met Ala Tyr Arg
    370                 375                 380
```

<210> SEQ ID NO 90
<211> LENGTH: 384
<212> TYPE: PRT
<213> ORGANISM: Artificial Sequence
<220> FEATURE:
<223> OTHER INFORMATION: Mutant ligase (Stenotrophomonas phage IME13
      backbone) protein sequence

<400> SEQUENCE: 90

```
Met Ser Arg Thr Ile Glu Leu Phe Asn Asn Leu Met Ser Val Val Glu
1               5                   10                  15
```

-continued

```
Lys Ser Glu Lys Gly Asn Phe Tyr Phe Lys Asp Val Ile Thr Ser Met
            20                  25                  30

Gly Thr Lys Ala Arg Ile Phe Ser Tyr Phe Ile Ala Ser Tyr Thr Asp
            35                  40                  45

Trp Leu Gln Asp Asp Ala Leu Glu Cys Arg Gly Ile Met Phe Glu Leu
        50                  55                  60

Asn Asp Lys Asn Glu Pro Val Arg Ile Met Ala Arg Pro Met Gln Lys
65                  70                  75                  80

Phe Phe Asn Leu Lys Glu Asn Pro Met Thr Ile Gly Leu Asp Leu Thr
                85                  90                  95

Lys Met Ile Gly Leu Met Glu Lys Ala Asp Gly Ser Leu Ile Ser Ser
                100                 105                 110

Tyr His Asp Gln Gly Tyr Val Tyr Leu Lys Ser Lys Thr Ser Ile Phe
            115                 120                 125

Ser Asp Gln Ala Asn Lys Ala Met Ala Leu Leu Asn Ser Pro Ala Tyr
    130                 135                 140

Glu Lys Leu Arg Asp Ala Ile Val Arg Ala Gly Ser Asp Phe Thr Phe
145                 150                 155                 160

Asn Met Glu Tyr Val Gly Pro Ser Asn Arg Val Val Leu Pro Tyr Glu
                165                 170                 175

Glu Glu Glu Leu Ile Val Leu Asn Val Arg His Asn Glu Thr Gly Gln
                180                 185                 190

Tyr Val Glu Phe Ser Thr Leu Leu Asp Asp Pro Leu Ile Arg His Arg
            195                 200                 205

Met Ile Gly Val Tyr Pro Cys Pro Asp Trp Ser Lys Val Thr Pro Glu
    210                 215                 220

Glu Trp Glu Ala Ala Thr Arg Ala Glu Thr Asp Ile Glu Gly Val Ile
225                 230                 235                 240

Gly Ile Met Pro Asp Gly Gln Leu Phe Lys Leu Lys Thr Asp Trp Tyr
                245                 250                 255

Ser Ser Leu Gly Arg Thr Lys Tyr Ser Ile Asn Asn Asn Lys Ala Leu
            260                 265                 270

Asn Gln Ser Ile Lys Glu Arg Ala Ser Val Ala Leu Arg Gly Met Phe
            275                 280                 285

Ser Asp Asp Asn Ala Ala Leu Ala Lys Ile Glu Ala Phe Glu Ser Ala
    290                 295                 300

Tyr Ile Asp Thr Val Ala Lys Tyr His Lys Ile Cys Ala Glu Val Phe
305                 310                 315                 320

Leu Arg Phe Ala Arg Phe Leu Ile Val Glu Val Phe Ala Ile Glu Ala
                325                 330                 335

Gln Ala Arg Met Lys Asp Cys Arg Tyr Leu Phe Ser Ile Val Met Gln
            340                 345                 350

Gln Tyr Gly Arg Asp Trp Asp Gly Glu Leu Ala Val Glu Lys Ile Glu
            355                 360                 365

Glu His Ile Ile Lys Glu Tyr Ala Thr Tyr Val Pro Met Ala Tyr Arg
    370                 375                 380
```

<210> SEQ ID NO 91
<211> LENGTH: 384
<212> TYPE: PRT
<213> ORGANISM: Artificial Sequence
<220> FEATURE:
<223> OTHER INFORMATION: Mutant ligase (Stenotrophomonas phage IME13
      backbone) protein sequence

<400> SEQUENCE: 91

```
Met Ser Arg Thr Ile Glu Leu Phe Asn Asn Leu Met Ser Val Val Glu
1               5                   10                  15

Lys Ser Glu Lys Gly Asn Phe Tyr Phe Lys Asp Val Ile Thr Ser Met
            20                  25                  30

Gly Thr Lys Ala Arg Ile Phe Ser His Asn Ile Ala Ser Tyr Thr Asp
        35                  40                  45

Trp Leu Gln Asp Asp Ala Leu Glu Cys Arg Gly Ile Met Phe Glu Leu
    50                  55                  60

Asn Asp Lys Asn Glu Pro Val Arg Ile Met Ala Arg Pro Met Gln Lys
65                  70                  75                  80

Phe Phe Asn Leu Lys Glu Asn Pro Met Thr Ile Gly Leu Asp Leu Thr
                85                  90                  95

Lys Met Ile Gly Leu Met Glu Lys Ala Asp Gly Ser Leu Ile Ser Ser
            100                 105                 110

Tyr His Asp Gln Gly Tyr Val Tyr Leu Lys Ser Lys Thr Thr Ile Phe
        115                 120                 125

Ser Asp Gln Ala Asn Lys Ala Met Ala Leu Leu Asn Ser Pro Ala Tyr
    130                 135                 140

Glu Lys Leu Arg Asp Ala Ile Val Arg Ala Gly Ser Asp Phe Thr Phe
145                 150                 155                 160

Asn Met Glu Tyr Val Gly Pro Ser Asn Arg Val Val Leu Pro Tyr Glu
                165                 170                 175

Glu Glu Glu Leu Ile Val Leu Asn Val Arg His Asn Glu Thr Gly Gln
            180                 185                 190

Tyr Val Glu Phe Ser Thr Leu Leu Asp Asp Pro Leu Ile Arg His Arg
        195                 200                 205

Met Ile Gly Val Tyr Pro Cys Pro Asp Trp Ser Lys Val Thr Pro Glu
    210                 215                 220

Glu Trp Glu Ala Ala Thr Arg Ala Glu Thr Asp Ile Glu Gly Val Ile
225                 230                 235                 240

Gly Ile Met Pro Asp Gly Gln Leu Phe Lys Leu Lys Thr Asp Trp Tyr
                245                 250                 255

Ser Ser Leu Gly Arg Thr Lys Tyr Ser Ile Asn Asn Asn Lys Ala Leu
            260                 265                 270

His Gln Ser Ile Lys Glu Arg Ala Ser Val Asp Leu Arg Gly Met Phe
        275                 280                 285

Ser Asp Asp Asn Ala Ala Leu Ala Lys Ile Glu Ala Phe Glu Ser Ala
    290                 295                 300

Tyr Ile Asp Thr Val Ala Lys Tyr His Lys Ile Cys Ala Glu Val Phe
305                 310                 315                 320

Leu Arg Phe Ala Arg Phe Leu Ile Val Glu Val Phe Ala Ile Glu Ala
            325                 330                 335

Gln Ala Arg Met Lys Asp Cys Arg Tyr Leu Phe Ser Ile Val Met Gln
            340                 345                 350

Gln Tyr Gly Arg Asp Trp Asp Gly Glu Leu Ala Val Glu Lys Ile Glu
        355                 360                 365

Glu His Ile Ile Lys Glu Tyr Ala Thr Tyr Val Pro Met Ala Tyr Arg
    370                 375                 380
```

```
<210> SEQ ID NO 92
<211> LENGTH: 384
<212> TYPE: PRT
<213> ORGANISM: Artificial Sequence
<220> FEATURE:
```

-continued

<223> OTHER INFORMATION: Mutant ligase (Stenotrophomonas phage IME13
      backbone) protein sequence

<400> SEQUENCE: 92

Met Ser Arg Thr Ile Glu Leu Phe Asn Asn Leu Met Ser Val Val Glu
1               5                   10                  15

Lys Ser Glu Lys Gly Asn Phe Tyr Phe Lys Asp Val Ile Thr Ser Met
            20                  25                  30

Gly Thr Lys Ala Arg Ile Phe Ser His Lys Ile Ala Ser Tyr Thr Asp
        35                  40                  45

Trp Leu Gln Asp Asp Ala Leu Glu Cys Arg Gly Ile Met Phe Glu Leu
    50                  55                  60

Asn Asp Lys Asn Glu Pro Val Arg Ile Met Ala Arg Pro Met Gln Lys
65                  70                  75                  80

Phe Phe Asn Leu Lys Glu Asn Pro Met Thr Ile Gly Leu Asp Leu Thr
                85                  90                  95

Lys Met Ile Gly Leu Met Glu Lys Ala Asp Gly Ser Leu Ile Ser Ser
            100                 105                 110

Tyr His Asp Gln Gly Tyr Val Tyr Leu Lys Ser Lys Ala Ala Ile Phe
        115                 120                 125

Ser Asp Gln Ala Asn Lys Ala Met Ala Leu Leu Asn Ser Pro Ala Tyr
    130                 135                 140

Glu Lys Leu Arg Asp Ala Ile Val Arg Ala Gly Ser Asp Phe Thr Phe
145                 150                 155                 160

Asn Met Glu Tyr Val Gly Pro Ser Asn Arg Val Val Leu Pro Tyr Glu
                165                 170                 175

Glu Glu Glu Leu Ile Val Leu Asn Val Arg His Asn Glu Thr Gly Gln
            180                 185                 190

Tyr Val Glu Phe Ser Thr Leu Leu Asp Asp Pro Leu Ile Arg His Arg
        195                 200                 205

Met Ile Gly Val Tyr Pro Cys Pro Asp Trp Ser Lys Val Thr Pro Glu
    210                 215                 220

Glu Trp Glu Ala Ala Thr Arg Ala Glu Thr Asp Ile Glu Gly Val Ile
225                 230                 235                 240

Gly Ile Met Pro Asp Gly Gln Leu Phe Lys Leu Lys Thr Asp Trp Tyr
                245                 250                 255

Ser Ser Leu His Arg Thr Lys Asp Ser Ile Asn Asn Asn Lys Ala Leu
            260                 265                 270

Phe Gln Ser Ile Lys Glu Arg Ala Ser Asp Asp Leu Arg Gly Met Phe
        275                 280                 285

Ser Asp Asp Asn Ala Ala Leu Ala Lys Ile Glu Ala Phe Glu Ser Ala
    290                 295                 300

Tyr Ile Asp Thr Val Ala Lys Tyr His Lys Ile Cys Ala Glu Val Phe
305                 310                 315                 320

Leu Arg Phe Ala Arg Phe Leu Ile Val Glu Val Phe Ala Ile Glu Ala
                325                 330                 335

Gln Ala Arg Met Lys Asp Cys Arg Tyr Leu Phe Ser Ile Val Met Gln
            340                 345                 350

Gln Tyr Gly Arg Asp Trp Asp Gly Glu Leu Ala Val Glu Lys Ile Glu
        355                 360                 365

Glu His Ile Ile Lys Glu Tyr Ala Thr Tyr Val Pro Met Ala Tyr Arg
    370                 375                 380

<210> SEQ ID NO 93

```
<211> LENGTH: 11
<212> TYPE: DNA
<213> ORGANISM: Artificial Sequence
<220> FEATURE:
<223> OTHER INFORMATION: Example 26 product oligonucleotide sequence

<400> SEQUENCE: 93
actcatcgat c                                                          11

<210> SEQ ID NO 94
<211> LENGTH: 11
<212> TYPE: DNA
<213> ORGANISM: Artificial Sequence
<220> FEATURE:
<223> OTHER INFORMATION: Example 26 product oligonucleotide sequence

<400> SEQUENCE: 94
actcatcgat t                                                          11

<210> SEQ ID NO 95
<211> LENGTH: 477
<212> TYPE: PRT
<213> ORGANISM: Unknown
<220> FEATURE:
<223> OTHER INFORMATION: Description of Unknown:
      Wild type phosphatase (Pandalus borealis) protein sequence - 'SAP'

<400> SEQUENCE: 95

Met Glu Glu Asp Lys Ala Tyr Trp Asn Lys Asp Ala Gln Asp Ala Leu
1               5                   10                  15

Asp Lys Gln Leu Gly Ile Lys Leu Arg Glu Lys Gln Ala Lys Asn Val
            20                  25                  30

Ile Phe Phe Leu Gly Asp Gly Met Ser Leu Ser Thr Val Thr Ala Ala
        35                  40                  45

Arg Ile Tyr Lys Gly Gly Leu Thr Gly Lys Phe Glu Arg Glu Lys Ile
    50                  55                  60

Ser Trp Glu Glu Phe Asp Phe Ala Ala Leu Ser Lys Thr Tyr Asn Thr
65                  70                  75                  80

Asp Lys Gln Val Thr Asp Ser Ala Ala Ser Ala Thr Ala Tyr Leu Thr
                85                  90                  95

Gly Val Lys Thr Asn Gln Gly Val Ile Gly Leu Asp Ala Asn Thr Val
            100                 105                 110

Arg Thr Asn Cys Ser Tyr Gln Leu Asp Glu Ser Leu Phe Thr Tyr Ser
        115                 120                 125

Ile Ala His Trp Phe Gln Glu Ala Gly Arg Ser Thr Gly Val Val Thr
    130                 135                 140

Ser Thr Arg Val Thr His Ala Thr Pro Ala Gly Thr Tyr Ala His Val
145                 150                 155                 160

Ala Asp Arg Asp Trp Glu Asn Asp Ser Asp Val Val His Asp Arg Glu
                165                 170                 175

Asp Pro Glu Ile Cys Asp Asp Ile Ala Glu Gln Leu Val Phe Arg Glu
                180                 185                 190

Pro Gly Lys Asn Phe Lys Val Ile Met Gly Gly Gly Arg Arg Gly Phe
            195                 200                 205

Phe Pro Glu Glu Ala Leu Asp Ile Glu Asp Gly Ile Pro Gly Glu Arg
    210                 215                 220

Glu Asp Gly Lys His Leu Ile Thr Asp Trp Leu Asp Asp Lys Ala Ser
225                 230                 235                 240

Gln Gly Ala Thr Ala Ser Tyr Val Trp Asn Arg Asp Asp Leu Leu Ala
```

-continued

```
                    245                 250                 255

Val Asp Ile Arg Asn Thr Asp Tyr Leu Met Gly Leu Phe Ser Tyr Thr
            260                 265                 270

His Leu Asp Thr Val Leu Thr Arg Asp Ala Glu Met Asp Pro Thr Leu
            275                 280                 285

Pro Glu Met Thr Lys Val Ala Ile Glu Met Leu Thr Lys Asp Glu Asn
        290                 295                 300

Gly Phe Phe Leu Leu Val Glu Gly Gly Arg Ile Asp His Met His His
305                 310                 315                 320

Ala Asn Gln Ile Arg Gln Ser Leu Ala Glu Thr Leu Asp Met Glu Glu
                325                 330                 335

Ala Val Ser Met Ala Leu Ser Met Thr Asp Pro Glu Glu Thr Ile Ile
            340                 345                 350

Leu Val Thr Ala Asp His Gly His Thr Leu Thr Ile Thr Gly Tyr Ala
            355                 360                 365

Asp Arg Asn Thr Asp Ile Leu Asp Phe Ala Gly Ile Ser Asp Leu Asp
        370                 375                 380

Asp Arg Arg Tyr Thr Ile Leu Asp Tyr Gly Ser Gly Pro Gly Tyr His
385                 390                 395                 400

Ile Thr Glu Asp Gly Lys Arg Tyr Glu Pro Thr Glu Glu Asp Leu Lys
                405                 410                 415

Asp Ile Asn Phe Arg Tyr Ala Ser Ala Ala Pro Lys His Ser Ala Thr
            420                 425                 430

His Asp Gly Thr Asp Val Gly Ile Trp Val Asn Gly Pro Phe Ala His
            435                 440                 445

Leu Phe Thr Gly Val Tyr Glu Glu Asn Tyr Ile Pro His Ala Leu Ala
        450                 455                 460

Tyr Ala Ala Cys Val Gly Thr Gly Arg Thr Phe Cys Asp
465                 470                 475
```

<210> SEQ ID NO 96
<211> LENGTH: 11
<212> TYPE: DNA
<213> ORGANISM: Artificial Sequence
<220> FEATURE:
<223> OTHER INFORMATION: Example 27 product oligonucleotide sequence

<400> SEQUENCE: 96

```
actcatcgat a                                                     11
```

<210> SEQ ID NO 97
<211> LENGTH: 12
<212> TYPE: DNA
<213> ORGANISM: Artificial Sequence
<220> FEATURE:
<223> OTHER INFORMATION: Example 27 product oligonucleotide sequence

<400> SEQUENCE: 97

```
actcatcgat aa                                                    12
```

<210> SEQ ID NO 98
<211> LENGTH: 12
<212> TYPE: DNA
<213> ORGANISM: Artificial Sequence
<220> FEATURE:
<223> OTHER INFORMATION: Example 27 product oligonucleotide sequence

<400> SEQUENCE: 98

```
actcatcgat aa                                                    12
```

-continued

<210> SEQ ID NO 99
<211> LENGTH: 12
<212> TYPE: DNA
<213> ORGANISM: Artificial Sequence
<220> FEATURE:
<223> OTHER INFORMATION: Example 28 product oligonucleotide sequence
<220> FEATURE:
<221> NAME/KEY: misc_feature
<222> LOCATION: (4)..(4)
<223> OTHER INFORMATION: n = 2' deoxyInosine

<400> SEQUENCE: 99
actnagacca cg                                                                          12

<210> SEQ ID NO 100
<211> LENGTH: 221
<212> TYPE: PRT
<213> ORGANISM: Unknown
<220> FEATURE:
<223> OTHER INFORMATION: Description of Unknown:
      Wild type Archaeoglobus fulgidus endonuclease V endonuclease

<400> SEQUENCE: 100

Met Leu Gln Met Asn Leu Glu Glu Leu Arg Arg Ile Gln Glu Glu Met
1               5                   10                  15

Ser Arg Ser Val Val Leu Glu Asp Leu Ile Pro Leu Glu Glu Leu Glu
            20                  25                  30

Tyr Val Val Gly Val Asp Gln Ala Phe Ile Ser Asp Glu Val Val Ser
        35                  40                  45

Cys Ala Val Lys Leu Thr Phe Pro Glu Leu Glu Val Val Asp Lys Ala
    50                  55                  60

Val Arg Val Glu Lys Val Thr Phe Pro Tyr Ile Pro Thr Phe Leu Met
65                  70                  75                  80

Phe Arg Glu Gly Glu Pro Ala Val Asn Ala Val Lys Gly Leu Val Asp
                85                  90                  95

Asp Arg Ala Ala Ile Met Val Asp Gly Ser Gly Ile Ala His Pro Arg
            100                 105                 110

Arg Cys Gly Leu Ala Thr Tyr Ile Ala Leu Lys Leu Arg Lys Pro Thr
        115                 120                 125

Val Gly Ile Thr Lys Lys Arg Leu Phe Gly Glu Met Val Glu Val Glu
        130                 135                 140

Asp Gly Leu Trp Arg Leu Leu Asp Gly Ser Glu Thr Ile Gly Tyr Ala
145                 150                 155                 160

Leu Lys Ser Cys Arg Arg Cys Lys Pro Ile Phe Ile Ser Pro Gly Ser
                165                 170                 175

Tyr Ile Ser Pro Asp Ser Ala Leu Glu Leu Thr Arg Lys Cys Leu Lys
            180                 185                 190

Gly Tyr Lys Leu Pro Glu Pro Ile Arg Ile Ala Asp Lys Leu Thr Lys
        195                 200                 205

Glu Val Lys Arg Glu Leu Thr Pro Thr Ser Lys Leu Lys
    210                 215                 220

<210> SEQ ID NO 101
<211> LENGTH: 7
<212> TYPE: DNA

-continued

```
<213> ORGANISM: Artificial Sequence
<220> FEATURE:
<223> OTHER INFORMATION: Example 28 product oligonucleotide sequence

<400> SEQUENCE: 101 gaccacg                                                                7
```